(12) United States Patent
Gray et al.

(10) Patent No.: US 9,868,744 B2
(45) Date of Patent: Jan. 16, 2018

(54) HETEROAROMATIC COMPOUNDS AND THEIR USE AS DOPAMINE D1 LIGANDS

(71) Applicant: PFIZER INC., New York, NY (US)

(72) Inventors: David Lawrence Firman Gray, Groton, MA (US); Lei Zhang, Auburndale, MA (US); Jennifer Elizabeth Davoren, Cambridge, MA (US); Amy Beth Dounay, Colorado Springs, CO (US); Ivan Viktorovich Efremov, Brookline, MA (US); Chewah Lee, Wallingford, CT (US); Scot Richard Mente, Arlington, MA (US); Steven Victor O'Neil, East Lyme, CT (US); Bruce Nelsen Rogers, Belmont, MA (US); Chakrapani Subramanyam, South Glastonbury, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 15/305,372

(22) PCT Filed: Apr. 13, 2015

(86) PCT No.: PCT/IB2015/052672
§ 371 (c)(1),
(2) Date: Oct. 20, 2016

(87) PCT Pub. No.: WO2015/162518
PCT Pub. Date: Oct. 29, 2015

(65) Prior Publication Data
US 2017/0037053 A1    Feb. 9, 2017

Related U.S. Application Data

(60) Provisional application No. 61/984,086, filed on Apr. 25, 2014.

(51) Int. Cl.
*C07D 471/04* (2006.01)
*C07D 491/048* (2006.01)
*C07D 498/04* (2006.01)

(52) U.S. Cl.
CPC ........ *C07D 491/048* (2013.01); *C07D 471/04* (2013.01); *C07D 498/04* (2013.01)

(58) Field of Classification Search
CPC .................. C07D 471/04; C07D 491/048
See application file for complete search history.

(56) References Cited

U.S. PATENT DOCUMENTS

| | | |
|---|---|---|
| 5,137,879 A | 8/1992 | Edie et al. |
| 6,106,864 A | 8/2000 | Dolan et al. |
| 6,124,300 A | 9/2000 | Rajagopalan et al. |
| 6,232,320 B1 | 5/2001 | Stewart et al. |
| 6,448,261 B1 | 9/2002 | Bakthavatchalam et al. |
| 6,589,950 B1 | 7/2003 | Collingwood et al. |
| 7,122,669 B1 | 10/2006 | Haesslein |
| 7,273,864 B2 | 9/2007 | Wu et al. |
| 7,294,633 B2 | 11/2007 | Bold et al. |
| 7,763,731 B2 | 7/2010 | Rockway et al. |
| 7,977,345 B2 | 7/2011 | Bannen et al. |
| 8,207,178 B2 | 6/2012 | Shaginian et al. |
| 8,518,396 B2 | 8/2013 | Van Epps et al. |
| 8,772,504 B2 | 7/2014 | Gijsen et al. |
| 8,822,494 B2 * | 9/2014 | Davoren .............. C07D 401/04 514/300 |

(Continued)

FOREIGN PATENT DOCUMENTS

| | | |
|---|---|---|
| CN | 102558147 | 9/2014 |
| EP | 1746096 | 7/2005 |

(Continued)

OTHER PUBLICATIONS

Abou-Zeid, K. A. M. et al, "synthesis of 6-(4-(substituted amino)phenyl)-4,5-dihydropyridazin-3(2H)-ones as potential positive inotropic agents," Egyptian Journal of Pharmaceutical Sciences (1998), vol. Date 1997, 38(4-6), 319-331.
Almarsson and M. J. Zaworotko, Chem. Commun. 2004, 17, 1889-1896.
Bioreversible Carriers in Drug Design, Pergamon Press, 1987 (Ed. E. B. Roche, American Pharmaceutical Association).
Bischoff, F. et. al, "Design and Synthesis of a Novel Series of Bicyclic Heterocycles As Potent y-Secretase Modulators," Journal of Medicinal Chemistry (2012), 55(21), 9089-9106.
Bringmann, G. et al., Atroposelective Synthesis of Axially Chiral Biaryl Compounds. Angew. Chem., Int. Ed. 2005, 44, 5384-5427.
Crystals and the Polarizing Microscope by N. H. Hartshorne and a. Stuart, 4th Edition (Edward Arnold, 1970).

(Continued)

*Primary Examiner* — Bruck Kifle
(74) *Attorney, Agent, or Firm* — Feng Shao

(57) ABSTRACT

The present invention provides, in part, compounds of Formula (I) and pharmaceutically acceptable salts thereof; processes for the preparation of; intermediates used in the preparation of; and compositions containing such compounds or salts, and their uses for treating D1-mediated (or D1-associated) disorders including, e.g., schizophrenia (e.g., its cognitive and negative symptoms), schizotypal personality disorder, cognitive impairment (e.g., cognitive impairment associated with schizophrenia, AD, PD, or pharmacotherapy therapy), ADHD, Parkinson's disease, anxiety, and depression.

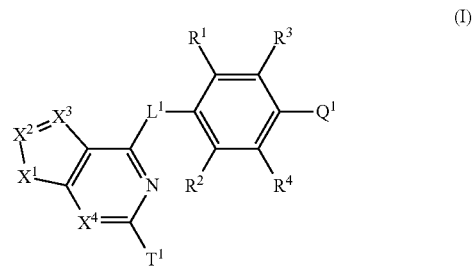

(I)

14 Claims, No Drawings

(56) References Cited

U.S. PATENT DOCUMENTS

| | | |
|---|---|---|
| 9,527,831 B2 | 12/2016 | Brodney et al. |
| 9,527,843 B2 | 12/2016 | Davoren et al. |
| 9,540,352 B2 | 1/2017 | Gray et al. |
| 9,617,275 B2 | 4/2017 | Coe et al. |
| 9,688,698 B2 | 6/2017 | Gray et al. |
| 2004/0204429 A1 | 10/2004 | Yuan |
| 2005/0153989 A1 | 7/2005 | Grotzfeld |
| 2007/0021446 A1 | 1/2007 | Ehlert et al. |
| 2007/0135452 A1 | 6/2007 | Gyorkos |
| 2007/0197558 A1 | 8/2007 | Betebenner |
| 2007/0275984 A1 | 11/2007 | Imogai |
| 2008/0194557 A1 | 8/2008 | Barbosa |
| 2009/0053192 A1 | 2/2009 | Millan |
| 2009/0163545 A1 | 6/2009 | Goldfarb |
| 2010/0010016 A1 | 1/2010 | Gangjee |
| 2010/0063047 A1 | 3/2010 | Borchardt |
| 2010/0143341 A1 | 6/2010 | Taylor et al. |
| 2010/0222352 A1 | 9/2010 | Jorgensen |
| 2010/0247517 A1 | 9/2010 | Austen |
| 2010/0317646 A1 | 12/2010 | Meiver |
| 2011/0092491 A1 | 4/2011 | Cheng et al. |
| 2011/0281881 A1 | 11/2011 | Gijsen |
| 2012/0022090 A1 | 1/2012 | Gijsen |
| 2012/0045420 A1 | 2/2012 | Van Epps |
| 2012/0258948 A1 | 10/2012 | Brown |
| 2013/0079323 A1 | 3/2013 | Creighton et al. |
| 2013/0123284 A1 | 5/2013 | Arnold et al. |
| 2013/0267513 A1 | 10/2013 | Chan |
| 2017/0037049 A1 | 2/2017 | Gray et al. |
| 2017/0044174 A1 | 2/2017 | Gray et al. |

FOREIGN PATENT DOCUMENTS

| | | |
|---|---|---|
| WO | 9111172 | 8/1991 |
| WO | 9402518 | 2/1994 |
| WO | 9855148 | 12/1998 |
| WO | 0132632 | 5/2001 |
| WO | 2005080377 | 1/2005 |
| WO | 2007009524 | 2/2007 |
| WO | 2007059905 | 5/2007 |
| WO | 08057402 | 5/2008 |
| WO | 2010118367 | 10/2010 |
| WO | 2011073845 | 6/2011 |
| WO | 2011119894 | 9/2011 |
| WO | 2013026516 | 2/2013 |
| WO | 2014072881 | 5/2014 |
| WO | 2014072882 | 5/2014 |

OTHER PUBLICATIONS

Demange, L., et al., Synthesis and evaluation of new potent inhibitors of CK1 and DCK5, two kinases involved in Alzheimer's disease, Med. Chem. Res., vol. 22, pp. 3247-3258 (2013).
Design of Prodrugs by H. Bundgaard (Elsevier, 1985).
Erdik, Tetrahedron 1992, 48, 9577-9648.
Farina et al., Organic Reactions 1997, 50, 1-652.
Finnin and Morgan, J. Pharm. Sci. 1999, 88, 955-958.
Freedman, T B et al.' Absolute Configuration Determination of Chiral Molecules in the Solution State Using Vibrational Circular Dichroism. Chirality2003, 15, 743-758.
Goldman-Rakic PS et al., "Targeting the dopamine D1 receptor in schizophrenia: insights for cognitive dysfunction", Psychopharmacology 174(1):3-16 (2004).
Goulet M, Madras BK "0(1) dopamine receptor agonists are more effective in alleviatingadvanced than mild parkinsonism in 1-methyl-4-phenyl-1,2, 3,6-tetrahydropyridinetreatedmonkeys", Journal of Pharmacology and Experimental Therapy 292(2):714-24(2000).
Greene and P. G. M. Wuts, Protective Groups in Organic Synthesis, 3rd Ed., Wiley & Sons, Inc., New York (1999).
Haleblian, J. K., J. Pharm. Sci. 1975, 64, 1269-1288.
Harris et al., Tetrahedron 2011, 67, 9063-9066.
Kalaitzakis et al., Tetrahedron: Asymmetry 2007, 18, 2418-2426.
Lewis, JPET 286:345-353, 1998.
Liang and Chen, Expert Opinion in Therapeutic Patents 2001, 11, 981-986.
Littke et al., J. Am. Chem. Soc. 2000, 122, 4020-4028.
Missale C, Nash SR, Robinson SW, Jaber M, Caron MG Dopamine receptors: from structure to Function, Physiological Reviews, vol. 78, No. 1, 1998.
Miyaura and A. Suzuki, Chem. Rev. 1995, 95, 2457-2483.
Pharmaceutical Dosage Forms: Tablets, vol. 1, by H. Lieberman and L. Lachman (Marcel Dekker, New York, 1980).
Pro-drugs as Novel Delivery Systems, vol. 14, ACS Symposium Series (T. Higuchi and W. Stella).
Prodrugs: Challenges and Reward, 2007 edition, edited by Valentino Stella, Ronald Borchardt, Michael Hageman, Reza Oliyai, Hans Maag, Jefferson Tilley, pp. 134-175 (Springer, 2007).
Remington's Pharmaceutical Sciences, 19th Edition (Mack Publishing Company, 1995).
Ryman-Rasmussen et al., "Differential activation of adenylate cyclase and receptor internalization by novel dopamine 01 receptor agonists", Molecular Pharmacology 68(4):1039-1048 (2005).
Stereochemistry of Organic Compounds by E. L. Eliel and S. H. Wilen (Wiley, New York, 1994).
Surmeier Dj et al., "The role of dopamine in modulating the structure and function of striatal circuits", Prog. Brain Res. 183: 149-67 (2010).
Suzuki, J. Organomet. Chem. 1999, 576, 147-168.
Verma et al., Pharmaceutical Technology On-line, 25(2), 1-14 (2001).
Handbook of Pharmaceutical Salts: Properties, Selection, and Use by Stahl and Wermuth (Wiley-VCH, 2002).
He, Gu, et al., 'Multicomplex-based pharmacophore-guided 3D-Qsar studies of N-substituted 2'-(aminoaryl) benzothiazoles as aurora-A inhibitors,' Chemical Biology & Drug Design (2012), 79(6), 960-971.
Tasler, Stefan, et al., 'N-substituted 2'-(aminoaryl)benzothiazoles as kinase inhibitors: Hit identification and scaffold hopping,' Bioorganic & Medicinal Chemistry Letters (2009), 19(5), 1349-1356.
Dumata, Nassima, et al., 'Roscovitine-Derived, Dual-Specificity Inhibitors of Cyclin-Dependent Kinases and Casein Kinases 1,' Journal of Medicinal Chemistry (2008), 51(17), 5229-5242.
Compound 1; Chemical Abstracts Services (CAS): American Chemical Society, Columbus, Ohio, Jun. 24, 2008; Registry No. 1030098-60-2; Chemical name: Isoxazolo[5,4-d]pyrimidine-6-carboxylic acid, 4-[[4-(5-isoxazolyl) phenyl]amino]-3-methyl-, ethyl ester.
Compound 2; Chemical Abstracts Services (CAS): American Chemical Society, Columbus, Ohio, Jun. 22, 2008; Registry No. 1029780-94-6; Chemical name: Isoxazolo[5,4-d]pyrimidine-3-carboxylic acid, 4-[[4-(5-isoxazolyl) phenyl]amino]-, ethyl ester.
Compound 3; Chemical Abstracts Services (CAS): American Chemical Society, Columbus, Ohio, Oct. 26, 2007; Registry No. 951529-82-1; Chemical name: Isoxazolo[5,4-d]pyrimidine-6-carboxylic acid, 3-methyl-4-[[4-(4-methyl-1-piperidinyl)phenyl]amino]-, ethyl ester.
Compound 4; Chemical Abstracts Services (CAS): American Chemical Society, Columbus, Ohio, Apr. 26, 2007; Registry No. 932551-11-6; Chemical name: Furo[2,3-d]pyrimidine-5-carboxylic acid, 2,6-dimethyl-4-[[4-(4-methyl-1-piperidinyl)phenyl]amino]-, ethyl ester.
Compound 5; Chemical Abstracts Services (CAS): American Chemical Society, Columbus, Ohio, Apr. 25, 2007; Registry No. 932480-83-6; Chemical name: Isoxazolo[5,4-d]pyrimidine-3-carboxylic acid, 4-[[4-(4-methyl-1-piperidinyl)phenyl]aminol]-, ethyl ester.
Compound 6; Chemical Abstracts Services (CAS): American Chemical Society, Columbus, Ohio, Apr. 25, 2007; Registry No. 932454-20-1; Chemical name: Isoxazolo[5,4-d]pyrimidine-3-carboxylic acid, 6-methyl-4-[[4-(4-methyl-1-piperidinyl)phenyl]amino]-, ethyl ester.
Compound 7; Chemical Abstracts Services (CAS): American Chemical Society, Columbus, Ohio, Jul. 19, 2006; Registry No.

(56) References Cited

OTHER PUBLICATIONS 894591-34-5; Chemical name: Isoxazolo[5,4-d]pyrimidine-3-carboxylic acid, 6-methyl-4-[[4-(4-methyl-1-piperidinyl)phenyl]amino]-, ethyl ester.
Compound 8; Chemical Abstracts Services (CAS): American Chemical Society, Columbus, Ohio, Oct. 11, 2011; Registry No. 1335051-48-3; Chemical name: 3H-Imidazo[4,5-c]pyridine, 2-methyl-4-[4-(1-methyl-1H-pyrazol-5-yl)phenoxy]-.
Compound 9; Chemical Abstracts Services (CAS): American Chemical Society, Columbus, Ohio, Oct. 11, 2011; Registry No. 1335051-54-1; Chemical name: Oxazolo[4,5-c]pyridine, 2-methyl-4-[4-(1-methyl-1H-pyrazol-5-yl) phenoxy]-.

* cited by examiner

HETEROAROMATIC COMPOUNDS AND THEIR USE AS DOPAMINE D1 LIGANDS

This application is a national phase filing under 35 U.S.C. § 371 of international patent application number PCT/IB2015/052672 filed Apr. 13, 2015, which in turn claims the benefit of priority to U.S. Provisional Patent Application Ser. No. 61/984,086 filed Apr. 25, 2014, the disclosure of each of these applications is hereby incorporated by reference in its entirety.

FIELD OF THE INVENTION

The present invention generally relates to heteroaromatic compounds, which are dopamine D1 ligands, for example dopamine D1 agonists or partial agonists.

BACKGROUND OF THE INVENTION

Dopamine acts upon neurons through two families of dopamine receptors, D1-like receptors (D1Rs) and D2-like receptors (D2Rs). The D1-like receptor family consists of D1 and D5 receptors which are expressed in many regions of the brain. D1 mRNA has been found, for example, in the striatum and nucleus accumbens. See e.g., Missale C, Nash S R, Robinson S W, Jaber M, Caron M G "Dopamine receptors: from structure to function", *Physiological Reviews* 78:189-225 (1998). Pharmacological studies have reported that D1 and D5 receptors (D1/D5), namely D1-like receptors, are linked to stimulation of adenylyl cyclase, whereas D2, D3, and D4 receptors, namely D2-like receptors, are linked to inhibition of cAMP production.

Dopamine D1 receptors are implicated in numerous neuropharmacological and neurobiological functions. For example, D1 receptors are involved in different types of memory function and synaptic plasticity. See e.g., Goldman-Rakic P S et al., "Targeting the dopamine D1 receptor in schizophrenia: insights for cognitive dysfunction", *Psychopharmacology* 174(1):3-16 (2004). Moreover, D1 receptors have been implicated in a variety of psychiatric, neurological, neurodevelopmental, neurodegenerative, mood, motivational, metabolic, cardiovascular, renal, ophthalmic, endocrine, and/or other disorders described herein including schizophrenia (e.g., cognitive and negative symptoms in schizophrenia), schizotypal personality disorder, cognitive impairment associated with D2 antagonist therapy, ADHD, impulsivity, autism spectrum disorder, mild cognitive impairment (MCI), age-related cognitive decline, Alzheimer's dementia, Parkinson's disease (PD), Huntington's chorea, depression, anxiety, treatment-resistant depression (TRD), bipolar disorder, chronic apathy, anhedonia, chronic fatigue, post-traumatic stress disorder, seasonal affective disorder, social anxiety disorder, post-partum depression, serotonin syndrome, substance abuse and drug dependence, Tourette's syndrome, tardive dyskinesia, drowsiness, sexual dysfunction, migraine, systemic lupus erythematosus (SLE), hyperglycemia, dislipidemia, obesity, diabetes, sepsis, post-ischemic tubular necrosis, renal failure, resistant edema, narcolepsy, hypertension, congestive heart failure, postoperative ocular hypotonia, sleep disorders, pain, and other disorders in a mammal. See e.g., Goulet M, Madras B K "D(1) dopamine receptor agonists are more effective in alleviating advanced than mild parkinsonism in 1-methyl-4-phenyl-1,2,3,6-tetrahydropyridine-treated monkeys", *Journal of Pharmacology and Experimental Therapy* 292 (2):714-24 (2000); Surmeier D J et al., "The role of dopamine in modulating the structure and function of striatal circuits", *Prog. Brain Res.* 183:149-67 (2010).

New or improved agents that modulate (such as agonize or partially agonize) D1R are needed for developing new and more effective pharmaceuticals to treat diseases or conditions associated with dysregulated activation of D1R, such as those described herein.

WO2013026516 reports bicyclic heteroaromatic compounds having the following structure

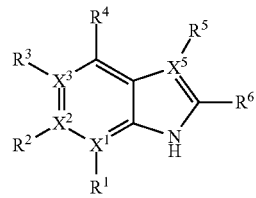

that are kinase inhibitors and can be used, for example, for treating tumors.

CN102558147 reports pyridinecarboxamide derivatives of the following formula:

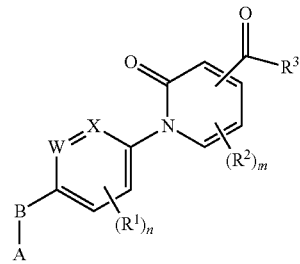

as inhibitors of tyrosine kinase and/or serine-threonine kinase for treating cancer.

WO2007009524 reports 2-arylbenzothiazoles of the following formula

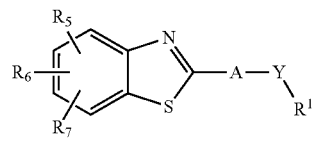

useful as protein kinase inhibitors for treating diseases such as those associated with abnormal and hyperproliferation of cells.

US2005/0153989 reports compounds of the following structure

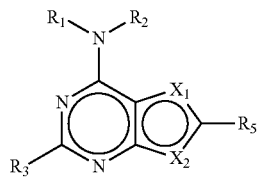

useful for treating and/or preventing conditions and diseases associated with kinase activity, e.g., EGFR activity, such as cancer, hyperplasia, psoriasis, cardiac hypertrophy, arthrosclerosis, dermatitis and/or diseases or conditions associated with undesired cellular hyperproliferation.

Abou-Zeid, K. A. M. et al, "synthesis of 6-(4-(substituted amino)phenyl)-4,5-dihydropyridazin-3(2H)-ones as potential positive inotropic agents," Egyptian Journal of Pharmaceutical Sciences (1998), Volume Date 1997, 38(4-6), 319-331, reports some pyridazinones, for example,

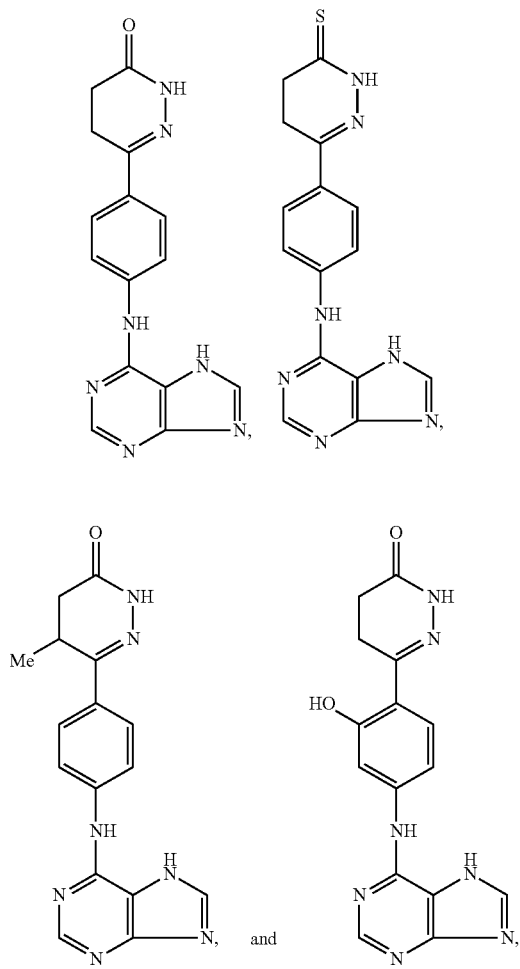

that were evaluated as inhibitors of cardiac cAMP phosphodiesterase.

Demange, L. et. al, "Synthesis and evaluation of new potent inhibitors of CK1 and CDK5, two kinases involved in Alzheimer's disease," Medicinal Chemistry Research (2013), 22(7), 3247-3258 reports compounds having one of following structures

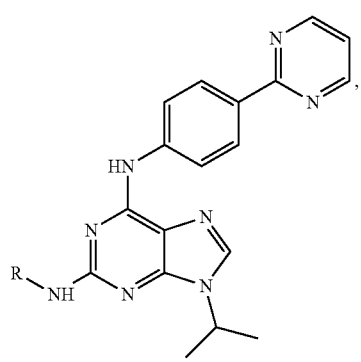

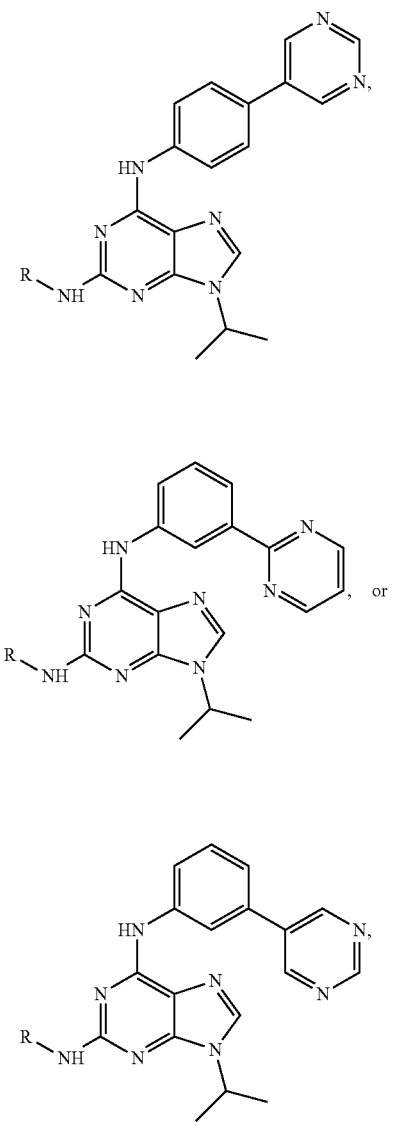

as inhibitors of CK1 and CDK5. In addition, it also reports certain intermediates having one of the following structures:

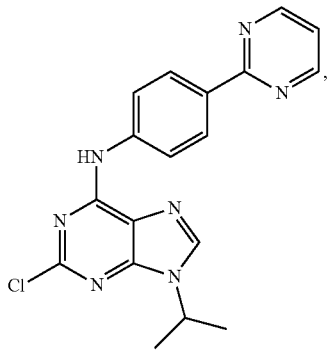

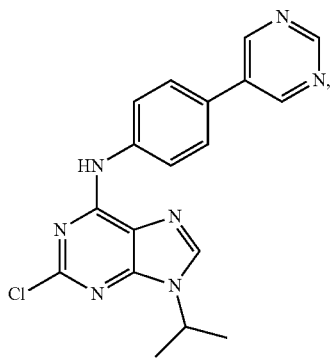

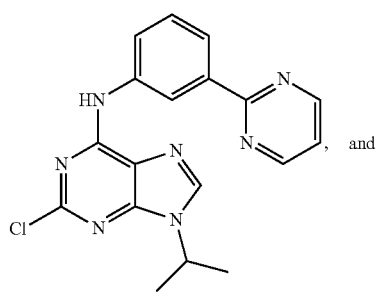

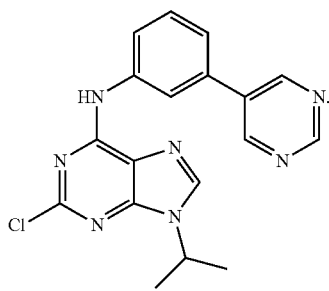

US20100317646 reports pyrazolopyridine compounds of the following structure

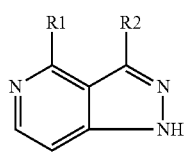

as kinase inhibitors (e.g., LRRK or LRRK2 inhibitors).

US20100247517 reports compounds having one of the following structures

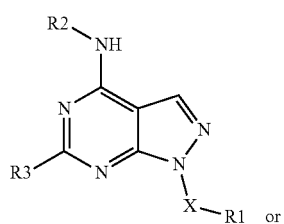

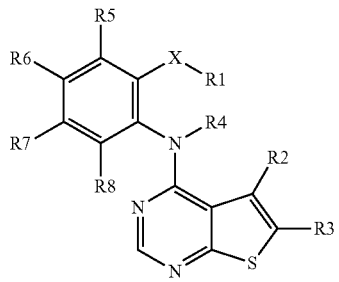

useful for the production of pharmaceutical compositions for the prophylaxis and/or treatment of diseases which can be influenced by the inhibition of the kinase activity of Mnk1 and/or Mnk2 (Mnk2a or Mnk2b) and/or variants thereof.

Bischoff, F. et. al, "Design and Synthesis of a Novel Series of Bicyclic Heterocycles As Potent γ-Secretase Modulators," Journal of Medicinal Chemistry (2012), 55(21), 9089-9106 reports certain imidazole containing compounds γ-secretase modulators including the following two compounds:

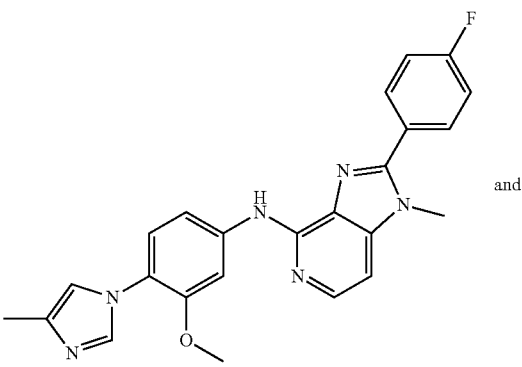

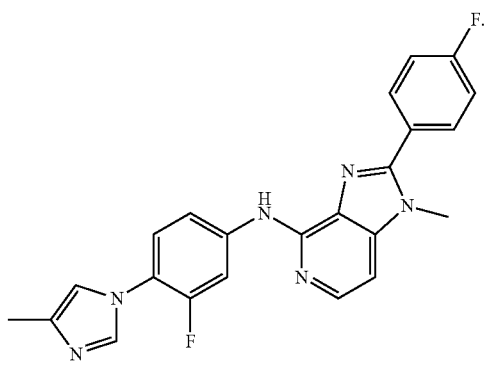

US2012/0022090 reports substituted benzoxazole, benzimidazole, oxazolopyridine, and imidazopyridine derivative of the following structure

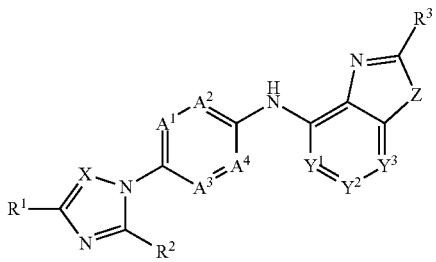

that are γ-secretase modulators useful in the treatment of diseases.

US2011/0281881 reports substituted bicyclic derivative of the following structure

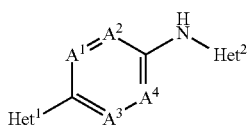

wherein $Het^2$ can be

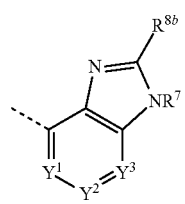

as γ-secretase modulators useful in the treatment of diseases such as Alzheimer's Disease.

WO2008067420 reports compounds of one of the flowing structures

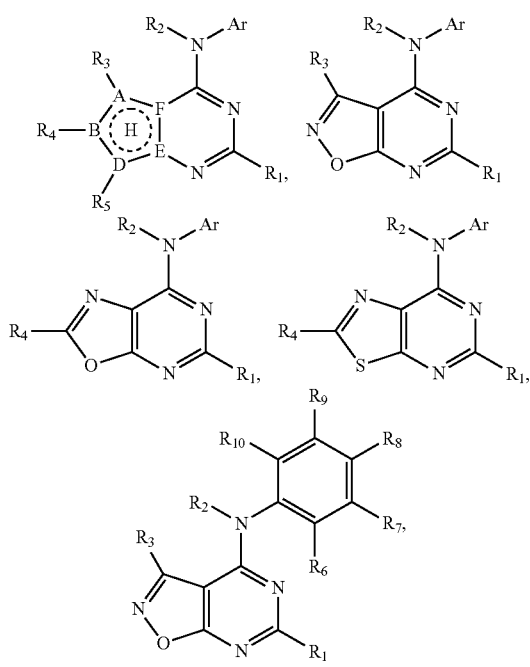

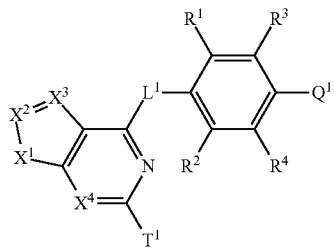

or pharmaceutically acceptable salts, proudrugs, or tautomers thererof, as caspase activators and inducers of apoptosis.

SUMMARY OF THE INVENTION

In a first aspect, the present invention provides a method for treating a D1-mediated (or D1-associated) disorder in a mammal, which method comprises administering to said mammal a therapeutically effective amount of a compound of Formula I:

I or a pharmaceutically acceptable salt thereof, wherein:
$L^1$ is O, S, $NR^N$, C(=O), CH(OH), or $CH(OCH_3)$;
$Q^1$ is an N-containing 5- to 10-membered heteroaryl, an N-containing 4- to 12-membered heterocycloalkyl, or phenyl, each optionally substituted with one $R^9$ and further optionally substituted with 1, 2, 3, or 4 $R^{10}$;
$X^1$ is O, S, NH, $N(C_{1-4}$ alkyl), N(cyclopropyl), or $N(-CH_2$-cyclopropyl);
$X^2$ is N or $C-T^2$;
$X^3$ is N or $C-T^3$;
provided that when $X^1$ is O or S, then at least one of $X^2$ and $X^3$ is not N;
$X^4$ is N or $C-T^4$;
$T^1$ is H, —OH, halogen, —CN, or optionally substituted $C_{1-2}$ alkyl;
each of $T^2$, $T^3$, and $T^4$ is independently selected from the group consisting of H, —OH, halogen, —CN, optionally substituted $C_{1-4}$ alkyl, optionally substituted $C_{3-4}$ cycloalkyl, optionally substituted cyclopropylmethyl, and optionally substituted $C_{1-4}$ alkoxy;

$R^N$ is H, $C_{1-4}$ alkyl, $C_{3-4}$ cycloalkyl, or —$C_{1-2}$ alkyl-$C_{3-4}$ cycloalkyl, each of $R^1$ and $R^2$ is independently selected from the group consisting of H, halogen, —CN, $C_{1-6}$ alkyl, $C_{1-6}$ haloalkyl, $C_{1-6}$ alkoxy, $C_{1-6}$ haloalkoxy, and $C_{3-6}$ cycloalkyl, wherein each of said $C_{1-6}$ alkyl and $C_{3-6}$ cycloalkyl is optionally substituted with 1, 2, 3, 4, or 5 substituents each independently selected from halo, —OH, —CN, $C_{1-4}$ alkyl, $C_{1-4}$ haloalkyl, $C_{1-4}$ alkoxy, and $C_{1-4}$ haloalkoxy;

each of $R^3$ and $R^4$ is independently selected from the group consisting of H, halogen, —OH, —$NH_2$, —$NH(CH_3)$, —$N(CH_3)_2$, —$NO_2$, —CN, —$SF_5$, $C_{1-6}$ alkyl, $C_{1-6}$ haloalkyl, $C_{1-6}$ haloalkoxy, $C_{2-6}$ alkenyl, $C_{2-6}$ alkynyl, $C_{3-7}$ cycloalkyl, a 4- to 10-membered heterocycloalkyl, —$N(R^5)(R^6)$, —$N(R^7)(C(=O)R^8)$, —$C(=O)$—$N(R^5)(R^6)$, —$C(=O)$—$R^8$, —$C(=O)$—$OR^8$, —$N(R^7)(S(=O)_2R^8)$, —$S(=O)_2$—$N(R^5)(R^6)$, —$SR^8$, and —$OR^8$, wherein each of said $C_{1-6}$ alkyl, $C_{3-7}$ cycloalkyl, and heterocycloalkyl is optionally substituted with 1, 2, or 3 substituents each independently selected from the group consisting of halogen, —CN, —OH, $C_{1-4}$ alkyl, $C_{1-4}$ alkoxy, $C_{1-4}$ haloalkyl, $C_{1-4}$ haloalkoxy, $C_{3-6}$ cycloalkyl, —$N(R^5)(R^6)$, —$N(R^7)(C(=O)R^8)$, —$C(=O)$—$OR^8$, —$C(=O)H$, —$C(=O)R^8$, —$C(=O)N(R^5)(R^6)$, —$N(R^7)(S(=O)_2R^8)$, —$S(=O)_2$—$N(R^5)(R^6)$, —$SR^8$, and —$OR^8$;

or $R^1$ and $R^3$ together with the two carbon atoms to which they are attached form a fused N-containing 5- or 6-membered heteroaryl, a fused N-containing 5- or 6-membered heterocycloalkyl, a fused 5- or 6-membered cycloalkyl, or a fused benzene ring, each optionally substituted with 1, 2, or 3 substituents each independently selected from the group consisting of halo, —CN, —OH, —$NH_2$, —$NH(CH_3)$, —$N(CH_3)_2$, $C_{1-3}$ alkyl, $C_{1-3}$ alkoxy, $C_{1-3}$ haloalkyl, and $C_{1-3}$ haloalkoxy;

$R^5$ is H, $C_{1-4}$ alkyl, $C_{1-4}$ haloalkyl, or $C_{3-7}$ cycloalkyl;

$R^6$ is H or selected from the group consisting of $C_{1-4}$ alkyl, $C_{1-4}$ haloalkyl, $C_{3-7}$ cycloalkyl, a 4- to 10-membered heterocycloalkyl, $C_{6-10}$ aryl, a 5- to 10-membered heteroaryl, ($C_{3-7}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, and (5- to 10-membered heteroaryl)-$C_{1-4}$ alkyl-, wherein each of the selections from the group is optionally substituted with 1, 2, 3, or 4 substituents each independently selected from the group consisting of —OH, —$NH_2$, —$NH(CH_3)$, —$N(CH_3)_2$, —CN, $C_{1-4}$ alkyl, $C_{3-7}$ cycloalkyl, $C_{1-4}$ hydroxylalkyl, —S—$C_{1-4}$ alkyl, —$C(=O)H$, —$C(=O)$—$C_{1-4}$ alkyl, —$C(=O)$—$O$—$C_{1-4}$ alkyl, —$C(=O)$—$NH_2$, —$C(=O)$—$N(C_{1-4}$ alkyl$)_2$, $C_{1-4}$ haloalkyl, $C_{1-4}$ alkoxy, and $C_{1-4}$ haloalkoxy;

or $R^5$ and $R^6$ together with the N atom to which they are attached form a 4- to 10-membered heterocycloalkyl or a 5- to 10-membered heteroaryl, each optionally substituted with 1, 2, 3, 4, or 5 substituents each independently selected from the group consisting of halogen, —OH, —$NH_2$, —$NH(CH_3)$, —$N(CH_3)_2$, oxo, —$C(=O)H$, —$C(=O)OH$, —$C(=O)$—$C_{1-4}$ alkyl, —$C(=O)$—$NH_2$, —$C(=O)$—$N(C_{1-4}$ alkyl$)_2$, —CN, $C_{1-4}$ alkyl, $C_{1-4}$ alkoxy, $C_{1-4}$ hydroxylalkyl, $C_{1-4}$ haloalkyl, and $C_{1-4}$ haloalkoxy;

$R^7$ is selected from the group consisting of H, $C_{1-4}$ alkyl, and $C_{3-7}$ cycloalkyl;

$R^8$ is selected from the group consisting of $C_{1-6}$ alkyl, $C_{3-7}$ cycloalkyl, a 4- to 14-membered heterocycloalkyl, $C_{6-10}$ aryl, a 5- to 10-membered heteroaryl, ($C_{3-7}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, and (5- to 10-membered heteroaryl)-$C_{1-4}$ alkyl-, wherein each of the selections from the group is optionally substituted with 1, 2, or 3 substituents each independently selected from the group consisting of halogen, —$CF_3$, —CN, —OH, —$NH_2$, —$NH(CH_3)$, —$N(CH_3)_2$, oxo, —S—$C_{1-4}$ alkyl, $C_{1-4}$ alkyl, $C_{1-4}$ haloalkyl, $C_{2-6}$ alkenyl, $C_{2-6}$ alkynyl, $C_{3-7}$ cycloalkyl, $C_{1-4}$ alkoxy, and $C_{1-4}$ haloalkoxy;

each of $R^9$ and $R^{10}$ is independently selected from the group consisting of halogen, —OH, —CN, —$SF_5$, —$NO_2$, Oxo, thiono, $C_{1-6}$ alkyl, $C_{1-6}$ haloalkyl, $C_{1-6}$ hydroxylalkyl, $C_{1-6}$ alkoxy, $C_{1-6}$ haloalkoxy, $C_{3-7}$ cycloalkyl, $C_{2-6}$ alkenyl, $C_{2-6}$ alkynyl, $C_{6-10}$ aryl, a 4- to 10-membered heterocycloalkyl, a 5- to 10-membered heteroaryl, ($C_{3-7}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, (5- to 10-membered heteroaryl)-$C_{1-4}$ alkyl-, —$N(R^5)(R^6)$, —$N(R^7)(C(=O)R^8)$, —$S(=O)_2N(R^5)(R^6)$, —$C(=O)$—$N(R^5)(R^6)$, —$C(=O)$—$R^8$, —$C(=O)$—$OR^8$, —$SR^8$, and —$OR^8$, wherein each of said $C_{1-6}$ alkyl, $C_{3-7}$ cycloalkyl, $C_{6-10}$ aryl, 4- to 10-membered heterocycloalkyl, 5- to 10-membered heteroaryl, ($C_{3-7}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, and (5- to 10-membered heteroaryl)-$C_{1-4}$ alkyl- is optionally substituted with 1, 2, 3, or 4 substituents each independently selected from the group consisting of halogen, OH, —CN, —$NO_2$, $C_{1-4}$ alkyl, $C_{1-4}$ hydroxylalkyl, $C_{1-4}$ alkoxy, —$N(R^5)(R^6)$, —S—($C_{1-4}$ alkyl), —$S(=O)_2$—($C_{1-4}$ alkyl), $C_{6-10}$ aryloxy, [($C_{6-10}$ aryl)-$C_{1-4}$ alkyloxy-optionally substituted with 1 or 2 $C_{1-4}$ alkyl], oxo, —$C(=O)H$, —$C(=O)$—$C_{1-4}$ alkyl, —$C(=O)O$—$C_{1-4}$ alkyl, —$C(=O)NH_2$, —$NHC(=O)H$, —$NHC(=O)$—($C_{1-4}$ alkyl), $C_{3-7}$ cycloalkyl, a 5- or 6-membered heteroaryl, $C_{1-4}$ haloalkyl, and $C_{1-4}$ haloalkoxy;

or $R^9$ and an adjacent $R^{10}$ together with the two ring atoms on $Q^1$ to which they are attached form a fused benzene ring or a fused 5- or 6-membered heteroaryl, each optionally substituted with 1, 2, 3, 4, or 5 independently selected $R^{10a}$; and each $R^{10a}$ is independently selected from the group consisting of halogen, —OH, —$N(R^5)(R^6)$, —$C(=O)OH$, —$C(=O)$—$C_{1-4}$ alkyl, —$C(=O)$—$NH_2$, —$C(=O)$—$N(C_{1-4}$ alkyl$)_2$, —CN, —$SF_5$, $C_{1-4}$ alkyl, $C_{1-4}$ alkoxy, $C_{1-4}$ hydroxylalkyl, $C_{1-4}$ haloalkyl, and $C_{1-4}$ haloalkoxy, with the provisos that (1) when $X^4$ is N and $X^1$ is NH, N($C_{1-4}$ alkyl), N(cyclopropyl), N(—$CH_2$-cyclopropyl), or S, then $L^1$ is other than $NR^N$;

(2) when $X^1$ is NH then $X^3$ is other than N;

(3) when $X^2$ is N, $X^3$ is C-$T^3$, $X^4$ is C-$T^4$, $T^3$ is not H, and $X^1$ is NH, then $L^1$ is other than O or $NR^N$;

(4) when $X^2$ is C-$T^2$, $X^3$ is C-$T^3$, $X^4$ is C-$T^4$, then $X^1$ is other than S or O;

(5) when $L^1$ is O, $X^3$ is C-$T^3$, and $X^4$ is C-$T^4$, then $X^1$ is other than NH;

(6) when $X^1$ is NH, N($C_{1-4}$ alkyl), N(cyclopropyl), N(—$CH_2$-cyclopropyl), or O, and $X^3$ is N then $L^1$ is other than $NR^N$; and (7) $Q^1$ is other than an optionally substituted benzo[d]thiazolyl (e.g., benzo[d]thiazol-2-yl) or an optionally substituted monocyclic 2-oxo-1H-pyridin-1-yl.

In some embodiments, when $X^4$ is N, then $L^1$ is other than $NR^N$.

In some embodiments, $L^1$ is other than $NR^N$.

In some embodiments, when $X^4$ is N, then $X^1$ is other than NH, N($C_{1-4}$ alkyl), N(cyclopropyl), or N(—$CH_2$-cyclopropyl).

In some embodiments, when $X^4$ is N, then $X^1$ is other than S.

In some embodiments, when $X^4$ is N, then $X^1$ is other than NH, N($C_{1-4}$ alkyl), N(cyclopropyl), N(—$CH_2$-cyclopropyl), or S.

In some embodiments, $Q^1$ is other than an optionally substituted monocyclic 2-oxo-1H-pyridin-1-yl.

In some embodiments, when $X^2$ is N, $X^3$ is C-$T^3$, and $X^4$ is C-$T^4$, then $X^1$ is other than NH.

In some embodiments, when $X^3$ is C-$T^3$, and $X^4$ is C-$T^4$, then $X^1$ is other than NH.

In some embodiments, $L^1$ is other than $NR^N$; $Q^1$ is other than an optionally substituted benzo[d]thiazolyl; $Q^1$ is other than an optionally substituted phenyl; when $X^4$ is N, then $X^1$ is other than NH, N($C_{1-4}$ alkyl), N(cyclopropyl), N(—$CH_2$-cyclopropyl) or S; and when $X^3$ is C-$T^3$, and $X^4$ is C-$T^4$, then $X^1$ is other than NH. In some further embodiments, $Q^1$ is other than an optionally substituted monocyclic 2-oxo-1H-pyridin-1-yl. In some yet further embodiments, $L^1$ is O or S. In still further embodiments, $L^1$ is O.

In some embodiments, the disorder is selected from schizophrenia (e.g., cognitive and negative symptoms in schizophrenia), schizotypal personality disorder, cognitive impairment [e.g., cognitive impairment associated with schizophrenia, cognitive impairment associated with AD, cognitive impairment associated with PD, cognitive impairment associated with pharmacotherapy therapy (e.g., D2 antagonist therapy)], attention deficit hyperactivity disorder (ADHD), impulsivity, compulsive gambling, overeating, autism spectrum disorder, mild cognitive impairment (MCI), age-related cognitive decline, dementia (e.g., senile dementia, HIV-associated dementia, Alzheimer's dementia, Lewy body dementia, vascular dementia, or frontotemporal dementia), restless leg syndrome (RLS), Parkinson's disease, Huntington's chorea, anxiety, depression (e.g., age-related depression), major depressive disorder (MDD), treatment-resistant depression (TRD), bipolar disorder, chronic apathy, anhedonia, chronic fatigue, post-traumatic stress disorder, seasonal affective disorder, social anxiety disorder, post-partum depression, serotonin syndrome, substance abuse and drug dependence, drug abuse relapse, Tourette's syndrome, tardive dyskinesia, drowsiness, excessive daytime sleepiness, cachexia, inattention, sexual dysfunction (e.g., erectile dysfunction or post-SSRI sexual dysfunction), migraine, systemic lupus erythematosus (SLE), hyperglycemia, atherosclerosis, dislipidemia, obesity, diabetes, sepsis, post-ischemic tubular necrosis, renal failure, hyponatremia, resistant edema, narcolepsy, hypertension, congestive heart failure, postoperative ocular hypotonia, sleep disorders, and pain.

In some embodiments, $L^1$ is O or S. In some further embodiments, $L^1$ is S.

In some embodiments, $L^1$ is O.

In some embodiments, $L^1$ is NH.

In some embodiments, $L^1$ is C(=O), CH(OH), or CH(OCH$_3$). In some further embodiments, $L^1$ is C(=O) or CH(OH).

In some embodiments, $T^1$ is H, F, Cl, methyl, or $C_1$ fluoroalkyl; and each of $T^2$, $T^3$, and $T^4$ is independently selected from the group consisting of H, halogen, —CN, $C_{1-4}$ alkyl, $C_{1-4}$ haloalkyl, $C_{3-4}$ cycloalkyl, $C_{3-4}$ halocycloalkyl, cyclopropylmethyl, $C_{1-4}$ alkoxy, and $C_{1-4}$ haloalkoxy. In some further embodiments, each of $T^2$, $T^3$, and $T^4$ is independently selected from the group consisting of H, halogen, —CN, methoxy, $C_1$ fluoroalkoxy, methyl, and $C_1$ fluoroalkyl, In some embodiments, $T^1$ is H, F, Cl, methyl, or $C_1$ fluoroalkyl.

In some embodiments, $T^1$ is H and $T^4$ is H.

In some embodiments, each of $T^2$ and $T^3$ is independently H, CN, F, Cl, Br, methyl, methoxy, $C_1$ fluoroalkoxy, or $C_1$ fluoroalkyl.

In some embodiments, $X^1$ is O.

In some embodiments, $X^1$ is O; and 0 or 1 of $X^2$ and $X^3$ is N. In some further embodiments, $X^4$ is N.

In some embodiments, $X^1$ is O; 1 of $X^2$ and $X^3$ is N, and $X^4$ is C-$T^4$.

In some embodiments, $X^1$ is S.

In some embodiments, $X^1$ is S; and 0 or 1 of $X^2$ and $X^3$ is N. In some further embodiments, $X^4$ is N.

In some embodiments, $X^1$ is S; 1 of $X^2$ and $X^3$ is N, and $X^4$ is C-$T^4$.

In some embodiments, $X^1$ is NH.

In some embodiments, $X^1$ is NH; and 0 or 1 of $X^2$ and $X^3$ is N. In some further embodiments, $X^4$ is C-$T^4$.

In some embodiments, $X^1$ is NH; $X^2$ is C-$T^2$; and $X^3$ is N.

In some embodiments, $X^4$ is N; and $X^1$ is O or S. In some further embodiments, 0 or 1 of $X^2$ and $X^3$ is N.

In some embodiments, $X^4$ is N; and $X^1$ is O. In some further embodiments, 0 or 1 of $X^2$ and $X^3$ is N.

In some embodiments, the compound of Formula I or a pharmaceutically acceptable salt thereof is a compound of Formula I-a:

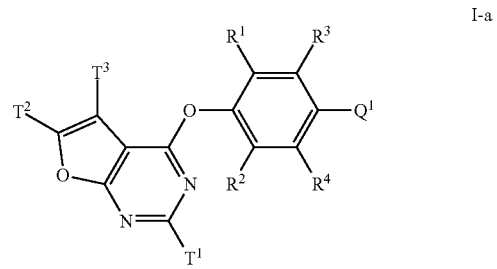

I-a or a pharmaceutically acceptable salt thereof.

In some embodiments, the compound of Formula I or a pharmaceutically acceptable salt thereof is a compound of Formula I-b:

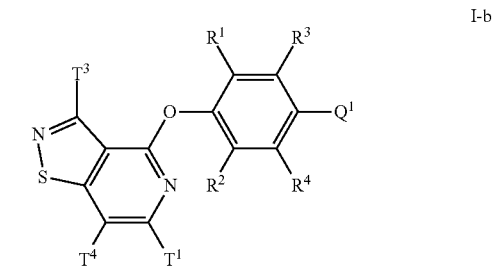

I-b or a pharmaceutically acceptable salt thereof.

In some embodiments, the compound of Formula I or a pharmaceutically acceptable salt thereof is a compound of Formula I-c:

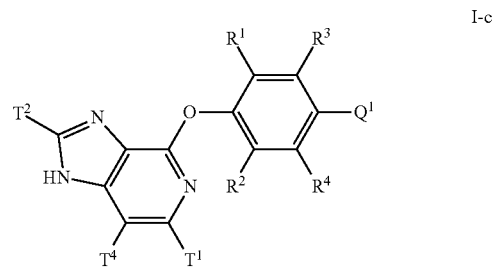

I-c or a pharmaceutically acceptable salt thereof.

In some embodiments, the compound of Formula I or a pharmaceutically acceptable salt thereof is a compound of Formula I-d:

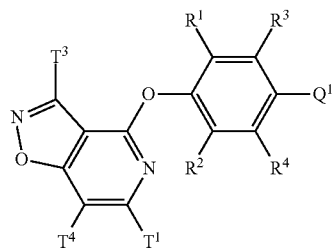

or a pharmaceutically acceptable salt thereof.

In some embodiments, the compound of Formula I or a pharmaceutically acceptable salt thereof is a compound of Formula I-e:

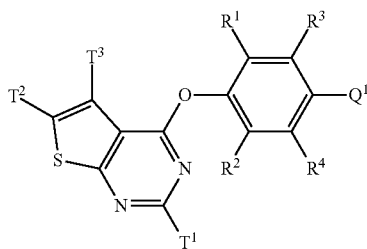

or a pharmaceutically acceptable salt thereof.

The embodiments described herein in the first aspect of the invention, unless specified otherwisely, include the methods for use of a compound of Formula I, I-a, I-b, I-c, I-d, or I-e, or a pharmaceutically acceptable salt thereof.

In some embodiments, each of $R^1$ and $R^2$ is independently H or halogen. In some further embodiments, each of $R^1$ and $R^2$ is H.

In some embodiments, each of $R^3$ and $R^4$ is independently H, halogen, —CN, methyl, $C_1$ haloalkyl, methoxy, or $C_1$ haloalkoxy.

In some embodiments, $R^3$ is H and $R^4$ is H, halogen, —CN, methyl, or $C_1$ haloalkyl.

In some embodiments, $R^3$ is H and $R^4$ is methyl.

In some embodiments, $Q^1$ is an N-containing 5- to 6-membered heteroaryl or an N-containing 5- to 6-membered heterocycloalkyl, each optionally substituted with one $R^9$ and 1, 2, 3, or 4 $R^{10}$.

In some embodiments, $Q^1$ is an N-containing 5- to 6-membered heteroaryl or an N-containing 5- to 6-membered heterocycloalkyl, each substituted with one $R^9$ and further optionally substituted with 1, 2, 3, or 4 $R^{10}$.

In some embodiment:
$R^9$ is halogen(e.g. Cl), $C_{1-4}$ alkyl, $C_{1-4}$ haloalkyl, —CN, —SF$_5$, —N($R^5$)($R^6$), $C_{1-6}$ alkoxy, $C_{1-6}$ haloalkoxy, $C_{3-7}$ cycloalkoxy, or $C_{3-7}$ cycloalkyl, wherein each of the $C_{1-4}$ alkyl and $C_{3-7}$ cycloalkyl is optionally substituted with 1, 2, 3, 4, or 5 substituents each independently selected from the group consisting of halogen, —N($R^5$)($R^6$), $C_{1-4}$ alkyl, $C_{1-4}$ haloalkyl, $C_{3-7}$ cycloalkyl, $C_{1-4}$ alkoxy, and $C_{1-4}$ haloalkoxy;

each $R^{10}$ is independently selected from the group consisting of halogen, —OH, —CN, —SF$_5$, —NO$_2$, Oxo, thiono, $C_{1-6}$ alkyl, $C_{1-6}$ haloalkyl, $C_{1-6}$ hydroxylalkyl, $C_{1-6}$ alkoxy, $C_{1-6}$ haloalkoxy, $C_{3-7}$ cycloalkyl, $C_{2-6}$ alkenyl, $C_{2-6}$ alkynyl, $C_{6-10}$ aryl, a 4- to 10-membered heterocycloalkyl, a 5- to 10-membered heteroaryl, ($C_{3-7}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, (5- to 10-membered heteroaryl)-$C_{1-4}$ alkyl-, —N($R^5$)($R^6$), —N($R^7$)(C(=O)$R^8$), —S(=O)$_2$N($R^5$)($R^6$), —C(=O)—N($R^5$)($R^6$), —C(=O)—$R^8$, —C(=O)—OR$^8$, —SR$^8$, and —OR$^8$, wherein each of said $C_{1-6}$ alkyl, $C_{3-7}$ cycloalkyl, $C_{6-10}$ aryl, 4- to 10-membered heterocycloalkyl, 5- to 10-membered heteroaryl, ($C_{3-7}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, and (5- to 10-membered heteroaryl)-$C_{1-4}$ alkyl- is optionally substituted with 1, 2, 3, or 4 substituents each independently selected from the group consisting of halogen, OH, —CN, —NO$_2$, $C_{1-4}$ alkyl, $C_{1-4}$ hydroxylalkyl, $C_{1-4}$ alkoxy, —N($R^5$)($R^6$), —S—($C_{1-4}$ alkyl), —S(=O)$_2$—($C_{1-4}$ alkyl), $C_{6-10}$ aryloxy, [($C_{6-10}$ aryl)-$C_{1-4}$ alkyloxy-optionally substituted with 1 or 2 $C_{1-4}$ alkyl], oxo, —C(=O)H, —C(=O)—$C_{1-4}$ alkyl, —C(=O)O—$C_{1-4}$ alkyl, —C(=O)NH$_2$, —NHC(=O)H, —NHC(=O)—($C_{1-4}$ alkyl), $C_{3-7}$ cycloalkyl, a 5- or 6-membered heteroaryl, $C_{1-4}$ haloalkyl, and $C_{1-4}$ haloalkoxy;

or $R^9$ and an adjacent $R^{10}$ together with the two ring atoms on $Q^1$ to which they are attached form a fused benzene ring or a fused 5- or 6-membered heteroaryl, each optionally substituted with 1, 2, 3, 4, or 5 independently selected $R^{10a}$.

In some embodiment, $R^9$ is halogen (e.g. Cl), $C_{1-4}$ alkyl, $C_{1-4}$ haloalkyl, —CN, —SF$_5$, —N($R^5$)($R^6$), $C_{1-6}$ alkoxy, $C_{1-6}$ haloalkoxy, $C_{3-7}$ cycloalkoxy, or $C_{3-7}$ cycloalkyl, wherein each of the $C_{1-4}$ alkyl and $C_{3-7}$ cycloalkyl is optionally substituted with 1, 2, 3, 4, or 5 substituents each independently selected from the group consisting of halogen, —N($R^5$)($R^6$), $C_{1-4}$ alkyl, $C_{1-4}$ haloalkyl, $C_{3-7}$ cycloalkyl, $C_{1-4}$ alkoxy, and $C_{1-4}$ haloalkoxy. In some further embodiments, $R^9$ is $C_{1-4}$ alkyl, $C_{1-4}$ haloalkyl, —CN, —SF$_5$, —N($R^5$)($R^6$), $C_{1-6}$ alkoxy, $C_{1-6}$ haloalkoxy, $C_{3-7}$ cycloalkoxy, or $C_{3-7}$ cycloalkyl, wherein each of the $C_{1-4}$ alkyl and $C_{3-7}$ cycloalkyl is optionally substituted with 1, 2, 3, 4, or 5 substituents each independently selected from the group consisting of halogen, —N($R^5$)($R^6$), $C_{1-4}$ alkyl, $C_{1-4}$ haloalkyl, $C_{3-7}$ cycloalkyl, $C_{1-4}$ alkoxy, and $C_{1-4}$ haloalkoxy.

In some embodiments:
$Q^1$ is a moiety of

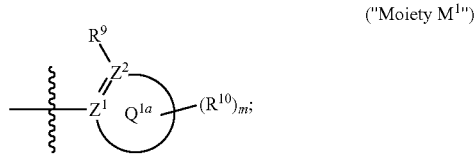

("Moiety M$^1$")

ring $Q^{1a}$ is an N-containing 5- to 6-membered heteroaryl or an N-containing 5- to 6-membered heterocycloalkyl;

‾‾‾‾‾‾ represents a single bond or double bond;

each of $Z^1$ and $Z^2$ is independently C or N;

$R^9$ is halogen (e.g. Cl), $C_{1-4}$ alkyl, $C_{1-4}$ haloalkyl, $C_{3-7}$ cycloalkyl, —CN, —N($R^5$)($R^6$), $C_{1-6}$ alkoxy, $C_{1-6}$ haloalkoxy, or $C_{3-7}$ cycloalkoxy, wherein each of the $C_{1-4}$ alkyl and $C_{3-7}$ cycloalkyl is optionally substituted with 1, 2, 3, 4, or 5 substituents each independently selected from the group consisting of halogen, —N($R^5$)($R^6$), $C_{1-4}$ alkyl, $C_{1-4}$ haloalkyl, $C_{3-7}$ cycloalkyl, $C_{1-4}$ alkoxy, and $C_{1-4}$ haloalkoxy;

each $R^{10}$ is independently selected from the group consisting of halogen, —OH, —CN, —NO$_2$, oxo, thiono, $C_{1-6}$ alkyl, $C_{1-6}$ haloalkyl, $C_{1-6}$ hydroxylalkyl, $C_{1-6}$ alkoxy, $C_{1-6}$ haloalkoxy, C$_{3-7}$ cycloalkyl, C$_{2-6}$ alkenyl, C$_{2-6}$ alkynyl, C$_{6-10}$ aryl, a 4- to 10-membered heterocycloalkyl, a 5- to 10-membered heteroaryl, (C$_{3-7}$ cycloalkyl)-C$_{1-4}$ alkyl-, (4- to 10-membered heterocycloalkyl)-C$_{1-4}$ alkyl-, (C$_{6-10}$ aryl)-C$_{1-4}$ alkyl-, (5- to 10-membered heteroaryl)-C$_{1-4}$ alkyl-, (5- to 10-membered heteroaryl)-C$_{2-4}$ alkenyl-, —N(R$^5$)(R$^6$), —N(R$^7$)(C(=O)R$^8$), —S(=O)$_2$N(R$^5$)(R$^6$), —C(=O)—N(R$^5$)(R$^6$), —C(=O)—R$^8$, —C(=O)—OR$^8$, and —OR$^8$, wherein each of said C$_{1-6}$ alkyl, C$_{3-7}$ cycloalkyl, C$_{6-10}$ aryl, 4- to 10-membered heterocycloalkyl, 5- to 10-membered heteroaryl, (C$_{3-7}$ cycloalkyl)-C$_{1-4}$ alkyl-, (4- to 10-membered heterocycloalkyl)-C$_{1-4}$ alkyl-, (C$_{6-10}$ aryl)-C$_{1-4}$ alkyl-, (5- to 10-membered heteroaryl)-C$_{1-4}$ alkyl-, and (5- to 10-membered heteroaryl)-C$_{2-4}$ alkenyl- is optionally substituted with 1, 2, 3, or 4 substituents each independently selected from the group consisting of halogen, OH, —CN, —NO$_2$, C$_{1-4}$ alkyl, C$_{1-4}$ hydroxylalkyl, C$_{1-4}$ alkoxy, —N(R$^5$)(R$^6$), —S—(C$_{1-4}$ alkyl), —S(=O)$_2$—(C$_{1-4}$ alkyl), C$_{6-10}$ aryloxy, (C$_{6-10}$ aryl)-C$_{1-4}$ alkyloxy-optionally substituted with 1 or 2 C$_{1-4}$ alkyl, oxo, —C(=O)H, —C(=O)—C$_{1-4}$ alkyl, —C(=O)O—C$_{1-4}$ alkyl, —C(=O)NH$_2$, —NHC(=O)H, —NHC(=O)—(C$_{1-4}$ alkyl), C$_{3-7}$ cycloalkyl, a 5- or 6-membered heteroaryl, C$_{1-4}$ haloalkyl, and C$_{1-4}$ haloalkoxy;

or R$^9$ and the adjacent R$^{10}$ together with the two ring atoms on ring Q$^{1a}$ to which they are attached form a fused benzene ring or a fused 5- or 6-membered heteroaryl, each optionally substituted with 1, 2, 3, 4, or 5 independently selected R$^{R10a}$;

each R$^{10a}$ is independently selected from the group consisting of halogen, —OH, —C(=O)OH, —C(=O)—C$_{1-4}$ alkyl, —C(=O)—NH$_2$, —C(=O)—N(C$_{1-4}$ alkyl)$_2$, —CN, C$_{1-4}$ alkyl, C$_{1-4}$ alkoxy, C$_{1-4}$ hydroxylalkyl, (C$_{1-2}$ alkoxy)-C$_{1-4}$ alkyl-, C$_{1-4}$ haloalkyl, and C$_{1-4}$ haloalkoxy; and m is 0, 1, 2, 3, or 4.

In some embodiments, Q$^1$ is a moiety of Moiety M$^1$ and Z$^1$ is C.

In some embodiments, Q$^1$ or ring Q$^{1a}$ is an optionally substituted N-containing 6-membered heteroaryl.

In some embodiments, Q$^1$ or ring Q$^{1a}$ is an optionally substituted pyridinyl, pyrimidinyl, pyridazinyl, or pyrazinyl. In some further embodiments, Q$^1$ or ring Q$^{1a}$ is an optionally substituted pyrimidinyl, pyridazinyl, or pyrazinyl.

In some embodiments, Q$^1$ or ring Q$^{1a}$ is pyrimidinyl, pyridazinyl, or pyrazinyl, each of which is optionally substituted with 1, 2, 3, or 4 substituents each independently selected from the group consisting of OH, halogen (e.g., Cl), CN, C$_{1-4}$ alkyl, C$_{1-4}$ haloalkyl, (C$_{1-2}$ alkoxy)-C$_{1-4}$ alkyl-, and C$_{3-7}$ cycloalkyl. In some further embodiments, Q$^1$ or ring Q$^{1a}$ is pyrimidinyl, pyridazinyl, or pyrazinyl, each of which is optionally substituted with 1, 2, 3, or 4 substituents each independently selected from the group consisting of CN, C$_{1-4}$ alkyl, C$_{1-4}$ haloalkyl, (C$_{1-2}$ alkoxy)-C$_{1-4}$ alkyl-, and C$_{3-7}$ cycloalkyl. In still further embodiments, Q$^1$ or ring Q$^{1a}$ is pyrimidinyl, pyridazinyl, or pyrazinyl, each of which is optionally substituted with 1 or 2 substituents each independently selected from the group consisting of CN, C$_{1-4}$ alkyl, and C$_{1-4}$ haloalkyl.

In some embodiments, Moiety M$^1$ is selected from the group consisting of quinolinyl, isoquinolinyl, 1H-imidazo[4,5-c]pyridinyl, imidazo[1,2-a]pyridinyl, 1H-pyrrolo[3,2-c]pyridinyl, imidazo[1,2-a]pyrazinyl, imidazo[2,1-c][1,2,4]triazinyl, imidazo[1,5-a]pyrazinyl, imidazo[1,2-a]pyrimidinyl, 1H-indazolyl, 9H-purinyl, imidazo[1,2-a]pyrimidinyl, [1,2,4]triazolo[1,5-a]pyrimidinyl, isoxazolo[5,4-c]pyridinyl, isoxazolo[3,4-c]pyridinyl, and [1,2,4]triazolo[4,3-b]pyridazinyl, each optionally substituted with 1, 2, or 3 R$^{10}$ and further optionally substituted with 1 or 2 R$^{10a}$; or wherein Moiety M$^1$ is selected from the group consisting of pyrimidinyl, pyrazinyl, pyridinyl, pyridazinyl, 1H-pyrazolyl, 1H-pyrrolyl, 4H-pyrazolyl, 1H-imidazolyl, 1H-imidazolyl, 3-oxo-2H-pyridazinyl, 1H-2-oxo-pyrimidinyl, 1H-2-oxo-pyridinyl, 2,4(1H,3H)-dioxo-pyrimidinyl, and 1H-2-oxo-pyrazinyl, each substituted with R$^9$ and further optionally substituted with 1, 2, or 3 R$^{10}$.

In some embodiments:

Moiety M$^1$ is

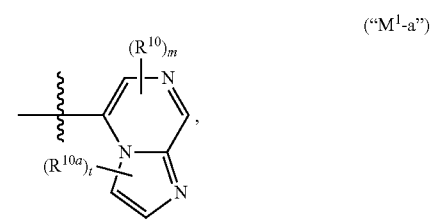
("M$^1$-a")

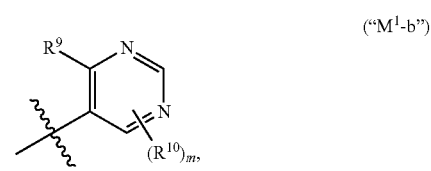
("M$^1$-b")

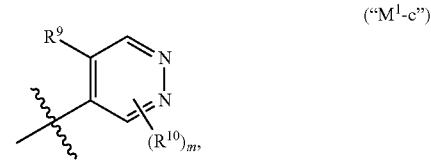
("M$^1$-c")

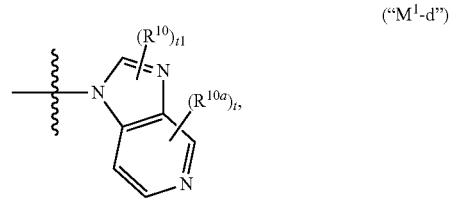
("M$^1$-d")

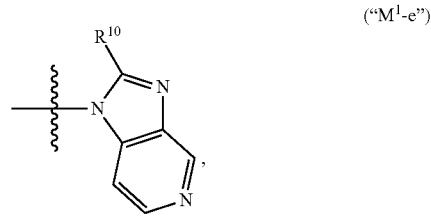
("M$^1$-e")

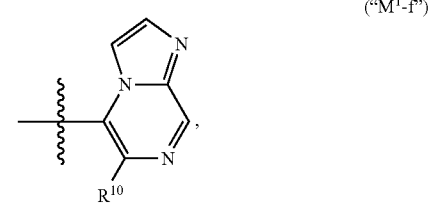
("M$^1$-f")

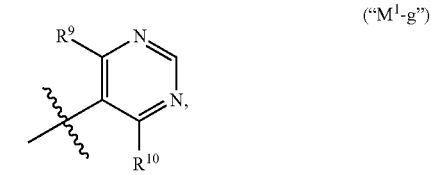
("M$^1$-g")

-continued

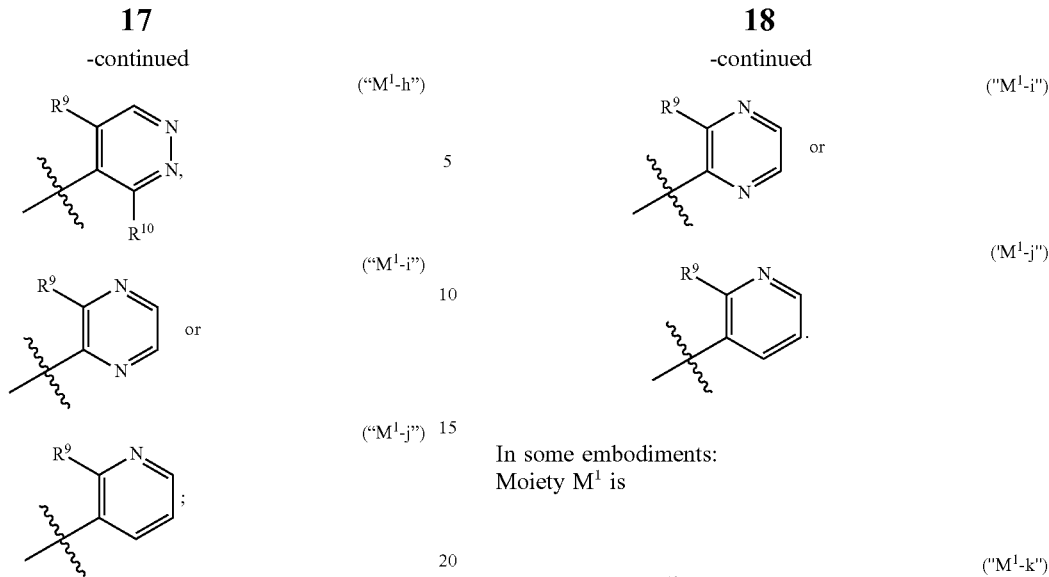

$R^{10a}$ is $C_{1-4}$ alkyl, $C_{1-4}$ haloalkyl, $(C_{1-2}$ alkoxy)-$C_{1-4}$ alkyl-, or $C_{3-7}$ cycloalkyl;

t1 is 0 or 1; and t is 0 or 1.

In some embodiments, Moiety $M^1$ is

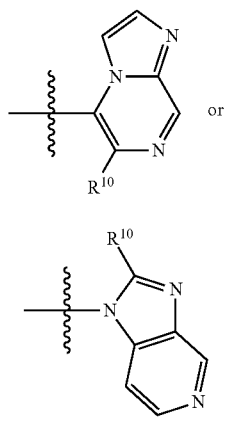

e").

In some embodiments, Moiety $M^1$ is

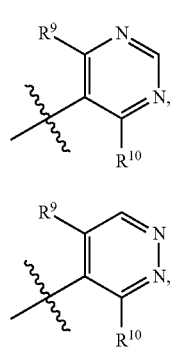

In some embodiments:

Moiety $M^1$ is and $R^{11}$ is H, $C_{1-4}$ alkyl, $C_{1-4}$ haloalkyl, $(C_{1-2}$ alkoxy)-$C_{1-4}$ alkyl-, or $C_{3-7}$ cycloalkyl.

In some embodiments, $R^9$ is halogen (e.g., Cl), $C_{3-6}$ cycloalkyl (e.g., cyclopropyl), $C_{1-4}$ alkyl, or —CN. In some further embodiments, $R^9$ is halogen (e.g., Cl), $C_{1-4}$ alkyl, or —CN.

In some embodiments, $R^9$ is $C_{1-4}$ alkyl or —CN. In some further embodiments, $R^9$ is $C_{1-4}$ alkyl. In some yet further embodiments, $R^9$ is methyl.

In some embodiments, each $R^{10}$ is independently selected from the group consisting of halogen (e.g., Cl), $C_{1-4}$ alkyl, $C_{1-4}$ haloalkyl, $(C_{1-2}$ alkoxy)-$C_{1-4}$ alkyl-, —CN, and —N($R^5$)($R^6$), wherein each of $R^5$ and $R^6$ independently is H or selected from the group consisting of $C_{1-4}$ alkyl, $C_{1-4}$ haloalkyl, and $C_{3-7}$ cycloalkyl; or $R^5$ and $R^6$ together with the N atom to which they are attached form a 4- to 7-membered heterocycloalkyl or a 5-membered heteroaryl, each optionally substituted with 1, 2, or 3 substituents each independently selected from the group consisting of halogen, —CN, $C_{1-4}$ alkyl, $C_{1-4}$ alkoxy, $C_{3-6}$ cycloalkyl, $C_{1-4}$ haloalkyl, and $C_{1-4}$ haloalkoxy. In some further embodiments, each $R^{10}$ is independently halogen (e.g., Cl), $C_{1-4}$ alkyl or CN. In yet further embodiments, each $R^{10}$ is independently $C_{1-4}$ alkyl or CN. In still yet further embodiments, each $R^{10}$ is $C_{1-4}$ alkyl (e.g., methyl). In further embodiments, each $R^{10}$ is $C_{1-4}$ alkyl methyl.

In some embodiments, each of $R^9$ and $R^{10}$ is independently halogen (e.g., Cl), $C_{3-6}$ cycloalkyl (e.g., cyclopropyl), $C_{1-4}$ alkyl, or —CN. In some further embodiments, each of $R^9$ and $R^{10}$ is independently halogen (e.g., Cl), $C_{1-4}$ alkyl, or —CN.

In some embodiments, each of $R^9$ and $R^{10}$ is independently $C_{1-4}$ alkyl or CN. In some further embodiments, each of $R^9$ and $R^{10}$ is independently methyl or CN.

In some embodiments, $X^1$ is O; 0 or 1 of $X^2$ and $X^3$ is N (e.g., neither of $X^2$ and $X^3$ is N); $X^4$ is N; $X^4$ is N; $Q^1$ is $M^1$; and $M^1$ is as described in one of the embodiments provided herein (e.g., $M^1$-g, $M^1$-k, $M^1$-m, or $M^1$-n). In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is O; 0 or 1 of $X^2$ and $X^3$ is N (e.g., neither of $X^2$ and $X^3$ is N); $X^4$ is N; $Q^1$ is $M^1$; and $M^1$ is $M^1$-g. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is O; 0 or 1 of $X^2$ and $X^3$ is N (e.g., neither of $X^2$ and $X^3$ is N); $X^4$ is N; $Q^1$ is $M^1$; and $M^1$ is $M^1$-k. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is O; 0 or 1 of $X^2$ and $X^3$ is N (e.g., neither of $X^2$ and $X^3$ is N); $X^4$ is N; $Q^1$ is $M^1$; and $M^1$ is $M^1$-m. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is O; 0 or 1 of $X^2$ and $X^3$ is N (e.g., neither of $X^2$ and $X^3$ is N); $X^4$ is N; $Q^1$ is $M^1$; and $M^1$ is $M^1$-n. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is O; $X^2$ is C-$T^2$, $X^3$ is C-$T^3$; $X^4$ is N; $Q^1$ is $M^1$; and $M^1$ is $M^1$-g. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is O; $X^2$ is C-$T^2$, $X^3$ is C-$T^3$; $X^4$ is N; $Q^1$ is $M^1$; and $M^1$ is $M^1$-k. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is O; $X^2$ is C-$T^2$, $X^3$ is C-$T^3$; $X^4$ is N; $Q^1$ is $M^1$; and $M^1$ is $M^1$-m. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is O; $X^2$ is C-$T^2$, $X^3$ is C-$T^3$; $X^4$ is N; $Q^1$ is $M^1$; and $M^1$ is $M^1$-n. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is O; 1 of $X^2$ and $X^3$ is N (e.g., $X^2$ is N and $X^3$ is C-$T^3$); $X^4$ is C-$T^4$; $Q^1$ is $M^1$; and $M^1$ is as described in one of the embodiments provided herein (e.g., $M^1$-g, $M^1$-k, $M^1$-m, or $M^1$-n). In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is O; 1 of $X^2$ and $X^3$ is N (e.g., $X^2$ is N and $X^3$ is C-$T^3$); $X^4$ is C-$T^4$; $Q^1$ is $M^1$; and $M^1$ is $M^1$-g. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is O; 1 of $X^2$ and $X^3$ is N (e.g., $X^2$ is N and $X^3$ is C-$T^3$); $X^4$ is C-$T^4$; $Q^1$ is $M^1$; and $M^1$ is $M^1$-k. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is O; 1 of $X^2$ and $X^3$ is N (e.g., $X^2$ is N and $X^3$ is C-$T^3$); $X^4$ is C-$T^4$; $Q^1$ is $M^1$; and $M^1$ is $M^1$-m. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is O; 1 of $X^2$ and $X^3$ is N (e.g., $X^2$ is N and $X^3$ is C-$T^3$); $X^4$ is C-$T^4$; $Q^1$ is $M^1$; and $M^1$ is $M^1$-n. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is O; $X^2$ is N, $X^3$ is C-$T^3$; $X^4$ is N; $Q^1$ is $M^1$; and $M^1$ is $M^1$-g. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is O; $X^2$ is C-$T^2$, $X^3$ is C-$T^3$; $X^4$ is N; $Q^1$ is $M^1$; and $M^1$ is $M^1$-k. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or C haloalkoxy. In yet still further embodiments, each of $R^1$ and $R^2$ is H; $R^3$ is H; and $R^4$ is methyl.

In some embodiments, $X^1$ is O; $X^2$ is C-$T^2$, $X^3$ is C-$T^3$; $X^4$ is N; $Q^1$ is $M^1$; and $M^1$ is $M^1$-m. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is O; $X^2$ is C-$T^2$, $X^3$ is C-$T^3$; $X^4$ is N; $Q^1$ is $M^1$; and $M^1$ is $M^1$-n. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is S; 0 or 1 of $X^2$ and $X^3$ is N (e.g., neither of $X^2$ and $X^3$ is N); $X^4$ is N; $X^4$ is N; $Q^1$ is $M^1$; and $M^1$ is as described in one of the embodiments provided herein (e.g., $M^1$-g, $M^1$-k, $M^1$-m, or $M^1$-n). In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is S; 0 or 1 of $X^2$ and $X^3$ is N (e.g., neither of $X^2$ and $X^3$ is N); $X^4$ is N; $Q^1$ is $M^1$; and $M^1$ is $M^1$-g. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is S; 0 or 1 of $X^2$ and $X^3$ is N (e.g., neither of $X^2$ and $X^3$ is N); $X^4$ is N; $Q^1$ is $M^1$; and $M^1$ is $M^1$-k. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is S; 0 or 1 of $X^2$ and $X^3$ is N (e.g., neither of $X^2$ and $X^3$ is N); $X^4$ is N; $Q^1$ is $M^1$; and $M^1$ is $M^1$-m. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is S; 0 or 1 of $X^2$ and $X^3$ is N (e.g., neither of $X^2$ and $X^3$ is N); $X^4$ is N; $Q^1$ is $M^1$; and $M^1$ is $M^1$-n. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is S; $X^2$ is C-$T^2$, $X^3$ is C-$T^3$; $X^4$ is N; $Q^1$ is $M^1$; and $M^1$ is $M^1$-g. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is S; $X^2$ is C-$T^2$, $X^3$ is C-$T^3$; $X^4$ is N; $Q^1$ is $M^1$; and $M^1$ is $M^1$-k. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is S; $X^2$ is C-$T^2$, $X^3$ is C-$T^3$; $X^4$ is N; $Q^1$ is $M^1$; and $M^1$ is M-m. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is S; $X^2$ is C-$T^2$, $X^3$ is C-$T^3$; $X^4$ is N; $Q^1$ is $M^1$; and $M^1$ is $M^1$-n. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is S; 1 of $X^2$ and $X^3$ is N (e.g., $X^2$ is N and $X^3$ is C-$T^3$); $X^4$ is C-$T^4$; $Q^1$ is $M^1$; and $M^1$ is as described in one of the embodiments provided herein (e.g., $M^1$-g, $M^1$-k, $M^1$-m, or $M^1$-n). In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is S; 1 of $X^2$ and $X^3$ is N (e.g., $X^2$ is N and $X^3$ is C-$T^3$); $X^4$ is C-$T^4$; $Q^1$ is $M^1$; and $M^1$ is $M^1$-g. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is S; 1 of $X^2$ and $X^3$ is N (e.g., $X^2$ is N and $X^3$ is C-$T^3$); $X^4$ is C-$T^4$; $Q^1$ is $M^1$; and $M^1$ is $M^1$-k. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is S; 1 of $X^2$ and $X^3$ is N (e.g., $X^2$ is N and $X^3$ is C-$T^3$); $X^4$ is C-$T^4$; $Q^1$ is $M^1$; and $M^1$ is $M^1$-m. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is S; 1 of $X^2$ and $X^3$ is N (e.g., $X^2$ is N and $X^3$ is C-$T^3$); $X^4$ is C-$T^4$; $Q^1$ is $M^1$; and $M^1$ is $M^1$-n. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is S; $X^2$ is N, $X^3$ is C-$T^3$; $X^4$ is N; $Q^1$ is $M^1$; and $M^1$ is $M^1$-g. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or C haloalkoxy. In yet still further embodiments, each of $R^1$ and $R^2$ is H; $R^3$ is H; and $R^4$ is methyl.

In some embodiments, $X^1$ is S; $X^2$ is C-$T^2$, $X^3$ is C-$T^3$; $X^4$ is N; $Q^1$ is $M^1$; and $M^1$ is $M^1$-k. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is S; $X^2$ is C-$T^2$, $X^3$ is C-$T^3$; $X^4$ is N; $Q^1$ is $M^1$; and $M^1$ is $M^1$-m. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is S; $X^2$ is C-$T^2$, $X^3$ is C-$T^3$; $X^4$ is N; $Q^1$ is $M^1$; and $M^1$ is $M^1$-n. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is NH; 0 or 1 of $X^2$ and $X^3$ is N (e.g., $X^2$ is C-$T^2$ and $X^3$ is N); $X^4$ is C-$T^4$; $Q^1$ is $M^1$; and $M^1$ is as described in one of the embodiments provided herein (e.g., $M^1$-g, $M^1$-k, $M^1$-m, or $M^1$-n). In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is NH; 0 or 1 of $X^2$ and $X^3$ is N (e.g., $X^2$ is C-$T^2$ and $X^3$ is N); $X^4$ is C-$T^4$; $Q^1$ is $M^1$; and $M^1$ is $M^1$-g. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is NH; 0 or 1 of $X^2$ and $X^3$ is N (e.g., $X^2$ is C-$T^2$ and $X^3$ is N); $X^4$ is C-$T^4$; $Q^1$ is $M^1$; and $M^1$ is $M^1$-k. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is NH; 0 or 1 of $X^2$ and $X^3$ is N (e.g., $X^2$ is C-$T^2$ and $X^3$ is N); $X^4$ is C-$T^4$; $Q^1$ is $M^1$; and $M^1$ is $M^1$-m. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is NH; 0 or 1 of $X^2$ and $X^3$ is N (e.g., $X^2$ is C-$T^2$ and $X^3$ is N); $X^4$ is C-$T^4$; $Q^1$ is $M^1$; and $M^1$ is $M^1$-n. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is NH; $X^2$ is C-$T^2$, $X^3$ is N; $X^4$ is N; $Q^1$ is $M^1$; and $M^1$ is $M^1$-g. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is NH; $X^2$ is C-$T^2$, $X^3$ is N; $X^4$ is N; $Q^1$ is $M^1$; and $M^1$ is $M^1$-k. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is NH; $X^2$ is C-$T^2$, $X^3$ is N; $X^4$ is N; $Q^1$ is $M^1$; and $M^1$ is $M^1$-m. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is NH; $X^2$ is C-$T^2$, $X^3$ is N; $X^4$ is N; $Q^1$ is $M^1$; and $M^1$ is $M^1$-n. In some further embodiments, L¹ is O or S. In yet further embodiments, L¹ is O. In still further embodiments, each of R¹ and R² is independently H or halogen; and each of R³ and R⁴ is independently H, halogen, —CN, methyl, $C_1$ haloalkyl, methoxy, or $C_1$ haloalkoxy. In yet still further embodiments, each of R¹ and R² is H; R³ is H; and R⁴ is methyl.

The first aspect of the invention includes any subset of any embodiment described herein.

The first aspect of the invention includes combinations of two or more embodiments described herein, or any subset thereof.

The first aspect of the invention further provides the compound of Formula I or a pharmaceutically acceptable salt thereof (including all embodiments and combinations of two or more embodiments described herein or any subset thereof) for use in treating a D1-mediated (or D1-associated) disorder described herein.

The first aspect of the invention further provides use of the compound of Formula I or a pharmaceutically acceptable salt thereof (including all embodiments and combinations of two or more embodiments described herein or any subset thereof) for treating a D1-mediated (or D1-associated) disorder described herein.

The first aspect of the invention further provides use of the compound of Formula I or a pharmaceutically acceptable salt thereof (including all embodiments and combinations of two or more embodiments described herein or any subset thereof) in manufacturing a medicament for use in treating a D1-mediated (or D1-associated) disorder described herein.

The term "therapeutically effective amount" as used herein refers to that amount of the compound (including a pharmaceutically acceptable salt thereof) being administered which will relieve to some extent one or more of the symptoms of the disorder being treated. In reference to the treatment of a D1-mediated disorder (e.g., schizophrenia), a therapeutically effective amount refers to that amount which has the effect of relieving to some extent (or, for example, eliminating) one or more symptoms associated with a D1-mediated disorder (e.g., schizophrenia, or cognitive and negative symptoms in schizophrenia, or cognitive impairment associated with schizophrenia).

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined herein. The term "treating" also includes adjuvant and neo-adjuvant treatment of a subject.

The compound of Formula I or its salt used in the method for treating a D1-mediated (or D1-associated) disorder of present invention is a D1R modulator (e.g., a D1 agoninst for example, a D1 partial agonist). The amount of the compound of Formula I or a pharmaceutically acceptable amount used in the method of the present invention is effective in modulating (e.g., agonizing or partially agonizing) D1R.

The present invention further provides a method for modulating (such as agonizing or partially agonizing) an activity of D1R (either in vitro or in vivo), comprising contacting (including incubating) the D1R with a compound of Formula I or a pharmaceutically acceptable salt thereof (such as one selected from Examples 1-23 herein) described herein.

In a second aspect, the present invention provides a compound of Formula I:

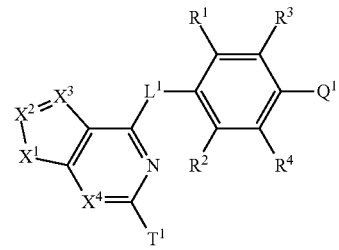

or a pharmaceutically acceptable salt thereof, wherein:
L¹ is O, S, NR$^N$, C(=O), or CH(OH);
Q¹ is an N-containing 5- to 6-membered heteroaryl or an N-containing 5- to 6-membered heterocycloalkyl, each optionally substituted with one R⁹ and further optionally substituted with 1, 2, 3, or 4 R¹⁰;
X¹ is O, S, or NH;
X² is N or C-T²;
X³ is N or C-T³;
provided that when X¹ is O or S, then at least one of X² and X² is not N;
X⁴ is N or C-T⁴;
T¹ is H, F, Cl, methyl, or $C_1$ fluoroalkyl;
each of T², T³, and T⁴ is independently selected from the group consisting of H, halogen, —CN, $C_{1-4}$ alkyl, $C_{1-4}$ haloalkyl, $C_{3-4}$ cycloalkyl, $C_{3-4}$ halocycloalkyl, cyclopropylmethyl, $C_{1-4}$ alkoxy, $C_{1-4}$ haloalkoxy;
R$^N$ is H, $C_{1-4}$ alkyl, $C_{3-4}$ cycloalkyl, or —$C_{1-2}$ alkyl-$C_{3-4}$ cycloalkyl,
each of R¹ and R² is independently selected from the group consisting of H, halogen, —CN, $C_{1-6}$ alkyl, $C_{1-6}$ haloalkyl, $C_{1-6}$ alkoxy, $C_{1-6}$ haloalkoxy, $C_{3-6}$ cycloalkyl, —C(=O)OH, and C(=O)—O—($C_{1-4}$ alkyl), wherein each of said $C_{1-6}$ alkyl and $C_{3-6}$ cycloalkyl is optionally substituted with 1, 2, 3, 4, or 5 substituents each independently selected from halo, —OH, —CN, $C_{1-4}$ alkyl, $C_{1-4}$ haloalkyl, $C_{1-4}$ alkoxy, and $C_{1-4}$ haloalkoxy;
each of R³ and R⁴ is independently selected from the group consisting of H, halogen, —OH, —NO₂, —CN, —SF₅, $C_{1-6}$ alkyl, $C_{1-6}$ haloalkyl, $C_{1-6}$ haloalkoxy, $C_{2-6}$ alkenyl, $C_{2-6}$ alkynyl, $C_{3-7}$ cycloalkyl, a 4- to 10-membered heterocycloalkyl, —N(R⁵)(R⁶), —N(R⁷)(C(=O)R⁸), —C(=O)—N(R⁵)(R⁶), —C(=O)—R⁸, —C(=O)—OR⁸, —OC(=O)R⁸, —N(R⁷)(S(=O)₂R⁸), —S(=O)₂—N(R⁵)(R⁶), —SR⁸, and —OR⁸, wherein each of said $C_{1-6}$ alkyl, $C_{3-7}$ cycloalkyl, and heterocycloalkyl is optionally substituted with 1, 2, or 3 substituents each independently selected from the group consisting of halogen, —CN, —OH, $C_{1-4}$ alkyl, $C_{1-4}$ alkoxy, $C_{1-4}$ haloalkyl, $C_{1-4}$ haloalkoxy, $C_{3-6}$ cycloalkyl, —N(R⁵)(R⁶), —N(R⁷)(C(=O)R⁸), —C(=O)—OR⁸, —C(=O)H, —C(=O)R⁸, —C(=O)N(R⁵)(R⁶), —N(R⁷)(S(=O)₂R⁸), —S(=O)₂—N(R⁵)(R⁶), —SR⁸, and —OR⁸;
or R¹ and R³ together with the two carbon atoms to which they are attached form a fused N-containing 5- or 6-membered heteroaryl, a fused N-containing 5- or 6-membered heterocycloalkyl, a fused 5- or 6-membered cycloalkyl, or a fused benzene ring, each optionally substituted with 1, 2, or 3 substituents each independently selected from the group consisting of halo, —CN, —OH, $C_{1-3}$ alkyl, $C_{1-3}$ alkoxy, $C_{1-3}$ haloalkyl, and $C_{1-3}$ haloalkoxy;
R⁵ is H, $C_{1-4}$ alkyl, $C_{1-4}$ haloalkyl, or $C_{3-7}$ cycloalkyl;
R⁶ is H or selected from the group consisting of $C_{1-4}$ alkyl, $C_{1-4}$ haloalkyl, $C_{3-7}$ cycloalkyl, a 4- to 10-membered heterocycloalkyl, $C_{6-10}$ aryl, a 5- to 10-membered heteroaryl, $(C_{3-7}$ cycloalkyl)-$C_{1-4}$ alkyl-, (4- to 10-membered heterocycloalkyl)-$C_{1-4}$ alkyl-, $(C_{6-10}$ aryl)-$C_{1-4}$ alkyl-, and (5- to 10-membered heteroaryl)-$C_{1-4}$ alkyl-, wherein each of the selections from the group is optionally substituted with 1, 2, 3, or 4 substituents each independently selected from the group consisting of —OH, —CN, $C_{1-4}$ alkyl, $C_{3-7}$ cycloalkyl, $C_{1-4}$ hydroxylalkyl, —S—$C_{1-4}$ alkyl, —C(=O)H, —C(=O)—$C_{1-4}$ alkyl, —C(=O)—O—$C_{1-4}$ alkyl, —C(=O)—NH$_2$, —C(=O)—N($C_{1-4}$ alkyl)$_2$, $C_{1-4}$ haloalkyl, $C_{1-4}$ alkoxy, and $C_{1-4}$ haloalkoxy;

or $R^5$ and $R^6$ together with the N atom to which they are attached form a 4- to 10-membered heterocycloalkyl or a 5- to 10-membered heteroaryl, each optionally substituted with 1, 2, 3, 4, or 5 substituents each independently selected from the group consisting of halogen, —OH, oxo, —C(=O)H, —C(=O)OH, —C(=O)—$C_{1-4}$ alkyl, —C(=O)—NH$_2$, —C(=O)—N($C_{1-4}$ alkyl)$_2$, —CN, $C_{1-4}$ alkyl, $C_{1-4}$ alkoxy, $C_{1-4}$ hydroxylalkyl, $C_{1-4}$ haloalkyl, and $C_{1-4}$ haloalkoxy;

$R^7$ is selected from the group consisting of H, $C_{1-4}$ alkyl, and $C_{3-7}$ cycloalkyl;

$R^8$ is selected from the group consisting of $C_{1-6}$ alkyl, $C_{3-7}$ cycloalkyl, a 4- to 14-membered heterocycloalkyl, $C_{6-10}$ aryl, a 5- to 10-membered heteroaryl, $(C_{3-7}$ cycloalkyl)-$C_{1-4}$ alkyl-, (4- to 10-membered heterocycloalkyl)-$C_{1-4}$ alkyl-, $(C_{6-10}$ aryl)-$C_{1-4}$ alkyl-, and (5- to 10-membered heteroaryl)-$C_{1-4}$ alkyl-, wherein each of the selections from the group is optionally substituted with 1, 2, or 3 substituents each independently selected from the group consisting of halogen, —CF$_3$, —CN, —OH, oxo, —S—$C_{1-4}$ alkyl, $C_{1-4}$ alkyl, $C_{1-4}$ haloalkyl, $C_{2-6}$ alkenyl, $C_{2-6}$ alkynyl, $C_{3-7}$ cycloalkyl, $C_{1-4}$ alkoxy, and $C_{1-4}$ haloalkoxy;

$R^9$ is halogen, $C_{1-4}$ alkyl, $C_{1-4}$ haloalkyl, —CN, —SF$_5$, —N(R$^5$)(R$^6$), $C_{1-6}$ alkoxy, $C_{1-6}$ haloalkoxy, $C_{3-7}$ cycloalkoxy, or $C_{3-7}$ cycloalkyl, wherein each of the $C_{1-4}$ alkyl and $C_{3-7}$ cycloalkyl is optionally substituted with 1, 2, 3, 4, or 5 substituents each independently selected from the group consisting of halogen, —N(R$^5$)(R$^6$), $C_{1-4}$ alkyl, $C_{1-4}$ haloalkyl, $C_{3-7}$ cycloalkyl, $C_{1-4}$ alkoxy, and $C_{1-4}$ haloalkoxy;

each $R^{10}$ is independently selected from the group consisting of halogen, —OH, —CN, —SF$_5$, —NO$_2$, Oxo, thiono, $C_{1-6}$ alkyl, $C_{1-6}$ haloalkyl, $C_{1-6}$ hydroxylalkyl, $C_{1-6}$ alkoxy, $C_{1-6}$ haloalkoxy, $C_{3-7}$ cycloalkyl, $C_{2-6}$ alkenyl, $C_{2-6}$ alkynyl, $C_{6-10}$ aryl, a 4- to 10-membered heterocycloalkyl, a 5- to 10-membered heteroaryl, $(C_{3-7}$ cycloalkyl)-$C_{1-4}$ alkyl-, (4- to 10-membered heterocycloalkyl)-$C_{1-4}$ alkyl-, $(C_{6-10}$ aryl)-$C_{1-4}$ alkyl-, (5- to 10-membered heteroaryl)-$C_{1-4}$ alkyl-, —N(R$^5$)(R$^6$), —N(R$^7$)(C(=O)R$^8$), —S(=O)$_2$N(R$^5$)(R$^6$), —C(=O)—N(R$^5$)(R$^6$), —C(=O)—R$^8$, —C(=O)—OR$^8$, —SR$^8$, and —OR$^8$, wherein each of said $C_{1-6}$ alkyl, $C_{3-7}$ cycloalkyl, $C_{6-10}$ aryl, 4- to 10-membered heterocycloalkyl, 5- to 10-membered heteroaryl, $(C_{3-7}$ cycloalkyl)-$C_{1-4}$ alkyl-, (4- to 10-membered heterocycloalkyl)-$C_{1-4}$ alkyl-, $(C_{6-10}$ aryl)-$C_{1-4}$ alkyl-, and (5- to 10-membered heteroaryl)-$C_{1-4}$ alkyl- is optionally substituted with 1, 2, 3, or 4 substituents each independently selected from the group consisting of halogen, OH, —CN, —NO$_2$, $C_{1-4}$ alkyl, $C_{1-4}$ hydroxylalkyl, $C_{1-4}$ alkoxy, —N(R$^5$)(R$^6$), —S—($C_{1-4}$ alkyl), —S(=O)$_2$—($C_{1-4}$ alkyl), $C_{6-10}$ aryloxy, [($C_{6-10}$ aryl)-$C_{1-4}$ alkyloxy-optionally substituted with 1 or 2 $C_{1-4}$ alkyl], oxo, —C(=O)H, —C(=O)—$C_{1-4}$ alkyl, —C(=O)O—$C_{1-4}$ alkyl, —C(=O)NH$_2$, —NHC(=O)H, —NHC(=O)—($C_{1-4}$ alkyl), $C_{3-7}$ cycloalkyl, a 5- or 6-membered heteroaryl, $C_{1-4}$ haloalkyl, and $C_{1-4}$ haloalkoxy;

or $R^9$ and an adjacent $R^{10}$ together with the two ring atoms on $Q^1$ to which they are attached form a fused benzene ring or a fused 5- or 6-membered heteroaryl, each optionally substituted with 1, 2, 3, 4, or 5 independently selected $R^{10a}$; and each $R^{10a}$ is independently selected from the group consisting of halogen, —OH, —N(R$^5$)(R$^6$), —C(=O)OH, —C(=O)—$C_{1-4}$ alkyl, —C(=O)—NH$_2$, —C(=O)—N($C_{1-4}$ alkyl)$_2$, —CN, —SF$_5$, $C_{1-4}$ alkyl, $C_{1-4}$ alkoxy, $C_{1-4}$ hydroxylalkyl, $C_{1-4}$ haloalkyl, and $C_{1-4}$ haloalkoxy, with the proviso that (1) when $X^4$ is N then $X^1$ is O;
(2) when $X^1$ is NH then $X^3$ is other than N;
(3) when $X^2$ is C-T$^2$, $X^3$ is C-T$^3$, and $X^4$ is C-T$^4$, then $X^1$ is other than S or O;
(4) when $L^1$ is O or NR$^N$, $X^3$ is C-T$^3$, and $X^4$ is C-T$^4$, then $X^1$ is other than NH;
(5) when $X^1$ is NH or O, and at least one of $X^3$ and $X^4$ is N, then $Q^1$ is not an optionally substituted monocyclic 5-membered ring; and
(6) when $X^4$ is N and $X^1$ is O, then $L^1$ is other than NR$^N$.

In some embodiments, when $X^3$ is C-T$^3$ and $X^4$ is C-T$^4$, then $X^1$ is other than NH.

In some embodiments, when $Q^1$ is an optionally substituted monocylic ring, then a ring-forming carbon atom of $Q^1$ is directly linked to the benzene ring of Formula I that is substituted by $R^1$, $R^2$, $R^3$, and $R^4$.

In some embodiments, when a ring-forming nitrogen atom of $Q^1$ is directly linked to the benzene ring of Formula I that is substituted by $R^1$, $R^2$, $R^3$, and $R^4$, then $Q^1$ is an optionally substituted bicyclic ring (e.g., an optionally substituted bicyclic heteroaryl).

In some embodiments, $Q^1$ is other than an optionally substituted monocyclic 5-membered ring.

In some embodiments, $L^1$ is other than NR$^N$.

In some embodiments, each of the ring-forming atoms of $Q^1$ is a nitrogen or carbon atom. In some further embodiment, when $Q^1$ is an optionally substituted monocylic ring, then a ring-forming carbon atom of $Q^1$ is directly linked to the benzene ring that is substituted by $R^1$, $R^2$, $R^3$, and $R^4$.

In some embodiments, $L^1$ is other than NR$^N$.

In some embodiments:
(1) when $X^4$ is N then $X^1$ is O;
(2) when $X^1$ is NH then $X^3$ is other than N;
(3) when $X^2$ is C-T$^2$, $X^3$ is C-T$^3$, and $X^4$ is C-T$^4$, then $X^1$ is other than S or O;
(4) when $X^3$ is C-T$^3$ and $X^4$ is C-T$^4$, then $X^1$ is other than NH;
(5) $Q^1$ is other than an optionally substituted monocyclic 5-membered ring;
(6) each of the ring-forming atoms of $Q^1$ is a nitrogen or carbon atom;
(7) when $Q^1$ is an optionally substituted monocylic ring, then a ring-forming carbon atom of $Q^1$ is directly linked to the benzene ring that is substituted by $R^1$, $R^2$, $R^3$, and $R^4$; and
(8) $L^1$ is other than NR$^N$.

In some embodiments, $L^1$ is O or S. In some further embodiments, $L^1$ is S.

In some embodiments, $L^1$ is O.

In some embodiments, $L^1$ is NH.

In some embodiments, $L^1$ is C(=O) or CH(OH).

In some embodiments, each of T$^2$, T$^3$, and T$^4$ is independently selected from the group consisting of H, halogen, —CN, methoxy, $C_1$ fluoroalkoxy, methyl, and $C_1$ fluoroalkyl.

In some embodiments, $T^1$ is H and $T^4$ is H.

In some embodiments, each of $T^2$ and $T^3$ is independently H, CN, F, Cl, Br, methoxy, $C_1$ fluoroalkoxy, methyl, or $C_1$ fluoroalkyl.

In some embodiments, $T^1$ is H; each of $T^2$ and $T^3$ is independently H, F, Cl, methoxy, $C_1$ fluoroalkoxy, methyl, or $C_1$ fluoroalkyl; and $T^4$ is H.

In some embodiments, $T^2$ is H and $T^3$ is H.

In some embodiments, $X^1$ is O.

In some embodiments, $X^1$ is O; and 0 or 1 of $X^2$ and $X^3$ is N. In some further embodiments, $X^4$ is N.

In some embodiments, $X^1$ is O; 0 or 1 of $X^2$ and $X^3$ is N, and $X^4$ is C-$T^4$.

In some embodiments, $X^1$ is S.

In some embodiments, $X^1$ is S; and 0 or 1 of $X^2$ and $X^3$ is N. In some further embodiments, $X^4$ is N.

In some embodiments, $X^1$ is S; 0 or 1 of $X^2$ and $X^3$ is N, and $X^4$ is C-$T^4$.

In some embodiments, $X^1$ is NH.

In some embodiments, $X^1$ is NH; and 0 or 1 of $X^2$ and $X^3$ is N. In some further embodiments, $X^4$ is C-$T^4$.

In some embodiments, $X^1$ is NH; $X^2$ is C-$T^2$; and $X^3$ is N.

In some embodiments, $X^4$ is N; and $X^1$ is O or S. In some further embodiments, 0 or 1 of $X^2$ and $X^3$ is N.

In some embodiments, $X^4$ is N; and $X^1$ is O. In some further embodiments, 0 or 1 of $X^2$ and $X^3$ is N.

In some embodiments, the compound of Formula I or a pharmaceutically acceptable salt thereof is a compound of Formula I-a:

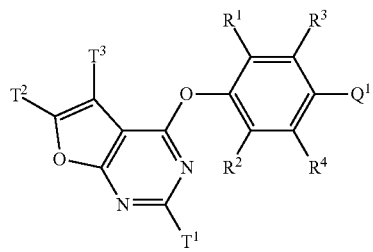

or a pharmaceutically acceptable salt thereof.

In some embodiments, the compound of Formula I or a pharmaceutically acceptable salt thereof is a compound of Formula I-b:

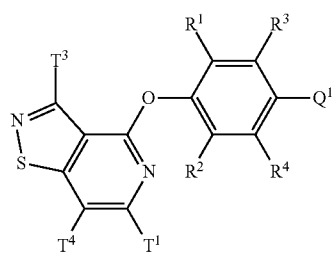

or a pharmaceutically acceptable salt thereof.

In some embodiments, the compound of Formula I or a pharmaceutically acceptable salt thereof is a compound of Formula I-c:

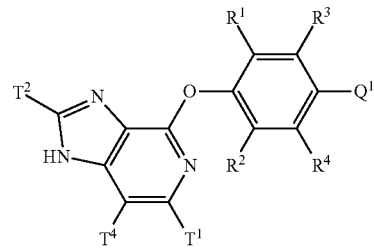

or a pharmaceutically acceptable salt thereof.

In some embodiments, the compound of Formula I or a pharmaceutically acceptable salt thereof is a compound of Formula I-d:

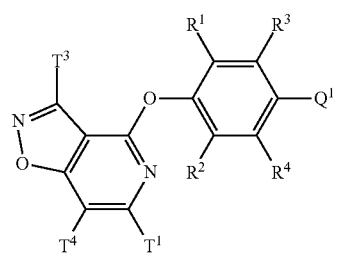

or a pharmaceutically acceptable salt thereof.

In some embodiments, the compound of Formula I or a pharmaceutically acceptable salt thereof is a compound of Formula I-e:

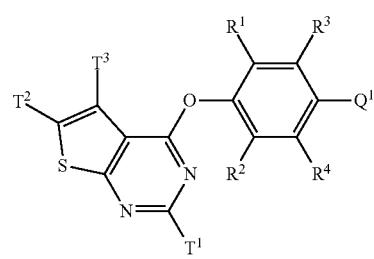

or a pharmaceutically acceptable salt thereof.

The embodiments described herein in the second aspect of the invention, unless specified otherwisely, include a compound of Formula I, I-a, I-b, I-c, I-d, or I-e, or a pharmaceutically acceptable salt thereof.

In some embodiments, each of $R^1$ and $R^2$ is independently H or halogen. In some further embodiments, each of $R^1$ and $R^2$ is H.

In some embodiments, each of $R^3$ and $R^4$ is independently H, halogen, —CN, methyl, $C_1$ haloalkyl, methoxy, or $C_1$ haloalkoxy.

In some embodiments, $R^3$ is H and $R^4$ is H, halogen, —CN, methyl, or $C_1$ haloalkyl.

In some embodiments, $R^3$ is H and $R^4$ is methyl.

In some embodiments, $Q^1$ is an N-containing 5- to 6-membered heteroaryl or an N-containing 5- to 6-membered heterocycloalkyl, each substituted with one $R^9$ and further optionally substituted with 1, 2, 3, or 4 $R^{10}$.

In some embodiments:
Q¹ is a moiety of

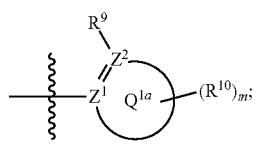

("Moiety M¹'")

ring $Q^{1a}$ is an N-containing 5- to 6-membered heteroaryl or an N-containing 5- to 6-membered heterocycloalkyl;

------ represents a single bond or double bond;

each of $Z^1$ and $Z^2$ is independently C or N;

$R^9$ is halogen (e.g. Cl), $C_{1-4}$ alkyl, $C_{1-4}$ haloalkyl, $C_{3-7}$ cycloalkyl, —CN, —N(R⁵)(R⁶), $C_{1-6}$ alkoxy, $C_{1-6}$ haloalkoxy, or $C_{3-7}$ cycloalkoxy, wherein each of the $C_{1-4}$ alkyl and $C_{3-7}$ cycloalkyl is optionally substituted with 1, 2, 3, 4, or 5 substituents each independently selected from the group consisting of halogen, —N(R⁵)(R⁶), $C_{1-4}$ alkyl, $C_{1-4}$ haloalkyl, $C_{3-7}$ cycloalkyl, $C_{1-4}$ alkoxy, and $C_{1-4}$ haloalkoxy;

each $R^{10}$ is independently selected from the group consisting of halogen, —OH, —CN, —NO₂, oxo, thiono, $C_{1-6}$ alkyl, $C_{1-6}$ haloalkyl, $C_{1-6}$ hydroxylalkyl, $C_{1-6}$ alkoxy, $C_{1-6}$ haloalkoxy, $C_{3-7}$ cycloalkyl, $C_{2-6}$ alkenyl, $C_{2-6}$ alkynyl, $C_{6-10}$ aryl, a 4- to 10-membered heterocycloalkyl, a 5- to 10-membered heteroaryl, ($C_{3-7}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, (5- to 10-membered heteroaryl)-$C_{1-4}$ alkyl-, (5- to 10-membered heteroaryl)-$C_{2-4}$ alkenyl-, —N(R⁵)(R⁶), —N(R⁷)(C(=O)R⁸), —S(=O)₂N(R⁵)(R⁶), —C(=O)—N(R⁵)(R⁶), —C(=O)—R⁸, —C(=O)—OR⁸, and —OR⁸, wherein each of said $C_{1-6}$ alkyl, $C_{3-7}$ cycloalkyl, $C_{6-10}$ aryl, 4- to 10-membered heterocycloalkyl, 5- to 10-membered heteroaryl, ($C_{3-7}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, (5- to 10-membered heteroaryl)-$C_{1-4}$ alkyl-, and (5- to 10-membered heteroaryl)-$C_{2-4}$ alkenyl- is optionally substituted with 1, 2, 3, or 4 substituents each independently selected from the group consisting of halogen, OH, —CN, —NO₂, $C_{1-4}$ alkyl, $C_{1-4}$ hydroxylalkyl, $C_{1-4}$ alkoxy, —N(R⁵)(R⁶), —S—($C_{1-4}$ alkyl), —S(=O)₂—($C_{1-4}$ alkyl), $C_{6-10}$ aryloxy, ($C_{6-10}$ aryl)-$C_{1-4}$ alkyloxy-optionally substituted with 1 or 2 $C_{1-4}$ alkyl, oxo, —C(=O)H, —C(=O)—$C_{1-4}$ alkyl, —C(=O)O—$C_{1-4}$ alkyl, —C(=O)NH₂, —NHC(=O)H, —NHC(=O)—($C_{1-4}$ alkyl), $C_{3-7}$ cycloalkyl, a 5- or 6-membered heteroaryl, $C_{1-4}$ haloalkyl, and $C_{1-4}$ haloalkoxy;

or $R^9$ and the adjacent $R^{10}$ together with the two ring atoms on ring $Q^{1a}$ to which they are attached form a fused benzene ring or a fused 5- or 6-membered heteroaryl, each optionally substituted with 1, 2, 3, 4, or 5 independently selected $R^{10a}$;

each $R^{10a}$ is independently selected from the group consisting of halogen, —OH, —C(=O)OH, —C(=O)—$C_{1-4}$ alkyl, —C(=O)—NH₂, —C(=O)—N($C_{1-4}$ alkyl)₂, —CN, $C_{1-4}$ alkyl, $C_{1-4}$ alkoxy, $C_{1-4}$ hydroxylalkyl, ($C_{1-2}$ alkoxy)-$C_{1-4}$ alkyl-, $C_{1-4}$ haloalkyl, and $C_{1-4}$ haloalkoxy; and m is 0, 1, 2, 3, or 4.

In some embodiment, each $R^{10}$ is independently selected from the group consisting of halogen, —OH, —CN, —SF₅, —NO₂, Oxo, thiono, $C_{1-6}$ alkyl, $C_{1-6}$ haloalkyl, $C_{1-6}$ hydroxylalkyl, $C_{1-6}$ alkoxy, $C_{1-6}$ haloalkoxy, $C_{3-7}$ cycloalkyl, $C_{2-6}$ alkenyl, $C_{2-6}$ alkynyl, and ($C_{3-7}$ cycloalkyl)-$C_{1-4}$ alkyl-, wherein each of said $C_{1-6}$ alkyl, $C_{3-7}$ cycloalkyl, $C_{2-6}$ alkenyl, $C_{2-6}$ alkynyl, and ($C_{3-7}$ cycloalkyl)-$C_{1-4}$ alkyl- is optionally substituted with 1, 2, 3, 4, or 5 substituents each independently selected from the group consisting of halogen, —N(R⁵)(R⁶), $C_{1-4}$ alkyl, $C_{1-4}$ haloalkyl, $C_{3-7}$ cycloalkyl, $C_{1-4}$ alkoxy, and $C_{1-4}$ haloalkoxy.

In some embodiments, $Z^1$ is C.

In some embodiments, $Q^1$ or ring $Q^{1a}$ is an optionally substituted N-containing 6-membered heteroaryl.

In some embodiments, $Q^1$ or ring $Q^{1a}$ is an optionally substituted pyridinyl, pyrimidinyl, pyridazinyl, or pyrazinyl.

In some further embodiments, $Q^1$ or ring $Q^{1a}$ is an optionally substituted pyrimidinyl, pyridazinyl, or pyrazinyl.

In some embodiments, $Q^1$ or ring $Q^{1a}$ is pyrimidinyl, pyridazinyl, or pyrazinyl, each of which is optionally substituted with 1, 2, 3, or 4 substituents each independently selected from the group consisting of OH, CN, $C_{1-4}$ alkyl, $C_{1-4}$ haloalkyl, ($C_{1-2}$ alkoxy)-$C_{1-4}$ alkyl-, and $C_{3-7}$ cycloalkyl. In some further embodiments, $Q^1$ or ring $Q^{1a}$ is pyrimidinyl, pyridazinyl, or pyrazinyl, each of which is optionally substituted with 1, 2, 3, or 4 substituents each independently selected from the group consisting of CN, $C_{1-4}$ alkyl, $C_{1-4}$ haloalkyl, ($C_{1-2}$ alkoxy)-$C_{1-4}$ alkyl-, and $C_{3-7}$ cycloalkyl. In still further embodiments, $Q^1$ or ring $Q^{1a}$ is pyrimidinyl, pyridazinyl, or pyrazinyl, each of which is optionally substituted with 1 or 2 substituents each independently selected from the group consisting of CN, $C_{1-4}$ alkyl, and $C_{1-4}$ haloalkyl. In yet still further embodiments, $Q^1$ or ring $Q^{1a}$ is pyrimidinyl, pyridazinyl, or pyrazinyl, each of which is optionally substituted with 1 or 2 substituents each independently selected from the group consisting of CN and $C_{1-4}$ alkyl.

In some embodiments, Moiety $M^1$ is selected from the group consisting of quinolinyl, isoquinolinyl, 1H-imidazo[4,5-c]pyridinyl, imidazo[1,2-a]pyridinyl, 1H-pyrrolo[3,2-c]pyridinyl, imidazo[1,2-a]pyrazinyl, imidazo[2,1-c][1,2,4]triazinyl, imidazo[1,5-a]pyrazinyl, imidazo[1,2-a]pyrimidinyl, 1H-indazolyl, 9H-purinyl, imidazo[1,2-a]pyrimidinyl, [1,2,4]triazolo[1,5-a]pyrimidinyl, isoxazolo[5,4-c]pyridinyl, isoxazolo[3,4-c]pyridinyl, and [1,2,4]triazolo[4,3-b]pyridazinyl, each optionally substituted with 1, 2, or 3 $R^{10}$ and further optionally substituted with 1 or 2 $R^{10a}$; or wherein Moiety $M^1$ is selected from the group consisting of pyrimidinyl, pyrazinyl, pyridinyl, pyridazinyl, 1H-pyrazolyl, 1H-pyrrolyl, 4H-pyrazolyl, 1H-imidazolyl, 1H-imidazolyl, 3-oxo-2H-pyridazinyl, 1H-2-oxo-pyrimidinyl, 1H-2-oxo-pyridinyl, 2,4(1H,3H)-dioxo-pyrimidinyl, and 1H-2-oxo-pyrazinyl, each substituted with $R^9$ and further optionally substituted with 1, 2, or 3 $R^{10}$.

In some embodiments:
Moiety $M^1$ is

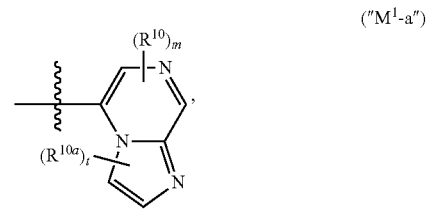

("M¹-a")

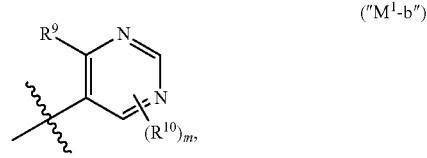

("M¹-b")

-continued
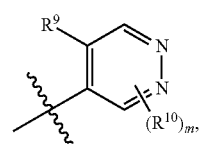
("M¹-c")
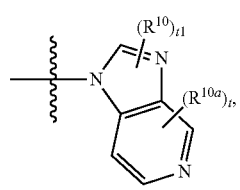
("M¹-d")
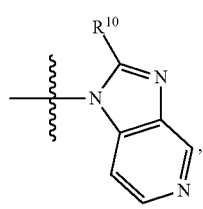
("M¹-e")
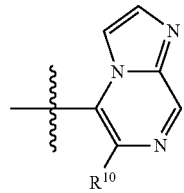
("M¹-f")
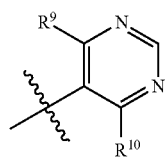
("M¹-g")
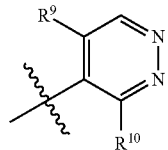
("M¹-h")
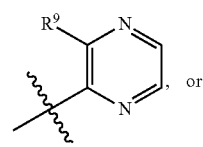
("M¹-i")
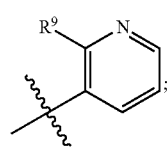
("M¹-j")
$R^{10a}$ is $C_{1-4}$ alkyl, $C_{1-4}$ haloalkyl, $(C_{1-2}$ alkoxy)-$C_{1-4}$ alkyl-, or $C_{3-7}$ cycloalkyl;
t1 is 0 or 1; and
t is 0 or 1.
In some embodiments, Moiety M¹ is
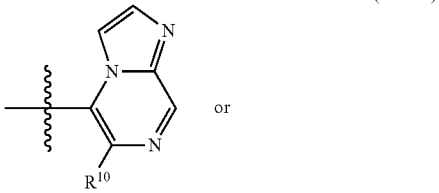
("M¹-f")
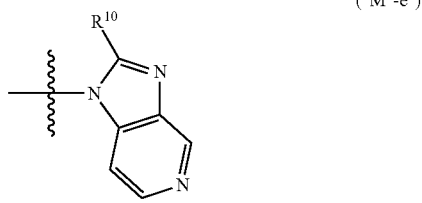
("M¹-e")
In some embodiments, Moiety M¹ is
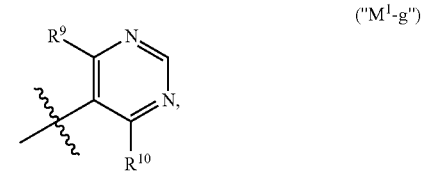
("M¹-g")
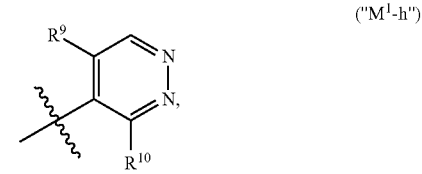
("M¹-h")
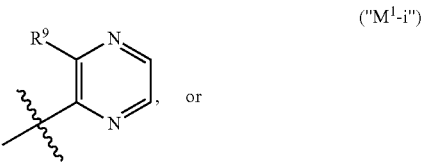
("M¹-i")
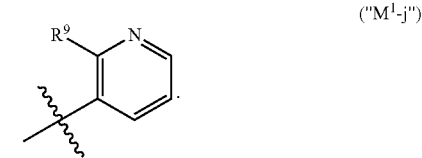
("M¹-j")
In some embodiments:
Moiety M¹ is
("M¹-k")

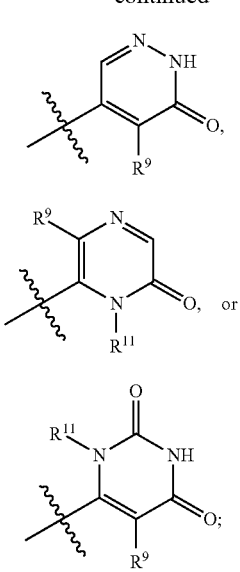

and

R$^{11}$ is H, C$_{1-4}$ alkyl, C$_{1-4}$ haloalkyl, (C$_{1-2}$ alkoxy)-C$_{1-4}$ alkyl-, or C$_{3-7}$ cycloalkyl.

In some embodiments, R$^9$ is halogen (e.g., Cl), C$_{3-6}$ cycloalkyl (e.g., cyclopropyl), C$_{1-4}$ alkyl, or —CN. In some further embodiments, R$^9$ is halogen (e.g., Cl), C$_{1-4}$ alkyl, or —CN.

In some embodiments, R$^9$ is C$_{1-4}$ alkyl or —CN. In some further embodiments, R$^9$ is C$_{1-4}$ alkyl. In some yet further embodiments, R$^9$ is methyl.

In some embodiments, each R$^{10}$ is independently selected from the group consisting of halogen, —OH, —CN, —SF$_5$, —NO$_2$, Oxo, thiono, C$_{1-6}$ alkyl, C$_{1-6}$ haloalkyl, C$_{1-6}$ hydroxylalkyl, C$_{1-6}$ alkoxy, C$_{1-6}$ haloalkoxy, C$_{3-7}$ cycloalkyl, C$_{2-6}$ alkenyl, C$_{2-6}$ alkynyl, and (C$_{3-7}$ cycloalkyl)-C$_{1-4}$ alkyl-, wherein each of said C$_{1-6}$ alkyl, C$_{3-7}$ cycloalkyl, C$_{2-6}$ alkenyl, C$_{2-6}$ alkynyl, and (C$_{3-7}$ cycloalkyl)-C$_{1-4}$ alkyl- is optionally substituted with 1, 2, 3, 4, or 5 substituents each independently selected from the group consisting of halogen, —N(R$^5$)(R$^6$), C$_{1-4}$ alkyl, C$_{1-4}$ haloalkyl, C$_{3-7}$ cycloalkyl, C$_{1-4}$ alkoxy, and C$_{1-4}$ haloalkoxy.

In some embodiments, each R$^{10}$ is independently selected from the group consisting of —CN, C$_{1-6}$ alkyl, C$_{1-6}$ haloalkyl, C$_{1-6}$ hydroxylalkyl, C$_{3-7}$ cycloalkyl, C$_{2-6}$ alkenyl, C$_{2-6}$ alkynyl, (C$_{3-7}$ cycloalkyl)-C$_{1-4}$ alkyl-, and —N(R$^5$)(R$^6$), wherein each of said C$_{1-6}$ alkyl, C$_{3-7}$ cycloalkyl, C$_{2-6}$ alkenyl, C$_{2-6}$ alkynyl, and (C$_{3-7}$ cycloalkyl)-C$_{1-4}$ alkyl- is optionally substituted with 1, 2, 3, 4, or 5 substituents each independently selected from the group consisting of halogen, C$_{1-4}$ alkoxy, and C$_{1-4}$ haloalkoxy. In some further embodiments, each R$^{10}$ is independently selected from the group consisting of —CN, C$_{1-4}$ alkyl, C$_{1-4}$ haloalkyl, C$_{1-4}$ hydroxylalkyl, (C$_{1-2}$ alkoxy)-C$_{1-4}$ alkyl-, and C$_{3-4}$ cycloalkyl, and —N(R$^5$)(R$^6$).

In some embodiments, each R$^{10}$ is independently selected from the group consisting of C$_{1-4}$ alkyl, C$_{1-4}$ haloalkyl, (C$_{1-2}$ alkoxy)-C$_{1-4}$ alkyl-, —CN, and —N(R$^5$)(R$^6$), wherein each of R$^5$ and R$^6$ independently is H or selected from the group consisting of C$_{1-4}$ alkyl, C$_{1-4}$ haloalkyl, and C$_{3-7}$ cycloalkyl; or R$^5$ and R$^6$ together with the N atom to which they are attached form a 4- to 7-membered heterocycloalkyl or a 5-membered heteroaryl, each optionally substituted with 1, 2, or 3 substituents each independently selected from the group consisting of halogen, —CN, C$_{1-4}$ alkyl, C$_{1-4}$ alkoxy, C$_{3-6}$ cycloalkyl, C$_{1-4}$ haloalkyl, and C$_{1-4}$ haloalkoxy. In some further embodiments, each R$^{10}$ is independently C$_{1-4}$ alkyl or CN. In yet further embodiments, each R$^{10}$ is independently C$_{1-4}$ alkyl. In still yet further embodiments, each R$^{10}$ is methyl.

In some embodiments, each of R$^9$ and R$^{10}$ is independently halogen (e.g., Cl), C$_{3-6}$ cycloalkyl (e.g., cyclopropyl), C$_{1-4}$ alkyl, or —CN. In some further embodiments, each of R$^9$ and R$^{10}$ is independently halogen (e.g., Cl), C$_{1-4}$ alkyl, or —CN.

In some embodiments, each of R$^9$ and R$^{10}$ is independently C$_{1-4}$ alkyl or CN. In some further embodiments, each of R$^9$ and R$^{10}$ is independently methyl or CN.

In some embodiments, X$^1$ is O; 0 or 1 of X$^2$ and X$^3$ is N (e.g., neither of X$^2$ and X$^3$ is N); X$^4$ is N; X$^4$ is N; Q$^1$ is M$^1$; and M$^1$ is as described in one of the embodiments provided herein (e.g., M$^1$-g, M$^1$-k, M$^1$-m, or M$^1$-n). In some further embodiments, L$^1$ is O or S. In yet further embodiments, L$^1$ is O. In still further embodiments, each of R$^1$ and R$^2$ is independently H or halogen; and each of R$^3$ and R$^4$ is independently H, halogen, —CN, methyl, C$_1$ haloalkyl, methoxy, or C$_1$ haloalkoxy. In yet still further embodiments, each of R$^1$ and R$^2$ is H; R$^3$ is H; and R$^4$ is methyl.

In some embodiments, X$^1$ is O; 0 or 1 of X$^2$ and X$^3$ is N (e.g., neither of X$^2$ and X$^3$ is N); X$^4$ is N; Q$^1$ is M$^1$; and M$^1$ is M$^1$-g. In some further embodiments, L$^1$ is O or S. In yet further embodiments, L$^1$ is O. In still further embodiments, each of R$^1$ and R$^2$ is independently H or halogen; and each of R$^3$ and R$^4$ is independently H, halogen, —CN, methyl, C$_1$ haloalkyl, methoxy, or C$_1$ haloalkoxy. In yet still further embodiments, each of R$^1$ and R$^2$ is H; R$^3$ is H; and R$^4$ is methyl.

In some embodiments, X$^1$ is O; 0 or 1 of X$^2$ and X$^3$ is N (e.g., neither of X$^2$ and X$^3$ is N); X$^4$ is N; Q$^1$ is M$^1$; and M$^1$ is M$^1$-k. In some further embodiments, L$^1$ is O or S. In yet further embodiments, L$^1$ is O. In still further embodiments, each of R$^1$ and R$^2$ is independently H or halogen; and each of R$^3$ and R$^4$ is independently H, halogen, —CN, methyl, C$_1$ haloalkyl, methoxy, or C$_1$ haloalkoxy. In yet still further embodiments, each of R$^1$ and R$^2$ is H; R$^3$ is H; and R$^4$ is methyl.

In some embodiments, X$^1$ is O; 0 or 1 of X$^2$ and X$^3$ is N (e.g., neither of X$^2$ and X$^3$ is N); X$^4$ is N; Q$^1$ is M$^1$; and M$^1$ is M$^1$-m. In some further embodiments, L$^1$ is O or S. In yet further embodiments, L$^1$ is O. In still further embodiments, each of R$^1$ and R$^2$ is independently H or halogen; and each of R$^3$ and R$^4$ is independently H, halogen, —CN, methyl, C$_1$ haloalkyl, methoxy, or C$_1$ haloalkoxy. In yet still further embodiments, each of R$^1$ and R$^2$ is H; R$^3$ is H; and R$^4$ is methyl.

In some embodiments, X$^1$ is O; 0 or 1 of X$^2$ and X$^3$ is N (e.g., neither of X$^2$ and X$^3$ is N); X$^4$ is N; Q$^1$ is M$^1$; and M$^1$ is M$^1$-n. In some further embodiments, L$^1$ is O or S. In yet further embodiments, L$^1$ is O. In still further embodiments, each of R$^1$ and R$^2$ is independently H or halogen; and each of R$^3$ and R$^4$ is independently H, halogen, —CN, methyl, C$_1$ haloalkyl, methoxy, or C$_1$ haloalkoxy. In yet still further embodiments, each of R$^1$ and R$^2$ is H; R$^3$ is H; and R$^4$ is methyl.

In some embodiments, X$^1$ is O; X$^2$ is C-T$^2$, X$^3$ is C-T$^3$; X$^4$ is N; Q$^1$ is M$^1$; and M$^1$ is M$^1$-g. In some further embodiments, L$^1$ is O or S. In yet further embodiments, L$^1$ is O. In still further embodiments, each of R$^1$ and R$^2$ is independently H or halogen; and each of R$^3$ and R$^4$ is independently H, halogen, —CN, methyl, C$_1$ haloalkyl, methoxy, or C haloalkoxy. In yet still further embodiments, each of $R^1$ and $R^2$ is H; $R^3$ is H; and $R^4$ is methyl.

In some embodiments, $X^1$ is O; $X^2$ is C-$T^2$, $X^3$ is C-$T^3$; $X^4$ is N; $Q^1$ is $M^1$; and $M^1$ is $M^1$-k. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or C haloalkoxy. In yet still further embodiments, each of $R^1$ and $R^2$ is H; $R^3$ is H; and $R^4$ is methyl.

In some embodiments, $X^1$ is O; $X^2$ is C-$T^2$, $X^3$ is C-$T^3$; $X^4$ is N; $Q^1$ is $M^1$; and $M^1$ is $M^1$-m. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is O; $X^2$ is C-$T^2$, $X^3$ is C-$T^3$; $X^4$ is N; $Q^1$ is $M^1$; and $M^1$ is $M^1$-n. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is O; 1 of $X^2$ and $X^3$ is N (e.g., $X^2$ is N and $X^3$ is C-$T^3$); $X^4$ is C-$T^4$; $Q^1$ is $M^1$; and $M^1$ is as described in one of the embodiments provided herein (e.g., $M^1$-g, $M^1$-k, $M^1$-m, or $M^1$-n). In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is O; 1 of $X^2$ and $X^3$ is N (e.g., $X^2$ is N and $X^3$ is C-$T^3$); $X^4$ is C-$T^4$; $Q^1$ is $M^1$; and $M^1$ is $M^1$-g. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is O; 1 of $X^2$ and $X^3$ is N (e.g., $X^2$ is N and $X^3$ is C-$T^3$); $X^4$ is C-$T^4$; $Q^1$ is $M^1$; and $M^1$ is $M^1$-k. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is O; 1 of $X^2$ and $X^3$ is N (e.g., $X^2$ is N and $X^3$ is C-$T^3$); $X^4$ is C-$T^4$; $Q^1$ is $M^1$; and $M^1$ is $M^1$-m. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is O; 1 of $X^2$ and $X^3$ is N (e.g., $X^2$ is N and $X^3$ is C-$T^3$); $X^4$ is C-$T^4$; $Q^1$ is $M^1$; and $M^1$ is $M^1$-n. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is O; $X^2$ is N, $X^3$ is C-$T^3$; $X^4$ is N; $Q^1$ is $M^1$; and $M^1$ is $M^1$-g. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is O; $X^2$ is C-$T^2$, $X^3$ is C-$T^3$; $X^4$ is N; $Q^1$ is $M^1$; and $M^1$ is $M^1$-k. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is O; $X^2$ is C-$T^2$, $X^3$ is C-$T^3$; $X^4$ is N; $Q^1$ is $M^1$; and $M^1$ is M-m. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is O; $X^2$ is C-$T^2$, $X^3$ is C-$T^3$; $X^4$ is N; $Q^1$ is $M^1$; and $M^1$ is $M^1$-n. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is S; 0 or 1 of $X^2$ and $X^3$ is N (e.g., neither of $X^2$ and $X^3$ is N); $X^4$ is N; $X^4$ is N; $Q^1$ is $M^1$; and $M^1$ is as described in one of the embodiments provided herein (e.g., $M^1$-g, $M^1$-k, $M^1$-m, or $M^1$-n). In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is S; 0 or 1 of $X^2$ and $X^3$ is N (e.g., neither of $X^2$ and $X^3$ is N); $X^4$ is N; $Q^1$ is $M^1$; and $M^1$ is $M^1$-g. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is S; 0 or 1 of $X^2$ and $X^3$ is N (e.g., neither of $X^2$ and $X^3$ is N); $X^4$ is N; $Q^1$ is $M^1$; and $M^1$ is $M^1$-k. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is S; 0 or 1 of $X^2$ and $X^3$ is N (e.g., neither of $X^2$ and $X^3$ is N); $X^4$ is N; $Q^1$ is $M^1$; and $M^1$ is $M^1$-m. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is S; 0 or 1 of $X^2$ and $X^3$ is N (e.g., neither of $X^2$ and $X^3$ is N); $X^4$ is N; $Q^1$ is $M^1$; and $M^1$ is $M^1$-n. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is S; $X^2$ is C-$T^2$, $X^3$ is C-$T^3$; $X^4$ is N; $Q^1$ is $M^1$; and $M^1$ is $M^1$-g. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or C haloalkoxy. In yet still further embodiments, each of $R^1$ and $R^2$ is H; $R^3$ is H; and $R^4$ is methyl.

In some embodiments, $X^1$ is S; $X^2$ is C-$T^2$, $X^3$ is C-$T^3$; $X^4$ is N; $Q^1$ is $M^1$; and $M^1$ is $M^1$-k. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is S; $X^2$ is C-$T^2$, $X^3$ is C-$T^3$; $X^4$ is N; $Q^1$ is $M^1$; and $M^1$ is $M^1$-m. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is S; $X^2$ is C-$T^2$, $X^3$ is C-$T^3$; $X^4$ is N; $Q^1$ is $M^1$; and $M^1$ is $M^1$-n. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is S; 1 of $X^2$ and $X^3$ is N (e.g., $X^2$ is N and $X^3$ is C-$T^3$); $X^4$ is C-$T^4$; $Q^1$ is $M^1$; and $M^1$ is as described in one of the embodiments provided herein (e.g., $M^1$-g, $M^1$-k, $M^1$-m, or $M^1$-n). In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is S; 1 of $X^2$ and $X^3$ is N (e.g., $X^2$ is N and $X^3$ is C-$T^3$); $X^4$ is C-$T^4$; $Q^1$ is $M^1$; and $M^1$ is $M^1$-g. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is S; 1 of $X^2$ and $X^3$ is N (e.g., $X^2$ is N and $X^3$ is C-$T^3$); $X^4$ is C-$T^4$; $Q^1$ is $M^1$; and $M^1$ is $M^1$-k. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is S; 1 of $X^2$ and $X^3$ is N (e.g., $X^2$ is N and $X^3$ is C-$T^3$); $X^4$ is C-$T^4$; $Q^1$ is $M^1$; and $M^1$ is $M^1$-m. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is S; 1 of $X^2$ and $X^3$ is N (e.g., $X^2$ is N and $X^3$ is C-$T^3$); $X^4$ is C-$T^4$; $Q^1$ is $M^1$; and $M^1$ is $M^1$-n. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is S; $X^2$ is N, $X^3$ is C-$T^3$; $X^4$ is N; $Q^1$ is $M^1$; and $M^1$ is $M^1$-g. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is S; $X^2$ is C-$T^2$, $X^3$ is C-$T^3$; $X^4$ is N; $Q^1$ is $M^1$; and $M^1$ is $M^1$-k. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is S; $X^2$ is C-$T^2$, $X^3$ is C-$T^3$; $X^4$ is N; $Q^1$ is $M^1$; and $M^1$ is $M^1$-m. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is S; $X^2$ is C-$T^2$, $X^3$ is C-$T^3$; $X^4$ is N; $Q^1$ is $M^1$; and $M^1$ is $M^1$-n. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is NH; 0 or 1 of $X^2$ and $X^3$ is N (e.g., $X^2$ is C-$T^2$ and $X^3$ is N); $X^4$ is C-$T^4$; $Q^1$ is $M^1$; and $M^1$ is as described in one of the embodiments provided herein (e.g., $M^1$-g, $M^1$-k, $M^1$-m, or $M^1$-n). In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is NH; 0 or 1 of $X^2$ and $X^3$ is N (e.g., $X^2$ is C-$T^2$ and $X^3$ is N); $X^4$ is C-$T^4$; $Q^1$ is $M^1$; and $M^1$ is $M^1$-g. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is NH; 0 or 1 of $X^2$ and $X^3$ is N (e.g., $X^2$ is C-$T^2$ and $X^3$ is N); $X^4$ is C-$T^4$; $Q^1$ is $M^1$; and $M^1$ is $M^1$-k. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is NH; 0 or 1 of $X^2$ and $X^3$ is N (e.g., $X^2$ is C-$T^2$ and $X^3$ is N); $X^4$ is C-$T^4$; $Q^1$ is $M^1$; and $M^1$ is $M^1$-m. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is NH; 0 or 1 of $X^2$ and $X^3$ is N (e.g., $X^2$ is C-$T^2$ and $X^3$ is N); $X^4$ is C-$T^4$; $Q^1$ is $M^1$; and $M^1$ is $M^1$-n. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is NH; $X^2$ is C-$T^2$, $X^3$ is N; $X^4$ is N; $Q^1$ is $M^1$; and $M^1$ is $M^1$-g. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is NH; $X^2$ is C-$T^2$, $X^3$ is N; $X^4$ is N; $Q^1$ is $M^1$; and $M^1$ is $M^1$-k. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is NH; $X^2$ is C-$T^2$, $X^3$ is N; $X^4$ is N; $Q^1$ is $M^1$; and $M^1$ is $M^1$-m. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, $X^1$ is NH; $X^2$ is C-$T^2$, $X^3$ is N; $X^4$ is N; $Q^1$ is $M^1$; and $M^1$ is $M^1$-n. In some further embodiments, $L^1$ is O or S. In yet further embodiments, $L^1$ is O. In still further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet still further embodiments, each of $R^1$ and $R^2$ is H; $R^3$ is H; and $R^4$ is methyl.

In some embodiments, the compound of Formula I or a salt thereof is a compound of Formula I-a or a salt thereof; and $Q^1$ is $M^1$; and $M^1$ is $M^1$-g. In some further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet further embodiments, each of $R^1$ and $R^2$ is H; $R^3$ is H; and $R^4$ is methyl. In some still further embodiments, each of $R^9$ and $R^{10}$ is independently $C_{1-4}$ alkyl or CN. In yet still further embodiments, each of $R^9$ and $R^{10}$ is independently methyl or CN.

In some embodiments, the compound of Formula I or a salt thereof is a compound of Formula I-a or a salt thereof; and $Q^1$ is $M^1$; and $M^1$ is $M^1$-k. In some further embodiments, each of $R^1$ and $R^2$ is independently H or halogen; and each of $R^3$ and $R^4$ is independently H, halogen, —CN, methyl, $C_1$ haloalkyl, methoxy, or C haloalkoxy. In yet further embodiments, each of $R^1$ and $R^2$ is H; $R^3$ is H; and $R^4$ is methyl. In some still further embodiments, each of $R^9$ and $R^{10}$ is independently $C_{1-4}$ alkyl or CN. In yet still further embodiments, each of $R^9$ and $R^{10}$ is independently methyl or CN.

In some embodiments, the compound of Formula I or a salt thereof is a compound of Formula I-a or a salt thereof; and $Q^1$ is $M^1$; and $M^1$ is $M^1$-m. In some further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet further embodiments, each of $R^1$ and $R^2$ is H; $R^3$ is H; and $R^4$ is methyl. In some still further embodiments, each of $R^9$ and $R^{10}$ is independently $C_{1-4}$ alkyl or CN. In yet still further embodiments, each of $R^9$ and $R^{10}$ is independently methyl or CN.

In some embodiments, the compound of Formula I or a salt thereof is a compound of Formula I-a or a salt thereof; and $Q^1$ is $M^1$; and $M^1$ is $M^1$-n. In some further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet further embodiments, each of $R^1$ and $R^2$ is H; $R^3$ is H; and $R^4$ is methyl. In some still further embodiments, each of $R^9$ and $R^{10}$ is independently $C_{1-4}$ alkyl or CN. In yet still further embodiments, each of $R^9$ and $R^{10}$ is independently methyl or CN.

In some embodiments, the compound of Formula I or a salt thereof is a compound of Formula I-b or a salt thereof; and $Q^1$ is $M^1$; and $M^1$ is $M^1$-g. In some further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet further embodiments, each of $R^1$ and $R^2$ is H; $R^3$ is H; and $R^4$ is methyl. In some still further embodiments, each of $R^9$ and $R^{10}$ is independently $C_{1-4}$ alkyl or CN. In yet still further embodiments, each of $R^9$ and $R^{10}$ is independently methyl or CN.

In some embodiments, the compound of Formula I or a salt thereof is a compound of Formula I-b or a salt thereof; and $Q^1$ is $M^1$; and $M^1$ is $M^1$-k. In some further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet further embodiments, each of $R^1$ and $R^2$ is H; $R^3$ is H; and $R^4$ is methyl. In some still further embodiments, each of $R^9$ and $R^{10}$ is independently $C_{1-4}$ alkyl or CN. In yet still further embodiments, each of $R^9$ and $R^{10}$ is independently methyl or CN.

In some embodiments, the compound of Formula I or a salt thereof is a compound of Formula I-b or a salt thereof; and $Q^1$ is $M^1$; and $M^1$ is $M^1$-m. In some further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet further embodiments, each of $R^1$ and $R^2$ is H; $R^3$ is H; and $R^4$ is methyl. In some still further embodiments, each of $R^9$ and $R^{10}$ is independently $C_{1-4}$ alkyl or CN. In yet still further embodiments, each of $R^9$ and $R^{10}$ is independently methyl or CN.

In some embodiments, the compound of Formula I or a salt thereof is a compound of Formula I-b or a salt thereof; and $Q^1$ is $M^1$; and $M^1$ is $M^1$-m. In some further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet further embodiments, each of $R^1$ and $R^2$ is H; $R^3$ is H; and $R^4$ is methyl. In some still further embodiments, each of $R^9$ and $R^{10}$ is independently $C_{1-4}$ alkyl or CN. In yet still further embodiments, each of $R^9$ and $R^{10}$ is independently methyl or CN.

In some embodiments, the compound of Formula I or a salt thereof is a compound of Formula I-c or a salt thereof; and $Q^1$ is $M^1$; and $M^1$ is $M^1$-g. In some further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet further embodiments, each of $R^1$ and $R^2$ is H; $R^3$ is H; and $R^4$ is methyl. In some still further embodiments, each of $R^9$ and $R^{10}$ is independently $C_{1-4}$ alkyl or CN. In yet still further embodiments, each of $R^9$ and $R^{10}$ is independently methyl or CN.

In some embodiments, the compound of Formula I or a salt thereof is a compound of Formula I-c or a salt thereof; and $Q^1$ is $M^1$; and $M^1$ is $M^1$-k. In some further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet further embodiments, each of $R^1$ and $R^2$ is H; $R^3$ is H; and $R^4$ is methyl. In some still further embodiments, each of $R^9$ and $R^{10}$ is independently $C_{1-4}$ alkyl or CN. In yet still further embodiments, each of $R^9$ and $R^{10}$ is independently methyl or CN.

In some embodiments, the compound of Formula I or a salt thereof is a compound of Formula I-c or a salt thereof; and $Q^1$ is $M^1$; and $M^1$ is $M^1$-m. In some further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet further embodiments, each of $R^1$ and $R^2$ is H; $R^3$ is H; and $R^4$ is methyl. In some still further embodiments, each of $R^9$ and $R^{10}$ is independently $C_{1-4}$ alkyl or CN. In yet still further embodiments, each of $R^9$ and $R^{10}$ is independently methyl or CN.

In some embodiments, the compound of Formula I or a salt thereof is a compound of Formula I-c or a salt thereof; and $Q^1$ is $M^1$; and $M^1$ is $M^1$-n. In some further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet further embodiments, each of $R^1$ and $R^2$ is H; $R^3$ is H; and $R^4$ is methyl. In some still further embodiments, each of $R^9$ and $R^{10}$ is independently $C_{1-4}$ alkyl or CN. In yet still further embodiments, each of $R^9$ and $R^{10}$ is independently methyl or CN.

In some embodiments, the compound of Formula I or a salt thereof is a compound of Formula I-d or a salt thereof; and $Q^1$ is $M^1$; and $M^1$ is $M^1$-g. In some further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet further embodiments, each of $R^1$ and $R^2$ is H; $R^3$ is H; and $R^4$ is methyl. In some still further embodiments, each of $R^9$ and $R^{10}$ is independently $C_{1-4}$ alkyl or CN. In yet still further embodiments, each of $R^9$ and $R^{10}$ is independently methyl or CN.

In some embodiments, the compound of Formula I or a salt thereof is a compound of Formula I-d or a salt thereof; and $Q^1$ is $M^1$; and $M^1$ is $M^1$-k. In some further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet further embodiments, each of $R^1$ and $R^2$ is H; $R^3$ is H; and $R^4$ is methyl. In some still further embodiments, each of $R^9$ and $R^{10}$ is independently $C_{1-4}$ alkyl or CN. In yet still further embodiments, each of $R^9$ and $R^{10}$ is independently methyl or CN.

In some embodiments, the compound of Formula I or a salt thereof is a compound of Formula I-d or a salt thereof; and $Q^1$ is $M^1$; and $M^1$ is $M^1$-m. In some further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet further embodiments, each of $R^1$ and $R^2$ is H; $R^3$ is H; and $R^4$ is methyl. In some still further embodiments, each of $R^9$ and $R^{10}$ is independently $C_{1-4}$ alkyl or CN. In yet still further embodiments, each of $R^9$ and $R^{10}$ is independently methyl or CN.

In some embodiments, the compound of Formula I or a salt thereof is a compound of Formula I-d or a salt thereof; and $Q^1$ is $M^1$; and $M^1$ is $M^1$-n. In some further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet further embodiments, each of $R^1$ and $R^2$ is H; $R^3$ is H; and $R^4$ is methyl. In some still further embodiments, each of $R^9$ and $R^{10}$ is independently $C_{1-4}$ alkyl or CN. In yet still further embodiments, each of $R^9$ and $R^{10}$ is independently methyl or CN.

In some embodiments, the compound of Formula I or a salt thereof is a compound of Formula I-e or a salt thereof; and $Q^1$ is $M^1$; and $M^1$ is $M^1$-g. In some further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet further embodiments, each of $R^1$ and $R^2$ is H; $R^3$ is H; and $R^4$ is methyl. In some still further embodiments, each of $R^9$ and $R^{10}$ is independently $C_{1-4}$ alkyl or CN. In yet still further embodiments, each of $R^9$ and $R^{10}$ is independently methyl or CN.

In some embodiments, the compound of Formula I or a salt thereof is a compound of Formula I-e or a salt thereof; and $Q^1$ is $M^1$; and $M^1$ is $M^1$-k. In some further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet further embodiments, each of $R^1$ and $R^2$ is H; $R^3$ is H; and $R^4$ is methyl. In some still further embodiments, each of $R^9$ and $R^{10}$ is independently $C_{1-4}$ alkyl or CN. In yet still further embodiments, each of $R^9$ and $R^{10}$ is independently methyl or CN.

In some embodiments, the compound of Formula I or a salt thereof is a compound of Formula I-e or a salt thereof; and $Q^1$ is $M^1$; and $M^1$ is $M^1$-m. In some further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet further embodiments, each of $R^1$ and $R^2$ is H; $R^3$ is H; and $R^4$ is methyl. In some still further embodiments, each of $R^9$ and $R^{10}$ is independently $C_{1-4}$ alkyl or CN. In yet still further embodiments, each of $R^9$ and $R^{10}$ is independently methyl or CN.

In some embodiments, the compound of Formula I or a salt thereof is a compound of Formula I-e or a salt thereof;

and $Q^1$ is $M^1$; and $M^1$ is $M^1$-n. In some further embodiments, each of $R^1$ and $R^2$ is independently H or halogen; and each of $R^3$ and $R^4$ is independently H, halogen, —CN, methyl, $C_1$ haloalkyl, methoxy, or $C_1$ haloalkoxy. In yet further embodiments, each of $R^1$ and $R^2$ is H; $R^3$ is H; and $R^4$ is methyl. In some still further embodiments, each of $R^9$ and $R^{10}$ is independently $C_{1-4}$ alkyl or CN. In yet still further embodiments, each of $R^9$ and $R^{10}$ is independently methyl or CN.

In some embodiments, the invention also provides one or more of the compounds described in Examples 1-23 in the Examples section of the subject application, pharmaceutically acceptable salts of the compounds; or the N-oxides of the compound or salt.

In some embodiments, the present invention provides a compound selected from the group consisting of:

4-[4-(4,6-dimethylpyrimidin-5-yl)-3-methylphenoxy]furo[2,3-d]pyrimidine;

6-[4-(furo[2,3-d]pyrimidin-4-yloxy)-2-methylphenyl]-1,5-dimethylpyrazin-2(1H)-one;

(−)-6-[4-(furo[2,3-d]pyrimidin-4-yloxy)-2-methylphenyl]-1,5-dimethylpyrazin-2(1H)-one;

(+)-6-[4-(furo[2,3-d]pyrimidin-4-yloxy)-2-methylphenyl]-1,5-dimethylpyrazin-2(1H)-one;

5-[4-(furo[2,3-d]pyrimidin-4-yloxy)-2-methylphenyl]-4,6-dimethylpyridazin-3(2H)-one;

(+)-5-[4-(furo[2,3-d]pyrimidin-4-yloxy)-2-methylphenyl]-4,6-dimethylpyridazin-3(2H)-one;

(−)-5-[4-(furo[2,3-d]pyrimidin-4-yloxy)-2-methylphenyl]-4,6-dimethylpyridazin-3(2H)-one;

6-[4-(furo[2,3-d]pyrimidin-4-yloxy)phenyl]-1,5-dimethylpyrimidine-2,4(1H,3H)-dione;

5-[4-(furo[2,3-d]pyrimidin-4-yloxy)phenyl]-4,6-dimethylpyridazin-3(2H)-one;

5-ethyl-6-[4-(furo[2,3-d]pyrimidin-4-yloxy)phenyl]-1-methylpyrimidine-2,4(1H,3H)-dione;

1-ethyl-6-[4-(furo[2,3-d]pyrimidin-4-yloxy)phenyl]-5-methylpyrimidine-2,4(1H,3H)-dione; and 1-cyclopropyl-6-[4-(furo[2,3-d]pyrimidin-4-yloxy)phenyl]-5-methylpyrimidine-2,4(1H,3H)-dione, or a pharmaceutically acceptable salt thereof.

The second aspect of the invention includes any subset of any embodiment described herein.

The second aspect of the invention includes combinations of two or more embodiments described hereinabove, or any subset thereof.

The second aspect of the invention further provides the compound of Formula I or a pharmaceutically acceptable salt thereof (including all embodiments and combinations of two or more embodiments described herein or any subcombination thereof) for use in treating a D1-mediated (or D1-associated) disorder described herein. The second aspect of the invention further provides use of the compound of Formula I or a pharmaceutically acceptable salt thereof (including all embodiments and combinations of two or more embodiments described herein or any subcombination thereof) for treating a D1-mediated (or D1-associated) disorder described herein.

The second aspect of the invention further provides use of the compound of Formula I or a pharmaceutically acceptable salt thereof (including all embodiments and combinations of two or more embodiments described herein or any subcombination thereof) in manufacturing a medicament for use in treating a D1-mediated (or D1-associated) disorder described herein.

The compound of Formula I or its salt of the second aspect of present invention is a D1R modulator (e.g., a D1R agoninst for example, a D1R partial agonist). Thus, the second aspect of present invention further provides a method for modulating (such as agonizing or partially agonizing) an activity of D1R (either in vitro or in vivo), comprising contacting (including incubating) the D1R with a compound of Formula I or a pharmaceutically acceptable salt thereof (such as one selected from Examples 1-23 herein) described herein.

As used herein, the term "n-membered" where n is an integer typically describes the number of ring-forming atoms in a moiety where the number of ring-forming atoms is n. For example, pyridine is an example of a 6-membered heteroaryl ring and thiophene is an example of a 5-membered heteroaryl group.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to include $C_1$ alkyl (methyl), $C_2$ alkyl (ethyl), $C_3$ alkyl, $C_4$ alkyl, $C_5$ alkyl, and $C_6$ alkyl. For another example, the term "a 5- to 10-membered heteroaryl group" is specifically intended to include any 5-, 6-, 7-, 8-, 9- or 10-membered heteroaryl group.

As used herein, the term "alkyl" is defined to include saturated aliphatic hydrocarbons including straight chains and branched chains. In some embodiments, the alkyl group has 1 to 20 carbon atoms, 1 to 10 carbon atoms, 1 to 6 carbon atoms, or 1 to 4 carbon atoms. For example, the term "$C_{1-6}$ alkyl," as well as the alkyl moieties of other groups referred to herein (e.g., $C_{1-6}$ alkoxy) refers to linear or branched radicals of 1 to 6 carbon atoms (e.g., methyl, ethyl, n-propyl, isopropyl, n-butyl, isobutyl, sec-butyl, tert-butyl, n-pentyl, or n-hexyl). For yet another example, the term "$C_{1-4}$ alkyl" refers to linear or branched aliphatic hydrocarbon chains of 1 to 4 carbon atoms; the term "$C_{1-3}$ alkyl" refers to linear or branched aliphatic hydrocarbon chains of 1 to 3 carbon atoms; the term "$C_{1-2}$ alkyl" refers to linear or branched aliphatic hydrocarbon chains of 1 to 2 carbon atoms; and the term "$C_1$ alkyl" refers to methyl. An alkyl group optionally can be substituted by one or more (e.g. 1 to 5) suitable substituents.

As used herein, the term "alkenyl" refers to aliphatic hydrocarbons having at least one carbon-carbon double bond, including straight chains and branched chains having at least one carbon-carbon double bond. In some embodiments, the alkenyl group has 2 to 20 carbon atoms, 2 to 10 carbon atoms, 2 to 6 carbon atoms, 3 to 6 carbon atoms, or 2 to 4 carbon atoms. For example, as used herein, the term "$C_{2-6}$ alkenyl" means straight or branched chain unsaturated radicals (having at least one carbon-carbon double bond) of 2 to 6 carbon atoms, including, but not limited to, ethenyl, 1-propenyl, 2-propenyl (allyl), isopropenyl, 2-methyl-1-propenyl, 1-butenyl, 2-butenyl, and the like. An alkenyl group optionally can be substituted by one or more (e.g. 1 to 5) suitable substituents. When the compounds of Formula I contain an alkenyl group, the alkenyl group may exist as the pure E form, the pure Z form, or any mixture thereof.

As used herein, the term "alkynyl" refers to aliphatic hydrocarbons having at least one carbon-carbon triple bond, including straight chains and branched chains having at least one carbon-carbon triple bond. In some embodiments, the alkynyl group has 2 to 20, 2 to 10, 2 to 6, or 3 to 6 carbon atoms. For example, as used herein, the term "$C_{2-6}$ alkynyl" refers to straight or branched hydrocarbon chain alkynyl radicals as defined above, having 2 to 6 carbon atoms. An alkynyl group optionally can be substituted by one or more (e.g. 1 to 5) suitable substituents.

As used herein, the term "cycloalkyl" refers to saturated or unsaturated, non-aromatic, monocyclic or polycyclic (such as bicyclic) hydrocarbon rings (e.g., monocyclics such as cyclopropyl, cyclobutyl, cyclopentyl, cyclohexyl, cycloheptyl, cyclooctyl, cyclononyl, or bicyclics including spiro, fused, or bridged systems (such as bicyclo[1.1.1]pentanyl, bicyclo[2.2.1]heptanyl, bicyclo[3.2.1]octanyl or bicyclo[5.2.0]nonanyl, decahydronaphthalenyl, etc.). The cycloalkyl group has 3 to 15 carbon atoms. In some embodiments the cycloalkyl may optionally contain one, two or more non-cumulative non-aromatic double or triple bonds and/or one to three oxo groups. In some embodiments, the bicycloalkyl group has 6 to 14 carbon atoms. For example, the term "$C_{3-14}$ cycloalkyl" refers to saturated or unsaturated, non-aromatic, monocyclic or polycyclic (such as bicyclic) hydrocarbon rings of 3 to 14 ring-forming carbon atoms (e.g., cyclopropyl, cyclobutyl, cyclopentyl, cyclohexyl, bicyclo[1.1.1]pentanyl, or cyclodecanyl); and the term "$C_{3-7}$ cycloalkyl" refers to saturated or unsaturated, non-aromatic, monocyclic or polycyclic (such as bicyclic) hydrocarbon rings of 3 to 7 ring-forming carbon atoms (e.g., cyclopropyl, cyclobutyl, cyclopentyl, cyclohexyl, bicyclo[1.1.1]pentan-1-yl, or bicyclo[1.1.1]pentan-2-yl). For another example, the term "$C_{3-6}$ cycloalkyl" refers to saturated or unsaturated, non-aromatic, monocyclic or polycyclic (such as bicyclic) hydrocarbon rings of 3 to 6 ring-forming carbon atoms. For yet another example, the term "$C_{3-4}$ cycloalkyl" refers to cyclopropyl or cyclobutyl. Also included in the definition of cycloalkyl are moieties that have one or more aromatic rings (including aryl and heteroaryl) fused to the cycloalkyl ring, for example, benzo or thienyl derivatives of cyclopentane, cyclopentene, cyclohexane, and the like (e.g., 2,3-dihydro-1H-indene-1-yl, or 1H-inden-2(3H)-one-1-yl). The cycloalkyl group optionally can be substituted by 1 or more (e.g., 1 to 5) suitable substituents.

As used herein, the term "aryl" refers to all-carbon monocyclic or fused-ring polycyclic aromatic groups having a conjugated pi-electron system. The aryl group has 6 or 10 carbon atoms in the ring(s). Most commonly, the aryl group has 6 carbon atoms in the ring. For example, as used herein, the term "$C_{6-10}$ aryl" means aromatic radicals containing from 6 to 10 carbon atoms such as phenyl or naphthyl. The aryl group optionally can be substituted by 1 or more (e.g., 1 to 5) suitable substituents.

As used herein, the term "heteroaryl" refers to monocyclic or fused-ring polycyclic aromatic heterocyclic groups with one or more heteroatom ring members (ring-forming atoms) each independently selected from O, S and N in at least one ring. The heteroaryl group has 5 to 14 ring-forming atoms, including 1 to 13 carbon atoms, and 1 to 8 heteroatoms selected from O, S, and N. In some embodiments, the heteroaryl group has 5 to 10 ring-forming atoms including one to four heteroatoms. The heteroaryl group can also contain one to three oxo or thiono (i.e. =S) groups. In some embodiments, the heteroaryl group has 5 to 8 ring-forming atoms including one, two or three heteroatoms. For example, the term "5-membered heteroaryl" refers to a monocyclic heteroaryl group as defined above with 5 ring-forming atoms in the monocyclic heteroaryl ring; the term "6-membered heteroaryl" refers to a monocyclic heteroaryl group as defined above with 6 ring-forming atoms in the monocyclic heteroaryl ring; and the term "5- or 6-membered heteroaryl" refers to a monocyclic heteroaryl group as defined above with 5 or 6 ring-forming atoms in the monocyclic heteroaryl ring. For another example, term "5- or 10-membered heteroaryl" refers to a monocyclic or bicyclic heteroaryl group as defined above with 5, 6, 7, 8, 9 or 10 ring-forming atoms in the monocyclic or bicyclic heteroaryl ring. A heteroaryl group optionally can be substituted by 1 or more (e.g., 1 to 5) suitable substituents. Examples of monocyclic heteroaryls include those with 5 ring-forming atoms including one to three heteroatoms or those with 6 ring-forming atoms including one, two or three nitrogen heteroatoms. Examples of fused bicyclic heteroaryls include two fused 5- and/or 6-membered monocyclic rings including one to four heteroatoms.

Examples of heteroaryl groups include pyridinyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, indolyl, 1H-imidazo[4,5-c]pyridinyl, imidazo[1,2-a]pyridinyl, 1H-pyrrolo[3,2-c]pyridinyl, imidazo[1,2-a]pyrazinyl, imidazo[2,1-c][1,2,4]triazinyl, imidazo[1,5-a]pyrazinyl, imidazo[1,2-a]pyrimidinyl, 1H-indazolyl, 9H-purinyl, imidazo[1,2-a]pyrimidinyl, [1,2,4]triazolo[1,5-a]pyrimidinyl, [1,2,4]triazolo[4,3-b]pyridazinyl, isoxazolo[5,4-c]pyridazinyl, isoxazolo[3,4-c]pyridazinyl, pyridone, pyrimidone, pyrazinone, pyrimidinone, 1H-imidazol-2(3H)-one, 1H-pyrrole-2,5-dione, 3-oxo-2H-pyridazinyl, 1H-2-oxo-pyrimidinyl, 1H-2-oxo-pyridinyl, 2,4(1H,3H)-dioxo-pyrimidinyl, 1H-2-oxo-pyrazinyl, and the like. The heteroaryl group optionally can be substituted by 1 or more (e.g., 1 to 5) suitable substituents.

As used herein, the term "heterocycloalkyl" refers to a monocyclic or polycyclic [including 2 or more rings that are fused together, including spiro, fused, or bridged systems, for example, a bicyclic ring system], saturated or unsaturated, non-aromatic 4- to 15-membered ring system (such as a 4- to 14-membered ring system, 4- to 12-membered ring system, 5- to 10-membered ring system, 4- to 7-membered ring system, 4- to 6-membered ring system, or 5- to 6-membered ring system), including 1 to 14 ring-forming carbon atoms and 1 to 10 ring-forming heteroatoms each independently selected from O, S and N. The heterocycloalkyl group can also optionally contain one or more oxo or thiono (i.e. =S) groups. For example, the term "4- to 12-membered heterocycloalkyl" refers to a monocyclic or polycyclic, saturated or unsaturated, non-aromatic 4- to 12-membered ring system that comprises one or more ring-forming heteroatoms each independently selected from O, S and N; and the term "4- to 10-membered heterocycloalkyl" refers to a monocyclic or polycyclic, saturated or unsaturated, non-aromatic 4- to 10-membered ring system that comprises one or more ring-forming heteroatoms each independently selected from O, S and N. For another example, the term "4- to 6-membered heterocycloalkyl" refers to a monocyclic or polycyclic, saturated or unsaturated, non-aromatic 4- to 6-membered ring system that comprises one or more ring-forming heteroatoms each independently selected from O, S and N; and the term "5- to 6-membered heterocycloalkyl" refers to a monocyclic or polycyclic, saturated or unsaturated, non-aromatic 5- to 6-membered ring system that comprises one or more ring-forming heteroatoms each independently selected from O, S and N. Also included in the definition of heterocycloalkyl are moieties that have one or more aromatic rings (including aryl and heteroaryl) fused to the nonaromatic heterocycloalkyl ring, for example pyridinyl, pyrimidinyl, thiophenyl, pyrazolyl, phthalimidyl, naphthalimidyl, and benzo derivatives of the nonaromatic heterocycloalkyl rings. The heterocycloalkyl group optionally can be substituted by 1 or more (e.g., 1 to 5) suitable substituents.

Examples of such heterocycloalkyl rings include azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydrothiadiazinyl, morpholinyl, oxetanyl, tetrahydrodiazinyl, oxazinyl, oxathiazinyl, quinuclidinyl, chromanyl, isochromanyl, benzoxazinyl, 7-azabicyclo[2.2.1]heptan-1-yl, 7-azabicyclo[2.2.1]heptan-2-yl, 7-azabicyclo[2.2.1]heptan-7-yl, 2-azabicyclo[2.2.1]heptan-3-on-2-yl, 3-azabicyclo[3.1.0]hexanyl, 3-azabicyclo[4.1.0]heptanyl and the like. Further examples of heterocycloalkyl rings include tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperidin-4-yl, piperazin-1-yl, piperazin-2-yl, 1,3-oxazolidin-3-yl, 1,4-oxazepan-1-yl, isothiazolidinyl, 1,3-thiazolidin-3-yl, 1,2-pyrazolidin-2-yl, 1,2-tetrahydrothiazin-2-yl, 1,3-thiazinan-3-yl, 1,2-tetrahydrodiazin-2-yl, 1,3-tetrahydrodiazin-1-yl, 1,4-oxazin-4-yl, oxazolidinonyl, 2-oxo-piperidinyl (e.g., 2-oxo-piperidin-1-yl), and the like. Some examples of aromatic-fused heterocycloalkyl groups include indolinyl, isoindolinyl, isoindolin-1-one-3-yl, 5,7-dihydro-6H-pyrrolo[3,4-b]pyridin-6-yl, 6,7-dihydro-5H-pyrrolo[3,4-d]pyrimidin-6-yl, 4,5,6,7-tetrahydrothieno[2,3-c]pyridine-5-yl, 5,6-dihydrothieno[2,3-c]pyridin-7(4H)-one-5-yl, 1,4,5,6-tetrahydropyrrolo[3,4-c]pyrazol-5-yl, and 3,4-dihydroisoquinolin-1(2H)-one-3-yl groups. The heterocycloalkyl group is optionally substituted by 1 or more (e.g., 1 to 5) suitable substituents. Examples of heterocycloalkyl groups include 5- or 6-membered monocyclic rings and 9- or 10-membered fused bicyclic rings.

As used herein, the term "halo" or "halogen" group is defined to include fluorine, chlorine, bromine or iodine.

As used herein, the term "haloalkyl" refers to an alkyl group having one or more halogen substituents (up to perhaloalkyl, i.e., every hydrogen atom of the alkyl group has been replaced by a halogen atom). For example, the term "$C_{1-6}$ haloalkyl" refers to a $C_{1-6}$ alkyl group having one or more halogen substituents (up to perhaloalkyl, i.e., every hydrogen atom of the alkyl group has been replaced by a halogen atom). For another example, the term "$C_{1-4}$ haloalkyl" refers to a $C_{1-4}$ alkyl group having one or more halogen substituents (up to perhaloalkyl, i.e., every hydrogen atom of the alkyl group has been replaced by a halogen atom); the term "$C_{1-3}$ haloalkyl" refers to a $C_{1-3}$ alkyl group having one or more halogen substituents (up to perhaloalkyl, i.e., every hydrogen atom of the alkyl group has been replaced by a halogen atom); and the term "$C_{1-2}$ haloalkyl" refers to a $C_{1-2}$ alkyl group (i.e. methyl or ethyl) having one or more halogen substituents (up to perhaloalkyl, i.e., every hydrogen atom of the alkyl group has been replaced by a halogen atom). For yet another example, the term "$C_1$ haloalkyl" refers to a methyl group having one, two, or three halogen substituents. Examples of haloalkyl groups include $CF_3$, $C_2F_5$, $CHF_2$, $CH_2F$, $CH_2CF_3$, $CH_2Cl$ and the like.

As used herein, the term "halocycloalkyl" refers to a cycloalkyl group having one or more halogen substituents (up to perhalocycloalkyl, i.e., every hydrogen atom of the cycloalkyl group has been replaced by a halogen atom). For example, the term "$C_{3-4}$ halocycloalkyl" refers to a cyclopropyl or cyclobutyl group having one or more halogen substituents. An example of halocycloalkyl is 2-fluorocyclopropan-1-yl.

As used herein, the term "alkoxy" or "alkyloxy" refers to an —O-alkyl group. For example, the term "$C_{1-6}$ alkoxy" or "$C_{1-6}$ alkyloxy" refers to an —O—($C_{1-6}$ alkyl) group; and the term "$C_{1-4}$ alkoxy" or "$C_{1-4}$ alkyloxy" refers to an —O—($C_{1-4}$ alkyl) group; For another example, the term "$C_{1-2}$ alkoxy" or "$C_{1-2}$ alkyloxy" refers to an —O—($C_{1-2}$ alkyl) group. Examples of alkoxy include methoxy, ethoxy, propoxy (e.g., n-propoxy and isopropoxy), tert-butoxy, and the like. The alkoxy or alkyloxy group optionally can be substituted by 1 or more (e.g., 1 to 5) suitable substituents.

As used here, the term "haloalkoxy" refers to an —O-haloalkyl group. For example, the term "$C_{1-6}$ haloalkoxy" refers to an —O—($C_{1-6}$ haloalkyl) group. For another example, the term "$C_{1-4}$ haloalkoxy" refers to an —O—($C_{1-4}$ haloalkyl) group; and the term "$C_{1-2}$ haloalkoxy" refers to an —O—($C_{1-2}$ haloalkyl) group. For yet another example, the term "$C_1$ haloalkoxy" refers to a methoxy group having one, two, or three halogen substituents. An example of haloalkoxy is —OCF$_3$ or —OCHF$_2$.

As used herein, the term "cycloalkoxy" or "cycloalkyloxy" refers to an —O— cycloalkyl group. For example, the term "$C_{3-7}$ cycloalkoxy" or "$C_{3-7}$ cycloalkyloxy" refers to an —O—($C_{3-7}$ cycloalkyl) group. For another example, the term "$C_{3-6}$ cycloalkoxy" or "$C_{3-6}$ cycloalkyloxy" refers to an —O—($C_{3-6}$ cycloalkyl) group. Examples of cycloalkoxy include $C_{3-6}$ cycloalkoxy (e.g., cyclopropoxy, cyclobutoxy, cyclopentoxy, cyclohexanoxy, and the like). The cycloalkoxy or cycloalkyloxy group optionally can be substituted by 1 or more (e.g., 1 to 5) suitable substituents.

As used here, the term "$C_{6-10}$ aryloxy" refers to an —O—($C_{6-10}$ aryl) group. An example of a $C_{6-10}$ aryloxy group is —O-phenyl [i.e., phenoxy]. The $C_{6-10}$ aryloxy y group optionally can be substituted by 1 or more (e.g., 1 to 5) suitable substituents.

As used herein, the term "fluoroalkyl" refers to an alkyl group having one or more fluorine substituents (up to perfluoroalkyl, i.e., every hydrogen atom of the alkyl group has been replaced by fluorine). For example, the term "$C_{1-2}$ fluoroalkyl" refers to a $C_{1-2}$ alkyl group having one or more fluorine substituents (up to perfluoroalkyl, i.e., every hydrogen atom of the $C_{1-2}$ alkyl group has been replaced by fluorine). For another example, the term "$C_1$ fluoroalkyl" refers to a $C_1$ alkyl group (i.e., methyl) having 1, 2, or 3 fluorine substituents). Examples of fluoroalkyl groups include $CF_3$, $C_2F_5$, $CH_2CF_3$, $CHF_2$, $CH_2F$, and the like.

As used here, the term "fluoroalkoxy" refers to an —O-fluoroalkyl group. For example, the term "$C_{1-2}$ fluoroalkoxy" refers to an —O—$C_{1-2}$ fluoroalkyl group. For another example, the term "$C_1$ fluoroalkoxy" refers to a methoxy group having one, two, or three fluorine substituents. An example of $C_1$ fluoroalkoxy is —OCF$_3$ or —OCHF$_2$.

As used herein, the term "hydroxylalkyl" or "hydroxyalkyl" refers to an alkyl group having one or more (e.g., 1, 2, or 3) OH substituents. The term "$C_{1-6}$ hydroxylalkyl" or "$C_{1-6}$ hydroxyalkyl" refers to a $C_{1-6}$ alkyl group having one or more (e.g., 1, 2, or 3) OH substituents. The term "$C_{1-4}$ hydroxylalkyl" or "$C_{1-4}$ hydroxyalkyl" refers to a $C_{1-4}$ alkyl group having one or more (e.g., 1, 2, or 3) OH substituents; the term "$C_{1-3}$ hydroxylalkyl" or "$C_{1-3}$ hydroxyalkyl" refers to a $C_{1-3}$ alkyl group having one or more (e.g., 1, 2, or 3) OH substituents; and the term "$C_{1-2}$ hydroxylalkyl" or "$C_{1-2}$ hydroxyalkyl" refers to a $C_{1-2}$ alkyl group having one or more (e.g., 1, 2, or 3) OH substituents. An example of hydroxylalkyl is —CH$_2$OH or —CH$_2$CH$_2$OH.

As used herein, the term "oxo" refers to =O. When an oxo is substituted on a carbon atom, they together form a carbonyl moiety [—C(=O)—]. When an oxo is substituted on a sulfur atom, they together form a sulfinyl moiety [—S(=O)—]; when two oxo groups are substituted on a sulfur atom, they together form a sulfonyl moiety [—S(=O)$_2$—].

As used herein, the term "thiono" refers to =S. When an thiono is substituted on a carbon atom, they together form moiety of [—C(=S)—].

As used herein, the term "optionally substituted" means that substitution is optional and therefore includes both unsubstituted and substituted atoms and moieties. A "substituted" atom or moiety indicates that any hydrogen on the designated atom or moiety can be replaced with a selection from the indicated substituent group (up to that every hydrogen atom on the designated atom or moiety is replaced with a selection from the indicated substituent group), provided that the normal valency of the designated atom or moiety is not exceeded, and that the substitution results in a stable compound. For example, if a methyl group (i.e., CH$_3$) is optionally substituted, then up to 3 hydrogen atoms on the carbon atom can be replaced with substituent groups.

As used herein, the term "optionally substituted C$_{1-4}$ alkyl" refers to C$_{1-4}$ alkyl optionally substituted by one or more (e.g. 1 to 5) substituents each independently selected from the group consisting of —OH, halogen, —CN, —NH$_2$, —NH(C$_{1-4}$ alkyl), —N(C$_{1-4}$ alkyl)$_2$, C$_{1-4}$ alkoxy, and C$_{1-4}$ haloalkoxy.

As used herein, the term "optionally substituted C$_{1-2}$ alkyl" refers to C$_{1-2}$ alkyl optionally substituted by one or more (e.g. 1 to 5) substituents each independently selected from the group consisting of —OH, halogen, —CN, —NH$_2$, —NH(C$_{1-4}$ alkyl), —N(C$_{1-4}$ alkyl)$_2$, C$_{1-4}$ alkoxy, and C$_{1-4}$ haloalkoxy.

As used herein, the term "optionally substituted C$_{3-4}$ cycloalkyl" refers to C$_{3-4}$ cycloalkyl optionally substituted by one or more (e.g. 1 to 5) substituents each independently selected from the group consisting of —OH, halogen, —CN, —NH$_2$, —NH(C$_{1-4}$ alkyl), —N(C$_{1-4}$ alkyl)$_2$, C$_{1-4}$ alkyl, C$_{1-4}$ haloalkyl, C$_{1-4}$ hydroxylalkyl, C$_{1-4}$ alkoxy, and C$_{1-4}$ haloalkoxy.

As used herein, the term "optionally substituted cyclopropylmethyl" refers to cyclopropylmethyl optionally substituted by one or more (e.g. 1 to 5) substituents each independently selected from the group consisting of —OH, halogen, —CN, —NH$_2$, —NH(C$_{1-4}$ alkyl), —N(C$_{1-4}$ alkyl)$_2$, C$_{1-4}$ alkyl, C$_{1-4}$ haloalkyl, C$_{1-4}$ hydroxylalkyl, C$_{1-4}$ alkoxy, and C$_{1-4}$ haloalkoxy.

As used herein, the term "optionally substituted C$_{1-4}$ alkoxy" refers to C$_{1-4}$ alkoxy optionally substituted by one or more (e.g. 1 to 5) substituents each independently selected from the group consisting of —OH, halogen, —CN, —NH$_2$, —NH(C$_{1-4}$ alkyl), —N(C$_{1-4}$ alkyl)$_2$, C$_{1-4}$ alkoxy, and C$_{1-4}$ haloalkoxy.

As used herein, unless specified, the point of attachment of a substituent can be from any suitable position of the substituent. For example, piperidinyl can be piperidin-1-yl (attached through the N atom of the piperidinyl), piperidin-2-yl (attached through the C atom at the 2-position of the piperidinyl), piperidin-3-yl (attached through the C atom at the 3-position of the piperidinyl), or piperidin-4-yl (attached through the C atom at the 4-position of the piperidinyl). For another example, pyridinyl (or pyridyl) can be 2-pyridinyl (or pyridin-2-yl), 3-pyridinyl (or pyridin-3-yl), or 4-pyridinyl (or pyridin-4-yl).

When a bond to a substituent is shown to cross a bond connecting two atoms in a ring, then such substituent may be bonded to any of the ring-forming atoms in that ring that are substitutable (i.e., bonded to one or more hydrogen atoms), unless otherwise specified or otherwise implicit from the context. For example, as shown in Formula a-101 below, R$^{10}$ may be bonded to either of the two ring carbon atoms each of which bears a hydrogen atom (but not shown). For another example, as shown in Formula a-102 below, R$^{10}$ may be bonded to either of the two ring carbon atoms on the pyrazine ring each of which bears a hydrogen atom (but not shown); and R$^{10a}$ may be bonded to either of the two ring carbon atoms on the imidazole ring each of which bears a hydrogen atom (but not shown).

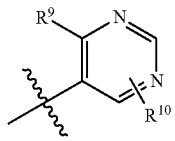

a-101

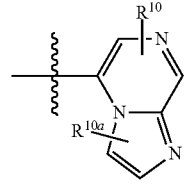

a-102

When a substituted or optionally substituted moiety is described without indicating the atom via which such moiety is bonded to a substituent, then the substituent may be bonded via any appropriate atom in such moiety. For example in a substituted arylalkyl, a substituent on the arylalkyl [e.g., (C$_{6-10}$ aryl)-C$_{1-4}$ alkyl-] can be bonded to any carbon atom on the alkyl part or on the aryl part of the arylalkyl. Combinations of substituents and/or variables are permissible only if such combinations result in stable compounds.

As noted above, the compounds of Formula I may exist in the form of pharmaceutically acceptable salts such as acid addition salts and/or base addition salts of the compounds of Formula I. The phrase "pharmaceutically acceptable salt(s)", as used herein, unless otherwise indicated, includes acid addition or base salts which may be present in the compounds of Formula I.

Pharmaceutically acceptable salts of the compounds of Formula I include the acid addition and base salts thereof.

Suitable acid addition salts are formed from acids which form non-toxic salts. Examples include the acetate, adipate, aspartate, benzoate, besylate, bicarbonate/carbonate, bisulfate/sulfate, borate, camphorsulfonate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulfate and hemicalcium salts.

For a review on suitable salts, see "Handbook of Pharmaceutical Salts: Properties, Selection, and Use" by Stahl and Wermuth (Wiley-VCH, 2002). Methods for making pharmaceutically acceptable salts of compounds of Formula I are known to one of skill in the art.

As used herein the terms "Formula I", "Formula I or pharmaceutically acceptable salts thereof", "pharmaceutically acceptable salts of the compound or the salt [of Formula I]" are defined to include all forms of the compound of Formula I, including hydrates, solvates, isomers (including for example rotational stereoisomers), crystalline and non-crystalline forms, isomorphs, polymorphs, metabolites, and prodrugs thereof.

As it is known to the person skilled in the art, amine compounds (i.e., those comprising one or more nitrogen atoms), for example tertiary amines, can form N-oxides (also known as amine oxides or amine N-oxides). An N-oxide has the formula of $(R^{100}R^{200}R^{300})N^+$—$O^-$ wherein the parent amine $(R^{100}R^{200}R^{300})N$ can be for example, a tertiary amine (for example, each of $R^{100}$, $R^{200}$, $R^{300}$ is independently alkyl, arylalkyl, aryl, heteroaryl, or the like), a heterocyclic or heteroaromatic amine [for example, $(R^{100}R^{200}R^{300})N$ together forms 1-alkylpiperidine, 1-alkylpyrrolidine, 1-benzylpyrrolidine, or pyridine]. For instance, an imine nitrogen, especially heterocyclic or heteroaromatic imine nitrogen, or pyridine-type nitrogen

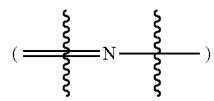 [SMILES: *N=*]

atom [such as a nitrogen atom in pyridine, pyridazine, or pyrazine], can be N-oxidized to form the N-oxide comprising the group

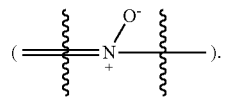

Thus, a compound according to the present invention comprising one or more nitrogen atoms (e.g., an imine nitrogen atom) may be capable of forming an N-oxide thereof (e.g., mono-N-oxides, bis-N-oxides or multi-N-oxides, or mixtures thereof depending on the number of nitrogen atoms suitable to form stable N-oxides).

As used herein, the term "N-oxide(s)" refer to all possible, and in particular all stable, N-oxide forms of the amine compounds (e.g., compounds comprising one or more imine nitrogen atoms) described herein, such as mono-N-oxides (including different isomers when more than one nitrogen atom of an amine compound can form a mono-N-oxide) or multi-N-oxides (e.g., bis-N-oxides), or mixtures thereof in any ratio.

Compounds of Formula I and their salts described herein further include N-oxides thereof.

Compounds of Formula I (including salts thereof) may exist in a continuum of solid states ranging from fully amorphous to fully crystalline. The term 'amorphous' refers to a state in which the material lacks long-range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from apparent solid to a material with liquid properties occurs, which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ('melting point').

Compounds of Formula I (including salts thereof) may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of Formula I (including salts thereof) may exist as clathrates or other complexes (e.g., co-crystals). Included within the scope of the invention are complexes such as clathrates, drug-host inclusion complexes wherein the drug and host are present in stoichiometric or non-stoichiometric amounts. Also included are complexes of the compounds of Formula I containing two or more organic and/or inorganic components, which may be in stoichiometric or non-stoichiometric amounts. The resulting complexes may be ionized, partially ionized, or non-ionized. Co-crystals are typically defined as crystalline complexes of neutral molecular constituents that are bound together through non-covalent interactions, but could also be a complex of a neutral molecule with a salt. Co-crystals may be prepared by melt crystallization, by recrystallization from solvents, or by physically grinding the components together; see O. Almarsson and M. J. Zaworotko, *Chem. Commun.* 2004, 17, 1889-1896. For a general review of multi-component complexes, see J. K. Haleblian, *J. Pharm. Sci.* 1975, 64, 1269-1288.

The compounds of the invention (including salts thereof) may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —$COO^-Na^+$, —$COO^-K^+$, or —$SO_3^-$—$Na^+$) or non-ionic (such as —$N^-N^+(CH_3)_3$) polar head group. For more information, see *Crystals and the Polarizing Microscope* by N. H. Hartshorne and A. Stuart, 4$^{th}$ Edition (Edward Arnold, 1970).

The invention also relates to prodrugs of the compounds of Formula I. Thus certain derivatives of compounds of Formula I which may have little or no pharmacological activity themselves can, when administered into or onto the body, be converted into compounds of Formula I having the desired activity, for example, by hydrolytic cleavage. Such derivatives are referred to as "prodrugs". Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (Ed. E. B. Roche, American Pharmaceutical Association).

Prodrugs in accordance with the invention can, for example, be produced by replacing appropriate functionalities present in the compounds of Formula I with certain moieties known to those skilled in the art as 'pro-moieties' as described, for example, in Design of Prodrugs by H. Bundgaard (Elsevier, 1985), or in Prodrugs: Challenges and Reward, 2007 edition, edited by Valentino Stella, Ronald Borchardt, Michael Hageman, Reza Oliyai, Hans Maag, Jefferson Tilley, pages 134-175 (Springer, 2007).

Moreover, certain compounds of Formula I may themselves act as prodrugs of other compounds of Formula I.

Also included within the scope of the invention are metabolites of compounds of Formula I, that is, compounds formed in vivo upon administration of the drug.

The compounds of Formula I (including salts thereof) include all stereoisomers and tautomers. Stereoisomers of Formula I include cis and trans isomers, optical isomers such as R and S enantiomers, diastereomers, geometric isomers, rotational isomers, atropisomers, and conformational isomers of the compounds of Formula I, including compounds exhibiting more than one type of isomerism; and mixtures thereof (such as racemates and diastereomeric pairs). Also included are acid addition or base addition salts wherein the counterion is optically active, for example, D-lactate or L-lysine, or racemic, for example, DL-tartrate or DL-arginine.

In some embodiments, the compounds of Formula I (including salts thereof) may have asymmetric carbon atoms. The carbon-carbon bonds of the compounds of Formula I may be depicted herein using a solid line (—), a solid wedge (▬), or a dotted wedge (⋯⫿⫿⫿). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of Formula I may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of Formula I can exist as enantiomers and diastereomers or as racemates and mixtures thereof. The use of a solid line to depict bonds to one or more asymmetric carbon atoms in a compound of Formula I and the use of a solid or dotted wedge to depict bonds to other asymmetric carbon atoms in the same compound is meant to indicate that a mixture of diastereomers is present.

In some embodiments, the compounds of Formula I (including salts thereof) may exist in and/or be isolated as atropisomers (e.g., one or more atropenantiomers). Those skilled in the art would recognize that atropisomerism may exist in a compound that has two or more aromatic rings (for example, two aromatic rings linked through a single bond). See e.g., Freedman, T. B. et al., Absolute Configuration Determination of Chiral Molecules in the Solution State Using Vibrational Circular Dichroism. *Chirality* 2003, 15, 743-758; and Bringmann, G. et al., Atroposelective Synthesis of Axially Chiral Biaryl Compounds. *Angew. Chem., Int. Ed.* 2005, 44, 5384-5427.

When any racemate crystallizes, crystals of different types are possible. One type is the racemic compound (true racemate) wherein one homogeneous form of crystal is produced containing both enantiomers in equimolar amounts. Another type is a racemic mixture or conglomerate wherein two forms of crystal are produced in equal or different molar amounts each comprising a single enantiomer.

The compounds of Formula I (including salts thereof) may exhibit the phenomena of tautomerism and structural isomerism. For example, the compounds of Formula I may exist in several tautomeric forms, including the enol and imine form, the amide and imidic acid form, and the keto and enamine form and geometric isomers and mixtures thereof. All such tautomeric forms are included within the scope of the compounds of Formula I. Tautomers may exist as mixtures of a tautomeric set in solution. In solid form, usually one tautomer predominates. Even though one tautomer may be described, the present invention includes all tautomers of the compounds of Formula I. For example, when one of the following two tautomers of the invention is disclosed in the experimental section herein, those skilled in the art would readily recognize that the invention also includes the other.

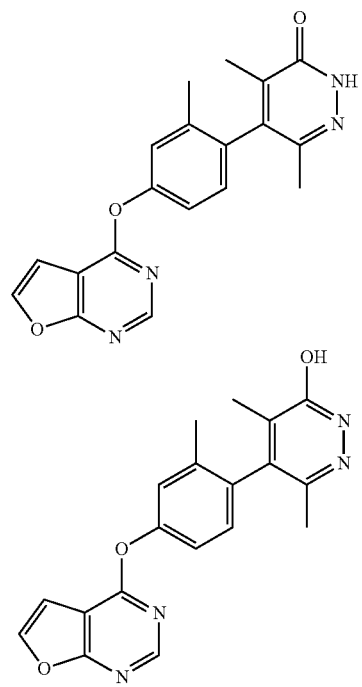

For another example, when one of the following three tautomers of the invention is disclosed in the experimental section herein, those skilled in the art would readily recognize that the invention also includes other tautomers such as the other two shown below.

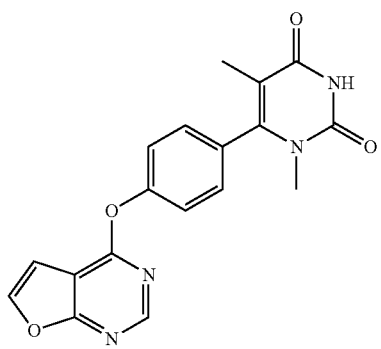

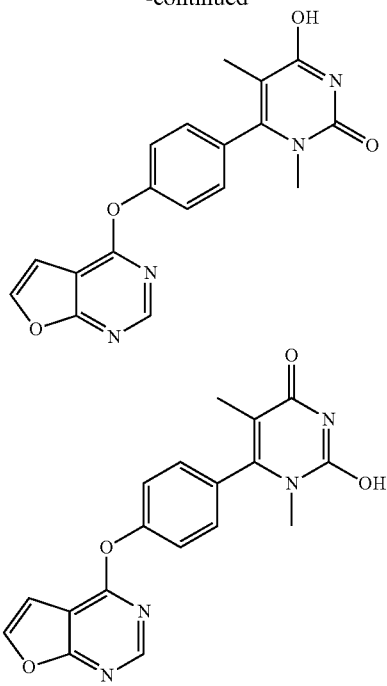

The present invention includes all pharmaceutically acceptable isotopically-labelled compounds of Formula I (including salts thereof) wherein one or more atoms are replaced by atoms having the same atomic number, but an atomic mass or mass number different from the atomic mass or mass number which predominates in nature.

Examples of isotopes suitable for inclusion in the compounds of the invention (including salts thereof) include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of Formula I, for example, those incorporating a radioactive isotope, are useful in drug and/or substrate tissue distribution studies. The radioactive isotopes tritium, i.e., $^3H$, and carbon-14, i.e., $^{14}C$, are particularly useful for this purpose in view of their ease of incorporation and ready means of detection.

Substitution with heavier isotopes such as deuterium, i.e., $^2H$, may afford certain therapeutic advantages resulting from greater metabolic stability, for example, increased in vivo half-life or reduced dosage requirements, and hence may be preferred in some circumstances.

Substitution with positron-emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of Formula I (including salts thereof) can generally be prepared by conventional techniques known to those skilled in the art or by processes analogous to those described in the accompanying Examples and Preparations using an appropriate isotopically-labeled reagent in place of the non-labeled reagent previously employed.

The present invention also provides compositions (e.g., pharmaceutical compositions) comprising a novel compound of Formula I (including a pharmaceutically acceptable salt thereof) in the second aspect of the invention.

Accordingly, in one embodiment, the invention provides a pharmaceutical composition comprising (a therapeutically effective amount of) a novel compound of Formula I (or a pharmaceutically acceptable salt thereof) and optionally comprising a pharmaceutically acceptable carrier. In one further embodiment, the invention provides a pharmaceutical composition comprising (a therapeutically effective amount of) a compound of Formula I (or a pharmaceutically acceptable salt thereof), optionally comprising a pharmaceutically acceptable carrier and, optionally, at least one additional medicinal or pharmaceutical agent (such as an antipsychotic agent or anti-schizophrenia agent described below). In one embodiment, the additional medicinal or pharmaceutical agent is an anti-schizophrenia agent as described below.

The pharmaceutically acceptable carrier may comprise any conventional pharmaceutical carrier or excipient. Suitable pharmaceutical carriers include inert diluents or fillers, water and various organic solvents (such as hydrates and solvates). The pharmaceutical compositions may, if desired, contain additional ingredients such as flavorings, binders, excipients and the like. Thus for oral administration, tablets containing various excipients, such as citric acid, may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Non-limiting examples of materials, therefore, include lactose or milk sugar and high molecular weight polyethylene glycols. When aqueous suspensions or elixirs are desired for oral administration, the active compound therein may be combined with various sweetening or flavoring agents, coloring matters or dyes and, if desired, emulsifying agents or suspending agents, together with diluents such as water, ethanol, propylene glycol, glycerin, or combinations thereof.

The pharmaceutical composition may, for example, be in a form suitable for oral administration as a tablet, capsule, pill, powder, sustained release formulation, solution or suspension, for parenteral injection as a sterile solution, suspension or emulsion, for topical administration as an ointment or cream or for rectal administration as a suppository.

Exemplary parenteral administration forms include solutions or suspensions of active compounds in sterile aqueous solutions, for example, aqueous propylene glycol or dextrose solutions. Such dosage forms may be suitably buffered, if desired.

The pharmaceutical composition may be in unit dosage forms suitable for single administration of precise dosages. One of ordinary skill in the art would appreciate that the composition may be formulated in sub-therapeutic dosage such that multiple doses are envisioned.

In one embodiment the composition comprises a therapeutically effective amount of a compound of Formula I (or a pharmaceutically acceptable salt thereof) and a pharmaceutically acceptable carrier.

Compounds of Formula I (including pharmaceutically acceptable salts thereof) are D1R modulators. In some embodiments, a compound of Formula I is a D1R agonist [i.e., binding (having affinity for) and activating D1R receptors]. In some embodiments, using dopamine as a reference full D1R agonist, a compound of Formula I is a super agonist (i.e., a compound that is capable of producing a greater maximal response than the endogenous D1R agonist, dopamine, for a D1R receptor, and thus exhibiting an efficacy of more than about 100%, for example 120%). In some embodiments, using dopamine as a reference full agonist, a compound of Formula I is a full D1R agonist (i.e., having an efficacy of about 100%, for example, 90%-100%, compared to that of dopamine). In some embodiments, using dopamine as a reference full D1R agonist, a compound of Formula I is a partial agonist [i.e., a compound having only partial efficacy (i.e., less than 100%, for example 10%-80% or 50%-70%) at a D1 receptor relative to the full agonist, dopamine, although it binds and activates a D1 receptor]. A D1R agonist (including superagonist, full agonist, and partial agonist) can agonize or partially agonize an activity of D1R. In some embodiments, the $EC_{50}$ of a compound of Formula I with respect to D1R is less than about 10 µM, 5 µM, 2 µM, 1 µM, 500 nM, 200 nM, 100 nM, 50, 40, 30, 20, 10, 5, 2, or 1 nM.

As used herein, when referencing to a compound, the term "D1R modulator" or "D1R agonist" (including a super D1R agonist, a full D1R agonist, or a partial D1R agonist) refers to a compound that is a D1-like receptor modulator or a D1-like receptor agonist respectively (i.e., not necessarily selective between/among subtypes of D1-like receptors). See Lewis, JPET 286:345-353, 1998. D1Rs include, for example, D1 and D5 in humans and D1A and D1B in rodents.

Administration of the compounds of Formula I may be effected by any method that enables delivery of the compounds to the site of action. These methods include, for example, enteral routes (e.g., oral routes, buccal routes, sublabial routes, sublingual routes), oral routes, intranasal routes, inhaled routes, intraduodenal routes, parenteral injection (including intravenous, subcutaneous, intramuscular, intravascular or infusion),intrathecal routes, epidural routes, intracerebral routes, intracerbroventricular routes, topical, and rectal administration.

In one embodiment of the present invention, the compounds of Formula I may be administered/effected by oral routes.

Dosage regimens may be adjusted to provide the optimum desired response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. The specifications for the dosage unit forms of the invention are dictated by a variety of factors such as the unique characteristics of the therapeutic agent and the particular therapeutic or prophylactic effect to be achieved. In one embodiment of the present invention, the compounds of Formula I may be used to treat humans.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens for administration of the chemotherapeutic agent is well-known in the relevant art and would be understood to be encompassed by the skilled artisan once provided the teachings disclosed herein.

The amount of the compound of Formula I or a pharmaceutically acceptable salt thereof administered will be dependent on the subject being treated, the severity of the disorder or condition, the rate of administration, the disposition of the compound and the discretion of the prescribing physician. Generally, an effective dosage is in the range of about 0.0001 to about 50 mg per kg body weight per day, for example about 0.01 to about 10 mg/kg/day, in single or divided doses. For a 70 kg human, this would amount to about 0.007 mg to about 3500 mg/day, for example about 0.7 mg to about 700 mg/day. In some instances, dosage levels below the lower limit of the aforesaid range may be more than adequate, while in other cases still larger doses may be employed without causing any harmful side effect, provided that such larger doses are first divided into several small doses for administration throughout the day.

As used herein, the term "combination therapy" refers to the administration of a compound of Formula I or a pharmaceutically acceptable salt thereof together with an at least one additional pharmaceutical or medicinal agent (e.g., an anti-schizophrenia agent), either sequentially or simultaneously.

The present invention includes the use of a combination of a compound of Formula I (or a pharmaceutically acceptable salt thereof) and one or more additional pharmaceutically active agent(s). If a combination of active agents is administered, then they may be administered sequentially or simultaneously, in separate dosage forms or combined in a single dosage form. Accordingly, the present invention also includes pharmaceutical compositions comprising an amount of: (a) a first agent comprising a compound of Formula I (including an N-oxide thereof or a pharmaceutically acceptable salt of the compound or the N-oxide); (b) a second pharmaceutically active agent; and (c) a pharmaceutically acceptable carrier, vehicle or diluent.

Various pharmaceutically active agents may be selected for use in conjunction with the compounds of Formula I (including or pharmaceutically acceptable salts thereof), depending on the disease, disorder, or condition to be treated.

Pharmaceutically active agents that may be used in combination with the compositions of the present invention include, without limitation:

(i) acetylcholinesterase inhibitors such as donepezil hydrochloride (ARICEPT, MEMAC); or Adenosine $A_{2A}$ receptor antagonists such as Preladenant (SCH 420814) or SCH 412348;

(ii) amyloid-β (or fragments thereof), such as $Aβ_{1-15}$ conjugated to pan HLA DR-binding epitope (PADRE) and ACC-001 (Elan/Wyeth);

(iii) antibodies to amyloid-β (or fragments thereof), such as bapineuzumab (also known as AAB-001) and AAB-002 (Wyeth/Elan);

(iv) amyloid-lowering or -inhibiting agents (including those that reduce amyloid production, accumulation and fibrillization) such as colostrinin and bisnorcymserine (also known as BNC);

(v) alpha-adrenergic receptor agonists such as clonidine (CATAPRES);

(vi) beta-adrenergic receptor blocking agents (beta blockers) such as carteolol;

(vii) anticholinergics such as amitriptyline (ELAVIL, ENDEP);

(viii) anticonvulsants such as carbamazepine (TEGRETOL, CARBATROL);

(ix) antipsychotics, such as lurasidone (also known as SM-13496; Dainippon Sumitomo);

(x) calcium channel blockers such as nilvadipine (ESCOR, NIVADIL);

(xi) catechol O-methyltransferase (COMT) inhibitors such as tolcapone (TASMAR);

(xii) central nervous system stimulants such as caffeine;

(xiii) corticosteroids such as prednisone (STERAPRED, DELTASONE);

(xiv) dopamine receptor agonists such as apomorphine (APOKYN);

(xv) dopamine receptor antagonists such as tetrabenazine (NITOMAN, XENAZINE, dopamine D2 antagonist such as Quetiapine);

(xvi) dopamine reuptake inhibitors such as nomifensine maleate (MERITAL);

(xvii) gamma-aminobutyric acid (GABA) receptor agonists such as baclofen (LIORESAL, KEMSTRO);

(xviii) histamine 3 ($H_3$) antagonists such as ciproxifan;

(xix) immunomodulators such as glatiramer acetate (also known as copolymer-1; COPAXONE);

(xx) immunosuppressants such as methotrexate (TREXALL, RHEUMATREX);

(xxi) interferons, including interferon beta-1a (AVONEX, REBIF) and interferon beta-1b (BETASERON, BETAFERON);

(xxii) levodopa (or its methyl or ethyl ester), alone or in combination with a DOPA decarboxylase inhibitor (e.g., carbidopa (SINEMET, CARBILEV, PARCOPA));

(xxiii) N-methyl-D-aspartate (NMDA) receptor antagonists such as memantine (NAMENDA, AXURA, EBIXA);

(xxiv) monoamine oxidase (MAO) inhibitors such as selegiline (EMSAM);

(xxv) muscarinic receptor (particularly M1 subtype) agonists such as bethanechol chloride (DUVOID, URECHOLINE);

(xxvi) neuroprotective drugs such as 2,3,4,9-tetrahydro-1H-carbazol-3-one oxime;

(xxvii) nicotinic receptor agonists such as epibatidine;

(xxviii) norepinephrine (noradrenaline) reuptake inhibitors such as atomoxetine (STRATTERA);

(xxix) phosphodiesterase (PDE) inhibitors, for example, PDE9 inhibitors such as BAY 73-6691 (Bayer AG) and PDE 10 (e.g. PDE10A) inhibitors such as papaverine;

(xxx) other PDE inhibitors including (a) PDE1 inhibitors (e.g., vinpocetine), (b) PDE2 inhibitors (e.g., erythro-9-(2-hydroxy-3-nonyl)adenine (EHNA)), (c) PDE4 inhibitors (e.g., rolipram), and (d) PDE5 inhibitors (e.g., sildenafil (VIAGRA, REVATIO));

(xxxi) quinolines such as quinine (including its hydrochloride, dihydrochloride, sulfate, bisulfate and gluconate salts);

(xxxii) β-secretase inhibitors such as WY-25105;

(xxxiii) γ-secretase inhibitors such as LY-411575 (Lilly);

(xxxiv) serotonin (5-hydroxytryptamine) 1A ($5-HT_{1A}$) receptor antagonists such as spiperone;

(xxxv) serotonin (5-hydroxytryptamine) 4 ($5-HT_4$) receptor agonists such as PRX-03140 (Epix);

(xxxvi) serotonin (5-hydroxytryptamine) 6 ($5-HT_6$) receptor antagonists such as mianserin (TORVOL, BOLVIDON, NORVAL);

(xxxvii) serotonin (5-HT) reuptake inhibitors such as alaproclate, citalopram (CELEXA, CIPRAMIL);

(xxxviii) trophic factors, such as nerve growth factor (NGF), basic fibroblast growth factor (bFGF; ERSOFERMIN), neurotrophin-3 (NT-3), cardiotrophin-1, brain-derived neurotrophic factor (BDNF), neublastin, meteorin, and glial-derived neurotrophic factor (GDNF), and agents that stimulate production of trophic factors, such as propentofylline;

and the like.

The compound of Formula I (including a pharmaceutically acceptable salt thereof) is optionally used in combination with another active agent. Such an active agent may be, for example, an atypical antipsychotic or an anti-Parkinson's disease agent or an anti-Alzheimer's agent. Accordingly, another embodiment of the invention provides methods of treating a D1-mediated disorder (e.g., a neurological and psychiatric disorder associated with D1), comprising administering to a mammal an effective amount of a compound of Formula I (including an N-oxide thereof or a pharmaceutically acceptable salt of the compound or the N-oxide) and further comprising administering another active agent.

As used herein, the term "another active agent" refers to any therapeutic agent, other than the compound of Formula I (including or a pharmaceutically acceptable salt thereof) that is useful for the treatment of a subject disorder. Examples of additional therapeutic agents include antidepressants, antipsychotics (such as anti-schizophrenia), anti-pain, anti-Parkinson's disease agents, anti-LID (levodopa-induced dyskinesia), anti-Alzheimer's and anti-anxiety agents. Examples of particular classes of antidepressants that can be used in combination with the compounds of the invention include norepinephrine reuptake inhibitors, selective serotonin reuptake inhibitors (SSRIs), NK-1 receptor antagonists, monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, and atypical antidepressants. Suitable norepinephrine reuptake inhibitors include tertiary amine tricyclics and secondary amine tricyclics. Examples of suitable tertiary amine tricyclics and secondary amine tricyclics include amitriptyline, clomipramine, doxepin, imipramine, trimipramine, dothiepin, butriptyline, iprindole, lofepramine, nortriptyline, protriptyline, amoxapine, desipramine and maprotiline. Examples of suitable selective serotonin reuptake inhibitors include fluoxetine, fluvoxamine, paroxetine, and sertraline. Examples of monoamine oxidase inhibitors include isocarboxazid, phenelzine, and tranylcypramine. Examples of suitable reversible inhibitors of monoamine oxidase include moclobemide. Examples of suitable serotonin and noradrenaline reuptake inhibitors of use in the present invention include venlafaxine. Examples of suitable atypical anti-depressants include bupropion, lithium, nefazodone, trazodone and viloxazine. Examples of anti-Alzheimer's agents include Dimebon, NMDA receptor antagonists such as memantine; and cholinesterase inhibitors such as donepezil and galantamine. Examples of suitable classes of anti-anxiety agents that can be used in combination with the compounds of the invention include benzodiazepines and serotonin 1A (5-HT1A) agonists or antagonists, especially 5-HT1A partial agonists, and corticotropin releasing factor (CRF) antagonists. Suitable benzodiazepines include alprazolam, chlordiazepoxide, clonazepam, chlorazepate, diazepam, halazepam, lorazepam, oxazepam, and prazepam. Suitable 5-HT1A receptor agonists or antagonists include buspirone, flesinoxan, gepirone, and ipsapirone. Suitable atypical antipsychotics include paliperidone, bifeprunox, ziprasidone, risperidone, aripiprazole, olanzapine, and quetiapine. Suitable nicotine acetylcholine agonists include ispronicline, varenicline and MEM 3454. Anti-pain agents include pregabalin, gabapentin, clonidine, neostigmine, baclofen, midazolam, ketamine and ziconotide. Examples of suitable anti-Parkinson's disease agents include L-DOPA (or its methyl or ethyl ester), a DOPA decarboxylase inhibitor (e.g., carbidopa (SINEMET, CARBILEV, PARCOPA), an Adenosine $A_{2A}$ receptor antagonist [e.g., Preladenant (SCH 420814) or SCH 412348], benserazide (MADOPAR), α-methyldopa, monofluoromethyldopa, difluoromethyldopa, brocresine, or m-hydroxybenzylhydrazine), a dopamine agonist [such as apomorphine (APOKYN), bromocriptine (PARLODEL), cabergoline (DOSTINEX), dihydrexidine, dihydroergocryptine, fenoldopam (CORLOPAM), lisuride (DOPERGIN), pergolide (PERMAX), piribedil (TRIVASTAL, TRASTAL), pramipexole (MIRAPEX), quinpirole, ropinirole (REQUIP), rotigotine (NEUPRO), SKF-82958 (GlaxoSmithKline), and sarizotan], a monoamine oxidase (MAO) inhibitor [such as selegiline (EMSAM), selegiline hydrochloride (L-deprenyl, ELDEPRYL, ZELAPAR), dimethylselegilene, brofaromine, phenelzine (NARDIL), tranylcypromine (PARNATE), moclobemide (AURORIX, MANERIX), befloxatone, safinamide, isocarboxazid (MARPLAN), nialamide (NIAMID), rasagiline (AZILECT), iproniazide (MARSILID, IPROZID, IPRONID), CHF-3381 (Chiesi Farmaceutici), iproclozide, toloxatone (HUMORYL, PERENUM), bifemelane, desoxypeganine, harmine (also known as telepathine or banasterine), harmaline, linezolid (ZYVOX, ZYVOXID), and pargyline (EUDATIN, SUPIRDYL)], a catechol O-methyltransferase (COMT) inhibitor [such as tolcapone (TASMAR), entacapone (COMTAN), and tropolone], an N-methyl-D-aspartate (NMDA) receptor antagonist [such as amantadine (SYMMETREL)], anticholinergics [such as amitriptyline (ELAVIL, ENDEP), butriptyline, benztropine mesylate (COGENTIN), trihexyphenidyl (ARTANE), diphenhydramine (BENADRYL), orphenadrine (NORFLEX), hyoscyamine, atropine (ATROPEN), scopolamine (TRANSDERM-SCOP), scopolamine methylbromide (PARMINE), dicycloverine (BENTYL, BYCLOMINE, DIBENT, DILOMINE, tolterodine (DETROL), oxybutynin (DITROPAN, LYRINEL XL, OXYTROL), penthienate bromide, propantheline (PRO-BANTHINE), cyclizine, imipramine hydrochloride (TOFRANIL), imipramine maleate (SURMONTIL), lofepramine, desipramine (NORPRAMIN), doxepin (SINEQUAN, ZONALON), trimipramine (SURMONTIL), and glycopyrrolate (ROBINUL)], or a combination thereof. Examples of anti-schizophrenia agents include ziprasidone, risperidone, olanzapine, quetiapine, aripiprazole, asenapine, blonanserin, or iloperidone. Some additional "another active agent" examples include rivastigmine (Exelon), Clozapine, Levodopa, Rotigotine, Aricept, Methylphenidate, memantine. milnacipran, guanfacine, bupropion, and atomoxetine.

As noted above, the compounds of Formula I (including pharmaceutically acceptable salts thereof) may be used in combination with one or more additional anti-schizophrenia agents which are described herein. When a combination therapy is used, the one or more additional anti-schizophrenia agents may be administered sequentially or simultaneously with the compound of the invention. In one embodiment, the additional anti-schizophrenia agent is administered to a mammal (e.g., a human) prior to administration of the compound of the invention. In another embodiment, the additional anti-schizophrenia agent is administered to the mammal after administration of the compound of the invention. In another embodiment, the additional anti-schizophrenia agent is administered to the mammal (e.g., a human) simultaneously with the administration of the compound of the invention (or an N-oxide thereof or a pharmaceutically acceptable salt of the foregoing).

The invention also provides a pharmaceutical composition for the treatment of schizophrenia in a mammal, including a human, which comprises an amount of a compound of Formula I (or a pharmaceutically acceptable salt thereof), as defined above (including hydrates, solvates and polymorphs of said compound or pharmaceutically acceptable salts thereof), in combination with one or more (for example one to three) anti-schizophrenia agents such as ziprasidone, risperidone, olanzapine, quetiapine, aripiprazole, asenapine, blonanserin, or iloperidone, wherein the amounts of the active agent and the combination when taken as a whole are therapeutically effective for treating schizophrenia.

The invention also provides a pharmaceutical composition for the treatment of Parkinson's disease in a mammal (including cognition impairment associated with PD), including a human, which comprises an amount of a compound of Formula I (or a pharmaceutically acceptable salt thereof), as defined above (including hydrates, solvates and polymorphs of said compound or pharmaceutically acceptable salts thereof), in combination with one or more (for example one to three) anti-Parkinson's disease agents such as L-DOPA, wherein the amounts of the active agent and the combination when taken as a whole are therapeutically effective for treating Parkinson's disease.

It will be understood that the compounds of Formula I depicted above are not limited to a particular stereoisomer (e.g. enantiomer or atropisomer) shown, but also include all stereoisomers and mixtures thereof.

DETAILED DESCRIPTION OF THE INVENTION

Compounds of the invention, including N-oxides and salts of the compounds or N-oxides, can be prepared using known organic synthesis techniques and can be synthesized according to any of numerous possible synthetic routes.

The reactions for preparing compounds of the invention can be carried out in suitable solvents, which can be readily selected by one of skill in the art of organic synthesis. Suitable solvents can be substantially non-reactive with the starting materials (reactants), the intermediates, or products at the temperatures at which the reactions are carried out, e.g., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3$^{rd}$ Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high-performance liquid chromatography (HPLC) or thin layer chromatography (TLC).

Compounds of Formula I and intermediates thereof may be prepared according to the following reaction schemes and accompanying discussion. Unless otherwise indicated, $R^1$, $R^2$, $R^3$, $R^4$, $R^5$, $R^6$, $R^7$, $R^8$, $R^9$, $R^{10}$, $R^{11}$, $L^1$, $X^1$, $X^2$, $X^3$, $X^4$, $Q^1$, and structural Formula I in the reaction schemes and discussion that follow are as defined above. In general, the compounds of this invention may be made by processes which include processes analogous to those known in the chemical arts, particularly in light of the description contained herein. Certain processes for the manufacture of the compounds of this invention and intermediates thereof are provided as further features of the invention and are illustrated by the following reaction schemes. Other processes are described in the experimental section. The schemes and examples provided herein (including the corresponding description) are for illustration only, and not intended to limit the scope of the present invention.

Scheme 1

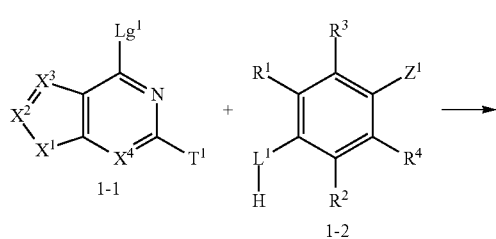

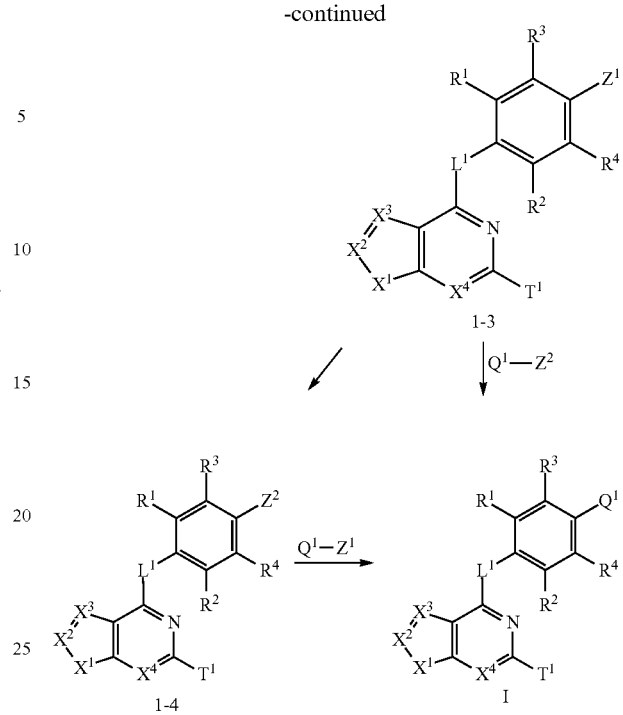

Scheme 1 refers to preparation of compounds of Formula I. Referring to Scheme 1, compounds of Formula 1-1 [where Lg$^1$ is a suitable leaving group such as halo (e.g., F, Cl or Br)] and 1-2 [wherein Z$^1$ can be, e.g., halogen (e.g., Br or I) or trifluoromethanesulfonate (triflate)] are commercially available or can be made by methods described herein or other methods well known to those skilled in the art. A compound of Formula 1-3 can be prepared by coupling a compound of Formula 1-1 with a compound of Formula 1-2 under suitable conditions. The coupling can be accomplished, for example, by heating a mixture of a compound of Formula 1-1 with a compound of Formula 1-2 in the presence of a base, such as Cs$_2$CO$_3$, in an appropriate solvent, such as dimethyl sulfoxide (DMSO). Alternatively, a metal-catalyzed (such as using a palladium or copper catalyst) coupling may be employed to accomplish the aforesaid coupling. In this variant of the coupling, a mixture of a compound of Formula 1-1 and a compound of Formula 1-2 can be heated in the presence of a base (such as Cs$_2$CO$_3$), a metal catalyst [such as a palladium catalyst, e.g., Pd(OAc)$_2$], and a ligand [such as 1,1'-binaphthalene-2,2'-diylbis(diphenylphosphane) (BINAP)] in an appropriate solvent, such as 1,4-dioxane. A compound of Formula 1-3 can subsequently be reacted with a compound of Formula Q$^1$-Z$^2$ [wherein Z$^2$ can be Br; B(OH)$_2$; B(OR)$_2$ wherein each R is independently H or C$_{1-6}$ alkyl, or wherein the two (OR) groups, together with the B atom to which they are attached, form a 5- to 10-membered heterocycloalkyl optionally substituted with one or more C$_{1-6}$ alkyl; a trialkyltin moiety; or the like] by a metal-catalyzed (such as using a palladium catalyst) coupling reaction to obtain a compound of Formula I. Compounds of Formula Q$^1$-Z$^2$ are commercially available or can be made by methods described herein or by methods analogous to those described in the chemical art. Alternatively, a compound of Formula 1-3 can be converted to a compound of Formula 1-4 (wherein $Z^2$ is defined as above). For example, a compound of Formula 1-3 (wherein $Z^1$ is halogen such as Br or I) can be converted to a compound of Formula 1-4 [wherein $Z^2$ is B(OH)$_2$; B(OR)$_2$ wherein each R is independently H or C$_{1-6}$ alkyl, or wherein the two (OR) groups, together with the B atom to which they are attached, form a 5- to 10-membered heterocycloalkyl or heteroaryl optionally substituted with one or more C$_{1-6}$ alkyl] by methods described herein or other methods well known to those skilled in the art. In this example, this reaction can be accomplished, for example, by reacting a compound of Formula 1-3 (wherein $Z^1$ is halogen such as Br) with 4,4,4',4',5,5,5',5'-octamethyl-2,2'-bi-1,3,2-dioxaborolane, a suitable base (such as potassium acetate), and a palladium catalyst {such as [1,1'-bis(diphenylphosphino)ferrocene]dichloropalladium(II)} in a suitable solvent such as 1,4-dioxane. In another example, a compound of Formula 1-3 (wherein $Z^1$ is halogen such as Br) can be converted to a compound of Formula 1-4 (wherein $Z^2$ is a trialkyltin moiety) by alternate methods described herein or other methods well known to those skilled in the art. In this example, this reaction can be accomplished, for example, by reacting a compound of Formula 1-3 (wherein $Z^1$ is halogen such as Br) with a hexaalkyldistannane (such as hexamethyldistannane) in the presence of a palladium catalyst [such as tetrakis(triphenylphosphine)palladium(0)] in a suitable solvent such as 1,4-dioxane. A compound of Formula 1-4 can then be reacted with a compound of Formula $Q^1$-$Z^1$ (wherein $Z^1$ is defined as above) by a metal-catalyzed (such as using a palladium catalyst) coupling reaction to obtain a compound of Formula I. Compounds of Formula $Q^1$-$Z^1$ are commercially available or can be made by methods described herein or by methods analogous to those described in the chemical art. The type of reaction employed depends on the selection of $Z^1$ and $Z^2$. For example, when $Z^1$ is halogen or triflate and the $Q^1$-$Z^2$ reagent is a boronic acid or boronic ester, a Suzuki reaction may be used [A. Suzuki, *J. Organomet. Chem.* 1999, 576, 147-168; N. Miyaura and A. Suzuki, *Chem. Rev.* 1995, 95, 2457-2483; A. F. Littke et al., *J. Am. Chem. Soc.* 2000, 122, 4020-4028]. In some specific embodiments, an aromatic iodide, bromide, or triflate of Formula 1-3 is combined with an aryl or heteroaryl boronic acid or boronic ester of Formula $Q^1$-$Z^2$ and a suitable base, such as potassium phosphate, in a suitable organic solvent such as tetrahydrofuran (THF). A palladium catalyst is added, such as S-Phos precatalyst {also known as chloro(2-dicyclohexylphosphino-2',6'-dimethoxy-1,1'-biphenyl)[2-(2-aminoethylphenyl)]palladium(II)-tert-butyl methyl ether adduct}, and the reaction mixture is heated. Alternatively, when $Z^1$ is halogen or triflate and $Z^2$ is trialkyltin, a Stille coupling may be employed [V. Farina et al., *Organic Reactions* 1997, 50, 1-652]. More specifically, a compound of Formula 1-3 (wherein $Z^1$ is Br, I, or triflate) may be combined with a compound of Formula $Q^1$-$Z^2$ (wherein the $Q^1$-$Z^2$ compound is a $Q^1$-stannane compound) in the presence of a palladium catalyst, such as dichlorobis(triphenylphosphine)palladium(II), in a suitable organic solvent such as toluene, and the reaction may be heated. Where $Z^1$ is Br, I, or triflate and $Z^2$ is Br or I, a Negishi coupling may be used [E. Erdik, *Tetrahedron* 1992, 48, 9577-9648]. More specifically, a compound of Formula 1-3 (wherein $Z^1$ is Br, I, or triflate) may be transmetallated by treatment with 1 to 1.1 equivalents of an alkyllithium reagent followed by a solution of 1.2 to 1.4 equivalents of zinc chloride in an appropriate solvent such as THF at a temperature ranging from −80° C. to −65° C. After warming to a temperature between 10° C. and 30° C., the reaction mixture may be treated with a compound of Formula $Q^1$-$Z^2$ (wherein $Z^2$ is Br or I), and heated at 50° C. to 70° C. with addition of a catalyst such as tetrakis(triphenylphosphine)palladium(0). The reaction may be carried out for times ranging from 1 to 24 hours to yield the compound of Formula I.

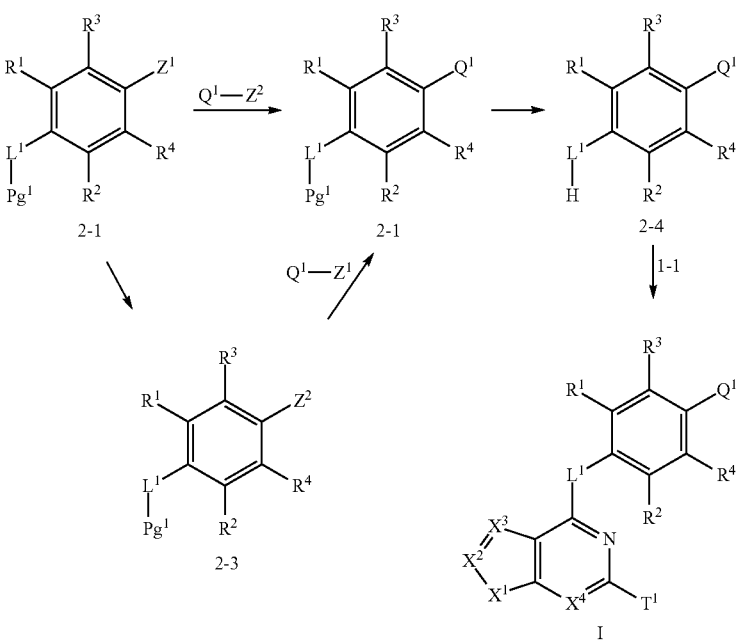

Scheme 2

Scheme 2 also refers to preparation of compounds of Formula I. Referring to Scheme 2, compounds of Formula I may be prepared utilizing analogous chemical transformations to those described in Scheme 1, but with a different ordering of steps. Compounds of Formula 2-1 [wherein $Pg^1$ is a suitable protecting group such as Boc or Cbz when $L^1$ is NH or methyl, benzyl, tetrahydropyranyl (THP), or tert-butyldimethyl (TBS) when $L^1$ is O] are commercially available or can be made by methods described herein or other methods well known to those skilled in the art. A compound of Formula 2-1 can be converted to a compound of Formula 2-2 either directly or after conversion to a compound of Formula 2-3 using methods analogous to those described in Scheme 1. A compound of Formula 2-2 may then be deprotected, using appropriate conditions depending on the selection of the $Pg^1$ group, to obtain a compound of Formula 2-4, which in turn can be coupled with a compound of Formula 1-1 in Scheme 1 to afford a compound of Formula I. The coupling conditions employed may be analogous to those described for the preparation of a compound of Formula 1-3 in Scheme 1.

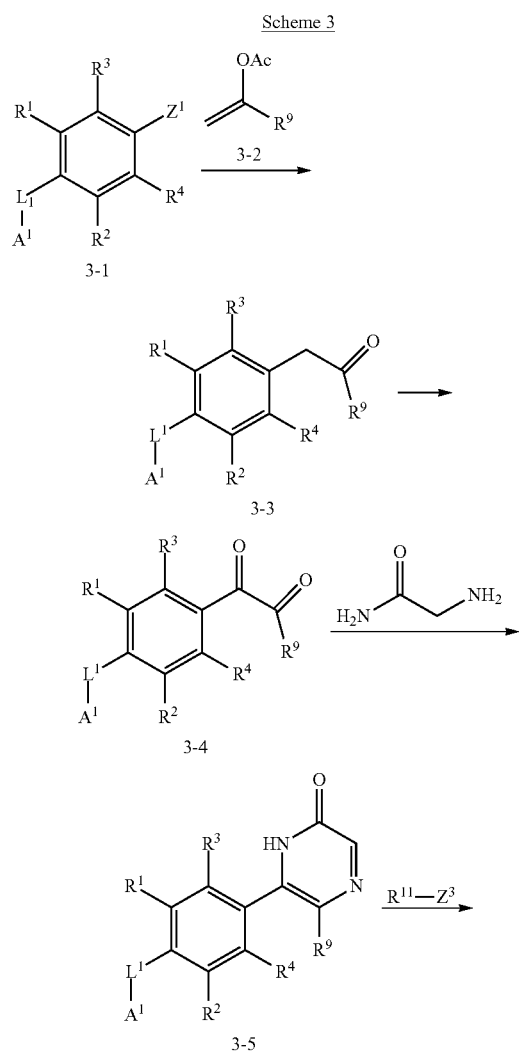

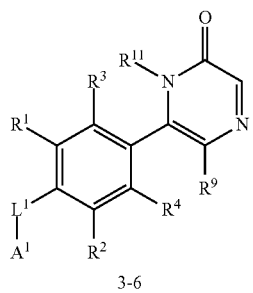

3-6

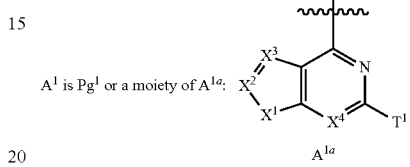

Scheme 3 refers to a preparation of a compound of Formula 3-6 wherein $A^1$ is a moiety of Formula $A^{1a}$ or a $Pg^1$. Referring to Scheme 3, compounds of Formula 3-1 are commercially available or can be made by methods described herein or other methods well known to those skilled in the art. A compound of Formula 3-3 can be prepared by reacting compound of Formula 3-1 with acylated enol of Formula 3-2 in the presence of a suitable palladium catalyst such as palladium(II) acetate, tributylmethoxystannane and a suitable phosphine ligand (such as tri-o-tolylphosphine). The resulting aryl ketone of Formula 3-3 can be converted to the diketone of Formula 3-4 upon treatment with a suitable oxidizing agent such as selenium dioxide. Diketones of Formula 3-4 can be reacted with glycinamide or a salt thereof (such as an acetic acid salt) in the presence of a base such as sodium hydroxide to obtain pyrazinones of Formula 3-5. Alkylation of the pyrazinone nitrogen to obtain a compound of Formula 3-6 can be achieved by treatment of a compound of Formula 3-5 with a base [such as lithium diisopropylamide (LDA), lithium bis(trimethylsilyl)amide (LHMDS), and the like] and a compound of the formula $R^{11}$—$Z^3$ [wherein $Z^3$ is an acceptable leaving group such as Cl, Br, I, methanesulfonate (mesylate), and the like and wherein $R^{11}$ is for example $C_{1-3}$ alkyl (e.g., methyl)]. Suitable reaction solvents typically can be selected from polar aprotic solvents such as N,N-dimethylformamide (DMF), 1,4-dioxane, or THF.

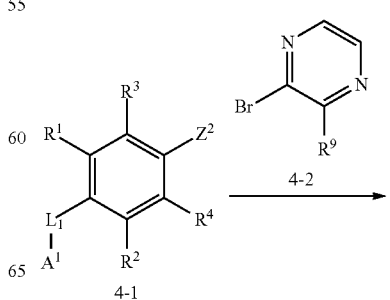

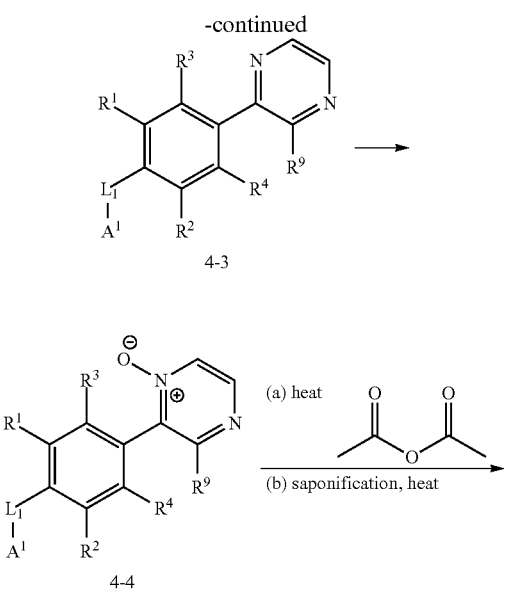

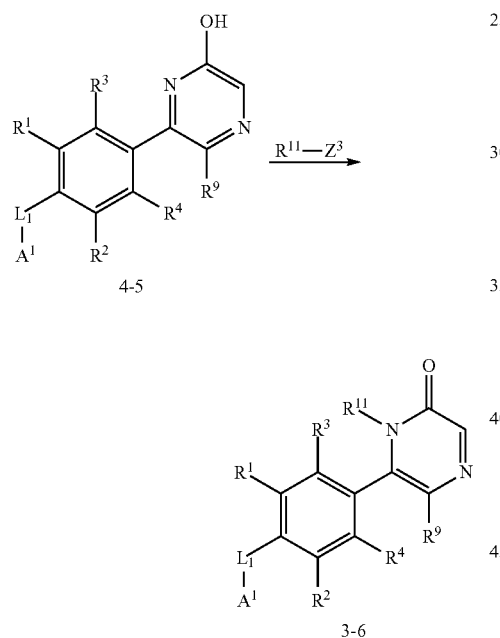

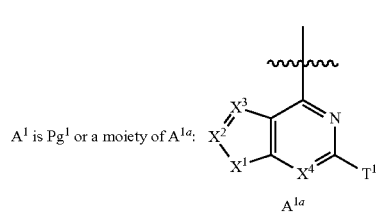

with a compound of Formula 4-2. The aforesaid coupling may be accomplished by reacting a compound of Formula 4-1 with a compound of Formula 4-2 in the presence of a suitable base (such as potassium carbonate), a suitable catalyst [such as tetrakis(triphenylphosphine)palladium(0)], and a suitable solvent (such as ethanol). A compound of Formula 4-3 can be reacted with maleic anhydride and hydrogen peroxide in a solvent (such as dichloromethane) to provide a compound of Formula 4-4, which may contain a mixture of N-oxide regioisomers. A compound of Formula 4-5 can be prepared from a compound of Formula 4-4 by heating with acetic anydride; the initial product can be saponified using a base (such as NaOH) in a suitable polar solvent (such as water or methanol). A compound of Formula 3-6 can be prepared from a compound of Formula 4-5 by reaction with a suitable base (such as LDA, LHMDS and the like), lithium bromide, and a compound of the formula $R^{11}$—$Z^3$ (wherein $Z^3$ is an acceptable leaving group such as Cl, Br, I, mesylate, and the like). Suitable reaction solvents typically can be selected from polar aprotic solvents (such as DMF, 1,4-dioxane, or THF).

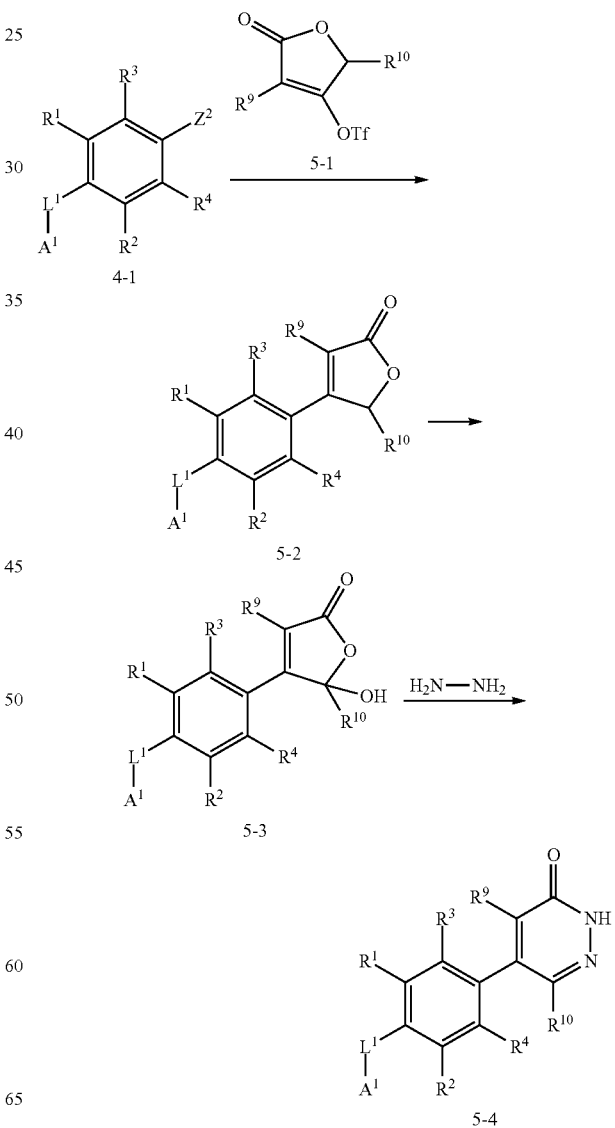

Alternatively, a compound of Formula 3-6 may be prepared as in Scheme 4 wherein $L^1$ is O, NH, N($C_{1-4}$ alkyl) and N($C_{3-6}$ cycloalkyl). Referring to Scheme 4, compounds of Formula 4-1 and 4-2 are commercially available or can be made by methods described herein or other methods well known to those skilled in the art. A compound of Formula 4-3 can be prepared by coupling a compound of Formula 4-1

$A^1$ is $Pg^1$ or a moiety of $A^{1a}$:

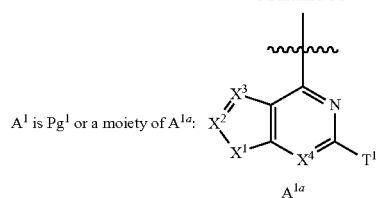

Scheme 5 refers to a preparation of a compound of Formula 5-4 wherein $L^1$ is O, NH, carbonyl, N(C$_{1-4}$ alkyl) and N(C$_{3-6}$ cycloalkyl) and $A^1$ is a moiety of Formula $A^{1a}$, or a $Pg^2$ (such as a benzyl group). Referring to Scheme 5, compounds of Formula 4-1 and 5-1 are commercially available or can be made by methods described herein or other methods well known to those skilled in the art. A compound of Formula 5-2 can be prepared by coupling a compound of Formula 4-1 with an enol trifluoromethanesulfonate of Formula 5-1. The aforesaid coupling may be accomplished by reacting a compound of Formula 4-1 with a trifluoromethanesulfonate of Formula 5-1 in the presence of a suitable base (such as potassium carbonate or sodium carbonate), a suitable catalyst [such as palladium(II) acetate], optionally a suitable ligand (such as tricyclohexylphosphine), and optionally a suitable phase-transfer catalyst such as tetrabutylammonium chloride. Suitable reaction solvents typically can be selected from polar aprotic solvents such as 1,4-dioxane or THF. A compound of Formula 5-2 can be reacted with 1 to 5 equivalents of a suitable base [such as 1,8-diazabicyclo[5.4.0]undec-7-ene (DBU)] under an oxygen atmosphere to obtain a compound of Formula 5-3. Suitable reaction solvents typically can be selected from polar aprotic solvents such as DMF, 1,4-dioxane, or THF. A compound of Formula 5-4 can be obtained by reacting a compound of Formula 5-3 with hydrazine in a suitable solvent such as 1-butanol.

Scheme 6

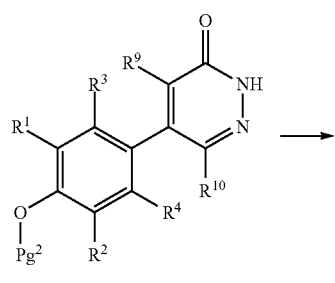

6-1

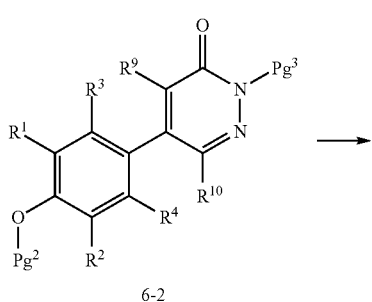

6-2

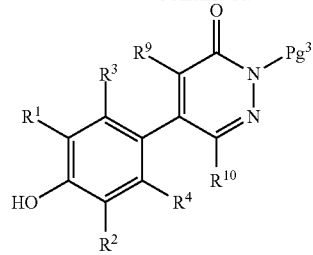

6-3

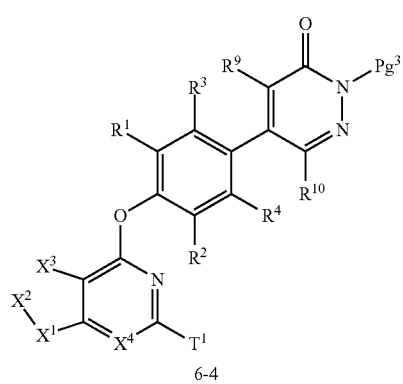

6-4

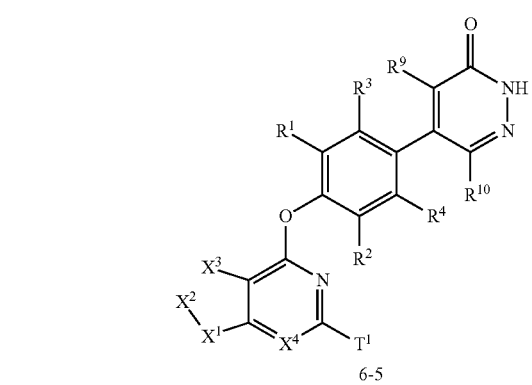

6-5

Scheme 6 refers to a preparation of a compound of Formula 6-5. Referring to Scheme 6, a compound of Formula 6-1 can be prepared as described in Scheme 5, wherein $Pg^2$ is a suitable protecting group (such as benzyl). A compound of Formula 6-1 can be converted to a suitably protected compound of Formula 6-2 using methods described herein or other methods well known to those skilled in the art, wherein $Pg^3$ is a suitable protecting group (such as THP) that can be removed under orthogonal reaction conditions to $Pg^2$. A compound of Formula 6-3 can be prepared by selective removal of $Pg^2$ under suitable deprotection conditions depending on the selection of $Pg^2$. For example, when $Pg^2$ is a benzyl group, it can be removed by treatment with palladium (10% on carbon) under hydrogenation condition in a suitable solvent, such as methanol and ethyl acetate. Using the aforementioned reaction conditions described in Scheme 1, a compound of Formula 6-3 can be coupled with a reagent of Formula 1-1 to yield a compound of Formula 6-4. A compound of Formula 6-5 can be obtained by removing Pg$^3$ under suitable deprotection conditions depending on the selection of Pg$^3$. For example, when Pg$^3$ is THP, it can be removed under acidic conditions, such as hydrogen chloride in a suitable solvent, such as dichloromethane.

Scheme 7

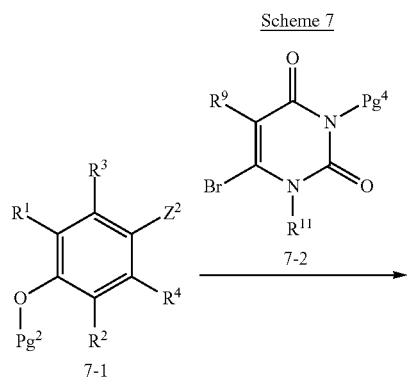

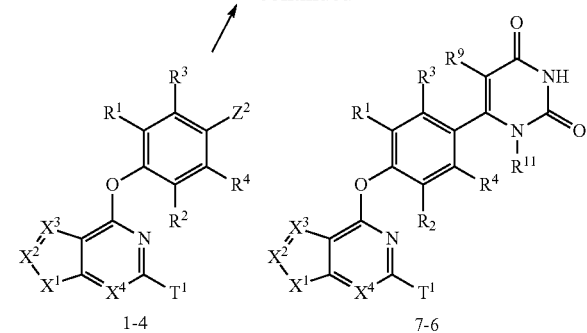

Scheme 7 refers to a preparation of a compound of Formula 7-6 [wherein R$^9$ is, for example, C$_{1-3}$ alkyl (e.g., methyl); R$^{11}$ is, for example, H or C$_{1-3}$ alkyl (e.g., methyl); and Pg$^4$ is a suitable protecting group [e.g., 2-(trimethylsilyl) ethoxymethyl (SEM), tert-butoxycarbonyl (Boc), or benzyloxymethyl acetal (BOM)]. Referring to Scheme 7, compounds of Formula 7-1 and 7-2 are commercially available or can be prepared by methods described herein or other methods well known to those skilled in the art. A compound of Formula 7-3 can be prepared by coupling a compound of Formula 7-1 with a compound of Formula 7-2, in the presence of a suitable base (such as potassium carbonate) and a suitable catalyst {such as [1,1'-bis(diphenylphosphino)ferrocene]dichloropalladium(II)}. A compound of Formula 7-4 can be prepared by selective removal of Pg$^2$ under suitable de-protection conditions depending on the selection of Pg$^2$. For example, when Pg$^2$ is a benzyl group, it can be removed by treatment with palladium (10% on carbon) under hydrogenation condition in a suitable solvent, such as methanol and ethyl acetate. Using the aforementioned reaction conditions described in Scheme 1, a compound of Formula 7-4 can be coupled with a reagent of Formula 1-1 to yield a compound of Formula 7-5. Alternatively, a compound of Formula 7-5 can be prepared from intermediate 1-4, following the coupling conditions described in Scheme 1. A compound of Formula 7-6 can then be obtained from a compound of Formula 7-5 by removing Pg$^4$ under suitable deprotection conditions that are known to those skilled in the art.

Scheme 8

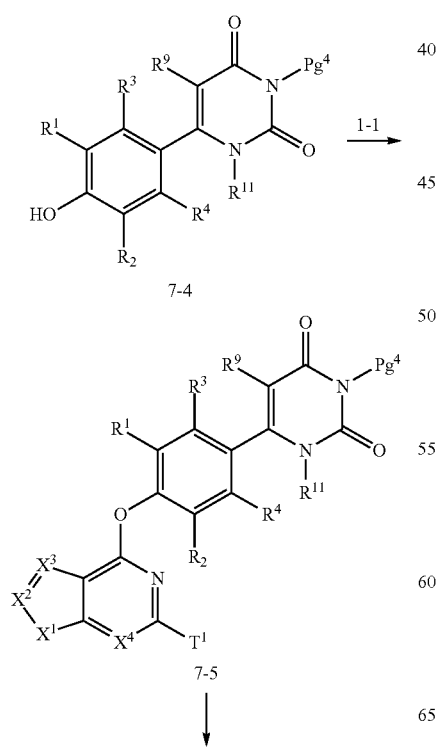

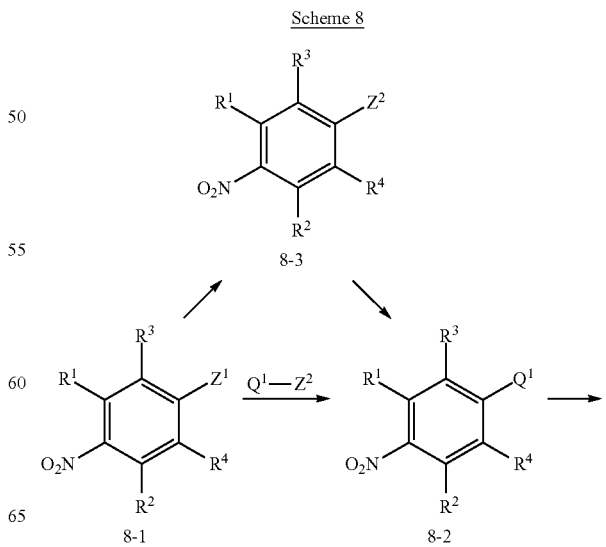

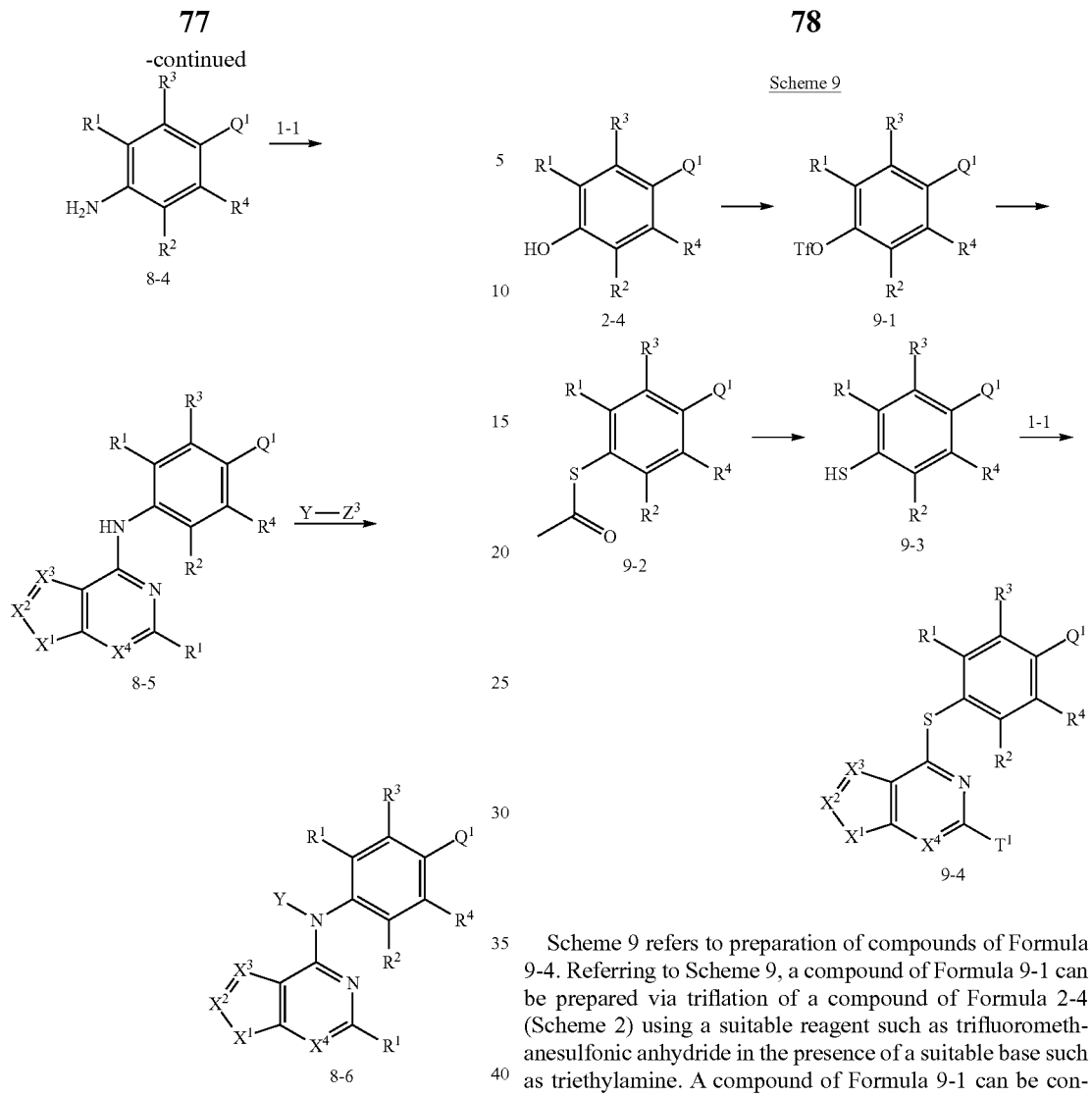

Scheme 8 refers to preparation of compounds of Formula 8-5 and 8-6. Referring to Scheme 8, compounds of Formula 8-1 are commercially available or can be made by methods described herein or other methods well known to those skilled in the art. A compound of Formula 8-1 can be converted to a compound of Formula 8-2 either directly or after conversion to a compound of Formula 8-3 using methods analogous to those described in Scheme 1. The nitro group of a compound of Formula 8-2 can then be converted to an amine via hydrogenation in the presence of a suitable catalyst, such as palladium (10% on carbon), to yield a compound of Formula 8-4. A compound of Formula 8-4 can then be coupled with a compound of Formula 1-1 in Scheme 1 to afford a compound of Formula 8-5. The coupling conditions employed may be analogous to those described for the preparation of a compound of Formula 1-3 in Scheme 1. A compound of Formula 8-6 can be prepared via N-alkylation of a compound of formula 8-5 using a reagent of Y—$Z^3$, wherein Y is $C_{1-4}$ alkyl, or $C_{3-6}$ cycloalkyl, and $Z^3$ is an acceptable leaving group such as Cl, Br, I, mesylate, and the like.

Scheme 9 refers to preparation of compounds of Formula 9-4. Referring to Scheme 9, a compound of Formula 9-1 can be prepared via triflation of a compound of Formula 2-4 (Scheme 2) using a suitable reagent such as trifluoromethanesulfonic anhydride in the presence of a suitable base such as triethylamine. A compound of Formula 9-1 can be converted to a compound of Formula 9-2 by coupling with potassium thioacetate, in the presence of a suitable metal catalyst, such as tris(dibenzylideneacetone)dipalladium(0), and a suitable ligand, such as (R)-(−)-1-[($S_P$)-2-(dicyclohexylphosphino)ferrocenyl]ethyldi-tert-butylphosphine, in a suitable solvent, such as toluene. A compound of Formula 9-2 can then be hydrolyzed to obtain a compound of Formula 9-3, which in turn can be coupled with a compound of Formula 1-1 in Scheme 1 to afford a compound of Formula 9-4. The coupling conditions employed may be analogous to those described for the preparation of a compound of Formula 1-3 in Scheme 1.

Scheme 10

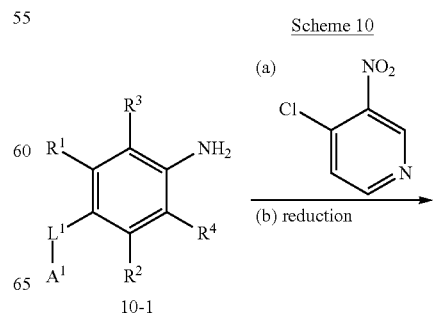

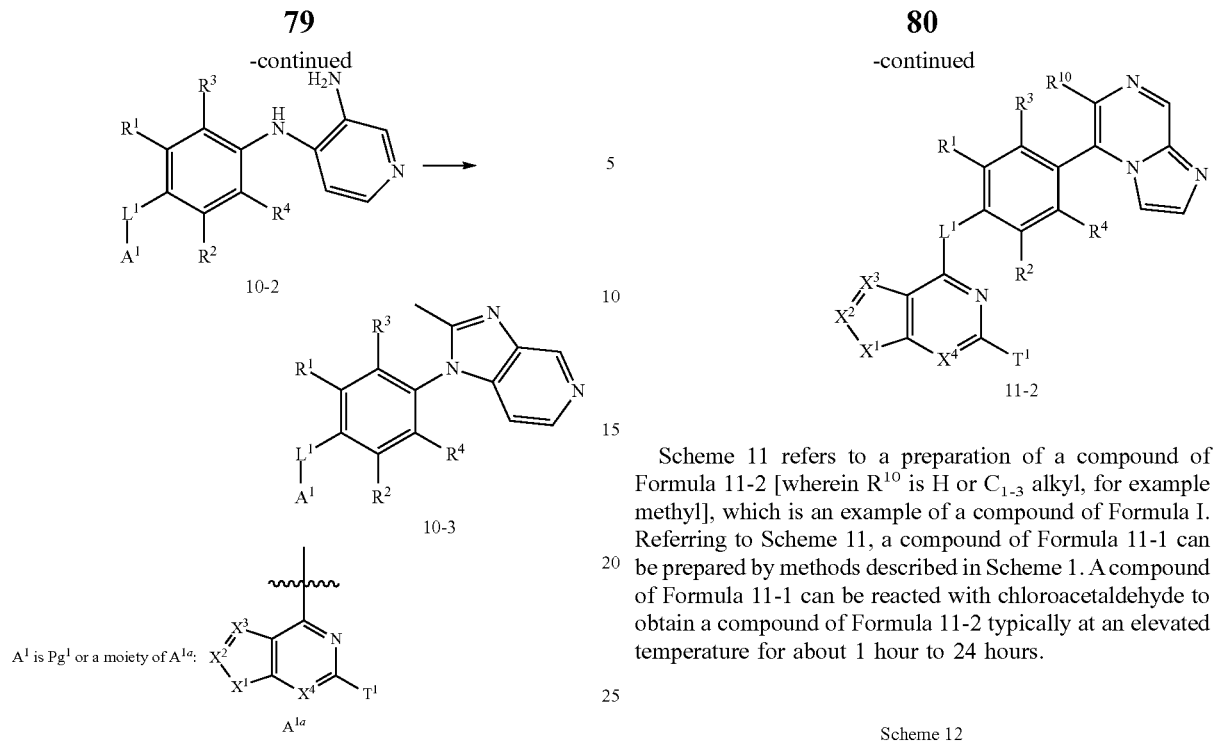

Scheme 10 refers to a preparation of a compound of Formula 10-3 [wherein $A^1$ is either $Pg^2$ as defined above or a moiety of Formula $A^{1a}$], which can be used in Scheme 2 as intermediate/starting material for the preparation of compounds of Formula I. Referring to Scheme 3, compounds of Formula 10-1 are commercially available or can be made by methods described herein or other methods well known to those skilled in the art. A compound of Formula 10-1 can be reacted with 4-chloro-3-nitropyridine and the initial product can be subsequently reduced to obtain a compound of Formula 10-2. Examples of suitable reaction conditions for the coupling of a compound of Formula 10-1 with 4-chloro-3-nitropyridine include mixing the two reactants with a suitable base, such as triethylamine, in a suitable reaction solvent such as ethanol. The subsequent reduction of the nitro group to afford a compound of Formula 10-2 can be achieved by, for example, hydrogenation in the presence of a catalyst such as palladium on carbon in a suitable solvent such as methanol. Suitable hydrogen pressures for the aforesaid reaction are typically between 1 atm and 4 atm. A compound of Formula 10-2 can then be heated with acetic anhydride and triethyl orthoformate to obtain a compound of Formula 10-3.

Scheme 11 refers to a preparation of a compound of Formula 11-2 [wherein $R^{10}$ is H or $C_{1-3}$ alkyl, for example methyl], which is an example of a compound of Formula I. Referring to Scheme 11, a compound of Formula 11-1 can be prepared by methods described in Scheme 1. A compound of Formula 11-1 can be reacted with chloroacetaldehyde to obtain a compound of Formula 11-2 typically at an elevated temperature for about 1 hour to 24 hours.

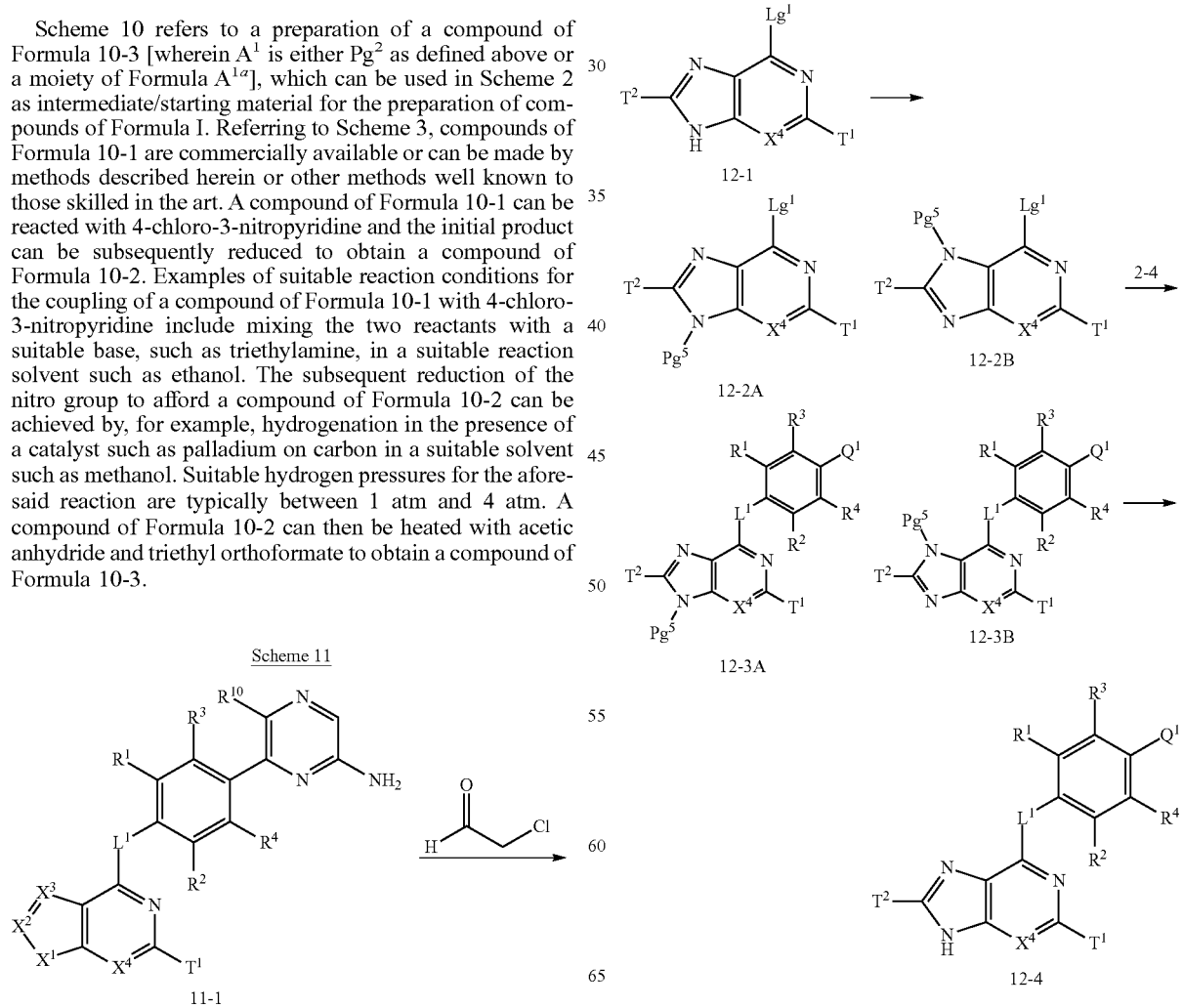

Scheme 12 refers to a preparation of a compound of Formula 12-4. Referring to Scheme 12, compounds of Formula 12-1 are commercially available or can be made by methods described herein or other methods well known to those skilled in the art. The free NH of a compound of Formula 12-1 can be protected by a suitable amine protecting group $Pg^5$ such as 2-(trimethylsilyl)ethoxymethyl (SEM) to give a mixture of regioisomers of Formula 12-2A and 12-2B. The mixture can be coupled with intermediate 2-4 under the conditions described in Scheme 1 to give a mixture of compounds of Formula 12-3A and 12-3B, which upon deprotection under suitable reaction conditions depending on the choice of $Pg^5$ yield a compound of Formula 12-4.

Additional starting materials and intermediates useful for making the compounds of the present invention can be obtained from chemical vendors such as Sigma-Aldrich or can be made according to methods described in the chemical art.

Those skilled in the art can recognize that in all of the Schemes described herein, if there are functional (reactive) groups present on a part of the compound structure such as a substituent group, for example $R^1$, $R^2$, $R^3$, $R^4$, $R^5$, $R^6$, $R^7$, $R^8$, $R^9$, $R^{10}$, $R^{11}$, $L^1$, $X^1$, $X^2$, $X^3$, $X^4$, and $Q^1$, etc., further modification can be made if appropriate and/or desired, using methods well known to those skilled in the art. For example, a —CN group can be hydrolyzed to afford an amide group; a carboxylic acid can be converted to an amide; a carboxylic acid can be converted to an ester, which in turn can be reduced to an alcohol, which in turn can be further modified. For another example, an OH group can be converted into a better leaving group such as a methanesulfonate, which in turn is suitable for nucleophilic substitution, such as by a cyanide ion ($CN^-$). For another example, an —S— can be oxidized to —S(=O)— and/or —S(=O)$_2$—. For yet another example, an unsaturated bond such as C=C or C≡C can be reduced to a saturated bond by hydrogenation. In some embodiments, a primary amine or a secondary amine moiety (present on a substituent group such as $R^3$, $R^4$, $R^9$, $R^{10}$, etc.) can be converted to an amide, sulfonamide, urea, or thiourea moiety by reacting it with an appropriate reagent such as an acid chloride, a sulfonyl chloride, an isocyanate, or a thioisocyanate compound. One skilled in the art will recognize further such modifications. Thus, a compound of Formula I having a substituent that contains a functional group can be converted to another compound of Formula I having a different substituent group.

Similarly, those skilled in the art can also recognize that in all of the schemes described herein, if there are functional (reactive) groups present on a substituent group such as $R^3$, $R^4$, $R^9$, $R^{10}$, etc., these functional groups can be protected/deprotected in the course of the synthetic scheme described here, if appropriate and/or desired. For example, an OH group can be protected by a benzyl, methyl, or acetyl group, which can be deprotected and converted back to the OH group in a later stage of the synthetic process. For another example, an $NH_2$ group can be protected by a benzyloxycarbonyl (Cbz) or Boc group; conversion back to the $NH_2$ group can be carried out at a later stage of the synthetic process via deprotection.

As used herein, the term "reacting" (or "reaction" or "reacted") refers to the bringing together of designated chemical reactants such that a chemical transformation takes place generating a compound different from any initially introduced into the system. Reactions can take place in the presence or absence of solvent.

Compounds of Formula I may exist as stereoisomers, such as atropisomers, racemates, enantiomers, or diastereomers. Conventional techniques for the preparation/isolation of individual enantiomers include chiral synthesis from a suitable optically pure precursor or resolution of the racemate using, for example, chiral high-performance liquid chromatography (HPLC). Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art. Chiral compounds of Formula I (and chiral precursors thereof) may be obtained in enantiomerically enriched form using chromatography, typically HPLC, on an asymmetric resin with a mobile phase consisting of a hydrocarbon, typically heptane or hexane, containing from 0% to 50% 2-propanol, typically from 2% to 20%, and from 0% to 5% of an alkylamine, typically 0.1% diethylamine. Concentration of the eluate affords the enriched mixture. Stereoisomeric conglomerates may be separated by conventional techniques known to those skilled in the art. See, e.g., *Stereochemistry of Organic Compounds* by E. L. Eliel and S. H. Wilen (Wiley, New York, 1994), the disclosure of which is incorporated herein by reference in its entirety. Suitable stereoselective techniques are well known to those of ordinary skill in the art.

Where a compound of Formula I contains an alkenyl or alkenylene (alkylidene) group, geometric cis/trans (or Z/E) isomers are possible. Cis/trans isomers may be separated by conventional techniques well known to those skilled in the art, for example, chromatography and fractional crystallization. Salts of the present invention can be prepared according to methods known to those of skill in the art.

The compounds of Formula I that are basic in nature are capable of forming a wide variety of salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the basic compounds of this invention can be prepared by treating the basic compound with a substantially equivalent amount of the selected mineral or organic acid in an aqueous solvent medium or in a suitable organic solvent, such as methanol or ethanol. Upon evaporation of the solvent, the desired solid salt is obtained. The desired acid salt can also be precipitated from a solution of the free base in an organic solvent by adding an appropriate mineral or organic acid to the solution.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, isonicotinic acid, lactic acid, pantothenic acid, bitartric acid, ascorbic acid, formic acid, 2,5-dihydroxybenzoic acid, gluconic acid, saccharic acid, formic acid, methanesulfonic acid, ethanesulfonic acid, benzenesulfonic acid, p-toluenesulfonic acid, and pamoic [i.e., 4,4'-methanediyl bis(3-hydroxynaphthalene-2-carboxylic acid)] acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as ethanesulfonic acid, or the like.

Those compounds of Formula I that are acidic in nature are capable of forming base salts with various pharmacologically acceptable cations. Examples of such salts include the alkali metal or alkaline earth metal salts, and particularly the sodium and potassium salts. These salts are all prepared by conventional techniques. The chemical bases which are used as reagents to prepare the pharmaceutically acceptable base salts of this invention are those which form non-toxic base salts with the acidic compounds of Formula I. These salts may be prepared by any suitable method, for example, treatment of the free acid with an inorganic or organic base, such as an amine (primary, secondary or tertiary), an alkali metal hydroxide or alkaline earth metal hydroxide, or the like. These salts can also be prepared by treating the corresponding acidic compounds with an aqueous solution containing the desired pharmacologically acceptable cations, and then evaporating the resulting solution to dryness, for example under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are, for example, employed in order to ensure completeness of reaction and maximum yields of the desired final product.

Pharmaceutically acceptable salts of compounds of Formula I (including compounds of Formula Ia or Ib) may be prepared by one or more of three methods:

(i) by reacting the compound of Formula I with the desired acid or base;
(ii) by removing an acid- or base-labile protecting group from a suitable precursor of the compound of Formula I or by ring-opening a suitable cyclic precursor, for example, a lactone or lactam, using the desired acid or base; or
(iii) by converting one salt of the compound of Formula I to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionization in the resulting salt may vary from completely ionized to almost non-ionized.

Polymorphs can be prepared according to techniques well-known to those skilled in the art, for example, by crystallization.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture may have almost identical physical properties, they may have different physical properties compared to the true racemate. Racemic mixtures may be separated by conventional techniques known to those skilled in the art—see, for example, *Stereochemistry of Organic Compounds* by E. L. Eliel and S. H. Wilen (Wiley, New York, 1994).

The invention also includes isotopically labeled compounds of Formula I wherein one or more atoms is replaced by an atom having the same atomic number, but an atomic mass or mass number different from the atomic mass or mass number usually found in nature. Isotopically labeled compounds of Formula I (or pharmaceutically acceptable salts thereof or N-oxides thereof) can generally be prepared by conventional techniques known to those skilled in the art or by processes analogous to those described herein, using an appropriate isotopically labeled reagent in place of the non-labeled reagent otherwise employed.

Prodrugs in accordance with the invention can, for example, be produced by replacing appropriate functionalities present in the compounds of Formula I with certain moieties known to those skilled in the art as 'pro-moieties' as described, for example, in *Design of Prodrugs* by H. Bundgaard (Elsevier, 1985).

The compounds of Formula I should be assessed for their biopharmaceutical properties, such as solubility and solution stability (across pH), permeability, etc., in order to select the most appropriate dosage form and route of administration for treatment of the proposed indication.

Compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention (or pharmaceutically acceptable salts thereof) and methods for their preparation will be readily apparent to those skilled in the art. Such compositions and methods for their preparation may be found, for example, in *Remington's Pharmaceutical Sciences*, 19th Edition (Mack Publishing Company, 1995).

The compounds of the invention (including pharmaceutically acceptable salts thereof and N-oxides thereof) may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropyl methyl cellulose) and typically comprise a carrier, for example, water, ethanol, polyethylene glycol, propylene glycol, methyl cellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described by Liang and Chen, *Expert Opinion in Therapeutic Patents* 2001, 11, 981-986.

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1 weight % to 25 weight %, for example, from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulfate. Lubricants generally comprise from 0.25 weight % to 10 weight %, for example, from 0.5 weight % to 3 weight % of the tablet.

Other possible ingredients include anti-oxidants, colorants, flavoring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt-congealed, or extruded before tabletting. The final formulation may comprise one or more layers and may be coated or uncoated; it may even be encapsulated.

The formulation of tablets is discussed in *Pharmaceutical Dosage Forms: Tablets*, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of Formula I, a film-forming polymer, a binder, a solvent, a humectant, a plasticizer, a stabilizer or emulsifier, a viscosity-modifying agent and a solvent. Some components of the formulation may perform more than one function.

The compound of Formula I (or pharmaceutically acceptable salts thereof or N-oxides thereof) may be water-soluble or insoluble. A water-soluble compound typically comprises from 1 weight % to 80 weight %, more typically from 20 weight % to 50 weight %, of the solutes. Less soluble compounds may comprise a smaller proportion of the composition, typically up to 30 weight % of the solutes. Alternatively, the compound of Formula I may be in the form of multiparticulate beads.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavorings and flavor enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Verma et al., *Pharmaceutical Technology On-line*, 25(2), 1-14 (2001). The use of chewing gum to achieve controlled release is described in WO 00/35298.

The compounds of the invention (including pharmaceutically acceptable salts thereof) may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (for example to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

The solubility of compounds of Formula I (including pharmaceutically acceptable salts thereof) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a suspension or as a solid, semi-solid, or thixotropic liquid for administration as an implanted depot providing modified release of the active compound. Examples of such formulations include drug-coated stents and semi-solids and suspensions comprising drug-loaded poly(DL-lactic-coglycolic acid) (PLGA) microspheres.

The compounds of the invention (including pharmaceutically acceptable salts thereof) may also be administered topically, (intra)dermally, or transdermally to the skin or mucosa. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated. See e.g., Finnin and Morgan, *J. Pharm. Sci.* 1999, 88, 955-958.

Other means of topical administration include delivery by electroporation, iontophoresis, phonophoresis, sonophoresis and microneedle or needle-free (e.g., Powderject™, Bioject™, etc.) injection.

Formulations for topical administration may be formulated to be immediate and/or modified release. Modified release formulations include delayed-, sustained-, pulsed-, controlled-, targeted and programmed release.

The compounds of the invention (including pharmaceutically acceptable salts thereof) can also be administered intranasally or by inhalation, typically in the form of a dry powder (either alone; as a mixture, for example, in a dry blend with lactose; or as a mixed component particle, for example, mixed with phospholipids, such as phosphatidylcholine) from a dry powder inhaler, as an aerosol spray from a pressurized container, pump, spray, atomizer (for example an atomizer using electrohydrodynamics to produce a fine mist), or nebulizer, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin.

The pressurized container, pump, spray, atomizer, or nebulizer contains a solution or suspension of the compound(s) of the invention comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules (made, for example, from gelatin or hydroxypropyl methyl cellulose), blisters and cartridges for use in an inhaler or insufflator may be formulated to contain a powder mix of the compound of the invention, a suitable powder base such as lactose or starch and a performance modifier such as L-leucine, mannitol, or magnesium stearate. The lactose may be anhydrous or in the form of the monohydrate. Other suitable excipients include dextran, glucose, maltose, sorbitol, xylitol, fructose, sucrose and trehalose.

A suitable solution formulation for use in an atomizer using electrohydrodynamics to produce a fine mist may contain from 1 µg to 20 mg of the compound of the invention per actuation and the actuation volume may vary from 1 µL to 100 µL. A typical formulation may comprise a compound of Formula I or a pharmaceutically acceptable salt thereof, propylene glycol, sterile water, ethanol and sodium chloride. Alternative solvents which may be used instead of propylene glycol include glycerol and polyethylene glycol.

Suitable flavors, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 0.01 to 100 mg of the compound of Formula I. The overall daily dose will typically be in the range 1 µg to 200 mg, which may be administered in a single dose or, more usually, as divided doses throughout the day.

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The compounds of the invention (including pharmaceutically acceptable salts thereof) may also be administered directly to the eye or ear, typically in the form of drops of a micronized suspension or solution in isotonic, pH-adjusted, sterile saline. Other formulations suitable for ocular and aural administration include ointments, gels, biodegradable (e.g., absorbable gel sponges, collagen) and non-biodegradable (e.g., silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropyl methyl cellulose, hydroxyethyl cellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

The compounds of the invention (including pharmaceutically acceptable salts thereof) may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e., as a carrier, diluent, or solubilizer. Most commonly used for these purposes are alpha-, beta- and gamma-cyclodextrins, examples of which may be found in International Patent Applications Nos. WO 91/11172, WO 94/02518 and WO 98/55148.

Since the present invention has an aspect that relates to the treatment of the disease/conditions described herein with a combination of active ingredients which may be administered separately, the invention also relates to combining separate pharmaceutical compositions in kit form. The kit comprises two separate pharmaceutical compositions: a compound of Formula I a prodrug thereof or a salt of such compound or prodrug and a second compound as described above. The kit comprises means for containing the separate compositions such as a container, a divided bottle or a divided foil packet. Typically the kit comprises directions for the administration of the separate components. The kit form is particularly advantageous when the separate components are for example administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. In some embodiments, the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, etc. . . . Second Week, Monday, Tuesday, . . . " etc. Other variations of memory aids will be readily apparent. A "daily dose" can be a single tablet or capsule or several pills or capsules to be taken on a given day. Also, a daily dose of Formula I compound can consist of one tablet or capsule while a daily dose of the second compound can consist of several tablets or capsules and vice versa. The memory aid should reflect this.

In another specific embodiment of the invention, a dispenser designed to dispense the daily doses one at a time in the order of their intended use is provided. For example, the dispenser is equipped with a memory aid, so as to further facilitate compliance with the regimen. An example of such a memory aid is a mechanical counter which indicates the number of daily doses that has been dispensed. Another example of such a memory aid is a battery-powered microchip memory coupled with a liquid crystal readout, or audible reminder signal which, for example, reads out the date that the last daily dose has been taken and/or reminds one when the next dose is to be taken.

The invention will be described in greater detail by way of specific examples. The following examples are offered for illustrative purposes, and are not intended to limit the invention in any manner. Those of skill in the art will readily recognize a variety of non-critical parameters that can be changed or modified to yield essentially the same results. Additional compounds within the scope of this invention may be prepared using the methods illustrated in these Examples, either alone or in combination with techniques generally known in the art. In the following Examples and Preparations, "DMSO" means dimethyl sulfoxide, "N" where referring to concentration means Normal, "M" means molar, "mL" means milliliter, "mmol" means millimoles, "μmol" means micromoles, "eq." means equivalent, "° C." means degrees Celsius, "MHz" means megahertz, "HPLC" means high-performance liquid chromatography.

EXAMPLES

The following illustrate the synthesis of various compounds of the present invention. Additional compounds within the scope of this invention may be prepared using the methods illustrated in these Examples, either alone or in combination with techniques generally known in the art.

Experiments were generally carried out under inert atmosphere (nitrogen or argon), particularly in cases where oxygen- or moisture-sensitive reagents or intermediates were employed. Commercial solvents and reagents were generally used without further purification. Anhydrous solvents were employed where appropriate, generally AcroSeal® products from Acros Organics or DriSolv® products from EMD Chemicals. In other cases, commercial solvents were passed through columns packed with 4 Å molecular sieves, until the following QC standards for water were attained: a) <100 ppm for dichloromethane, toluene, N,N-dimethylformamide and tetrahydrofuran; b)<180 ppm for methanol, ethanol, 1,4-dioxane and diisopropylamine. For very sensitive reactions, solvents were further treated with metallic sodium, calcium hydride or molecular sieves, and distilled just prior to use. Products were generally dried under vacuum before being carried on to further reactions or submitted for biological testing. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed. In some examples, chiral separations were carried out to separate enantiomers or atropisomers (or atropenantiomers) of certain compounds of the invention (in some examples, the separated atropisomers are designated as ENT-1 and ENT-2, according to their order of elution). In some examples, the optical rotation of an enantiomer or atropisomer was measured using a polarimeter. According to its observed rotation data (or its specific rotation data), an enantiomer or atropisomer (or atropenantiomer) with a clockwise rotation was designated as the (+)-enantiomer or (+)-atropisomer [or the (+) atropenantiomer] and an enantiomer or atropisomer (or atropenantiomer) with a counter-clockwise rotation was designated as the (−)-enantiomer or (−)-atropisomer [or the (−) atropenantiomer].

Reactions proceeding through detectable intermediates were generally followed by LCMS, and allowed to proceed to full conversion prior to addition of subsequent reagents. For syntheses referencing procedures in other Examples or Methods, reaction conditions (reaction time and temperature) may vary. In general, reactions were followed by thin layer chromatography or mass spectrometry, and subjected to work-up when appropriate. Purifications may vary between experiments: in general, solvents and the solvent ratios used for eluents/gradients were chosen to provide appropriate $R_f$s or retention times.

Example 1

4-[4-(4,6-Dimethylpyrimidin-5-yl)-3-methylphenoxy]furo[2,3-d]pyrimidine (1)

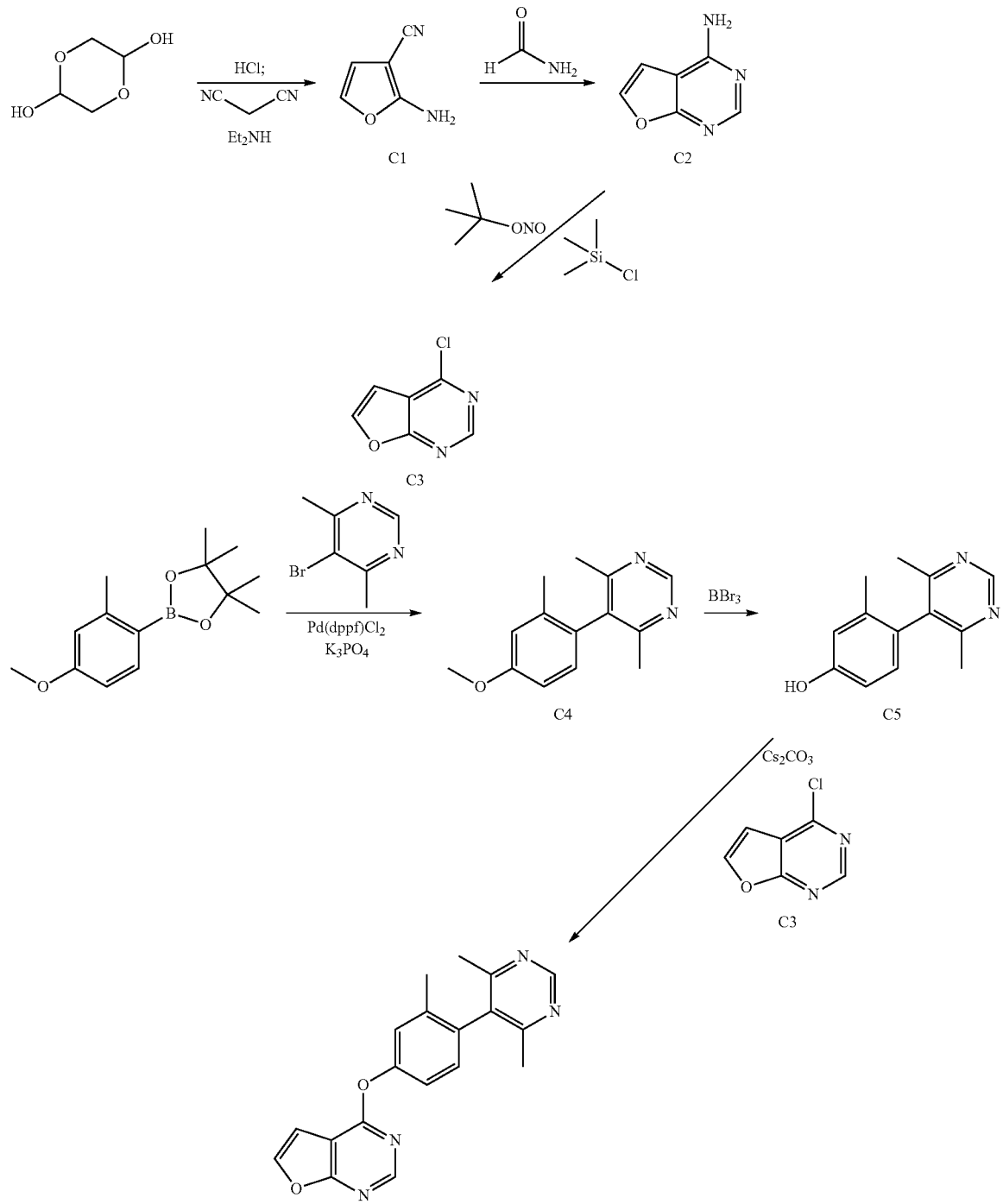

Step 1. Synthesis of 2-aminofuran-3-carbonitrile (C1)

1,4-Dioxane-2,5-diol (hydroxyacetaldehyde dimer, 5 g, 40 mmol) was dissolved in water (5 mL), treated with aqueous hydrochloric acid (0.1 M, 15 mL), and allowed to stir for 18 hours. Malononitrile (4.72 mL, 74.9 mmol) was added drop-wise, followed by the addition of diethylamine (7.72 mL, 74.9 mmol) drop-wise. The reaction mixture was stirred at room temperature for 3 hours and was then quenched with saturated aqueous sodium bicarbonate solution. The mixture was extracted with ethyl acetate, and the combined organic layers were dried over magnesium sulfate. After removal of solvent in vacuo, the residue was purified by silica gel chromatography (Gradient: 20% to 40% ethyl acetate in heptane) to provide the product as a yellow solid. Yield: 3.22 g, 28 mmol, 70%. LCMS m/z 108.8 [M+H]$^+$. $^1$H NMR (400 MHz, CDCl$_3$) δ 6.72 (d, J=2.1 Hz, 1H), 6.29 (d, J=2.3 Hz, 1H), 4.72 (br s, 2H).

Step 2. Synthesis of furo[2,3-d]pyrimidin-4-amine (C2)

Compound C1 (100 mg, 0.925 mmol) was dissolved in formamide (2 mL) and the reaction mixture was heated at 120° C. overnight. The reaction mixture was cooled to room temperature and partitioned between water and ethyl acetate. The aqueous layer was extracted with ethyl acetate and dichloromethane. The combined organic layers were dried over magnesium sulfate, filtered, and concentrated in vacuo to afford the product as a yellow solid. Yield: 21 mg, 0.16 mmol, 17%. LCMS m/z 135.9 [M+H]$^+$. $^1$H NMR (400 MHz, CD$_3$OD) δ 8.13 (s, 1H), 7.61 (d, J=2.5 Hz, 1H), 6.89 (d, J=2.5 Hz, 1H).

Step 3. Synthesis of 4-chlorofuro[2,3-d]pyrimidine (C3)

A mixture of C2 (660 mg, 4.88 mmol), tert-butyl nitrite (12.1 mL, 97.7 mmol), and trimethylsilyl chloride (3.12 mL, 24.4 mmol) in acetonitrile (20 mL) was stirred at 50° C. for 1 hour. The reaction was cooled to room temperature and quenched with aqueous sodium hydroxide solution (2 M, 30 mL). The aqueous layer was extracted with ethyl acetate (3×50 mL), and the combined organic layers were dried over sodium sulfate. The solvent was removed in vacuo and the residue was purified via chromatography on silica gel (Gradient: 0% to 30% ethyl acetate in heptane) to provide the product as a volatile white solid. Yield: 168 mg, 1.09 mmol, 22%. LCMS m/z 154.8 [M+H]+. $^1$H NMR (400 MHz, CDCl$_3$) δ 8.77 (s, 1H), 7.76 (d, J=0.8 Hz, 1H), 7.25 (d, J=0.8 Hz, 1H).

Step 4. Synthesis of 5-(4-methoxy-2-methylphenyl)-4,6-dimethylpyrimidine (C4)

[1,1'-Bis(diphenylphosphino)ferrocene]dichloropalladium(II)-dichloromethane complex (5 g, 6 mmol) was added to a degassed mixture of 2-(4-methoxy-2-methylphenyl)-4,4,5,5-tetramethyl-1,3,2-dioxaborolane (30 g, 120 mmol), 5-bromo-4,6-dimethylpyrimidine (22.5 g, 120 mmol), and potassium phosphate (76.3 g, 359 mmol) in 1,4-dioxane (300 mL) and water (150 mL). The reaction mixture was heated at reflux for 4 hours, whereupon it was filtered and concentrated in vacuo. Purification via silica gel chromatography (Gradient: ethyl acetate in petroleum ether) provided the product as a brown solid. Yield: 25 g, 110 mmol, 92%. LCMS m/z 229.3 [M+H]$^+$. $^1$H NMR (300 MHz, CDCl$_3$) δ 8.95 (s, 1H), 6.94 (d, J=8.2 Hz, 1H), 6.87-6.89 (m, 1H), 6.84 (dd, J=8.3, 2.5 Hz, 1H), 3.86 (s, 3H), 2.21 (s, 6H), 1.99 (s, 3H).

Step 5. Synthesis of 4-(4,6-dimethylpyrimidin-5-yl)-3-methylphenol (C5)

Boron tribromide (3.8 mL, 40 mmol) was added drop-wise to a solution of C4 (3.0 g, 13 mmol) in dichloromethane (150 mL) at −70° C. The reaction mixture was stirred at room temperature for 16 hours, then adjusted to pH 8 with saturated aqueous sodium bicarbonate solution. The aqueous layer was extracted with dichloromethane (3×200 mL), and the combined organic layers were dried over sodium sulfate, filtered, and concentrated in vacuo. Silica gel chromatography (Gradient: 60% to 90% ethyl acetate in petroleum ether) afforded the product as a yellow solid. Yield: 1.2 g, 5.6 mmol, 43%. LCMS m/z 215.0 [M+H$^+$]. $^1$H NMR (400 MHz, CDCl$_3$) δ 8.98 (s, 1H), 6.89 (d, J=8.0 Hz, 1H), 6.86 (d, J=2.3 Hz, 1H), 6.80 (dd, J=8.3, 2.5 Hz, 1H), 2.24 (s, 6H), 1.96 (s, 3H).

Step 6. Synthesis of 4-[4-(4,6-dimethylpyrimidin-5-yl)-3-methylphenoxy]furo[2,3-d]pyrimidine (1)

To a stirred solution of C3 (33 mg, 0.21 mmol) in dimethyl sulfoxide (1 mL) was added C5 (45 mg, 0.21 mmol) and cesium carbonate (205 mg, 0.63 mmol). The 5 reaction mixture was stirred at 120° C. for 3 hours, then was cooled to room temperature. The reaction mixture was partitioned between ethyl acetate and water, and the aqueous layer was extracted twice with ethyl acetate. The organic layers were combined and dried over magnesium sulfate. The solvent was removed in vacuo and the residue was purified via silica gel chromatography (Gradient: 0% to 40% [80:20:1 dichloromethane/methanol/concentrated ammonium hydroxide] in dichloromethane) to provide the product as a pale yellow solid. Yield: 30 mg, 0.09 mmol, 43%. LCMS m/z 333.1 [M+H]$^+$. $^1$H NMR (400 MHz, CDCl$_3$) δ 8.96 (s, 1H), 8.55 (s, 1H), 7.76 (d, J=2.3 Hz, 1H), 7.19 (m, 1H), 7.10 (m, 1H), 6.79 (d, J=2.5 Hz, 1H), 2.24 (s, 6H), 2.03 (s, 3H), 1.51 (s, 3H).

Example 2
4-[3-Methyl-4-(6-methylimidazo[1,2-a]pyrazin-5-yl)phenoxy]-1H-imidazo[4,5-c]pyridine (2)
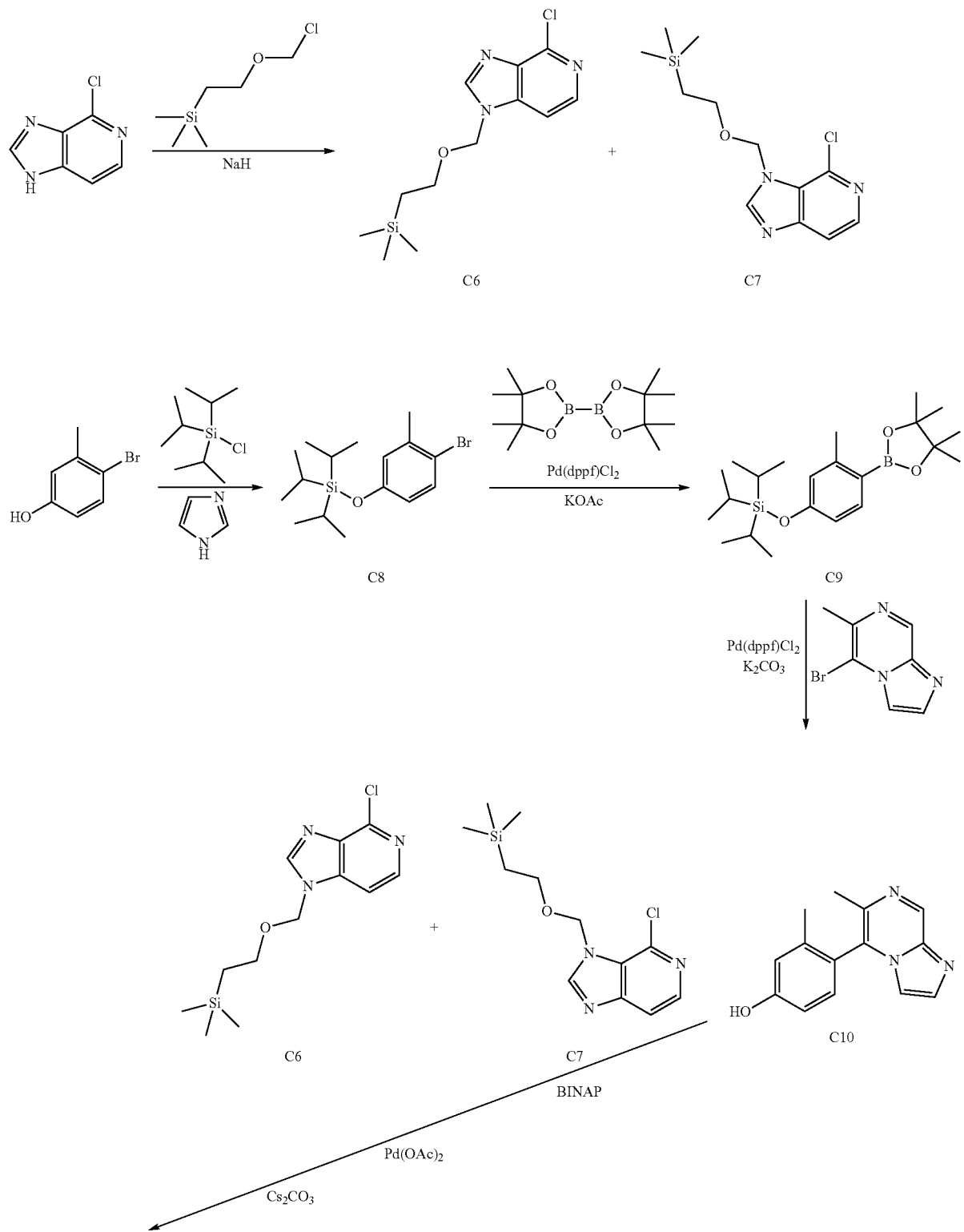

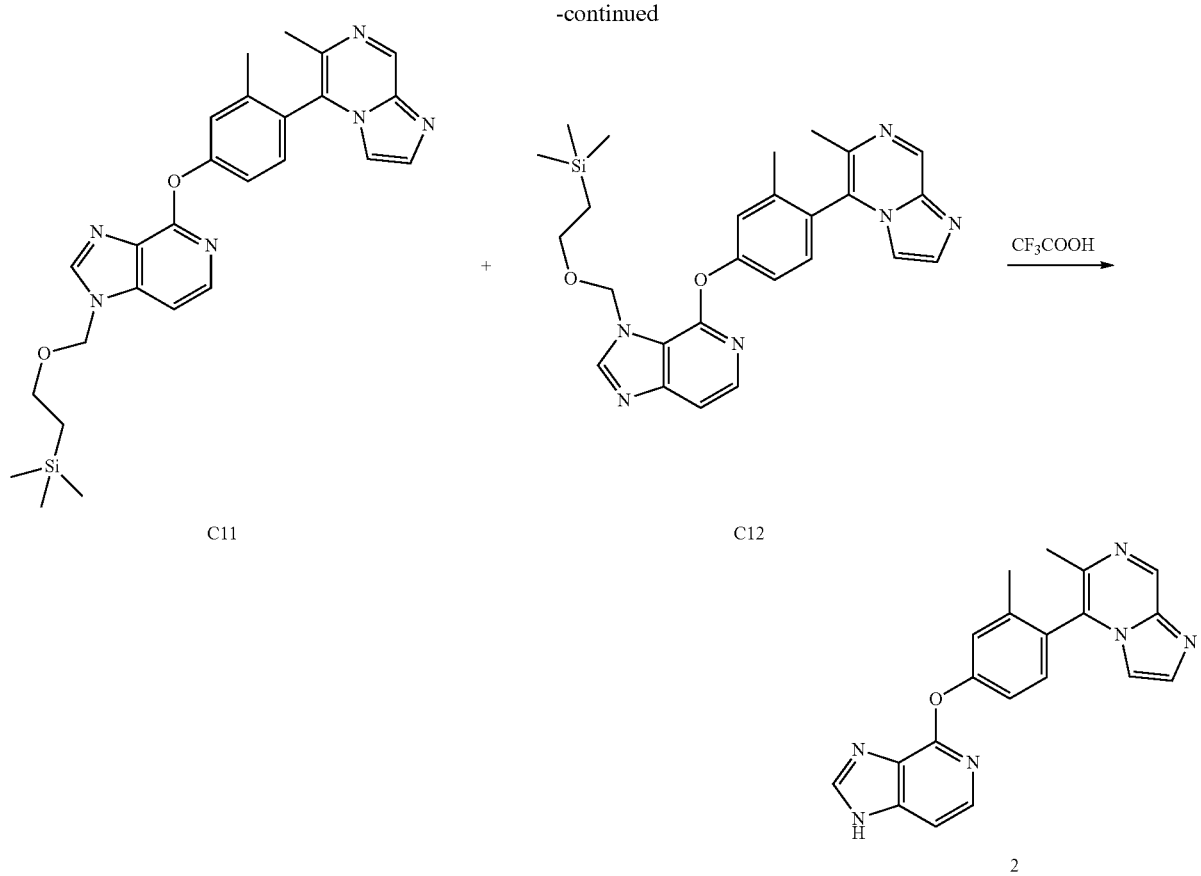

Step 1. Synthesis of 4-chloro-1-((2-(trimethylsilyl)ethoxy)methyl)-1H-imidazo[4,5-c]pyridine (C6) and 4-chloro-3-{[2-(trimethylsilyl)ethoxy]methyl}-3H-imidazo[4,5-c]pyridine (C7)

To a solution of 4-chloro-1H-imidazo[4,5-c]pyridine (4.64 g, 30.2 mmol) in tetrahydrofuran (200 mL) was added sodium hydride (1.57 g, 39.3 mmol) at 0° C. The reaction mixture was stirred for 45 minutes at 0° C., whereupon 2-(trimethylsilyl)ethoxymethyl chloride (6.55 g, 39.3 mmol) was added. Stirring was continued for 2 hours at 0° C., at which time the reaction mixture was quenched with saturated aqueous ammonium chloride solution and then extracted with dichloromethane (3×50 mL). The combined organic layers were dried over sodium sulfate and concentrated in vacuo to give a residue, which was purified by silica gel chromatography to afford a mixture of C6 and C7. Yield: 7.0 g, 24 mmol, 80%. $^1$H NMR (400 MHz, CDCl$_3$) δ 8.25 (t, J=5.1 Hz, 2H), 8.18 (s, 1H), 8.12 (s, 1H), 7.71 (d, J=5.6 Hz, 1H), 7.48 (d, J=5.6 Hz, 1H), 5.89 (s, 2H), 5.59 (s, 2H), 3.65 (t, J=8.0 Hz, 2H), 3.55 (t, J=8.0 Hz, 2H), 0.97 (m, 4H), 0.01 (s, 9H), 0.00 (s, 9H).

Step 2. Synthesis of (4-bromo-3-methylphenoxy)[tri(propan-2-yl)]silane (C8)

To a solution of 4-bromo-3-methylphenol (70 g, 0.374 mol) and 1H-imidazole (51.52 g, 0.748 mol) in N,N-dimethylformamide (420 mL) was added tri(propan-2-yl)silyl chloride (88 mL, 0.41 mol) drop-wise. The reaction mixture was stirred at room temperature overnight, then poured into water (1.5 L) and extracted with heptane (1.2 L). The organic layer was washed with water (1 L) and with saturated aqueous sodium chloride solution (400 mL), and dried over magnesium sulfate. The solvent was removed in vacuo to provide the product as a yellow oil. Yield: 137 g, 0.37 mmol, 100% yield. $^1$H NMR (400 MHz, CDCl$_3$) δ 7.32 (d, J=8.7 Hz, 1H), 6.76 (d, J=2.7 Hz, 1H), 6.64 (dd, J=8.5, 2.7 Hz, 1H), 2.32 (s, 3H), 1.22 (m, 3H), 1.09 (d, J=8.0 Hz, 18H).

Step 3. Synthesis of [3-methyl-4-(4,4,5,5-tetramethyl-1,3,2-dioxaborolan-2-yl)phenoxy][tri(propan-2-yl)]silane (C9)

To a degassed solution of C8 (137 g, 0.374 mol), 4,4,4',4',5,5,5',5'-octamethyl-2,2'-bi-1,3,2-dioxaborolane (190 g, 0.748 mol) and potassium acetate (147 g, 1.49 mol) in 1,4-dioxane (1.3 L) was added [1,1'-bis(diphenylphosphino)ferrocene]dichloropalladium(II) (12.2 g, 15 mmol), and the reaction mixture was heated at reflux overnight. The reaction mixture was filtered through diatomaceous earth, washing with ethyl acetate, and concentrated in vacuo. Silica gel chromatography (Gradient: 0% to 3% ethyl acetate in heptane) afforded the product as a yellow oil. Yield: 131 g, 0.34 mmol, 90%. $^1$H NMR (400 MHz, CDCl$_3$) δ 7.62 (d, J=7.8 Hz, 1H), 6.65 (m, 2H), 2.47 (s, 3H), 1.31 (s, 12H), 1.27 (m, 1H), 1.08 (d, J=8.0 Hz, 18H).

Step 4. Synthesis of 3-methyl-4-(6-methylimidazo[1,2-a]pyrazin-5-yl) phenol (C10)

Water (17 μL, 0.94 mmol) was added to a suspension of 5-bromo-6-methylimidazo[1,2-a]pyrazine (see A. R. Harris et al., *Tetrahedron* 2011, 67, 9063-9066) (100 mg, 0.472 mmol), C9 (368 mg, 0.943 mmol), [1,1'-bis(diphenylphosphino)ferrocene]dichloropalladium(II) (35 mg, 47 µmol) and potassium carbonate (130 mg, 0.943 mmol) in degassed 1,2-dimethoxyethane (2 mL). The reaction mixture was heated at reflux for 24 hours, then filtered through neutral diatomaceous earth, washing with acetone (20 mL). The solvent was removed in vacuo and the residue was purified by silica gel chromatography (Gradient: 0% to 10% methanol in ethyl acetate) to afford the product as a pale pink solid. Yield: 114 mg, 0.47 mmol, quantitative yield. $^1$H NMR (400 MHz, CD$_3$OD) δ 8.94 (s, 1H), 7.72 (d, J=1.4 Hz, 1H), 7.23 (s, 1H), 7.13 (d, J=8.2 Hz, 1H), 6.89 (d, J=2.7 Hz, 1H), 6.83 (dd, J=8.2, 2.3 Hz, 1H), 2.29 (s, 3H), 1.94 (s, 3H).

Step 5. Synthesis of 4-[3-methyl-4-(6-methylimidazo[1,2-a]pyrazin-5-yl)phenoxy]-1-{[2-(trimethylsilyl)ethoxy]methyl}-1H-imidazo[4,5-c]pyridine (C11) and 4-[3-methyl-4-(6-methylimidazo[1,2-a]pyrazin-5-yl)phenoxy]-3-{[2-(trimethylsilyl)ethoxy]methyl}-3H-imidazo[4,5-c]pyridine (C12)

To a solution of a mixture of C6 and C7 (100 mg, 0.35 mmol) in 1,4-dioxane (5 mL) were added C10 (84 mg, 0.35 mmol), 1,1'-binaphthalene-2,2'-diylbis(diphenylphosphane) (BINAP, 43.5 mg, 0.07 mmol), cesium carbonate (341 mg, 1.05 mmol), and palladium(II) acetate (7.84 mg, 35 µmol) at room temperature. The reaction mixture was degassed with nitrogen for 5 minutes and then heated to 120° C. for 4 hours. After cooling to room temperature, it was filtered through a pad of diatomaceous earth. The filtrate was concentrated in vacuo to provide the crude product (350 mg), which was used in the next step without further purification.

Step 6. Synthesis of 4-[3-methyl-4-(6-methylimidazo[1,2-a]pyrazin-5-yl)phenoxy]-1H-imidazo[4,5-c]pyridine (2)

To a mixture of C11 and C12 (from the previous step, 350 mg) was added trifluoroacetic acid (8 mL) at room temperature. The reaction mixture was stirred for 1 hour at 80° C. and was then concentrated in vacuo and purified by preparative HPLC to give the product. Yield: 46 mg, 0.13 mmol, 37% over two steps. LCMS m/z 357.0 [M+H]$^+$. $^1$H NMR (400 MHz, CD$_3$OD) 9.03 (s, 1H), 8.39 (s, 1H), 7.93 (d, J=5.8 Hz, 1H), 7.81 (d, J=1.0 Hz, 1H), 7.54 (s, 1H), 7.45 (m, 2H), 7.39 (s, 1H), 7.31 (dd, J=8.0, 1.8 Hz, 1H), 2.40 (s, 3H), 2.09 (s, 3H).

Examples 3, 4, and 5

6-[4-(Furo[2,3-d]pyrimidin-4-yloxy)-2-methylphenyl]-1,5-dimethylpyrazin-2(1H)-one (3), (−)-6-[4-(Furo[2,3-d]pyrimidin-4-yloxy)-2-methylphenyl]-1,5-dimethylpyrazin-2(1H)-one (4), and (+)-6-[4-(Furo[2,3-d]pyrimidin-4-yloxy)-2-methylphenyl]-1,5-dimethylpyrazin-2(1H)-one (5)

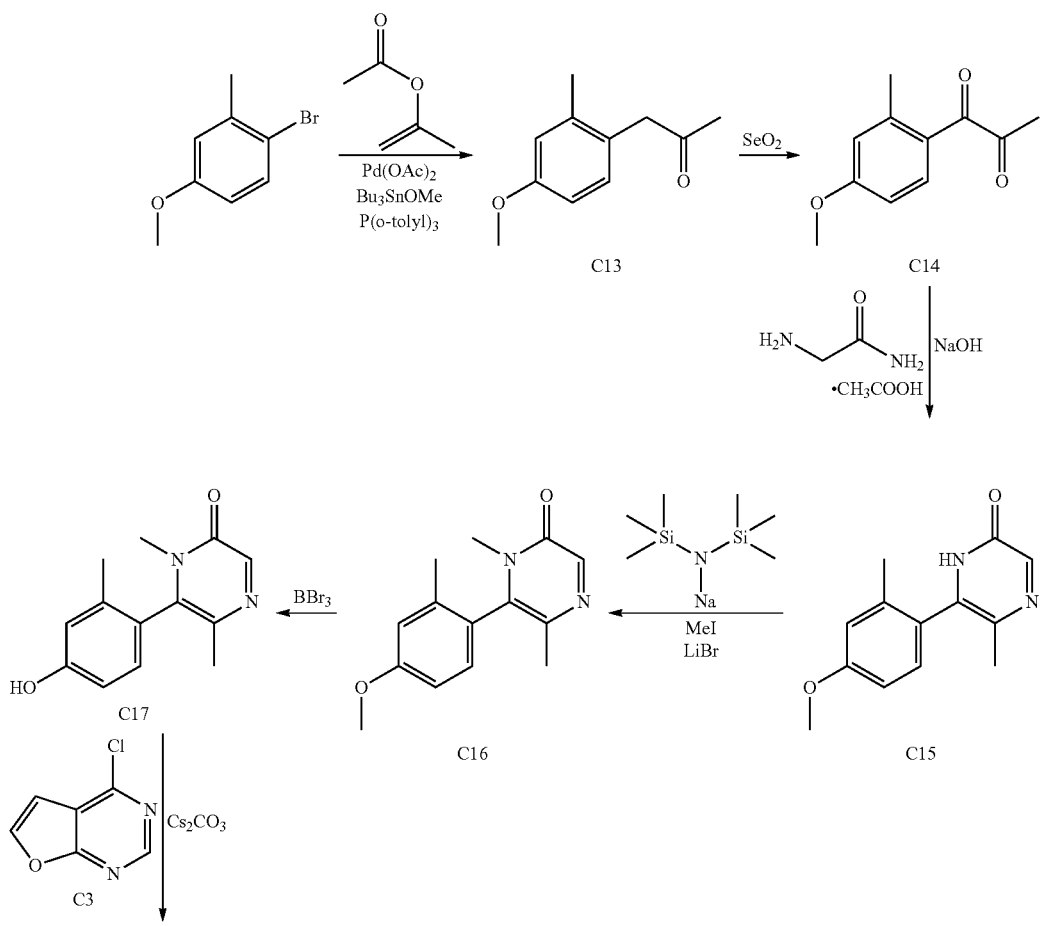

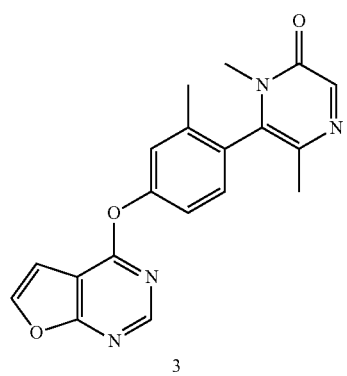
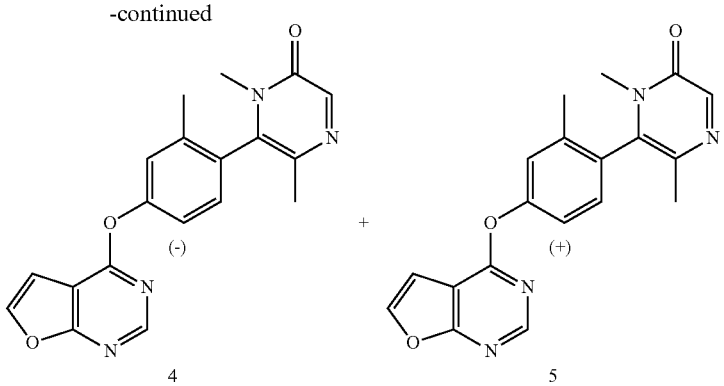

Step 1. Synthesis of 1-(4-methoxy-2-methylphenyl)propan-2-one (C13)

This experiment was carried out four times. Tributyl (methoxy)stannane (400 g, 1.24 mol), 1-bromo-4-methoxy-2-methylbenzene (250 g, 1.24 mol), prop-1-en-2-yl acetate (187 g, 1.87 mol), palladium(II) acetate (7.5 g, 33 mmol) and tri-o-tolylphosphine (10 g, 33 mmol) were stirred together in toluene (2 L) at 100° C. for 18 hours. After it had cooled to room temperature, the reaction mixture was treated with aqueous potassium fluoride solution (4 M, 400 mL) and stirred for 2 hours at 40° C. The resulting mixture was diluted with toluene (500 mL) and filtered through diatomaceous earth; the filter pad was thoroughly washed with ethyl acetate (2×1.5 L). The organic phase from the combined filtrates was dried over sodium sulfate, filtered, and concentrated in vacuo. Purification via silica gel chromatography (Gradient: 0% to 5% ethyl acetate in petroleum ether) provided the product as a yellow oil. Combined yield: 602 g, 3.38 mol, 68%. LCMS m/z 179.0 [M+H]$^+$. $^1$H NMR (400 MHz, CDCl$_3$) δ 7.05 (d, J=8.3 Hz, 1H), 6.70-6.77 (m, 2H), 3.79 (s, 3H), 3.65 (s, 2H), 2.22 (s, 3H), 2.14 (s, 3H).

Step 2. Synthesis of 1-(4-methoxy-2-methylphenyl)propane-1,2-dione (C14)

Compound C13 (6.00 g, 33.7 mmol) and selenium dioxide (7.47 g, 67.3 mmol) were suspended in 1,4-dioxane (50 mL) and heated at 100° C. for 18 hours. The reaction mixture was cooled to room temperature and filtered through diatomaceous earth; the filtrate was concentrated in vacuo. Silica gel chromatography (Eluent: 10% ethyl acetate in heptane) afforded the product as a bright yellow oil. Yield: 2.55 g, 13.3 mmol, 39%. LCMS m/z 193.1 [M+H]$^+$. $^1$H NMR (400 MHz, CDCl$_3$) δ 7.66 (d, J=8.6 Hz, 1H), 6.81 (br d, half of AB quartet, J=2.5 Hz, 1H), 6.78 (br dd, half of ABX pattern, J=8.7, 2.6 Hz, 1H), 3.87 (s, 3H), 2.60 (br s, 3H), 2.51 (s, 3H).

Step 3. Synthesis of 6-(4-methoxy-2-methylphenyl)-5-methylpyrazin-2(1H)-one (C15)

Compound C14 (4.0 g, 21 mmol) and glycinamide acetate (2.79 g, 20.8 mmol) were dissolved in methanol (40 mL) and cooled to −10° C. Aqueous sodium hydroxide solution (12 N, 3.5 mL, 42 mmol) was added, and the resulting mixture was slowly warmed to room temperature. After stirring for 3 days, the reaction mixture was concentrated in vacuo. The residue was diluted with water, and 1 M aqueous hydrochloric acid was added until the pH was approximately 7. The aqueous phase was extracted with ethyl acetate, and the combined organic extracts were washed with saturated aqueous sodium chloride solution, dried over magnesium sulfate, filtered, and concentrated under reduced pressure. The resulting residue was slurried with 3:1 ethyl acetate/heptane, stirred for 5 minutes, filtered, and concentrated in vacuo. Silica gel chromatography (Eluent: ethyl acetate) provided the product as a tan solid that contained 15% of an undesired regioisomer; this material was used without further purification. Yield: 2.0 g. LCMS m/z 231.1 [M+H]$^+$. $^1$H NMR (400 MHz, CDCl$_3$) δ 8.09 (s, 1H), 7.14 (d, J=8.2 Hz, 1H), 6.82-6.87 (m, 2H), 3.86 (s, 3H), 2.20 (s, 3H), 2.11 (s, 3H).

Step 4. Synthesis of 6-(4-methoxy-2-methylphenyl)-1,5-dimethylpyrazin-2(1H)-one (C16)

Compound C15 (from the previous step, 1.9 g) was dissolved in N,N-dimethylformamide (40 mL). Lithium bromide (0.86 g, 9.9 mmol) and sodium bis(trimethylsilyl)amide (95%, 1.91 g, 9.89 mmol) were added, and the resulting solution was stirred for 30 minutes. Methyl iodide (0.635 mL, 10.2 mmol) was added and stirring was continued at room temperature for 18 hours. The reaction mixture was then diluted with water and brought to a pH of approximately 7 by slow portion-wise addition of 1 M aqueous hydrochloric acid. The aqueous layer was extracted with ethyl acetate and the combined organic layers were washed several times with water, dried over magnesium sulfate, filtered, and concentrated. Silica gel chromatography (Gradient: 75% to 100% ethyl acetate in heptane) afforded the product as a viscous orange oil. Yield: 1.67 g, 6.84 mmol, 33% over two steps. LCMS m/z 245.1 [M+H]$^+$. $^1$H NMR (400 MHz, CDCl$_3$) δ 8.17 (s, 1H), 7.03 (br d, J=8 Hz, 1H), 6.85-6.90 (m, 2H), 3.86 (s, 3H), 3.18 (s, 3H), 2.08 (br s, 3H), 2.00 (s, 3H).

Step 5. Synthesis of 6-(4-hydroxy-2-methylphenyl)-1,5-dimethylpyrazin-2(1H)-one (C17)

To a −78° C. solution of C16 (1.8 g, 7.4 mmol) in dichloromethane (40 mL) was added a solution of boron tribromide in dichloromethane (1 M, 22 mL, 22 mmol). The cooling bath was removed after 30 minutes, and the reaction mixture was allowed to warm to room temperature and stir for 18 hours. The reaction was cooled to −78° C., and methanol (10 mL) was slowly added; the resulting mixture was gradually warmed to room temperature. After the solvent had been removed in vacuo, methanol (20 mL) was added, and the mixture was again concentrated under reduced pressure. The residue was diluted with ethyl acetate (300 mL) and water (200 mL), the aqueous layer was brought to pH 7 via portion-wise addition of saturated aqueous sodium carbonate solution, and the mixture was extracted with ethyl acetate (3×200 mL). The combined organic layers were washed with water and with saturated aqueous sodium chloride solution, dried over magnesium sulfate, filtered, and concentrated in vacuo to afford the product as a light tan solid. Yield: 1.4 g, 6.0 mmol, 81%. LCMS m/z 231.1 [M+H]$^+$. $^1$H NMR (400 MHz, CDCl$_3$) δ 8.21 (s, 1H), 6.98 (d, J=8.2 Hz, 1H), 6.87-6.89 (m, 1H), 6.85 (br dd, J=8.2, 2.5 Hz, 1H), 3.22 (s, 3H), 2.06 (br s, 3H), 2.03 (s, 3H).

Step 6. Synthesis of 6-[4-(furo[2,3-d]pyrimidin-4-yloxy)-2-methylphenyl]-1,5-dimethylpyrazin-2(1H)-one (3), (−)-6-[4-(furo[2,3-d]pyrimidin-4-yloxy)-2-methylphenyl]-1,5-dimethylpyrazin-2(1H)-one (4), and (+)-6-[4-(furo[2,3-d]pyrimidin-4-yloxy)-2-methylphenyl]-1,5-dimethylpyrazin-2(1H)-one (5)

To a stirred solution of C3 (60 mg, 0.39 mmol) in dimethyl sulfoxide (2 mL) was added C17 (121 mg, 0.39 mmol) and cesium carbonate (379 mg, 1.16 mmol). The reaction mixture was stirred at 120° C. for 3 hours, cooled to room temperature, and partitioned between ethyl acetate and water. The aqueous layer was extracted three times with ethyl acetate, and the combined organic layers were washed sequentially with water and with saturated aqueous sodium chloride solution, then dried over sodium sulfate. The solvent was removed in vacuo and the residue was purified via silica gel chromatography (Gradient: 0% to 30% [80:20:1 dichloromethane/methanol/concentrated ammonium hydroxide] in dichloromethane) to provide product 3, a mixture of atropenantiomers, as a light yellow foam. Yield: 108 mg, 0.31 mmol, 80%. LCMS m/z 349.1 [M+H]$^+$. $^1$H NMR (400 MHz, CDCl$_3$) δ 8.58 (s, 1H), 8.22 (s, 1H), 7.72 (d, J=2.5 Hz, 1H), 7.18-7.35 (m, 3H), 6.91 (d, J=2.4 Hz, 1H), 3.26 (s, 3H), 2.18 (s, 3H), 2.08 (s, 3H).

Compound Example 3 was separated into its atropenantiomers via supercritical fluid chromatography Column: Chiral Technologies Chiralcel OJ-H, 5 μm; Eluent: 3:1 carbon dioxide/2-propanol). Example 4 [designated the (−)-atropenantiomer according to its observed rotation data] was the first-eluting isomer, followed by Example 5. Example 5 was designated the (+)-atropenantiomer according to its observed rotation data.

4: LCMS m/z 349.1 [M+H]$^+$. $^1$H NMR (400 MHz, CD$_3$OD) δ 8.49 (s, 1H), 8.11 (s, 1H), 7.96 (d, J=2.5 Hz, 1H), 7.36-7.41 (m, 2H), 7.33 (br dd, half of ABX pattern, J=8, 2 Hz, 1H), 7.00 (d, J=2.5 Hz, 1H), 3.27 (s, 3H), 2.18 (s, 3H), 2.06 (s, 3H). 5: LCMS m/z 349.1 [M+H]$^+$. $^1$H NMR (400 MHz, CD$_3$OD) δ 8.49 (s, 1H), 8.11 (s, 1H), 7.96 (d, J=2.5 Hz, 1H), 7.36-7.41 (m, 2H), 7.33 (br dd, half of ABX pattern, J=8, 2 Hz, 1H), 7.00 (d, J=2.5 Hz, 1H), 3.27 (s, 3H), 2.18 (s, 3H), 2.06 (s, 3H).

Examples 6, 7, and 8

5-[4-(Furo[2,3-d]pyrimidin-4-yloxy)-2-methylphenyl]-4,6-dimethylpyridazin-3(2H)-one (6), (+)-5-[4-(Furo[2,3-d]pyrimidin-4-yloxy)-2-methylphenyl]-4,6-dimethylpyridazin-3(2H)-one (7), and (−)-5-[4-(Furo[2,3-d]pyrimidin-4-yloxy)-2-methylphenyl]-4,6-dimethylpyridazin-3(2H)-one (8)

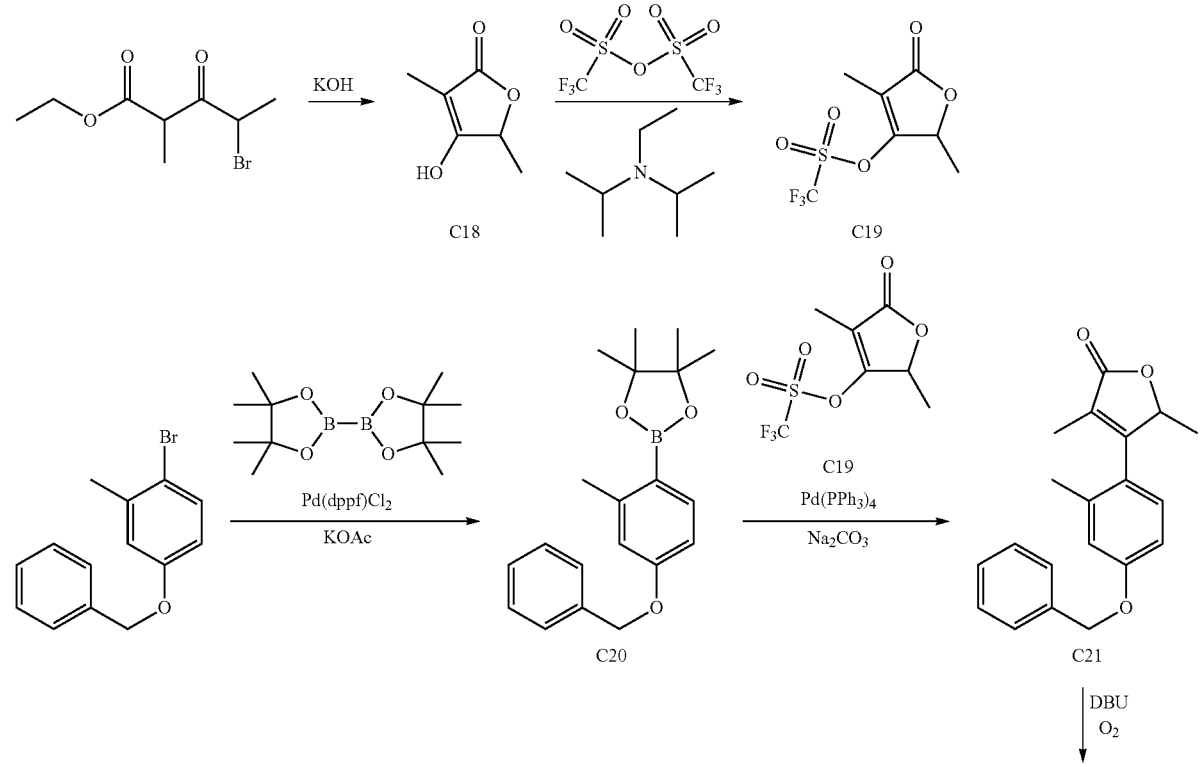

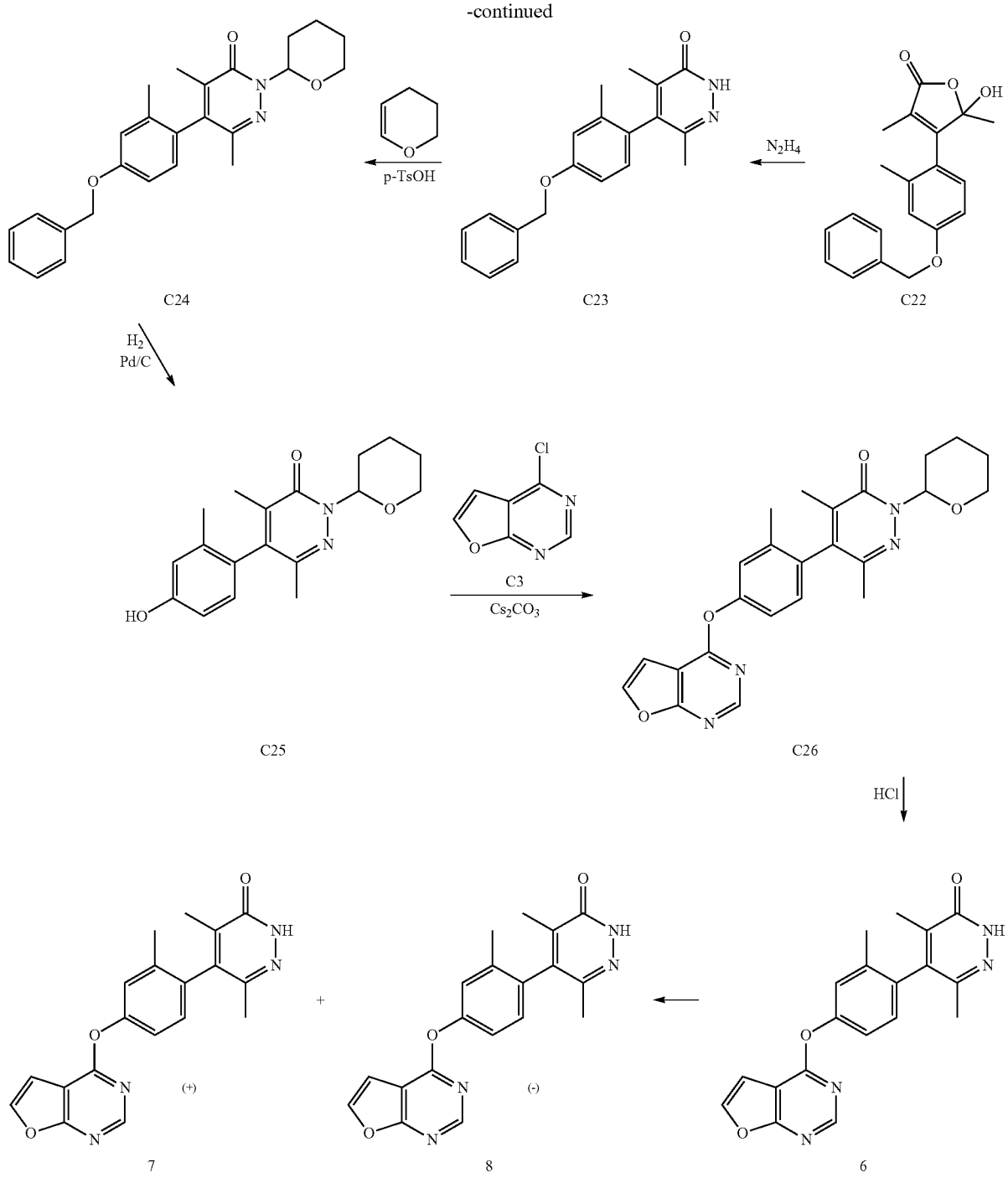

Step 1. Synthesis of
4-hydroxy-3,5-dimethylfuran-2(5H)-one (C18)

Methylation of ethyl 3-oxopentanoate according to the method of D. Kalaitzakis et al., *Tetrahedron: Asymmetry* 2007, 18, 2418-2426, afforded ethyl 2-methyl-3-oxopentanoate; subsequent treatment with 1 equivalent of bromine in chloroform provided ethyl 4-bromo-2-methyl-3-oxopentanoate. This crude material (139 g, 586 mmol) was slowly added to a 0° C. solution of potassium hydroxide (98.7 g, 1.76 mol) in water (700 mL). The internal reaction temperature rose to 30° C. during the addition. The reaction mixture was then subjected to vigorous stirring for 4 hours in an ice bath, at which point it was acidified via slow addition of concentrated hydrochloric acid. After extraction with ethyl acetate, the aqueous layer was saturated with solid sodium chloride and extracted three additional times with ethyl acetate. The combined organic layers were washed with saturated aqueous sodium chloride solution, dried over magnesium sulfate, filtered, and concentrated under reduced pressure to afford a mixture of oil and solid (81.3 g). This material was suspended in chloroform (200 mL); the solids were removed via filtration and washed with chloroform (2×50 mL). The combined filtrates were concentrated in vacuo and treated with a 3:1 mixture of heptane and diethyl ether (300 mL). The mixture was vigorously swirled until some of the oil began to solidify, whereupon it was concentrated under reduced pressure to afford an oily solid (60.2 g). After addition of a 3:1 mixture of heptane and diethyl ether (300 mL) and vigorous stirring for 10 minutes, filtration afforded the product as an off-white solid. Yield: 28.0 g, 219 mmol, 37%. $^1$H NMR (400 MHz, CDCl$_3$) δ 4.84 (br q, J=6.8 Hz, 1H), 1.74 (br s, 3H), 1.50 (d, J=6.8 Hz, 3H).

Step 2. Synthesis of 2,4-dimethyl-5-oxo-2,5-dihydrofuran-3-yl trifluoromethanesulfonate (C19)

Trifluoromethanesulfonic anhydride (23.7 mL, 140 mmol) was added portion-wise to a solution of C18 (15.0 g, 117 mmol) and N,N-diisopropylethylamine (99%, 24.8 mL, 140 mmol) in dichloromethane (500 mL) at −20° C., at a rate sufficient to maintain the internal reaction temperature below −10° C. The reaction mixture was allowed to warm gradually from −20° C. to 0° C. over 5 hours. It was then passed through a plug of silica gel, dried over magnesium sulfate, and concentrated in vacuo. The residue was suspended in diethyl ether and filtered; the filtrate was concentrated under reduced pressure. Purification using silica gel chromatography (Gradient: 0% to 17% ethyl acetate in heptane) afforded the product as a pale yellow oil. Yield: 21.06 g, 80.94 mmol, 69%. $^1$H NMR (400 MHz, CDCl$_3$) δ 5.09-5.16 (m, 1H), 1.94-1.96 (m, 3H), 1.56 (d, J=6.6 Hz, 3H).

Step 3. Synthesis of 2-[4-(benzyloxy)-2-methylphenyl]-4,4,5,5-tetramethyl-1,3,2-dioxaborolane (C20)

A mixture of benzyl 4-bromo-3-methylphenyl ether (19.0 g, 68.6 mmol), [1,1'-bis(diphenylphosphino)ferrocene]dichloropalladium(II) (7.5 g, 10 mmol), potassium acetate (26.9 g, 274 mmol) and 4,4,4',4',5,5,5',5'-octamethyl-2,2'-bi-1,3,2-dioxaborolane (20 g, 79 mmol) in 1,4-dioxane (500 mL) was heated at reflux for 2 hours. The reaction mixture was then filtered through diatomaceous earth, and the filtrate was concentrated in vacuo. Silica gel chromatography (Gradient: 0% to 1% ethyl acetate in petroleum ether) provided the product as a yellow gel. Yield: 15 g, 46 mmol, 67%. $^1$H NMR (400 MHz, CDCl$_3$) δ 7.73 (d, J=8.0 Hz, 1H), 7.30-7.46 (m, 5H), 6.76-6.82 (m, 2H), 5.08 (s, 2H), 2.53 (s, 3H), 1.34 (s, 12H).

Step 4. Synthesis of 4-[4-(benzyloxy)-2-methylphenyl]-3,5-dimethylfuran-2(5H)-one (C21)

Compound C19 (5.0 g, 19 mmol), C20 (7.48 g, 23.1 mmol), tetrakis(triphenylphosphine)palladium(0) (2.22 g, 1.92 mmol), and sodium carbonate (4.07 g, 38.4 mmol) were combined in 1,4-dioxane (100 mL) and water (5 mL), and heated at reflux for 2 hours. The reaction mixture was filtered and the filtrate was concentrated in vacuo. Silica gel chromatography (Eluents: 10:1, then 5:1 petroleum ether/ethyl acetate) provided the product as a white solid. Yield: 5.8 g, 19 mmol, 100%. NMR (400 MHz, CDCl$_3$) δ 7.33-7.49 (m, 5H), 6.98 (d, J=8.5 Hz, 1H), 6.94 (br d, J=2.5 Hz, 1H), 6.88 (br dd, J=8.3, 2.5 Hz, 1H), 5.20 (qq, J=6.7, 1.8 Hz, 1H), 5.09 (s, 2H), 2.21 (s, 3H), 1.78 (d, J=1.8 Hz, 3H), 1.31 (d, J=6.8 Hz, 3H).

Step 5. Synthesis of 4-[4-(benzyloxy)-2-methylphenyl]-5-hydroxy-3,5-dimethylfuran-2(5H)-one (C22)

A solution of C21 (5.4 g, 18 mmol) and 1,8-diazabicyclo[5.4.0]undec-7-ene (13.3 g, 87.4 mmol) in acetonitrile (100 mL) was cooled to −60° C. Oxygen was bubbled into the reaction mixture for 20 minutes at −60° C.; the solution was then stirred at 50° C. for 18 hours. The reaction mixture was concentrated in vacuo and purified via silica gel chromatography (Eluent: 5:1 petroleum ether/ethyl acetate) to provide the product as a colorless oil. Yield: 3.5 g, 11 mmol, 61%. $^1$H NMR (400 MHz, CDCl$_3$), characteristic peaks: δ 7.33-7.49 (m, 5H), 6.92-6.96 (m, 1H), 6.88 (dd, J=8.5, 2.5 Hz, 1H), 5.09 (s, 2H), 2.20 (s, 3H), 1.73 (s, 3H).

Step 6. Synthesis of 5-[4-(benzyloxy)-2-methylphenyl]-4,6-dimethylpyridazin-3(2H)-one (C23)

A mixture of C22 (3.5 g, 11 mmol) and hydrazine hydrate (85% in water, 1.9 g, 32 mmol) in n-butanol (60 mL) was heated at reflux for 18 hours. After removal of volatiles under reduced pressure, the residue was stirred with ethyl acetate (20 mL) for 30 minutes, whereupon filtration provided the product as a white solid. Yield: 2.0 g, 6.2 mmol, 56%. $^1$H NMR (400 MHz, CDCl$_3$) δ 10.93 (br s, 1H), 7.33-7.51 (m, 5H), 6.96 (s, 1H), 6.88-6.94 (m, 2H), 5.10 (s, 2H), 2.04 (s, 3H), 1.95 (s, 3H), 1.91 (s, 3H).

Step 7. Synthesis of 5-[4-(benzyloxy)-2-methylphenyl]-4,6-dimethyl-2-(tetrahydro-2H-pyran-2-yl)pyridazin-3(2H)-one (C24)

A mixture of C23 (17.8 g, 55.6 mmol), 3,4-dihydro-2H-pyran (233 g, 2.77 mol) and p-toluenesulfonic acid monohydrate (2.1 g, 11 mmol) in tetrahydrofuran (800 mL) was heated at reflux for 18 hours. Triethylamine (10 mL, 72 mmol) was added, and the mixture was concentrated in vacuo. Silica gel chromatography (Gradient: 0% to 25% ethyl acetate in petroleum ether) afforded the product as a solid, presumed to be a mixture of diastereomeric atropisomers from its $^1$H NMR spectrum. Yield: 20 g, 49 mmol, 88%. $^1$H NMR (400 MHz, CDCl$_3$), characteristic peaks: δ 7.32-7.50 (m, 5H), 6.82-6.96 (m, 3H), 6.15 (br d, J=10.3 Hz, 1H), 5.08 (s, 2H), 4.14-4.23 (m, 1H), 3.76-3.85 (m, 1H), 2.28-2.41 (m, 1H), 2.01 and 2.04 (2 s, total 3H), 1.97 and 1.98 (2 s, total 3H), 1.89 and 1.89 (2 s, total 3H).

Step 8. Synthesis of 5-(4-hydroxy-2-methylphenyl)-4,6-dimethyl-2-(tetrahydro-2H-pyran-2-yl)pyridazin-3(2H)-one (C25)

Palladium (10% on carbon, 1.16 g, 1.09 mmol) was added to a solution of C24 (1.47 g, 3.63 mmol) in methanol (30 mL) and ethyl acetate (10 mL), and the mixture was hydrogenated (50 psi) on a Parr shaker for 18 hours at room temperature. The reaction mixture was filtered through diatomaceous earth, and the filter pad was rinsed with ethyl acetate; the combined filtrates were concentrated in vacuo and triturated with heptane, affording the product as a white solid, judged to be a mixture of diastereomeric atropisomers from its 1H NMR spectrum. Yield: 1.01 g, 3.21 mmol, 88%. $^1$H NMR (400 MHz, CDCl$_3$), characteristic peaks: δ 6.74-6.85 (m, 3H), 6.12-6.17 (m, 1H), 4.15-4.23 (m, 1H), 3.76-

3.84 (m, 1H), 2.28-2.41 (m, 1H), 1.99 and 2.01 (2 s, total 3H), 1.97 and 1.98 (2 s, total 3H), 1.89 and 1.89 (2 s, total 3H).

Step 9. Synthesis of 5-(4-(furo[2,3-d]pyrimidin-4-yloxy)-2-methylphenyl)-4,6-dimethyl-2-(tetrahydro-2H-pyran-2-yl)pyridazin-3(2H)-one (C26)

To a resealable pressure tube were added C3 (38.9 mg, 0.25 mmol), C25 (66 mg, 0.21 mmol), cesium carbonate (205 mg, 0.63 mmol) and dimethyl sulfoxide (15 mL). The reaction mixture was heated to 120° C. for 6 hours, then cooled to room temperature and diluted with ethyl acetate. The mixture was washed sequentially with water and with saturated aqueous sodium chloride solution, then dried over magnesium sulfate. The solvent was removed in vacuo and the residue was used in the next step without further purification. LCMS m/z 433.1 [M+H]+.

Step 10. Synthesis of 5-[4-(furo[2,3-d]pyrimidin-4-yloxy)-2-methylphenyl]-4,6-dimethylpyridazin-3(2H)-one (6)

To a solution of C26 (from the previous step, <0.21 mmol) in dichloromethane was added a solution of hydrogen chloride in 1,4-dioxane (4 M, 1.61 mL, 6.45 mmol). The reaction mixture was stirred at room temperature overnight, whereupon it was partitioned between ethyl acetate and saturated aqueous sodium bicarbonate solution. The aqueous layer was extracted three times with ethyl acetate, and the combined organic layers were dried over sodium sulfate. The solvent was removed in vacuo and the resulting solid was triturated with diethyl ether to afford the product as a tan solid. Yield: 56.5 mg, 0.16 mmol, 76% over two steps. LCMS m/z 349.2 [M+H]+. 1H NMR (400 MHz, CDCl3) δ 8.56 (s, 1H), 7.68 (d, J=2.5 Hz, 1H), 7.26-7.28 (m, 1H, assumed; partially obscured by solvent peak), 7.23 (br dd, J=8, 2 Hz, 1H), 7.08 (d, J=8 Hz, 1H), 6.83 (d, J=2.5 Hz, 1H), 2.11 (s, 3H), 2.03 (s, 3H), 1.97 (s, 3H).

Step 11. Isolation of (+)-5-[4-(furo[2,3-d]pyrimidin-4-yloxy)-2-methylphenyl]-4,6-dimethylpyridazin-3(2H)-one (7) and (−)-5-[4-(furo[2,3-d]pyrimidin-4-yloxy)-2-methylphenyl]-4,6-dimethylpyridazin-3(2H)-one (8)

Compound 6 was separated into its atropenantiomers using supercritical fluid chromatography (Column: Chiral Tech OJ-H, 5 μm; Eluent: 4:1 carbon dioxide/methanol). Example 7 (designated the (+)-atropenantiomer according to its observed rotation data) was the first-eluting isomer, followed by Example 8. Example 8 was designated the (−)-atropenantiomer according to its observed rotation data. 7: 1H NMR (400 MHz, CDCl3) δ 8.58 (s, 1H), 7.70 (d, J=2.4 Hz, 1H), 7.21-7.27 (m, 2H), 7.10 (d, J=8.2 Hz, 1H), 6.84 (d, J=2.4 Hz, 1H), 2.13 (s, 3H), 2.04 (s, 3H), 1.99 (s, 3H). 8: 1H NMR (400 MHz, CDCl3) δ 10.83 (brs, 1H), 8.58 (s, 1H), 7.70 (d, J=2.4 Hz, 1H), 7.21-7.26 (m, 2H), 7.10 (d, J=8.2 Hz, 1H), 6.84 (d, J=2.4 Hz, 1H), 2.13 (s, 3H), 2.02 (s, 3H), 1.98 (s, 3H).

Example 9

6-[4-(Furo[2,3-d]pyrimidin-4-yloxy)phenyl]-1,5-dimethylpyrimidine-2,4(1H,3H)-dione (9)

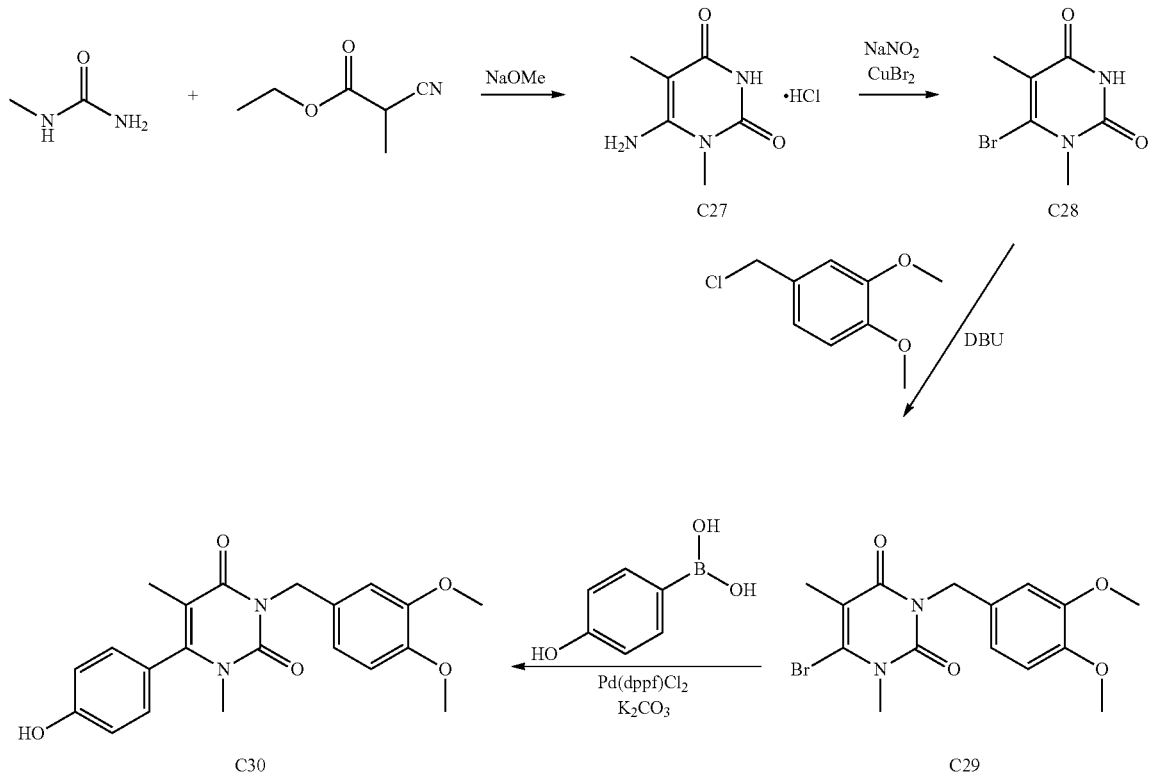

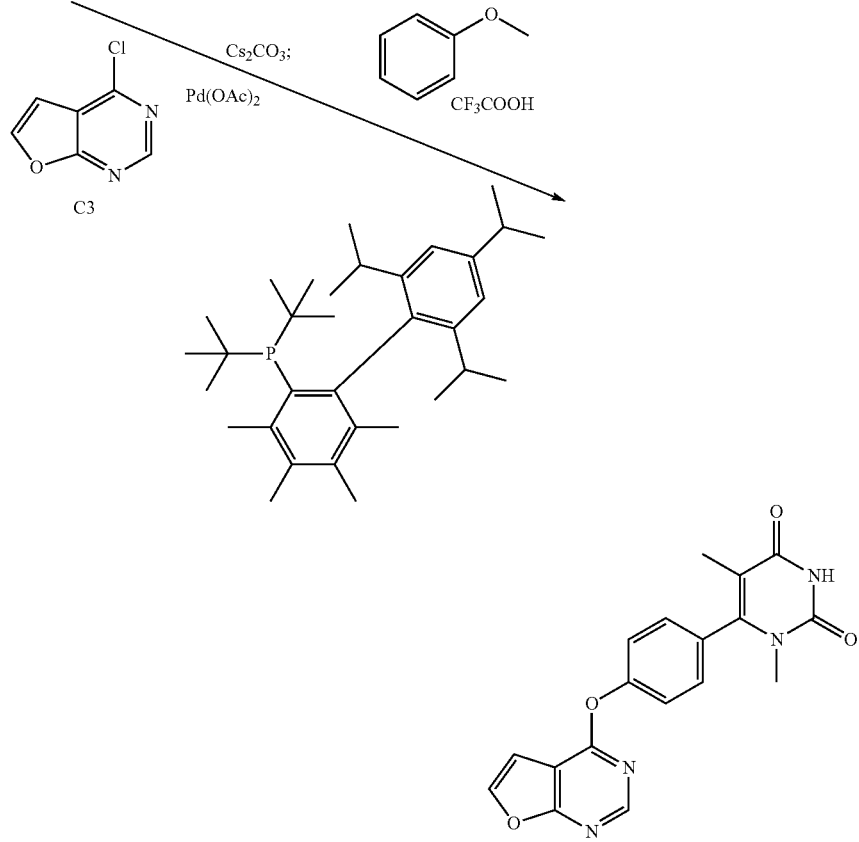

Step 1. Synthesis of 6-amino-1,5-dimethylpyrimidine-2,4(1H,3H)-dione, hydrochloride salt (C27)

A solution of sodium methoxide in methanol (4.4 M, 27 mL, 119 mmol) was added to a solution of ethyl 2-cyanopropanoate (95%, 13.2 mL, 99.6 mmol) and 1-methylurea (98%, 8.26 g, 109 mmol) in methanol (75 mL), and the reaction mixture was heated at reflux for 18 hours, then cooled to room temperature. After removal of solvent in vacuo, the residue was repeatedly evaporated under reduced pressure with acetonitrile (3×50 mL), then partitioned between acetonitrile (100 mL) and water (100 mL). Aqueous 6 M hydrochloric acid was slowly added until the pH had reached approximately 2; the resulting mixture was stirred for 1 hour. The precipitate was collected via filtration and washed with tert-butyl methyl ether, affording the product as a white solid. Yield: 15.2 g, 79.3 mmol, 80%. LCMS m/z 156.1 [M+H]$^+$. $^1$H NMR (400 MHz, DMSO-d$_6$) δ 10.38 (br s, 1H), 6.39 (s, 2H), 3.22 (s, 3H), 1.67 (s, 3H).

Step 2. Synthesis of 6-bromo-1,5-dimethylpyrimidine-2,4(1H,3H)-dione (C28)

A 1:1 mixture of acetonitrile and water (120 mL) was added to a mixture of C27 (9.50 g, 49.6 mmol), sodium nitrite (5.24 g, 76 mmol), and copper(II) bromide (22.4 g, 100 mmol) {Caution: bubbling and slight exotherm!}, and the reaction mixture was allowed to stir at room temperature for 66 hours. Addition of aqueous sulfuric acid (1 N, 200 mL) and ethyl acetate (100 mL) provided a precipitate, which was collected via filtration and washed with water and ethyl acetate to afford the product as a light yellow solid (7.70 g). The organic layer of the filtrate was concentrated to a smaller volume, during which additional precipitate formed; this was isolated via filtration and washed with 1:1 ethyl acetate/heptane to provide additional product (0.4 g). Total yield: 8.1 g, 37 mmol, 75%. GCMS m/z 218, 220 [M$^+$]. $^1$H NMR (400 MHz, DMSO-d$_6$) δ 11.58 (br s, 1H), 3.45 (s, 3H), 1.93 (s, 3H).

Step 3. Synthesis of 6-bromo-3-(3,4-dimethoxybenzyl)-1,5-dimethylpyrimidine-2,4(1H,3H)-dione (C29)

1,8-Diazabicyclo[5.4.0]undec-7-ene (DBU, 98%, 5.57 mL, 36.5 mmol) was added to a suspension of C28 (4.00 g, 18.3 mmol) and 4-(chloromethyl)-1,2-dimethoxybenzene (5.16 g, 27.6 mmol) in acetonitrile (80 mL), and the reaction mixture was heated at 60° C. for 18 hours. After removal of solvent in vacuo, the residue was purified via silica gel chromatography (Gradient: 25% to 50% ethyl acetate in heptane) to afford the product as a white solid. Yield: 5.70 g, 15.4 mmol, 84%. $^1$H NMR (400 MHz, CDCl$_3$) δ 7.08–7.12 (m, 2H), 6.80 (d, J=8.0 Hz, 1H), 5.07 (s, 2H), 3.88 (s, 3H), 3.85 (s, 3H), 3.65 (s, 3H), 2.14 (s, 3H).

Step 4. Synthesis of 3-(3, 4-dimethoxybenzyl)-6-(4-hydroxyphenyl)-1,5-dimethylpyrimidine-2,4(1H, 3H)-dione (C30)

To a solution of C29 (3.5 g, 9.5 mmol) in 1,4-dioxane (100 mL) were added 4-hydroxyphenyl boronic acid (2.7 g, 19 mmol), 1,1'-bis(diphenylphosphino)ferrocene palladium (II) chloride, dichloromethane complex (592 mg, 0.711 mmol), and aqueous potassium carbonate solution (3 M, 9 mL, 27 mmol). The reaction mixture was heated at 100° C. overnight, then cooled to room temperature, diluted with ethyl acetate and water, and filtered through diatomaceous earth to remove solids. The organic layer was washed sequentially with saturated aqueous sodium bicarbonate solution and saturated aqueous sodium chloride solution, then dried over magnesium sulfate. The solvent was removed in vacuo and the residue was purified by silica gel chromatography (Gradient: 25% to 50% ethyl acetate in heptane) to afford the product as a white solid. Yield: 3.4 g, 8.9 mmol, 94%. LCMS m/z 383.2 [M+H]$^+$. $^1$H NMR (400 MHz, CDCl$_3$) δ 7.20 (m, 2H), 7.05 (m, 2H), 6.96 (m, 2H), 6.82 (d, J=8.0 Hz, 1H), 5.15 (s, 2H), 3.89 (s, 3H), 3.86 (s, 3H), 3.06 (s, 3H), 1.70 (s, 3H).

Step 5. Synthesis of 6-[4-(furo[2,3-d]pyrimidin-4-yloxy)phenyl]-1,5-dimethylpyrimidine-2,4(1H,3H)-dione (9)

The title compound was generated as part of a library using the following protocol: to a 2-dram vial were added C3 (0.13 mmol), C30 (38.2 mg, 0.1 mmol), cesium carbonate (98 mg, 0.3 mmol), di-tert-butyl[3,4,5,6-tetramethyl-2',4',6'-tri(propan-2-yl)biphenyl-2-yl]phosphane (10 mg, 20 µmol) and degassed 1,4-dioxane (1 mL). The reaction was degassed with nitrogen and shaken and heated at 110° C. for 20 hours. The reaction mixture was then partitioned between water (1.5 mL) and ethyl acetate (2.5 mL) and filtered through diatomaceous earth; the organic layer was eluted through a solid-phase extraction cartridge charged with sodium sulfate, and the filtrate was concentrated in vacuo. The residue was treated with methoxybenzene (0.1 mL) and trifluoroacetic acid (1.25 mL), and this reaction mixture was shaken and heated at 90° C. for 48 hours, whereupon it was concentrated. The residue (35 mg) was purified via reversed phase HPLC (Column: Waters XBridge C18, 5 µm; Mobile phase A: 0.03% ammonium hydroxide in water (v/v); Mobile phase B: 0.03% ammonium hydroxide in acetonitrile (v/v); Gradient: 5% to 100% B). Yield: 2.6 mg, 7.4 µmol, 7%. LCMS m/z 351.2 [M+H]$^+$. $^1$H NMR (600 MHz, DMSO-d$_6$) δ 8.58 (s, 1H), 8.18 (d, J=2.4 Hz, 1H), 7.51 (br AB quartet, J$_{AB}$=8.7 Hz, Δν$_{AB}$=11.1 Hz, 4H), 7.07 (d, J=2.4 Hz, 1H), 2.94 (s, 3H), 1.56 (s, 3H).

Example 10

4,6-Dimethyl-5-[2-methyl-4-([1,2]thiazolo[4,5-c]pyridin-4-yloxy)phenyl]pyridazin-3(2H)-one (10)

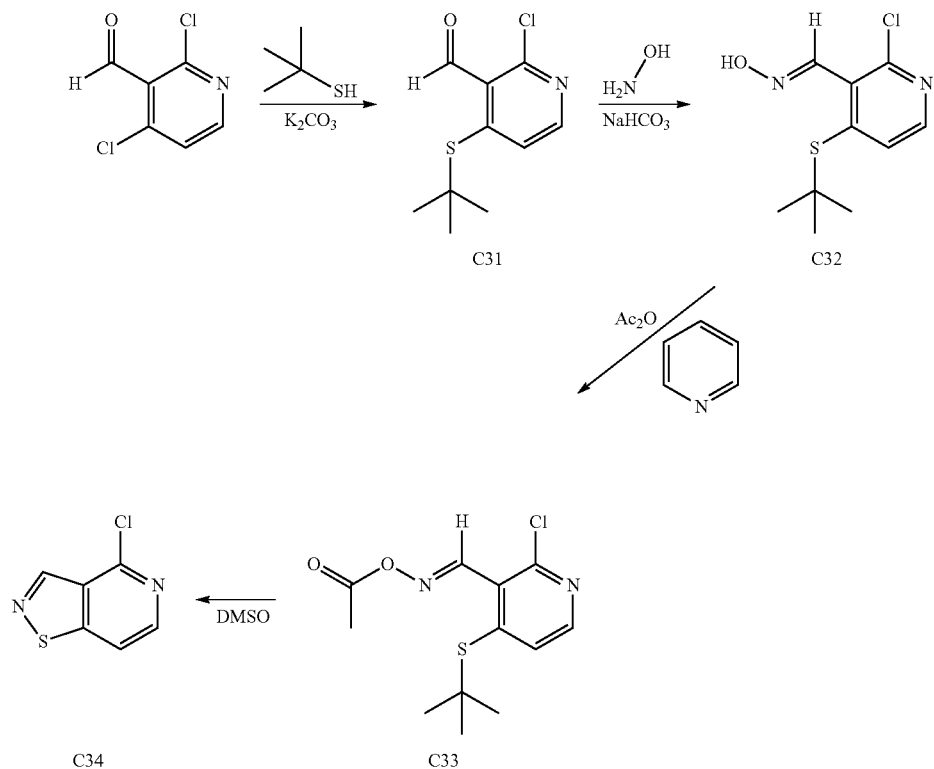

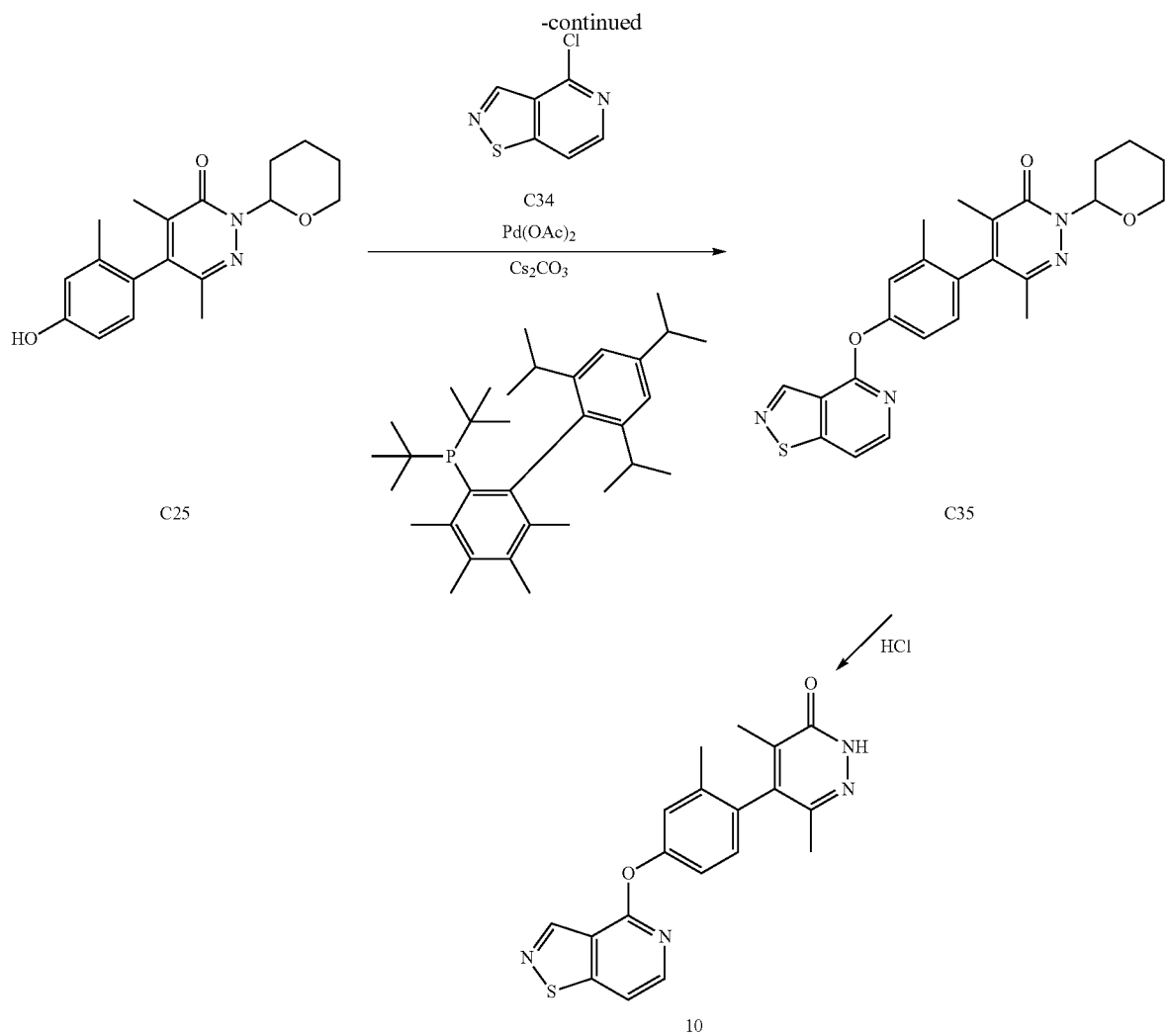

Step 1. Synthesis of 4-(tert-butylsulfanyl)-2-chloro-pyridine-3-carbaldehyde (C31)

A mixture of 2,4-dichloropyridine-3-carbaldehyde (838 mg, 4.76 mmol), 2-methylpropane-2-thiol (429 mg, 4.76 mmol), and potassium carbonate (987 mg, 4.76 mmol) in N,N-dimethylformamide (10 mL) was heated at 50° C. for 3 hours. After the reaction mixture had been cooled to room temperature, it was diluted with water and extracted with dichloromethane (3×30 mL). The combined organic layers were washed with water (3×15 mL) and dried over magnesium sulfate. The solvent was removed in vacuo and the residue was purified by silica gel chromatography (Gradient: 0% to 20% ethyl acetate in heptane) to afford the product as a yellow oil. Yield: 840 mg, 3.66 mmol, 77%. LCMS m/z 230.1 [M+H]+. 1H NMR (400 MHz, CDCl3) δ 10.56 (s, 1H), 8.30 (d, J=5.5 Hz, 1H), 7.52 (d, J=5.5 Hz, 1H), 1.55 (s, 9H).

Step 2. Synthesis of (E)-1-[4-(tert-butylsulfanyl)-2-chloropyridin-3-yl]-N-hydroxymethanimine (C32)

To a stirred solution of C31 (840 mg, 3.66 mmol) in N,N-dimethylformamide (10 mL) at room temperature were added hydroxylamine hydrochloride (145 mg, 4.39 mmol) and sodium bicarbonate (1.84 g, 21.9 mmol). The reaction mixture was stirred at room temperature overnight, and then heated to 50° C. for 2 hours. The reaction mixture was cooled to room temperature and diluted with ethyl acetate, washed with water and with saturated aqueous sodium chloride solution, and dried over magnesium sulfate. The solvent was removed in vacuo and the residue was purified by silica gel chromatography (Gradient: 0% to 20% ethyl acetate in heptane) to afford the product as a white solid. Yield: 482 mg, 1.97 mmol, 54%. LCMS m/z 245.1 [M+H]+. 1H NMR (400 MHz, CDCl3) δ 8.48 (s, 1H), 8.28 (d, J=5.5 Hz, 1H), 7.68 (d, J=5.5 Hz, 1H), 1.50 (s, 9H).

Step 3. Synthesis of 1-[({(E)-[4-(tert-butylsulfanyl)-2-chloropyridin-3-yl]methylidene}amino)oxy]etha-none (C33)

A mixture of C32 (250 mg, 1.02 mmol) and acetic anhydride (225 mg, 2.05 mmol) in pyridine (10 mL) was heated at reflux for 1 hour. The reaction mixture was cooled to room temperature, diluted with ethyl acetate, and washed with saturated aqueous potassium carbonate solution. The organic layer was dried over magnesium sulfate, filtered, and concentrated in vacuo; the residue was purified via chromatography on silica gel (Gradient: 0% to 20% ethyl acetate in heptane) to afford the product as a white solid. Yield: 199 mg, 0.69 mmol, 68%. LCMS m/z 284.9 [M−H]+. 1H NMR (400 MHz, CDCl3) δ 8.70 (s, 1H), 8.27 (d, J=5.5 Hz, 1H), 7.48 (d, J=5.5 Hz, 1H), 2.30 (s, 3H), 1.49 (s, 3H).

Step 4. Synthesis of 4-chloro[1,2]thiazolo[4,5-c]pyridine (C34)

A solution of C33 (170 mg, 0.59 mmol) in dimethyl sulfoxide (5 mL) was heated at 100° C. for 5 hours, whereupon it was cooled to room temperature and diluted with dichloromethane. The mixture was washed sequentially with water and with saturated aqueous sodium chloride solution, then dried over magnesium sulfate. The solvent was removed in vacuo and the residue was purified by silica gel chromatography (Gradient: 0% to 20% ethyl acetate in heptane) to afford the product as a white solid. Yield: 55 mg, 0.32 mmol, 54%. LCMS m/z 171.0 [M+H]$^+$. $^1$H NMR (400 MHz, CDCl$_3$) δ 9.11 (s, 1H), 8.36 (d, J=5.7 Hz, 1H), 7.83 (dd, J=5.7, 1 Hz, 1H).

Step 5. Synthesis of 4,6-dimethyl-5-[2-methyl-4-([1,2]thiazolo[4,5-c]pyridin-4-yloxy)phenyl]-2-(tetrahydro-2H-pyran-2-yl)pyridazin-3(2H)-one (C35)

To a solution of C25 (122 mg, 0.39 mmol) in 1,4-dioxane (5 mL) were added C34 (55 mg, 0.32 mmol), cesium carbonate (316 mg, 0.97 mmol), palladium(II) acetate (7.4 mg, 33 μmol) and di-tert-butyl[3,4,5,6-tetramethyl-2',4',6'-tri(propan-2-yl)biphenyl-2-yl]phosphane (31 mg, 62 μmol). The reaction mixture was heated to 80° C. overnight, then cooled to room temperature and filtered through diatomaceous earth. The filter pad was rinsed with ethyl acetate. The combined filtrates were concentrated in vacuo and the residue was purified first by chromatography on silica gel (Gradient: 0% to 100% ethyl acetate in heptane, followed by elution with 20% methanol in dichloromethane) and then via reversed phase HPLC (Column: Phenomenex Gemini NX-C18, 5 μm; Mobile phase A: 0.1% ammonium hydroxide in water; Mobile phase B: 0.1% ammonium hydroxide in methanol; Gradient: 50% to 100% B) to afford the product as a white solid. Yield: 16 mg, 36 μmol, 11%. LCMS m/z 447.2 [M−H$^+$]. $^1$H NMR (400 MHz, CDCl$_3$) δ 8.24 (d, J=5.5 Hz, 1H), 8.03 (d, J=5.5 Hz, 1H), 7.33 (d, J=5.5 Hz, 1H), 7.12 (m, 1H), 7.00 (m, 2H), 6.13 (m, 1H), 4.19 (m, 2H), 3.79 (m, 1H), 2.32 (m, 1H), 2.05 (s, 3H), 1.99 (s, 3H), 1.91 (s, 3H), 1.74 (m, 2H), 1.54 (m, 2H).

Step 6. Synthesis of 4,6-dimethyl-5-[2-methyl-4-([1,2]thiazolo[4,5-c]pyridin-4-yloxy)phenyl]pyridazin-3(2H)-one (10)

To a stirred solution of C35 (41 mg, 91 μmol) in dichloromethane (5 mL) was added a solution of hydrogen chloride in 1,4-dioxane (4 M, 0.68 mL, 2.7 mmol). The reaction mixture was stirred at room temperature for 3 hours, whereupon it was partitioned between ethyl acetate and saturated aqueous sodium bicarbonate solution. The aqueous layer was extracted three times with ethyl acetate, and the combined organic layers were dried over sodium sulfate. The solvent was removed in vacuo and the residue was triturated with diethyl ether to afford the product as a white solid. Yield: 29 mg, 79 μmol, 87%. LCMS m/z 365.2 [M+H]$^+$. $^1$H NMR (400 MHz, CDCl$_3$) δ 9.19 (s, 1H), 8.10 (d, J=5.7 Hz, 1H), 7.60 (dd, J=5.8, 0.9 Hz, 1H), 7.26 (m, 2H), 7.24 (m, 1H), 7.09 (d, J=8.2 Hz, 1H), 2.12 (s, 3H), 2.02 (s, 3H), 1.98 (s, 3H).

PREPARATIONS

Preparations below describe preparation of P1 that can be used as starting materials for preparation of certain examples of compounds of the invention.

Preparation P1

5-(4-Hydroxy-2-methylphenyl)-4-methyl-2-(tetrahydro-2H-pyran-2-yl)pyridazin-3(2H)-one (P1)

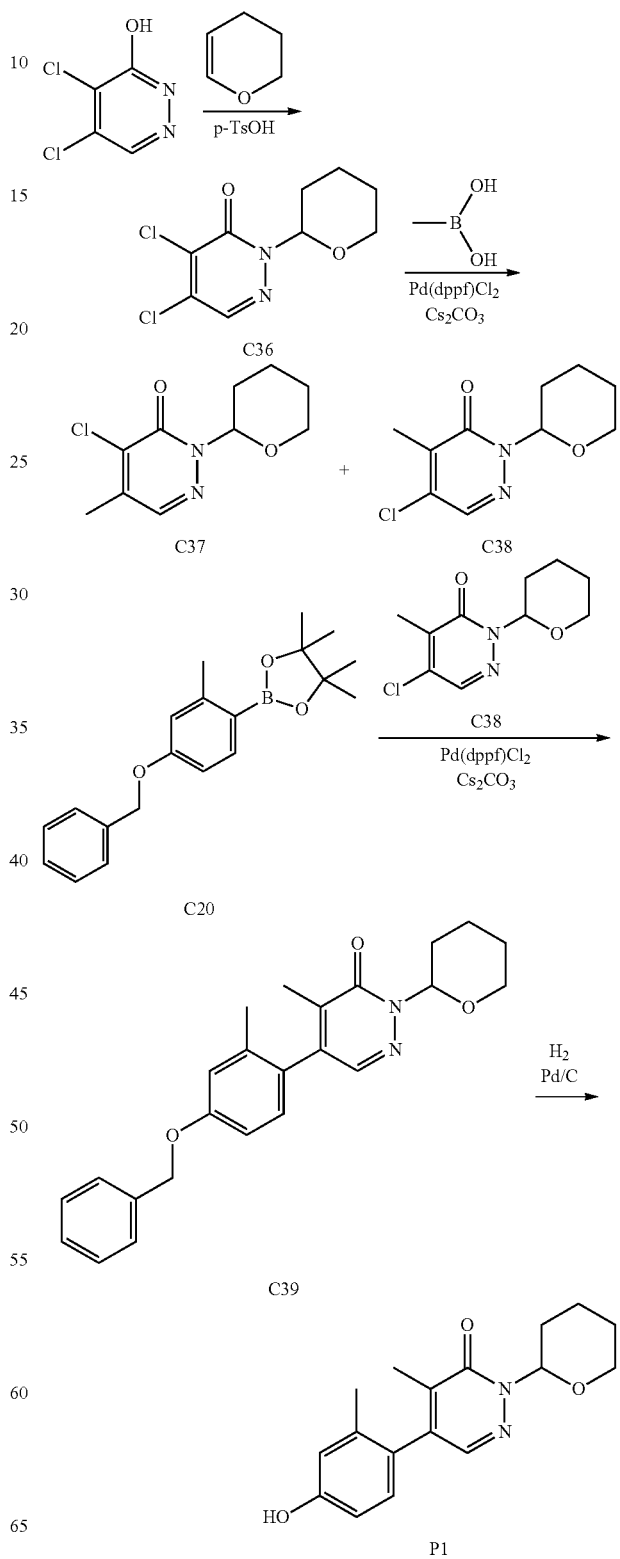

Step 1. Synthesis of 4, 5-dichloro-2-(tetrahydro-2H-pyran-2-yl)pyridazin-3(2H)-one (C36)

A mixture of 4,5-dichloropyridazin-3-ol (42 g, 250 mmol), 3,4-dihydro-2H-pyran (168 g, 2.00 mol) and p-toluenesulfonic acid (8.8 g, 51 mmol) in tetrahydrofuran (2 L) was heated at reflux for 2 days. After cooling to room temperature, the reaction mixture was concentrated in vacuo and purified by silica gel chromatography (Gradient: 3% to 5% ethyl acetate in petroleum ether). The product was obtained as a white solid. Yield: 42 g, 170 mmol, 68%. $^1$H NMR (400 MHz, CDCl$_3$) δ 7.84 (s, 1H), 6.01 (br d, J=11 Hz, 1H), 4.10-4.16 (m, 1H), 3.70-3.79 (m, 1H), 1.99-2.19 (m, 2H), 1.50-1.80 (m, 4H).

Step 2. Synthesis of 4-chloro-5-methyl-2-(tetrahydro-2H-pyran-2-yl)pyridazin-3(2H)-one (C37) and 5-chloro-4-methyl-2-(tetrahydro-2H-pyran-2-yl)pyridazin-3(2H)-one (C38)

To a mixture of C36 (40 g, 0.16 mol), methylboronic acid (9.6 g, 0.16 mol) and cesium carbonate (156 g, 479 mmol) in 1,4-dioxane (500 mL) and water (50 mL) was added [1,1'-bis(diphenylphosphino)ferrocene]dichloropalladium (II) (5 g, 7 mmol). The reaction mixture was stirred at 110° C. for 2 hours, whereupon it was cooled to room temperature and concentrated in vacuo. Purification via silica gel chromatography (Gradient: 3% to 6% ethyl acetate in petroleum ether) afforded compound C37 as a pale yellow solid. Yield: 9.0 g, 39 mmol, 24%. LCMS m/z 250.8 [M+Na$^+$]. $^1$H NMR (400 MHz, CDCl$_3$) δ 7.71 (s, 1H), 6.07 (dd, J=10.7, 2.1 Hz, 1H), 4.10-4.18 (m, 1H), 3.71-3.81 (m, 1H), 2.30 (s, 3H), 1.98-2.19 (m, 2H), 1.53-1.81 (m, 4H). Also obtained was C38, as a pale yellow solid. Yield: 9.3 g, 41 mmol, 26%. LCMS m/z 250.7 [M+Na$^+$]. $^1$H NMR (400 MHz, CDCl$_3$) δ 7.77 (s, 1H), 6.02 (dd, J=10.7, 2.1 Hz, 1H), 4.10-4.17 (m, 1H), 3.71-3.79 (m, 1H), 2.27 (s, 3H), 1.99-2.22 (m, 2H), 1.51-1.79 (m, 4H).

Step 3. Synthesis of 5-[4-(benzyloxy)-2-methylphenyl]-4-methyl-2-(tetrahydro-2H-pyran-2-yl)pyridazin-3(2H)-one (C39)

A solution of C20 (7.30 g, 22.5 mmol), C38 (2.7 g, 12 mmol), [1,1'-bis(diphenylphosphino)ferrocene]dichloropalladium(II) (1.3 g, 1.8 mmol) and cesium carbonate (7.7 g, 24 mmol) in 1,4-dioxane (100 mL) was heated at reflux for 7 hours. The reaction mixture was then filtered through a pad of diatomaceous earth, and the filtrate was concentrated in vacuo. Silica gel chromatography (Gradient: 10% to 50% ethyl acetate in petroleum ether) afforded the product as a brown gel, presumed to be a mixture of diastereomeric atropisomers from its $^1$H NMR spectrum. Yield: 2.5 g, 6.4 mmol, 53%. $^1$H NMR (400 MHz, CDCl$_3$), characteristic peaks: δ 7.66 (s, 1H), 7.35-7.49 (m, 5H), 6.96-7.03 (m, 1H), 6.94 (br d, J=2 Hz, 1H), 6.89 (dd, J=8.3, 2 Hz, 1H), 6.14-6.20 (m, 1H), 5.10 (s, 2H), 4.15-4.24 (m, 1H), 3.76-3.86 (m, 1H), 2.18-2.32 (m, 1H), 2.12 and 2.14 (2 s, total 3H), 2.00 (s, 3H), 1.71-1.86 (m, 3H).

Step 4. Synthesis of 5-(4-hydroxy-2-methylphenyl)-4-methyl-2-(tetrahydro-2H-pyran-2-yl)pyridazin-3(2H)-one (P1)

A mixture of C39 (2.5 g, 6.4 mmol) and wet palladium on carbon (0.8 g) in methanol (80 mL) was stirred under 50 psi of hydrogen for 3 days, whereupon the reaction mixture was filtered through diatomaceous earth. The filtrate was concentrated in vacuo, and the residue was purified via silica gel chromatography (Gradient: 10% to 60% ethyl acetate in petroleum ether) to provide the product as a white solid, judged to be a mixture of diastereomeric atropisomers from its $^1$H NMR spectrum. Yield: 1.6 g, 5.3 mmol, 83%. LCMS m/z 301 [M+H]+. $^1$H NMR (400 MHz, CDCl$_3$), characteristic peaks: δ 7.64-7.68 (s, 1H), 6.90-6.97 (m, 1H), 6.73-6.82 (m, 2H), 6.14-6.19 (m, 1H), 4.14-4.23 (m, 1H), 3.76-3.85 (m, 1H), 2.17-2.31 (m, 1H), 2.09 and 2.11 (2 s, total 3H), 2.00 (s, 3H), 1.72-1.85 (m, 3H).

Table 1 below lists some additional examples of compounds of invention (Examples 11-23) that were made using methods, starting materials or intermediates, and preparations described herein.

TABLE 1

Examples 11-23 (including Method of Preparation, Non-Commercial starting materials, Structures and Physicochemical Data).

| Example number | Method of Preparation; Non-commercial starting materials | Structure | $^1$H NMR (600 MHz, DMSO-d$_6$) δ (ppm); Mass spectrum, observed ion m/z [M + H]$^+$ or HPLC retention time; Mass spectrum m/z [M + H]$^+$ (unless otherwise indicated) |
|---|---|---|---|
| 11 | Example 2; C5 | 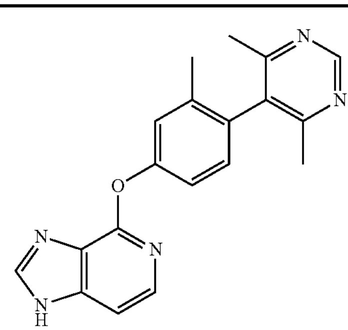 | $^1$H NMR (400 MHz, CD$_3$OD) δ 8.90 (s, 1H), 8.36 (s, 1H), 7.89 (d, J = 5.8 Hz, 1H), 7.42 (d, J = 5.6 Hz, 1H), 7.27 (s, 1H), 7.19 (s, 2H), 2.71 (s, 6H), 2.05 (s, 3H); 332.1 |

TABLE 1-continued

Examples 11-23 (including Method of Preparation, Non-Commercial starting materials, Structures and Physicochemical Data).

| Example number | Method of Preparation; Non-commercial starting materials | Structure | $^1$H NMR (600 MHz, DMSO-d$_6$) δ (ppm); Mass spectrum, observed ion m/z [M + H]$^+$ or HPLC retention time; Mass spectrum m/z [M + H]$^+$ (unless otherwise indicated) |
|---|---|---|---|
| 12 | Example 2[1] | 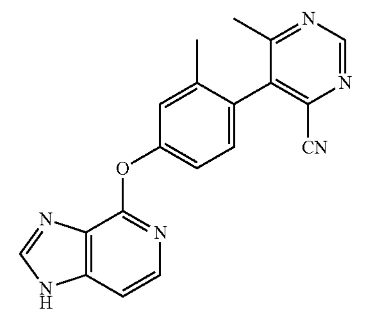 [SMILES: Cc1cc(Oc2nccc3[nH]cnc23)ccc1-c1c(C)ncnc1C#N] | $^1$H NMR (400 MHz, CD$_3$OD) δ 9.21 (s, 1H), 8.38 (s, 1H), 7.94 (d, J = 5.8 Hz, 1H), 7.45 (d, J = 4.0 Hz, 1H), 7.33 (m, 2H), 7.25 (d, J = 9.8 Hz, 1H), 2.47 (s, 3H), 2.15 (s, 3H); 343.0 |
| 13 | Example 6[2] | 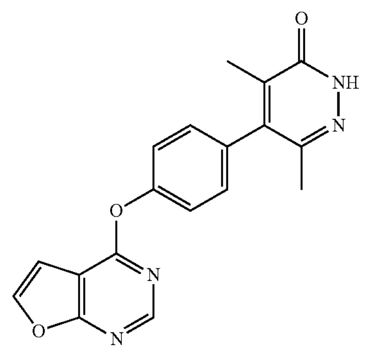 [SMILES: Cc1n[nH]c(=O)c(C)c1-c1ccc(Oc2ncnc3occc23)cc1] | $^1$H NMR (400 MHz, CD$_3$OD) δ 8.40 (s, 1H), 7.85 (d, J = 2.7 Hz, 1H), 7.36 (m, 2H), 7.26 (m, 2H), 7.33 (m, 2H), 6.86 (d, J = 2.5 Hz, 1H), 1.99 (s, 3H), 1.88 (s, 3H); 335.2 |
| 14 | Example 6[3]; P1 | 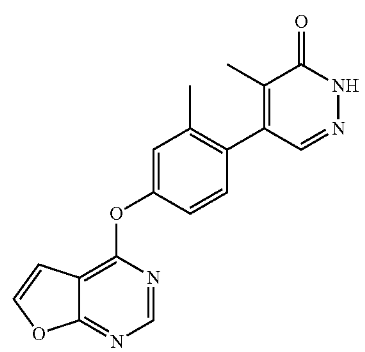 [SMILES: Cc1cc(Oc2ncnc3occc23)ccc1-c1cn[nH]c(=O)c1C] | Retention time, 2.44 minutes; 335.0 |
| 15 | Example 9[4]; C30 | 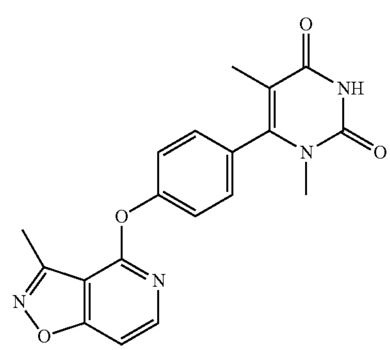 [SMILES: Cc1c(-c2ccc(Oc3nccc4onc(C)c34)cc2)n(C)c(=O)[nH]c1=O] | 8.19 (d, J = 6.1 Hz, 1H), 7.53 (d, J = 6.1 Hz, 1H), 7.49 (d, J = 8.6, 2H), 7.47 (d, J = 8.6 Hz, 1H), 2.94 (s, 3H), 2.71 (s, 3H), 1.58 (s, 3H); 365.0 |

TABLE 1-continued

Examples 11-23 (including Method of Preparation, Non-Commercial starting materials, Structures and Physicochemical Data).

| Example number | Method of Preparation; Non-commercial starting materials | Structure | $^1$H NMR (600 MHz, DMSO-$d_6$) δ (ppm); Mass spectrum, observed ion m/z [M + H]$^+$ or HPLC retention time; Mass spectrum m/z [M + H]$^+$ (unless otherwise indicated) |
|---|---|---|---|
| 16 | Example 6; C25 | 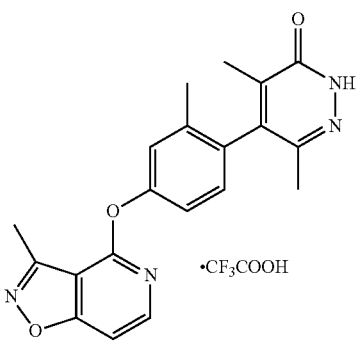 [SMILES: Cc1cc(Oc2nccc3onc(C)c23)ccc1-c1c(C)n[nH]c(=O)c1C ; "·CF3COOH"] | 8.19 (d, J = 6.1 Hz, 1H), 7.51 (d, J = 6.1 Hz, 1H), 7.32 (s, 1H), 7.26 (dd, J = 8.6, 2.2 Hz, 1H), 7.18 (d, J = 8.3 Hz, 1H), 2.69 (s, 3H), 2.49 (s, 3H), 2.04 (s, 3H), 1.88 (s, 3H); 363.1 |
| 17 | Example 3; C17 | 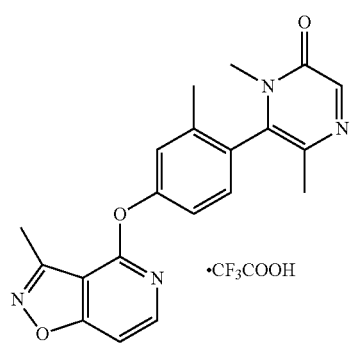 [SMILES: Cc1cc(Oc2nccc3onc(C)c23)ccc1-c1c(C)ncc(=O)n1C ; "·CF3COOH"] | 8.20 (d, J = 6.1 Hz, 1H), 8.03 (s, 1H), 7.52 (d, J = 6.1 Hz, 1H), 7.39 (dd, J = 8.3, 2.1 Hz, 1H), 7.33 (d, J = 8.1 Hz, 1H), 3.08 (s, 3H), 2.69 (s, 3H), 2.10 (s, 3H), 1.93 (s, 3H); 363.1 |
| 18 | Example 9[5] | 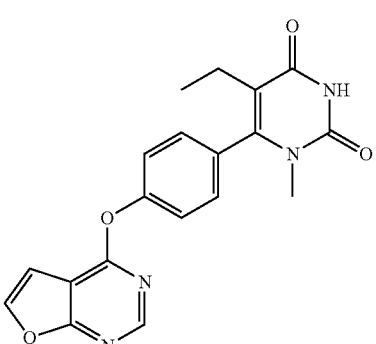 | 8.59 (s, 1H), 8.18 (d, J = 2.2 Hz, 1H), 7.52 (s, br, 4H), 7.05 (d, J = 2.2 Hz, 1H), 2.92 (s, 3H), 1.97 (q, J = 7.3 Hz, 2H), 0.86 (t, J = 7.3 Hz, 3H); 365.2 |
| 19 | Example 9[6] | 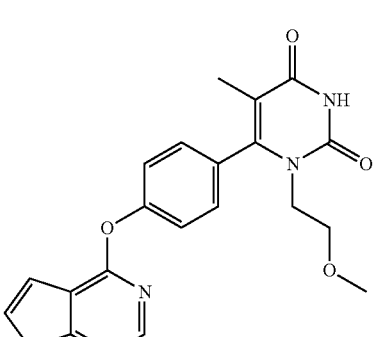 | 8.57 (s, 1H), 8.17 (d, J = 2.6 Hz, 1H), 7.49 (m, br, 4H), 7.03 (d, J = 2.6 Hz, 1H), 3.61 (t, J = 6.1 Hz, 2H), 3.34 (t, J = 6.1 Hz, 2H) 3.09 (s, 3H), 1.51 (s, 3H); 395.2 |

TABLE 1-continued

Examples 11-23 (including Method of Preparation, Non-Commercial starting materials, Structures and Physicochemical Data).

| Example number | Method of Preparation; Non-commercial starting materials | Structure | $^1$H NMR (600 MHz, DMSO-d$_6$) δ (ppm); Mass spectrum, observed ion m/z [M + H]$^+$ or HPLC retention time; Mass spectrum m/z [M + H]$^+$ (unless otherwise indicated) |
|---|---|---|---|
| 20 | Example 9[7] | 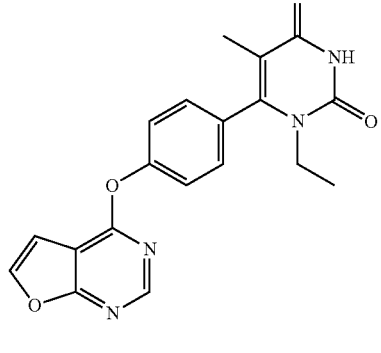 | 8.59 (s, 1H), 8.19 (d, J = 2.2 Hz, 1H), 7.53 (s, br, 4H), 7.05 (d, J = 2.2 Hz, 1H), 3.49 (q, J = 7.0 Hz, 2H), 1.52 (s, 3H), 0.98 (t, J = 7.0 Hz, 3H); 365.2 |
| 21 | Example 9[8] | 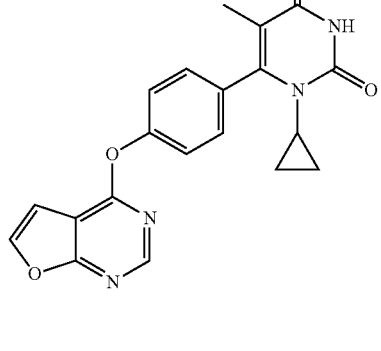 | 8.57 (s, 1H), 8.17 (d, J = 2.6 Hz, 1H), 7.54 (dt, J = 9.6, 0.7 Hz, 2H), 7.45 (dt, J = 9.6, 0.7 Hz, 2H), 7.03 (d, J = 2.6 Hz, 1H), 2.6 (m, 1H), 1.60 (s, 3H), 0.57 (m, 2H), 0.51 (m, 2H); 377.2 |
| 22 | Example 9[9] | 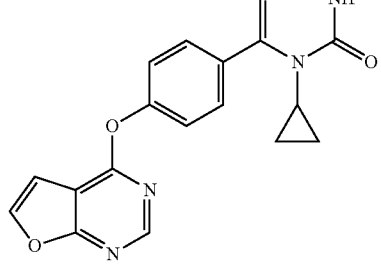 | 8.58 (s, 1H), 8.18 (d, J = 2.2 Hz, 1H), 7.57 (d, J = 8.8 Hz, 2H), 7.46 (d, J = 8.8 Hz, 2H), 7.01 (d, J = 2.2 Hz, 1H), 2.54 (q, J = 7.3 Hz, 2H), 2.03 (t, J = 7.3 Hz, 3H); 391.2 |

TABLE 1-continued

Examples 11-23 (including Method of Preparation, Non-Commercial starting materials, Structures and Physicochemical Data).

| Example number | Method of Preparation; Non-commercial starting materials | Structure | $^1$H NMR (600 MHz, DMSO-$d_6$) δ (ppm); Mass spectrum, observed ion m/z [M + H]$^+$ or HPLC retention time; Mass spectrum m/z [M + H]$^+$ (unless otherwise indicated) |
|---|---|---|---|
| 23 | Example 9[10] | 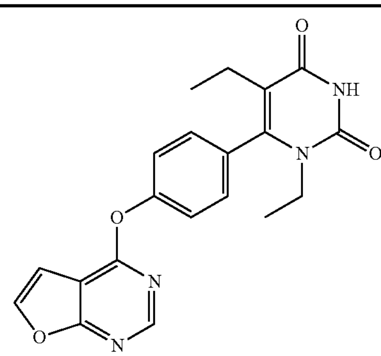 | 8.60 (s, 1H), 8.19 (d, J = 2.2 Hz, 1H), 7.55 (d, J = 8.8 Hz, 2H), 7.53 (d, J = 8.8 Hz, 2H), 7.02 (d, J = 2.2 Hz, 1H), 3.45 (q, J = 7.0 Hz, 2H), 1.93 (q, J = 7.5 Hz, 2H), 0.99 (t, J = 7.0 Hz, 3H), 0.85 (t, J = 7.5 Hz, 3H); 379.2 |

1. The requisite intermediate 5-(4-hydroxy-2-methylphenyl)-6-methylpyrimidine-4-carbonitrile was prepared following a procedure similar to that described for the preparation of C5 from 5-bromo-6-methylpyrimidine-4-carbonitrile. The final product was obtained following the coupling and deprotection conditions described in the preparation of Example 2.
2. The requisite 5-(4-hydroxyphenyl)-4,6-dimethyl-2-(tetrahydro-2H-pyran-2-yl)pyridazin-3(2H)-one was prepared from 1-(benzyloxy)-4-bromobenzene following the procedure described for preparation of C25.
3. Analytical HPLC conditions. Column: Waters Atlantis dC18, 4.6 x 50 mm, 5 μm; Mobile phase A: 0.05% trifluoroacetic acid in water (v/v); Mobile phase B: 0.05% trifluoroacetic acid in acetonitrile (v/v); Gradient: 5.0% to 95.0% B, linear, over 4.0 minutes; Flow rate: 2 mL/minute.
4. The final coupling step was carried out using cesium carbonate in dimethyl sulfoxide at 80° C.
5. The requisite 3-(3,4-dimethoxybenzyl)-5-ethyl-6-(4-hydroxyphenyl)-1-methylpyrimidine-2,4(1H,3H)-dione was prepared following a procedure similar to that described for the preparation of C30, starting from ethyl 2-cyanobutanoate and 1-methylurea.
6. The requisite 3-(3,4-dimethoxybenzyl)-6-(4-hydroxyphenyl)-1-(2-methoxyethyl)-5-methylpyrimidine-2,4(1H,3H)-dione was prepared following a procedure similar to that described for the preparation of C30, starting from ethyl 2-cyanopropanoate and 1-(2-methoxyethyl)urea.
7. The requisite 3-(3,4-dimethoxybenzyl)-1-ethyl-6-(4-hydroxyphenyl)-5-methylpyrimidine-2,4(1H,3H)-dione was prepared following a procedure similar to that described for the preparation of C30, starting from ethyl 2-cyanopropanoate and 1-ethylurea.
8. The requisite 1-cyclopropyl-3-(3,4-dimethoxybenzyl)-6-(4-hydroxyphenyl)-5-methylpyrimidine-2,4(1H,3H)-dione was prepared following a procedure similar to that described for the preparation of C30, starting from ethyl 2-cyanopropanoate and 1-cyclopropylurea.
9. The requisite 1-cyclopropyl-3-(3,4-dimethoxybenzyl)-5-ethyl-6-(4-hydroxyphenyl)pyrimidine-2,4(1H,3H)-dione was prepared following a procedure similar to that described for the preparation of C30, starting from ethyl 2-cyanobutanoate and 1-cyclopropylurea.
10. The requisite 3-(3,4-dimethoxybenzyl)-1,5-diethyl-6-(4-hydroxyphenyl)pyrimidine-2,4(1H,3H)-dione was prepared following a procedure similar to that described for the preparation of C30, starting from ethyl 2-cyanobutanoate and 1-ethylurea.

Example AA

Human D1 Receptor Binding Assay and Data

The affinity of the compounds described herein was determined by competition binding assays similar to those described in Ryman-Rasmussen et al., "Differential activation of adenylate cyclase and receptor internalization by novel dopamine D1 receptor agonists", Molecular Pharmacology 68(4):1039-1048 (2005). This radioligand binding assay used [$^3$H]-SCH23390, a radiolabeled D1 ligand, to evaluate the ability of a test compound to compete with the radioligand when binding to a D1 receptor.

D1 binding assays were performed using over-expressing LTK human cell lines. To determine basic assay parameters, ligand concentrations were determined from saturation binding studies where the $K_d$ for [$^3$H]-SCH23390 was found to be 1.3 nM. From tissue concentration curve studies, the optimal amount of tissue was determined to be 1.75 mg/mL per 96 well plate using 0.5 nM of [$^3$H]-SCH23390. These ligand and tissue concentrations were used in time course studies to determine linearity and equilibrium conditions for binding. Binding was at equilibrium with the specified amount of tissue in 30 minutes at 37° C. From these parameters, $K_i$ values were determined by homogenizing the specified amount of tissue for each species in 50 mM Tris (pH 7.4 at 4° C.) containing 2.0 mM MgCl$_2$ using a Polytron and spun in a centrifuge at 40,000×g for 10 minutes. The pellet was resuspended in assay buffer [50 mM Tris (pH 7.4@ RT) containing 4 mM MgSO$_4$ and 0.5 mM EDTA]. Incubations were initiated by the addition of 200 μL of tissue to 96-well plates containing test drugs (2.5 μL) and 0.5 nM [$^3$H]-SCH23390 (50 μL) in a final volume of 250 μL. Non-specific binding was determined by radioligand binding in the presence of a saturating concentration of (+)-Butaclamol (10 μM), a D1 antagonist. After a 30 minute incubation period at 37° C., assay samples were rapidly filtered through Unifilter-96 GF/B PEI-coated filter plates and rinsed with 50 mM Tris buffer (pH 7.4 at 4° C.). Membrane bound [$^3$H]-SCH23390 levels were determined by liquid scintillation counting of the filterplates in Ecolume. The IC$_{50}$ value (concentration at which 50% inhibition of specific binding occurs) was calculated by linear regression of the concentration-response data in Microsoft Excel. $K_i$ values were calculated according to the Cheng-Prusoff equation:

$$K_i = \frac{IC_{50}}{1 + ([L]/K_d)}$$

where [L]=concentration of free radioligand and $K_d$=dissociation constant of radioligand for D1 receptor (1.3 nM for [$^3$H]-SCH23390).

Example BB

D1 cAMP HTRF Assay and Data

The D1 cAMP (Cyclic Adenosine Monophosphate) HTRF (Homogeneous Time-Resolved Fluorescence) Assay used and described herein is a competitive immunoassay between native cAMP produced by cells and cAMP labeled with XL-665. This assay was used to determine the ability of a test compound to agonize (including partially agonize) D1. A Mab anti-cAMP labeled Cryptate visualizes the tracer. The maximum signal is achieved if the samples do not contain free cAMP due to the proximity of donor (Eucryptate) and acceptor (XL665) entities. The signal, therefore, is inversely proportional to the concentration of cAMP in the sample. A time-resolved and ratiometric measurement (em 665 nm/em 620 nm) minimizes the interference with medium. cAMP HTRF assays are commercially available, for example, from Cisbio Bioassays, IBA group.

Materials and Methods

Materials: The cAMP Dynamic kit was obtained from Cisbio International (Cisbio 62AM4PEJ). Multidrop Combi (Thermo Scientific) was used for assay additions. An EnVision (PerkinElmer) reader was used to read HTRF.

Cell Cuture: A HEK293T/hD1#1 stable cell line was constructed internally (Pfizer Ann Arbor). The cells were grown as adherent cells in NuncT$_{500}$ flasks in high glucose DMEM (Invitrogen 11995-065), 10% fetal bovine serum dialyzed (Invitrogen 26400-044), 1×MEM NEAA (Invitrogen 1140, 25 mM HEPES (Invitrogen 15630), 1×Pen/Strep (Invitrogen 15070-063) and 500 µg/mL Genenticin (Invitrogen 10131-035) at 37° C. and 5% $CO_2$. At 72 or 96 hours post-growth, cells were rinsed with DPBS, and 0.25% Trypsin-EDTA was added to dislodge the cells. Media was then added and cells were centrifuged and media removed. The cell pellets were re-suspended in Cell Culture Freezing Medium (Invitrogen 12648-056) at a density of 4e7 cells/mL. One mL aliquots of the cells were made in Cryo-vials and frozen at −80° C. for future use in the D1 HTRF assay.

D1 cAMP HTRF Assay Procedure: Frozen cells were quickly thawed, re-suspended in 50 mL warm media and allowed to sit for 5 min prior to centrifugation (1000 rpm) at room temperature. Media was removed and cell pellet was re-suspended in PBS/0.5 µM IBMX generating 2e5 cells/mL. Using a Multidrop Combi, 5 µL cells/well was added to the assay plate (Greiner 784085), which already contained 5 µL of a test compound. Compound controls [5 µM dopamine (final) and 0.5% DMSO (final)] were also included on every plate for data analysis. Cells and compounds were incubated at room temperature for 30 min. Working solutions of cAMP-D2 and anti-cAMP-cryptate were prepared according to Cisbio instructions. Using Multidrop, 5 µL cAMP-D2 working solution was added to the assay plate containing the test compound and cells. Using Multidrop, 5 µL anti-cAMP-cryptate working solutions was added to assay plate containing test compound, cells and cAMP-D2. The assay plate was incubated for 1 hour at room temperature. The assay plate was read on an EnVision plate reader using Cisbio recommended settings. A cAMP standard curve was generated using cAMP stock solution provided in the Cisbio kit.

Data Analysis: Data analysis was done using computer software. Percent effects were calculated from the compound controls. Ratio $EC_{50}$ was determined using the raw ratio data from the EnVision reader. The cAMP standard curve was used in an analysis program to determine cAMP concentrations from raw ratio data. cAMP $EC_{50}$ was determined using the calculated cAMP data.

TABLE 2

Biological Data and Compound Name for Examples 1-23.

| Example number | Human D1 Receptor Binding, $K_i$ (nM); Geometric mean of 2-4 determinations (unless otherwise indicated) | IUPAC Name |
|---|---|---|
| 1 | 166$^a$ | 4-[4-(4,6-dimethylpyrimidin-5-yl)-3-methylphenoxy]furo[2,3-d]pyrimidine |
| 2 | 374$^a$ | 4-[3-methyl-4-(6-methylimidazo[1,2-a]pyrazin-5-yl)phenoxy]-1H-imidazo[4,5-c]pyridine |
| 3 | 196$^a$ | 6-[4-(furo[2,3-d]pyrimidin-4-yloxy)-2-methylphenyl]-1,5-dimethylpyrazin-2(1H)-one |
| 4 | 127 | (−)-6-[4-(furo[2,3-d]pyrimidin-4-yloxy)-2-methylphenyl]-1,5-dimethylpyrazin-2(1H)-one |
| 5 | 400$^a$ | (+)-6-[4-(furo[2,3-d]pyrimidin-4-yloxy)-2-methylphenyl]-1,5-dimethylpyrazin-2(1H)-one |
| 6 | 44.7 | 5-[4-(furo[2,3-d]pyrimidin-4-yloxy)-2-methylphenyl]-4,6-dimethylpyridazin-3(2H)-one |
| 7 | 30.7 | (+)-5-[4-(furo[2,3-d]pyrimidin-4-yloxy)-2-methylphenyl]-4,6-dimethylpyridazin-3(2H)-one |
| 8 | 40.2 | (−)-5-[4-(furo[2,3-d]pyrimidin-4-yloxy)-2-methylphenyl]-4,6-dimethylpyridazin-3(2H)-one |
| 9 | 142$^a$ | 6-[4-(furo[2,3-d]pyrimidin-4-yloxy)phenyl]-1,5-dimethylpyrimidine-2,4(1H,3H)-dione |
| 10 | 32.7 | 4,6-dimethyl-5-[2-methyl-4-([1,2]thiazolo[4,5-c]pyridin-4-yloxy)phenyl]pyridazin-3(2H)-one |
| 11 | 912$^a$ | 4-[4-(4,6-dimethylpyrimidin-5-yl)-3-methylphenoxy]-1H-imidazo[4,5-c]pyridine |
| 12 | 367 | 5-[4-(1H-imidazo[4,5-c]pyridin-4-yloxy)-2-methylphenyl]-6-methylpyrimidine-4-carbonitrile |
| 13 | 70.3 | 5-[4-(furo[2,3-d]pyrimidin-4-yloxy)phenyl]-4,6-dimethylpyridazin-3(2H)-one |
| 14 | 372$^a$ | 5-[4-(furo[2,3-d]pyrimidin-4-yloxy)-2-methylphenyl]-4-methylpyridazin-3(2H)-one |

TABLE 2-continued

Biological Data and Compound Name for Examples 1-23.

| Example number | Human D1 Receptor Binding, $K_i$ (nM); Geometric mean of 2-4 determinations (unless otherwise indicated) | IUPAC Name |
|---|---|---|
| 15 | 280[a] | 1,5-dimethyl-6-{4-[(3-methyl[1,2]oxazolo[4,5-c]pyridin-4-yl)oxy]phenyl}pyrimidine-2,4(1H,3H)-dione |
| 16 | 326[a] | 4,6-dimethyl-5-{2-methyl-4-[(3-methyl[1,2]oxazolo[4,5-c]pyridin-4-yl)oxy]phenyl}pyridazin-3(2H)-one, trifluoroacetic acid salt |
| 17 | 1730[a] | 1,5-dimethyl-6-{2-methyl-4-[(3-methyl[1,2]oxazolo[4,5-c]pyridin-4-yl)oxy]phenyl}pyrazin-2(1H)-one, trifluoroacetic acid salt |
| 18 | 274[a] | 5-ethyl-6-[4-(furo[2,3-d]pyrimidin-4-yloxy)phenyl]-1-methylpyrimidine-2,4(1H,3H)-dione |
| 19 | 900[a] | 6-[4-(furo[2,3-d]pyrimidin-4-yloxy)phenyl]-1-(2-methoxyethyl)-5-methylpyrimidine-2,4(1H,3H)-dione |
| 20 | 179[a] | 1-ethyl-6-[4-(furo[2,3-d]pyrimidin-4-yloxy)phenyl]-5-methylpyrimidine-2,4(1H,3H)-dione |
| 21 | 122[a] | 1-cyclopropyl-6-[4-(furo[2,3-d]pyrimidin-4-yloxy)phenyl]-5-methylpyrimidine-2,4(1H,3H)-dione |
| 22 | 142[a] | 1-cyclopropyl-5-ethyl-6-[4-(furo[2,3-d]pyrimidin-4-yloxy)phenyl]pyrimidine-2,4(1H,3H)-dione |
| 23 | 309[a] | 1,5-diethyl-6-[4-(furo[2,3-d]pyrimidin-4-yloxy)phenyl]pyrimidine-2,4(1H,3H)-dione |

[a]$K_i$ value is from a single determination

Various modifications of the invention, in addition to those described herein, will be apparent to those skilled in the art from the foregoing description. Such modifications are also intended to fall within the scope of the appendant claims. Each reference (including all patents, patent applications, journal articles, books, and any other publications) cited in the present application is hereby incorporated by reference in its entirety.

What is claimed is:

1. A compound of Formula I-a:

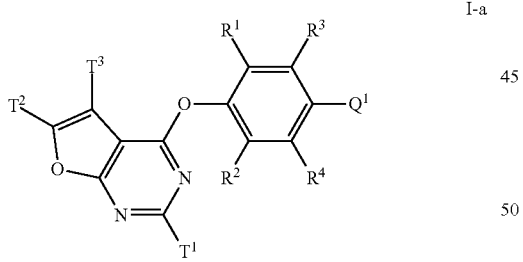

or a pharmaceutically acceptable salt thereof, wherein:
$Q^1$ is an N-containing 5- to 6-membered heteroaryl or an N-containing 5- to 6-membered heterocycloalkyl, each optionally substituted with one $R^9$ and further optionally substituted with 1, 2, 3, or 4 $R^{10}$;
$T^1$ is H, F, Cl, methyl, or $C_1$ fluoroalkyl;
each of $T^2$ and $T^3$ is independently selected from the group consisting of H, halogen, —CN, $C_{1-4}$ alkyl, $C_{1-4}$ haloalkyl, $C_{3-4}$ cycloalkyl, $C_{3-4}$ halocycloalkyl, cyclopropylmethyl, $C_{1-4}$ alkoxy, $C_{1-4}$ haloalkoxy;
each of $R^1$ and $R^2$ is independently selected from the group consisting of H, halogen, —CN, $C_{1-6}$ alkyl, $C_{1-6}$ haloalkyl, $C_{1-6}$ alkoxy, $C_{1-6}$ haloalkoxy, $C_{3-6}$ cycloalkyl, —C(=O)OH, and C(=O)—O—($C_{1-4}$ alkyl), wherein each of said $C_{1-6}$ alkyl and $C_{3-6}$ cycloalkyl is optionally substituted with 1, 2, 3, 4, or 5 substituents each independently selected from halo, —OH, —CN, $C_{1-4}$ alkyl, $C_{1-4}$ haloalkyl, $C_{1-4}$ alkoxy, and $C_{1-4}$ haloalkoxy;
each of $R^3$ and $R^4$ is independently selected from the group consisting of H, halogen, —OH, —NO$_2$, —CN, —SF$_5$, $C_{1-6}$ alkyl, $C_{1-6}$ haloalkyl, $C_{1-6}$ haloalkoxy, $C_{2-6}$ alkenyl, $C_{2-6}$ alkynyl, $C_{3-7}$ cycloalkyl, a 4- to 10-membered heterocycloalkyl, —N($R^5$)($R^6$), —N($R^7$)(C(=O)$R^8$), —C(=O)—N($R^5$)($R^6$), —C(=O)—$R^8$, —C(=O)—$OR^8$, —OC(=O)$R^8$, —N($R^7$)(S(=O)$_2R^8$), —S(=O)$_2$—N($R^5$)($R^6$), —$SR^8$, and —$OR^8$, wherein each of said $C_{1-6}$ alkyl, $C_{3-7}$ cycloalkyl, and heterocycloalkyl is optionally substituted with 1, 2, or 3 substituents each independently selected from the group consisting of halogen, —CN, —OH, $C_{1-4}$ alkyl, $C_{1-4}$ alkoxy, $C_{1-4}$ haloalkyl, $C_{1-4}$ haloalkoxy, $C_{3-6}$ cycloalkyl, —N($R^5$)($R^6$), —N($R^7$)(C(=O)$R^8$), —C(=O)—$OR^8$, —C(=O)H, —C(=O)$R^8$, —C(=O)N($R^5$)($R^6$), —N($R^7$)(S(=O)$_2R^8$), —S(=O)$_2$—N($R^5$)($R^6$), —$SR^8$, and —$OR^8$;
or $R^1$ and $R^3$ together with the two carbon atoms to which they are attached form a fused N-containing 5- or 6-membered heteroaryl, a fused N-containing 5- or 6-membered heterocycloalkyl, a fused 5- or 6-membered cycloalkyl, or a fused benzene ring, each optionally substituted with 1, 2, or 3 substituents each independently selected from the group consisting of halo, —CN, —OH, $C_{1-3}$ alkyl, $C_{1-3}$ alkoxy, $C_{1-3}$ haloalkyl, and $C_{1-3}$ haloalkoxy;
$R^5$ is H, $C_{1-4}$ alkyl, $C_{1-4}$ haloalkyl, or $C_{3-7}$ cycloalkyl;
$R^6$ is H or selected from the group consisting of $C_{1-4}$ alkyl, $C_{1-4}$ haloalkyl, $C_{3-7}$ cycloalkyl, a 4- to 10-membered heterocycloalkyl, $C_{6-10}$ aryl, a 5- to 10-membered heteroaryl, ($C_{3-7}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, and (5- to 10-membered heteroaryl)-$C_{1-4}$ alkyl-, wherein each of the selections from the group is optionally substituted with 1, 2, 3, or 4 substituents each independently selected from the group consisting of —OH, —CN, $C_{1-4}$ alkyl, $C_{3-7}$ cycloalkyl, $C_{1-4}$ hydroxylalkyl, —S—$C_{1-4}$ alkyl, —C(=O)H, —C(=O)—$C_{1-4}$ alkyl, —C(=O)—O—$C_{1-4}$ alkyl, —C(=O)—NH$_2$, —C(=O)—N($C_{1-4}$ alkyl)$_2$, $C_{1-4}$ haloalkyl, $C_{1-4}$ alkoxy, and $C_{1-4}$ haloalkoxy;

or $R^5$ and $R^6$ together with the N atom to which they are attached form a 4- to 10-membered heterocycloalkyl or a 5- to 10-membered heteroaryl, each optionally substituted with 1, 2, 3, 4, or 5 substituents each independently selected from the group consisting of halogen, —OH, oxo, —C(=O)H, —C(=O)OH, —C(=O)—$C_{1-4}$ alkyl, —C(=O)—NH$_2$, —C(=O)—N($C_{1-4}$ alkyl)$_2$, —CN, $C_{1-4}$ alkyl, $C_{1-4}$ alkoxy, $C_{1-4}$ hydroxylalkyl, $C_{1-4}$ haloalkyl, and $C_{1-4}$ haloalkoxy;

$R^7$ is selected from the group consisting of H, $C_{1-4}$ alkyl, and $C_{3-7}$ cycloalkyl;

$R^8$ is selected from the group consisting of $C_{1-6}$ alkyl, $C_{3-7}$ cycloalkyl, a 4- to 14-membered heterocycloalkyl, $C_{6-10}$ aryl, a 5- to 10-membered heteroaryl, ($C_{3-7}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, and (5- to 10-membered heteroaryl)-$C_{1-4}$ alkyl-, wherein each of the selections from the group is optionally substituted with 1, 2, or 3 substituents each independently selected from the group consisting of halogen, —CF$_3$, —CN, —OH, oxo, —S—$C_{1-4}$ alkyl, $C_{1-4}$ alkyl, $C_{1-4}$ haloalkyl, $C_{2-6}$ alkenyl, $C_{2-6}$ alkynyl, $C_{3-7}$ cycloalkyl, $C_{1-4}$ alkoxy, and $C_{1-4}$ haloalkoxy;

$R^9$ is halogen, $C_{1-4}$ alkyl, $C_{1-4}$ haloalkyl, —CN, —SF$_5$, —N($R^5$)($R^6$), $C_{1-6}$ alkoxy, $C_{1-6}$ haloalkoxy, $C_{3-7}$ cycloalkoxy, or $C_{3-7}$ cycloalkyl, wherein each of the $C_{1-4}$ alkyl and $C_{3-7}$ cycloalkyl is optionally substituted with 1, 2, 3, 4, or 5 substituents each independently selected from the group consisting of halogen, —N($R^5$)($R^6$), $C_{1-4}$ alkyl, $C_{1-4}$ haloalkyl, $C_{3-7}$ cycloalkyl, $C_{1-4}$ alkoxy, and $C_{1-4}$ haloalkoxy;

each $R^{10}$ is independently selected from the group consisting of halogen, —OH, —CN, —SF$_5$, —NO$_2$, oxo, thiono, $C_{1-6}$ alkyl, $C_{1-6}$ haloalkyl, $C_{1-6}$ hydroxylalkyl, $C_{1-6}$ alkoxy, $C_{1-6}$ haloalkoxy, $C_{3-7}$ cycloalkyl, $C_{2-6}$ alkenyl, $C_{2-6}$ alkynyl, $C_{6-10}$ aryl, a 4- to 10-membered heterocycloalkyl, a 5- to 10-membered heteroaryl, ($C_{3-7}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, (5- to 10-membered heteroaryl)-$C_{1-4}$ alkyl-, —N($R^5$)($R^6$), —N($R^7$)(C(=O)$R^8$), —S(=O)$_2$N($R^5$)($R^6$), —C(=O)—N($R^5$)($R^6$), —C(=O)—$R^8$, —C(=O)—$R^8$, —SR$^8$, and —OR$^8$, wherein each of said $C_{1-6}$ alkyl, $C_{3-7}$ cycloalkyl, $C_{6-10}$ aryl, 4- to 10-membered heterocycloalkyl, 5- to 10-membered heteroaryl, ($C_{3-7}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, and (5- to 10-membered heteroaryl)-$C_{1-4}$ alkyl- is optionally substituted with 1, 2, 3, or 4 substituents each independently selected from the group consisting of halogen, OH, —CN, —NO$_2$, $C_{1-4}$ alkyl, $C_{1-4}$ hydroxylalkyl, $C_{1-4}$ alkoxy, —N($R^5$)($R^6$), —S—($C_{1-4}$ alkyl), —S(=O)$_2$—($C_{1-4}$ alkyl), $C_{6-10}$ aryloxy, [($C_{6-10}$ aryl)-$C_{1-4}$ alkyloxy- optionally substituted with 1 or 2 $C_{1-4}$ alkyl], oxo, —C(=O)H, —C(=O)—$C_{1-4}$ alkyl, —C(=O)O—$C_{1-4}$ alkyl, —C(=O)NH$_2$, —NHC(=O)H, —NHC(=O)—($C_{1-4}$ alkyl), $C_{3-7}$ cycloalkyl, a 5- or 6-membered heteroaryl, $C_{1-4}$ haloalkyl, and $C_{1-4}$ haloalkoxy;

or $R^9$ and an adjacent $R^{10}$ together with the two ring atoms on $Q^1$ to which they are attached form a fused benzene ring or a fused 5- or 6-membered heteroaryl, each optionally substituted with 1, 2, 3, 4, or 5 independently selected $R^{10a}$; and each $R^{10a}$ is independently selected from the group consisting of halogen, —OH, —N($R^5$)($R^6$), —C(=O)OH, —C(=O)—$C_{1-4}$ alkyl, —C(=O)—NH$_2$, —C(=O)—N($C_{1-4}$ alkyl)$_2$, —CN, —SF$_5$, $C_{1-4}$ alkyl, $C_{1-4}$ alkoxy, $C_{1-4}$ hydroxylalkyl, $C_{1-4}$ haloalkyl, and $C_{1-4}$ haloalkoxy.

2. The compound of claim 1 or a pharmaceutically acceptable salt thereof, wherein each of $T^2$, $T^3$, and $T^4$ is independently selected from the group consisting of H, halogen, —CN, methoxy, $C_1$ fluoroalkoxy, methyl, and $C_1$ fluoroalkyl.

3. The compound of claim 1 or a pharmaceutically acceptable salt thereof, wherein $T^1$ is H and $T^4$ is H.

4. The compound of claim 1 or a pharmaceutically acceptable salt thereof, wherein each of $R^1$ and $R^2$ is independently H or halogen; and each of $R^3$ and $R^4$ is independently H, halogen, —CN, methyl, $C_1$ haloalkyl, methoxy, or $C_1$ haloalkoxy.

5. The compound of claim 1 or a pharmaceutically acceptable salt thereof, wherein each of $R^1$ and $R^2$ is H; $R^3$ is H; and $R^4$ is H, halogen, —CN, methyl, or $C_1$ haloalkyl.

6. The compound of claim 1 or a pharmaceutically acceptable salt thereof, wherein:

$Q^1$ is a moiety of

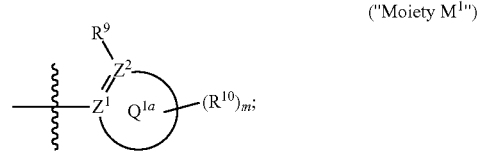

("Moiety M$^1$")

ring $Q^{1a}$ is an N-containing 5- to 6-membered heteroaryl or an N-containing 5- to 6-membered heterocycloalkyl;

====== represents a single bond or double bond;

each of $Z^1$ and $Z^2$ is independently C or N;

$R^9$ is halogen, $C_{1-4}$ alkyl, $C_{1-4}$ haloalkyl, $C_{3-7}$ cycloalkyl, —CN, —N($R^5$)($R^6$), $C_{1-6}$ alkoxy, $C_{1-6}$ haloalkoxy, or $C_{3-7}$ cycloalkoxy, wherein each of the $C_{1-4}$ alkyl and $C_{3-7}$ cycloalkyl is optionally substituted with 1, 2, 3, 4, or 5 substituents each independently selected from the group consisting of halogen, —N($R^5$)($R^6$), $C_{1-4}$ alkyl, $C_{1-4}$ haloalkyl, $C_{3-7}$ cycloalkyl, $C_{1-4}$ alkoxy, and $C_{1-4}$ haloalkoxy;

each $R^{10}$ is independently selected from the group consisting of halogen, —OH, —CN, —NO$_2$, oxo, thiono, $C_{1-6}$ alkyl, $C_{1-6}$ haloalkyl, $C_{1-6}$ hydroxylalkyl, $C_{1-6}$ alkoxy, $C_{1-6}$ haloalkoxy, $C_{3-7}$ cycloalkyl, $C_{2-6}$ alkenyl, $C_{2-6}$ alkynyl, $C_{6-10}$ aryl, a 4- to 10-membered heterocycloalkyl, a 5- to 10-membered heteroaryl, ($C_{3-7}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, (5- to 10-membered heteroaryl)-$C_{1-4}$ alkyl-, (5- to 10-membered heteroaryl)-$C_{2-4}$ alkenyl-, —N($R^5$)($R^6$), —N($R^7$)(C(=O)$R^8$), —S(=O)$_2$N($R^5$)($R^6$), —C(=O)—N($R^5$)($R^6$), —C(=O)—$R^8$, —C(=O)—OR$^8$, and —OR$^8$, wherein each of said $C_{1-6}$ alkyl, $C_{3-7}$ cycloalkyl, $C_{6-10}$ aryl, 4- to 10-membered heterocycloalkyl, 5- to 10-membered heteroaryl, ($C_{3-7}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, (5- to 10-membered heteroaryl)-$C_{1-4}$ alkyl-, and (5- to 10-membered heteroaryl)-$C_{2-4}$ alkenyl- is optionally substituted with 1, 2, 3, or 4 substituents each independently selected from the group consisting of halogen, OH, —CN, —NO$_2$, $C_{1-4}$ alkyl, $C_{1-4}$ hydroxylalkyl, $C_{1-4}$ alkoxy, —N($R^5$)($R^6$), —S—($C_{1-4}$ alkyl), —S(=O)$_2$—($C_{1-4}$ alkyl), $C_{6-10}$ aryloxy, ($C_{6-10}$ aryl)-$C_{1-4}$ alkyloxy- optionally substituted with 1 or 2 $C_{1-4}$ alkyl, oxo, —C(=O)H, —C(=O)—$C_{1-4}$ alkyl, —C(=O)O—$C_{1-4}$ alkyl, —C(=O)NH$_2$, —NHC(=O)H, —NHC(=O)—($C_{1-4}$ alkyl), $C_{3-7}$ cycloalkyl, a 5- or 6-membered heteroaryl, $C_{1-4}$ haloalkyl, and $C_{1-4}$ haloalkoxy;

or $R^9$ and the adjacent $R^{10}$ together with the two ring atoms on ring $Q^{1a}$ to which they are attached form a fused benzene ring or a fused 5- or 6-membered heteroaryl, each optionally substituted with 1, 2, 3, 4, or 5 independently selected $R^{10a}$;

each $R^{10a}$ is independently selected from the group consisting of halogen, —OH, —C(=O)OH, —C(=O)—$C_{1-4}$ alkyl, —C(=O)—NH$_2$, —C(=O)—N($C_{1-4}$ alkyl)$_2$, —CN, $C_{1-4}$ alkyl, $C_{1-4}$ alkoxy, $C_{1-4}$ hydroxylalkyl, ($C_{1-2}$ alkoxy)-$C_{1-4}$ alkyl-, $C_{1-4}$ haloalkyl, and $C_{1-4}$ haloalkoxy; and m is 0, 1, 2, 3, or 4.

7. The compound of claim 6 or a pharmaceutically acceptable salt thereof, wherein Moiety M$^1$ is selected from the group consisting of quinolinyl, isoquinolinyl, 1H-imidazo[4,5-c]pyridinyl, imidazo[1,2-a]pyridinyl, 1H-pyrrolo[3,2-c]pyridinyl, imidazo[1,2-a]pyrazinyl, imidazo[2,1-c][1,2,4]triazinyl, imidazo[1,5-a]pyrazinyl, imidazo[1,2-a]pyrimidinyl, 1H-indazolyl, 9H-purinyl, imidazo[1,2-a]pyrimidinyl, [1,2,4]triazolo[1,5-a]pyrimidinyl, isoxazolo[5,4-c]pyridazinyl, isoxazolo[3,4-c]pyridazinyl, and [1,2,4]triazolo[4,3-b]pyridazinyl, each optionally substituted with 1, 2, or 3 $R^{10}$ and further optionally substituted with 1 or 2 $R^{10a}$; or wherein Moiety M$^1$ is selected from the group consisting of pyrimidinyl, pyrazinyl, pyridinyl, pyridazinyl, 1H-pyrazolyl, 1H-pyrrolyl, 4H-pyrazolyl, 1H-imidazolyl, 1H-imidazolyl, 3-oxo-2H-pyridazinyl, 1H-2-oxo-pyrimidinyl, 1H-2-oxo-pyridinyl, 2,4(1H,3H)-dioxo-pyrimidinyl, and 1H-2-oxo-pyrazinyl, each substituted with $R^9$ and further optionally substituted with 1, 2, or 3 $R^{10}$.

8. The compound of claim 6 or a pharmaceutically acceptable salt thereof, wherein:

Moiety M$^1$ is

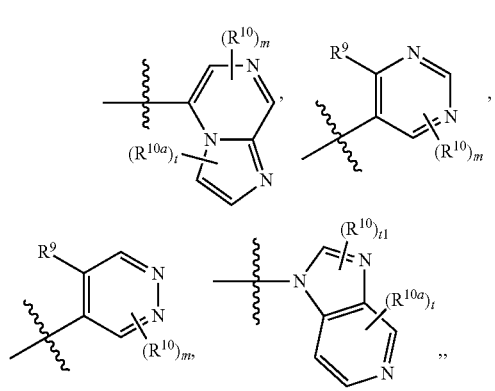

-continued

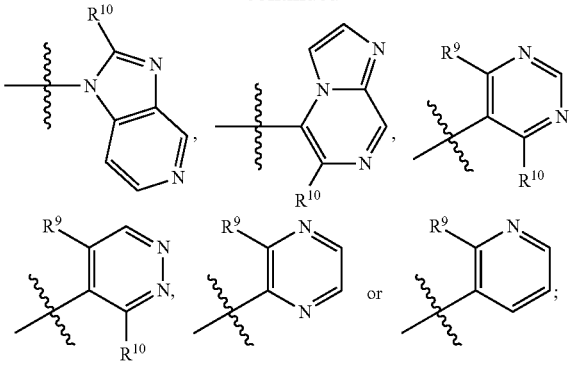

$R^{10a}$ is $C_{1-4}$ alkyl, $C_{1-4}$ haloalkyl, ($C_{1-2}$ alkoxy)-$C_{1-4}$ alkyl-, or $C_{3-7}$ cycloalkyl;

t1 is 0 or 1; and t is 0 or 1.

9. The compound of claim 6 or a pharmaceutically acceptable salt thereof, wherein Moiety M$^1$ is

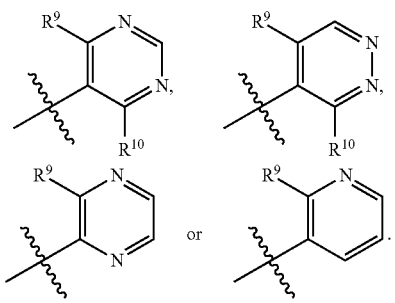

10. The compound of claim 6 or a pharmaceutically acceptable salt thereof, wherein:

Moiety M$^1$ is

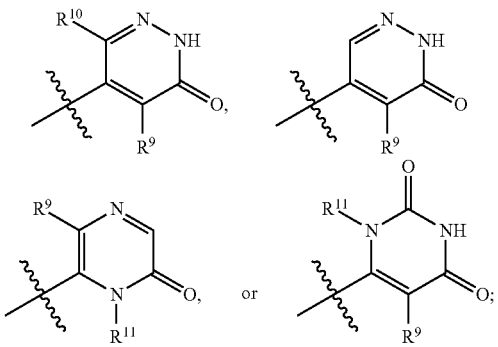

and $R^{11}$ is H, $C_{1-4}$ alkyl, $C_{1-4}$ haloalkyl, ($C_{1-2}$ alkoxy)-$C_{1-4}$ alkyl-, or $C_{3-7}$ cycloalkyl.

11. The compound of claim 1 or a pharmaceutically acceptable salt thereof, wherein $R^9$ is halogen, $C_{3-6}$ cycloalkyl, $C_{1-4}$ alkyl or —CN; and each $R^{10}$ is independently selected from the group consisting of $C_{1-4}$ alkyl, $C_{1-4}$ haloalkyl, ($C_{1-2}$ alkoxy)-$C_{1-4}$ alkyl-, —CN, and —N($R^5$)($R^6$), wherein each of $R^5$ and $R^6$ independently is H or selected from the group consisting of $C_{1-4}$ alkyl, $C_{1-4}$ haloalkyl, and $C_{3-7}$ cycloalkyl; or $R^5$ and $R^6$ together with the N atom to which they are attached form a 4- to 7-membered heterocycloalkyl or a 5-membered heteroaryl, each optionally substituted with 1, 2, or 3 substituents each independently selected from the group consisting of halogen, —CN, $C_{1-4}$ alkyl, $C_{1-4}$ alkoxy, $C_{3-6}$ cycloalkyl, $C_{1-4}$ haloalkyl, and $C_{1-4}$ haloalkoxy.

12. A compound of claim 1 selected from the group consisting of:
- 4-[4-(4,6-dimethylpyrimidin-5-yl)-3-methylphenoxy]furo[2,3-d]pyrimidine;
- (−)-6-[4-(furo[2,3-d]pyrimidin-4-yloxy)-2-methylphenyl]-1,5-dimethylpyrazin-2(1H)-one;
- (+)-6-[4-(furo[2,3-d]pyrimidin-4-yloxy)-2-methylphenyl]-1,5-dimethylpyrazin-2(1H)-one;
- (+)-5-[4-(furo[2,3-d]pyrimidin-4-yloxy)-2-methylphenyl]-4,6-dimethylpyridazin-3(2H)-one;
- (−)-5-[4-(furo[2, 3-d]pyrimidin-4-yloxy)-2-methylphenyl]-4,6-dimethylpyridazin-3(2H)-one;
- 6-[4-(furo[2,3-d]pyrimidin-4-yloxy)phenyl]-1,5-dimethylpyrimidine-2,4(1H,3H)-dione;
- 5-[4-(furo[2,3-d]pyrimidin-4-yloxy)phenyl]-4,6-dimethylpyridazin-3(2H)-one;
- 5-ethyl-6-[4-(furo[2,3-d]pyrimidin-4-yloxy)phenyl]-1-methylpyrimidine-2,4(1H,3H)-dione;
- 1-ethyl-6-[4-(furo[2,3-d]pyrimidin-4-yloxy)phenyl]-5-methylpyrimidine-2,4(1H,3H)-dione; and
- 1-cyclopropyl-6-[4-(furo[2,3-d]pyrimidin-4-yloxy)phenyl]-5-methylpyrimidine-2,4(1H,3H)-dione, or a pharmaceutically acceptable salt thereof.

13. A pharmaceutical composition comprising a compound of claim 1 or a pharmaceutically acceptable salt thereof, and a pharmaceutically acceptable carrier.

14. A method for treating Parkinson's disease in a mammal comprising administering to the mammal a therapeutically effective amount of a compound of claim 1 or a pharmaceutically acceptable salt thereof.

* * * * *